United States Patent
Carroll et al.

(10) Patent No.: US 6,593,335 B1
(45) Date of Patent: *Jul. 15, 2003

(54) POTASSIUM CHANNEL OPENERS

(75) Inventors: William A. Carroll, Evanston, IL (US); Yiyuan Chen, East Syracuse, NY (US); Mark W. Holladay, Tucson, AZ (US); Michael E. Kort, Lake Bluff, IL (US); Philip R. Kym, Grayslake, IL (US); James P. Sullivan, Deerfield, IL (US); Rui Tang, Gurnee, IL (US); Lin Yi, Milford, CT (US); Henry Q. Zhang, Grayslake, IL (US); Irene Drizin, Wadsworth, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 565 days.

(21) Appl. No.: 09/338,889

(22) Filed: Jun. 23, 1999

Related U.S. Application Data

(63) Continuation-in-part of application No. 09/216,651, filed on Dec. 18, 1998, now abandoned, which is a continuation-in-part of application No. 08/993,392, filed on Dec. 18, 1997, now abandoned.

(51) Int. Cl.[7] .................. A61K 31/4365; C07D 495/04; C07D 495/14; A61P 13/00
(52) U.S. Cl. .......................................... 514/291; 546/80
(58) Field of Search ........................... 546/80; 514/291

(56) References Cited

U.S. PATENT DOCUMENTS

| | | | | |
|---|---|---|---|---|
| 4,532,248 A | * | 7/1985 | Franckowiak | 514/302 |
| 4,879,384 A | | 11/1989 | Schwender | 546/114 |
| 5,270,308 A | * | 12/1993 | Shiraishi | 514/229.8 |
| 5,455,253 A | * | 10/1995 | Ohnmacht | 514/311 |

FOREIGN PATENT DOCUMENTS

| | | |
|---|---|---|
| DE | 26 16 995 | 10/1977 |
| DE | 2658804 | 7/1978 |
| DE | 2747513 | 5/1979 |
| DE | 4424678 | 1/1996 |
| EP | 0 145 956 | 6/1985 |
| EP | 0 189 060 | 7/1986 |
| EP | 0241281 | 10/1987 |
| EP | 0 400 660 | 12/1990 |
| EP | 0462696 | 12/1991 |
| EP | 0539154 | 4/1993 |
| EP | 0 705 830 | 4/1996 |
| WO | 9408966 | 4/1994 |
| WO | 96/02547 | 2/1996 |
| WO | 99/31059 | 6/1999 |
| WO | 00/24743 | 5/2000 |
| WO | 00/51986 | 9/2000 |

OTHER PUBLICATIONS

Berge, S.M.; Journal Pharmaceutical Sciences; 66: 1 et seq. (1977).

Dodd, John H.; "Synthesis of Novel Cyclic Sulfone Dihydropyridines Facilitated by a Selective Ethyl Diazoacetate Ring Expansion"; J. Heterocyclic Chem. 27:1453–1456 (1990).

Dodd, J. H., et al., "Synthesis and Biological Properties of FWJ 22108, A Bronchoselective Calcium Channel Blocker", Drug Design and Discovery, 10:65–75 (1993).

Fenk, C. J., et al., "Synthesis of a Novel Cyclic Sulfone Dihydropyridine: An Investigation of the Isomerization Reaction Converting an Exocyclic Double Bond Isomer into a 1,4–Dihydropyridine", J. Heterocyclic Chem., 31:351–355 (1993).

Freedman, Jonathan E. et al.; "ATP–sensitive Potassium Channels: Diverse Functions in the Central Nervous System"; The Neuroscientist 2:(3) 145–152 (1996).

Gehlert, Donald R.; "ATP Sensitive Potassium Channels: Potential Drug Targets in Neuropsychopharmacology"; Prog. Neuro–Psychopharmacol & Biol. Psychiat. 18:1093–1102 (1994).

Gopalakrishnan, M. et al.; "ATP–Sensitive $K^+$ Channels: Pharmacologic Properties, Regulation, and Therapeutic Potential"; Drug Development Research 28:95–127 (1993).

Howe, Burton B. et al.; "ZENECA ZD6169: A Novel $K_{ATP}$ Channel Opener with in Vivo Selectivity for Urinary Bladder"; The Journal of Pharmacology and Experimental Therapeutics 274:884–890 (1995).

Klockner, V. and Isenberg, G.; Pflugers Arch; 405;329–339 (1985).

Lawson, K.; "Potassium Channel Activation: A Potential Therapeutic Approach?"; Pharmacol Ther. 70: (1) 39–63 (1996).

Moore, Jr., J. B., et al., "RWJ–22108—a novel airway tissue—selective calcium channel blocker", Agents Actions, 40:57–61 (1993).

(List continued on next page.)

Primary Examiner—Evelyn Mei Huang
(74) Attorney, Agent, or Firm—B. Gregory Donner; Michael J. Ward

(57) ABSTRACT

Compounds having the formula I:

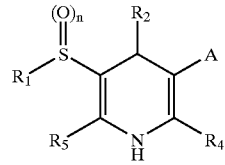

are useful in treating diseases prevented by or ameliorated with potassium channel openers. Also disclosed are potassium channel opening compositions and a method of opening potassium channels in a mammal.

54 Claims, No Drawings

OTHER PUBLICATIONS

Nurse, D.E. et al.; Br. J. Urol.; vol. 68; pp. 27–31 (1991).
Quast et al; Mol. Pharmacol; vol. 43; pp. 474–481 (1993).
Ritchie, D. M., et al., "Experimental Antiasthmatic Activity of FWJ 22108: A Bronchoselective Calcium Entry Blocker", *Int. Arch. Allergy Immunol.*, 100:274–282 (1993).

Spanswick, D. et al.; "Leptin inhibits hypothalamic neurons by activation of ATP–sensitive potassium channels"; *Nature* 390:521–25; (Dec. 4, 1997).

\* cited by examiner

POTASSIUM CHANNEL OPENERS

This application is a continuation-in-part of U.S. patent application Ser. No. 09/216,651, filed Dec. 18, 1998 abandoned, which is a continuation-in-part of U.S. patent application Ser. No. 08/993,392, filed Dec. 18, 1997, abandoned, both of which are hereby incorporated by reference.

1. Technical Field

Novel dihydropyridine compounds and their derivatives can open potassium channels and are useful for treating a variety of medical conditions.

2. Background of Invention

Potassium channels play an important role in regulating cell membrane excitability. When the potassium channels open, changes in the electrical potential across the cell membrane occur and result in a more polarized state. A number of diseases or conditions can be treated with therapeutic agents that open potassium channels. See K. Lawson, Pharmacol. Ther., v. 70, pp. 39–63 (1996); D.R. Gehlert et al., Pros. Neuro-Psychopharmacol & Biol. Psychiat., v. 18, pp. 1093–1102 (1994); M. Gopalakrishnan et al., Drug Development Research, v. 28, pp. 95–127 (1993); J.E. Freedman et al., The Neuroscientist, v. 2, pp. 145–152 (1996). Such diseases or conditions include asthma, epilepsy, hypertension, male sexual dysftmction, female sexual dysfunction, migraine, pain, urinary incontinence, stroke, Raynaud's Syndrome, eating disorders, functional bowel disorders, and neurodegeneration.

Potassium channel openers also act as smooth muscle relaxants. Because urinary incontinence can result from the spontaneous, uncontrolled contractions of the smooth muscle of the bladder, the ability of potassium channel openers to hyperpolarize bladder cells and relax bladder smooth muscle provides a method to ameliorate or prevent urinary incontinence.

WO 9408966 and EP 0539154 AI disclose a group of acridinedione and quinolone compounds that are claimed useful in the treatment of urinary incontinence. These compounds belong to the larger general chemical class of dihydropyridines. The compounds of the present invention are chemically distinct from those of W094/08966 and EP 0539154 Al since they have at least one sulfonyl group attached to the 3-position of the dihydropyridine ring.

Dihydropyridines of differing chemical structure may possess a variety of biological activities. For example, US 4,879,384 discloses a group of thiacycloalkeno[3,2-b] pyridines that belong to the dihydropyridine class and are calcium channel antagonists. The compounds of the present invention are chemically distinct from those of US 4,879,384 since they do not have a carboxylic acid derivative attached to the 3-position of the dihydropyridine ring.

Thus, the compounds of the present invention are chemically distinct from the prior art, hyperpolarize cell membranes, open potassium channels, relax smooth muscle cells, inhibit bladder contractions and are useful for treating diseases that can be ameliorated by opening potassium channels.

SUMMARY OF THE INVENTION

In its principle embodiment, the present invention discloses compounds having formula I:

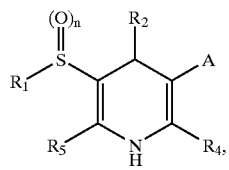

or a pharmaceutically acceptable salt, ester, amide, or prodrug thereof wherein, n is 0–2;

$R_1$ is selected from the group consisting of alkyl and haloalkyl;

$R_2$ is selected from the group consisting of optionally substituted aryl and optionally substituted heteroaryl;

A is selected from the group consisting of hydrogen, alkyl, haloalkyl, cyano, heteroaryl, nitro and —$XR_3$;

X is selected from the group consisting of C(O) and $S(O)_p$;

p is 1–2;

$R_3$ is selected from the group consisting of alkyl, haloalkyl, and hydroxy;

$R_4$ is selected from the group consisting of hydrogen, alkoxyalkoxyalkyl, alkoxyalkyl, alkyl, arylalkoxyalkyl, aryloxyalkyl, haloalkyl, heteroarylalkoxyalkyl, heteroaryloxyalkyl, ($NZ^1Z^2$) alkoxyalkyl, and ($NZ^1Z^2$)alkyl wherein $Z^1$ and $Z^2$ are independently selected from the group consisting of hydrogen, alkoxycarbonyl, alkyl, alkylcarbonyl, alkylsulfonyl, aminocarbonyl, aryl, arylalkyl, cycloalkyl, cycloalkylalkyl, formyl, heteroaryl, and heteroarylalkyl or $Z^1$, $Z^2$ and the nitrogen atom to which they are attached form a 3, 4, 5, 6, 7, or 8 membered ring; or $R_3$ and $R_4$ together form a ring selected from the group consisting of a 5-, 6-, or 7-membered carbocyclic ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo, and a 5-, 6- or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo; and $R_5$ is selected from the group consisting of hydrogen, alkyl and haloalkyl; or $R_1$ and $R_5$ together with the ring to which they are attached form a 5-, 6- or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo;

provided that at least one of $R_1$ and $R_5$ or $R_3$ and $R_4$ forms a ring.

Another embodiment of the present invention relates to pharmaceutical compositions comprising a therapeutically effective amount of a compound of formula I or a pharmaceutically acceptable salt, ester, amide, or prodrug thereof in combination with a pharmaceutically acceptable carrier.

Another embodiment of the invention relates to a method of treating male sexual dysfunction including, but not limited, to male erectile dysfunction and premature ejaculation.

Another embodiment of the invention relates to a method of treating female sexual dysfunction including, but not limited to, female anorgasmia, clitoral erectile insufficiency, vaginal engorgement, dyspareunia, and vaginismus.

Yet another embodiment of the invention relates to a method of treating asthma, epilepsy, hypertension, Raynaud's syndrome, migraine, pain, eating disorders, urinary incontinence, functional bowel disorders, neurodegeneration and stroke comprising administering a therapeutically effective amount of a compound of formula I or a pharmaceutically acceptable salt, ester, amide, or prodrug thereof.

DETAILED DESCRIPTION OF THE INVENTION

In its principle embodiment, the present invention discloses compounds having formula I:

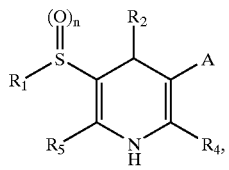

I or a pharmaceutically acceptable salt, ester, amide, or prodrug thereof wherein, n is 0–2;

$R_1$ is selected from the group consisting of alkyl and haloalkyl;

$R_2$ is selected from the group consisting of optionally substituted aryl and optionally substituted heteroaryl;

A is selected from the group consisting of hydrogen, alkyl, haloalkyl, cyano, heteroaryl, nitro and —$XR_3$;

X is selected from the group consisting of C(O) and $S(O)_p$;

p is 1–2;

$R_3$ is selected from the group consisting of alkyl, haloalkyl, and hydroxy;

$R_4$ is selected from the group consisting of hydrogen, alkoxyalkoxyalkyl, alkoxyalkyl, alkyl, arylalkoxyalkyl, aryloxyalkyl, haloalkyl, heteroarylalkoxyalkyl, heteroaryloxyalkyl, ($NZ^1Z^2$) alkoxyalkyl, and ($NZ^1Z^2$)alkyl wherein $Z^1$ and $Z^2$ are independently selected from the group consisting of hydrogen, alkoxycarbonyl, alkyl, alkylcarbonyl, alkylsulfonyl, aminocarbonyl, aryl, arylalkyl, cycloalkyl, cycloalkylalkyl, formyl, heteroaryl, and heteroarylalkyl or $Z^1$, $Z^2$ and the nitrogen atom to which they are attached form a 3, 4, 5, 6, 7, or 8 membered ring; or $R_3$ and $R_4$ together form a ring selected from the group consisting of a 5-, 6-, or 7-membered carbocyclic ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo, and a 5-, 6- or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo; and $R_5$ is selected from the group consisting of hydrogen, alkyl and haloalkyl; or $R_1$ and $R_5$ together with the ring to which they are attached form a 5-, 6- or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo;

provided that at least one of R. and $R_5$ or $R_3$ and $R_4$ forms a ring.

In another embodiment of the present invention, compounds have formula I wherein, A is —$XR_3$; X is C(O); $R_3$ and $R_4$ together form a 6-membered carbocyclic ring with 1 double bond; and $R_1$, $R_2$, $R_5$ and n are as defined above.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 6-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 6-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 6-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 5-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 5-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 5-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 5-membered sulfur-containing ring with 1 double bond; n is 1; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond; R, and $R_5$ together with the ring to which they are attached form a 5-membered sulfur-containing ring with 1 double bond; n is 1; and $R_2$ is an optionally substituted aryl group.

In another embodiment of the present invention, compounds have formula I wherein., A is —$XR_3$; X is C(O); $R_3$ and $R_4$ together form a 6-membered carbocyclic ring with 1 double bond; $R_1$ and $R_5$ together with the ring to which they are attached form a 5-membered sulfur-containing ring with 1 double bond; n is 1; and $R_2$ is an optionally substituted heteroaryl group.

In another embodiment of the present invention, compounds have formula I wherein, A is —$XR_3$; X is C(O); $R_3$ and $R_4$ together form a 6-membered carbocyclic ring with 1 double bond; R, and Rs together with the ring to which they are attached form a 7-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 7-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 6-membered carbocyclic ring with 1 double bond; $R_1$ and $R_5$ together with the ring to which they are attached form a 7-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 6-membered carbocyclic ring with 1 double bond; R, is alkyl; $R_5$ is alkyl; n is 2; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond; R, is alkyl; $R_5$ is alkyl; n is 2; and $R_2$ is an optionally substituted aryl group.

In another embodiment of the present invention, compounds have formula I wherein, A is —$XR_3$; X is C(O); $R_3$ and $R_4$ together form a 6-membered carbocyclic ring with 1 double bond; $R_1$ is alkyl; $R_5$ is alkyl; n is 2; and $R_2$ is an optionally substituted heteroaryl group.

In another embodiment of the present invention, compounds have formula I wherein, A is —$XR_3$; X is C(O); $R_3$ and $R_4$ together form a 5-membered carbocyclic ring with 1 double bond; and R., $R_2$, $R_5$ and n are as defined above.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 6-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 6-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 6-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 5-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 5-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 5-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 5-membered carbocyclic ring with 1 double bond; $R_1$ and $R_5$ together with the ring to which they are attached form a 7-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 5-membered carbocyclic ring with 1 double bond; R, and $R_5$ together with the ring to which they are attached form a 7-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 5-membered carbocyclic ring with 1 double bond; $R_1$ and R, together with the ring to which they are attached form a 7-membered sulfur-containing ring with 1 double bond; n is 2; and $R_2$ is an optionally substituted heteroaryl group.

In another embodiment of the present invention, compounds have formula I wherein, A is —$XR_3$; X is C(O); $R_3$ and $R_4$ together form a 5-membered carbocyclic ring with 1 double bond; R, is alkyl; $R_5$ is alkyl; n is 2; and $R_2$ is as defined above.

In another embodiment of the present invention, compounds have formula I wherein, A is —$XR_3$; X is C(O); $R_3$ and $R_4$ together form a 5-membered carbocyclic ring with 1 double bond; R, is alkyl; $R_5$ is alkyl; n is 2; and $R_2$ is an optionally substituted aryl group.

In another embodiment of the present invention, compounds have formula I wherein, A is —$XR_3$; X is C(O); $R_3$ and $R_4$ together form a 5-membered carbocyclic ring with 1 double bond; $R_1$ is alkyl; $R_5$ is alkyl; n is 2; and $R_2$ is an optionally substituted heteroaryl group.

In another embodiment of the present invention, compounds have formula I wherein, A is —$XR_3$; X is C(O); $R_3$ is alkyl; $R_4$ is alkyl; and R., $R_2$, $R_5$, and n are as defined above.

In another embodiment of the present invention, compounds have formula I wherein, A is —$XR_3$; X is C(O); $R_3$ is alkyl; $R_4$ is alkyl; $R_1$ and $R_5$ together with the ring to which they are attached form a 6-membered sulfur-containing ring with 1 double bond; n is 2; and $R_2$ is as defined above.

In another embodiment of the present invention, compounds have formula I wherein, A is —XR$_3$; X is C(O); R$_3$ is alkyl; R$_4$ is alkyl; R$_1$ and R$_5$ together with the ring to which they are attached form a 6-membered sulfur-containing ring with 1 double bond; n is 2; and R$_2$ is an optionally substituted aryl group.

In another embodiment of the present invention, compounds have formula I wherein, A is —XR$_3$; X is C(O); R$_3$ is alkyl; R$_4$ is alkyl; R$_1$ and R$_5$ together with the ring to which they are attached form a 6-membered sulfur-containing ring with 1 double bond; n is 2; and R$_2$ is an optionally substituted heteroaryl group.

In another embodiment of the present invention, compounds have formula I wherein, R$_1$ and R$_5$ together with the ring to which they are attached form a 6-membered sulfur-containing ring with 1 double bond; n is 2; and A, R$_2$ and R$_4$ are as defined above.

In another embodiment of the present invention, compounds have formula I wherein, R$_1$ and R$_5$ together with the ring to which they are attached form a 6-membered sulfur-containing ring with 1 double bond; n is 2; A is —XR$_3$; X is C(O); R$_3$ is hydroxy; R$_4$ is alkyl; and R$_2$ is as defined above.

In another embodiment of the present invention, compounds have formula I wherein, R$_1$ and R$_5$ together with the ring to which they are attached form a 6-membered sulfur-containing ring with 1 double bond; n is 2; A is —XR$_3$; X is C(O); R$_3$ is hydroxy; R$_4$ is alkyl; and R$_2$ is an optionally substituted aryl group.

In another embodiment of the present invention, compounds have formula I wherein, R$_1$ and R$_5$ together with the ring to which they are attached form a 6-membered sulfur-containing ring with 1 double bond; n is 2; A is —XR$_3$; X is C(O); R$_3$ is hydroxy; R$_4$ is alkyl; and R$_2$ is an optionally substituted heteroaryl group.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is haloalkyl; and R$_2$ is as defined above.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is haloalkyl; and R$_2$ is an optionally substituted aryl group.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is haloalkyl; and R$_2$ is an optionally substituted heteroaryl group.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is alkyl; and R$_2$ is as defined above.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is alkyl; and R$_2$ is an optionally substituted aryl group.

In another embodiment of the present invention, compounds have formula I wherein, R$_1$ and R$_5$ together with the ring to which they are attached form a 6-membered sulfur-containing ring with 1 double bond; n is 2; A is hydrogen; R$_4$ is alkyl; and R$_2$ is an optionally substituted heteroaryl group.

In another embodiment of the present invention, compounds have formula I wherein, R, and R$_5$ together with the ring to which they are attached form a 6-membered sulfur-containing ring with 1 double bond; n is 2; A is cyano; R$_4$ is alkyl; and R$_2$ is as defined above.

In another embodiment of the present invention, compounds have formula I wherein, R, and R$_5$ together with the ring to which they are attached form a 6-membered sulfur-containing ring with 1 double bond; n is 2; A is cyano; R$_4$ is alkyl; and R$_2$ is an optionally substituted aryl group.

In another embodiment of the present invention, compounds have formula I wherein, R$_1$, and R$_5$ together with the ring to which they are attached form a 6-membered sulfur-containing ring with 1 double bond; n is 2; A is cyano; R$_4$ is alkyl; and R$_2$ is an optionally substituted heteroaryl group.

In another embodiment of the present invention, compounds have formula I wherein, R$_1$ and R$_5$ together with the ring to which they are attached form a 6-membered sulfur-containing ring with 1 double bond; n is 2; A is alkyl; R$_4$ is haloalkyl; and R$_2$ is as 30 defined above.

In another embodiment of the present invention, compounds have formula I wherein, R$_1$ and R$_5$ together with the ring to which they are attached form a 6-membered sulfur-containing ring with 1 double bond; n is 2; A is alkyl; R$_4$ is haloalkyl; and R$_2$ is an optionally substituted aryl group.

In another embodiment of the present invention, compounds have formula I wherein, R$_1$ and R$_5$ together with the ring to which they are attached form a 6-membered sulfur-containing ring with 1 double bond; n is 2; A is alkyl; R$_4$ is haloalkyl; and R$_2$ is an optionally substituted heteroaryl group.

In another embodiment of the present invention, compounds have formula I wherein, A is —XR$_3$; X is S(O)$_p$; p is 1–2; R$_3$ and R$_4$ together form a 6-membered sulfur-containing ring with 1 double bond; and R., R$_2$, R$_5$, and n are as defined above.

In another embodiment of the present invention, compounds have formula I wherein, A is —XR$_3$; X is S(O)$_p$; p is 1–2; R$_3$ and R$_4$ together form a 6-membered sulfur-containing ring with 1 double bond; R$_1$ and R$_5$ together with the ring to which they are attached form a 6-membered sulfur-containing ring with 1 double bond; n is 2; and R$_2$ is as defined above.

In another embodiment of the present invention, compounds have formula I wherein, A is —XR$_3$; X is S(O)$_p$; p is 1–2; R$_3$ and R$_4$ together form a 6-membered sulfur-containing ring with 1 double bond; R$_1$ and R$_5$ together with the ring to which they are attached form a 6-membered sulfur-containing ring with 1 double bond; n is 2; and R$_2$ is an optionally substituted aryl group.

In another embodiment of the present invention, compounds have formula I wherein, A is —XR$_3$; X is S(O)$_p$; p is 1–2; R$_3$ and R$_4$ together form a 6-membered sulfur-containing ring with 1 double bond; R$_1$ and R$_5$ together with the ring to which they are attached form a 6-membered sulfur-containing ring with 1 double bond; n is 2; and R$_2$ is an optionally substituted heteroaryl group.

In another embodiment of the present invention, compounds have formula I wherein, A is —XR$_3$; X is S(O)$_p$; p is 1–2; R$_3$ and R$_4$ together form a 5-membered sulfur-containing ring with 1 double bond; and R., R$_2$, R$_5$, and n are as defined above.

In another embodiment of the present invention, compounds have formula I wherein, A is —XR$_3$; X is S(O)$_p$; p is 1–2; R$_3$ and R$_4$ together form a 5-membered sulfur-containing ring with 1 double bond; R$_1$ and R$_5$ together with the ring to which they are attached form a 5-membered sulfur-containing ring with 1 double bond; n is 2; and $R_2$ is as defined above.

In another embodiment of the present invention, compounds have formula I wherein, A is —$XR_3$; X is $S(O)_p$; p is 1–2; $R_3$ and $R_4$ together form a 5-membered sulfur-containing ring with 1 double bond; $R_1$ and $R_5$ together with the ring to which they are attached form a 5-membered sulfur-containing ring with 1 double bond; n is 2; and $R_2$ is an optionally substituted aryl group.

In another embodiment of the present invention, compounds have formula I wherein, A is —$XR_3$; X is $S(O)_p$; p is 1–2; $R_3$ and $R_4$ together form a 5-membered sulfur-containing ring with 1 double bond; $R_1$ and $R_5$ together with the ring to which they are attached form a 5-membered sulfur-containing ring with 1 double bond; n is 2; and $R_2$ is an optionally substituted heteroaryl group.

In another embodiment of the present invention, compounds have formula I wherein, $R_1$ and $R_5$ together with the ring to which they are attached form a 5-membered sulfur-containing ring with 1 double bond; n is 2; and A, $R_2$ and $R_4$ are as defined above.

In another embodiment of the present invention, compounds have formula I wherein, $R_1$ and $R_5$ together with the ring to which they are attached form a 5-membered sulfur-containing ring with 1 double bond; n is 2; A is —$XR_3$; X is C(O); $R_3$ is hydroxy; $R_4$ is alkyl; and $R_2$ is as defined above.

In another embodiment of the present invention, compounds have formula I wherein, $R_1$ and $R_5$ together with the ring to which they are attached form a 5-membered sulfur-containing ring with 1 double bond; n is 2; A is —$XR_3$; X is C(O); $R_3$ is hydroxy; $R_4$ is alkyl; and $R_2$ is an optionally substituted aryl group.

In another embodiment of the present invention, compounds have formula I wherein, $R_1$ and $R_5$ together with the ring to which they are attached form a 5-membered sulfur-containing ring with 1 double bond; n is 2; A is —$XR_3$; X is C(O); $R_3$ is hydroxy; $R_4$ is alkyl; and $R_2$ is an optionally substituted heteroaryl group.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is haloalkyl; and $R_2$ is as defined above.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is haloalkyl; and $R_2$ is an optionally substituted aryl group.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is haloalkyl; and $R_2$ is an optionally substituted heteroaryl group.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is alkyl; and $R_2$ is as defined above.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is alkyl; and $R_2$ is an optionally substituted aryl group.

In another embodiment of the present invention, compounds have formula I wherein, $R_1$ and $R_5$ together with the ring to which they are attached form a 5-membered sulfur-containing ring with 1 double bond; n is 2; A is hydrogen; $R_4$ is alkyl; and $R_2$ is an optionally substituted heteroaryl group.

In another embodiment of the present invention, compounds have formula I wherein, $R_1$ and $R_5$ together with the ring to which they are attached form a 5-membered sulfur-containing ring with 1 double bond; n is 2; A is alkyl; $R_4$ is haloalkyl; and $R_2$ is as defined above.

In another embodiment of the present invention, compounds have formula I wherein, $R_1$ and $R_5$ together with the ring to which they are attached form a 5-membered sulfur-containing ring with 1 double bond; n is 2; A is alkyl; $R_4$ is haloalkyl; and $R_2$ is an optionally substituted aryl group.

In another embodiment of the present invention, compounds have formula I wherein, $R_1$ and $R_5$ together with the ring to which they are attached form a 5-membered sulfur-containing ring with 1 double bond; n is 2; A is alkyl; $R_4$ is haloalkyl; and $R_2$ is an optionally substituted heteroaryl group.

In another embodiment of the present invention, compounds have formula I wherein, R, and $R_5$ together with the ring to which they are attached form a 5-membered sulfur-containing ring with 1 double bond; n is 2; A is cyano; $R_4$ is alkyl; and $R_2$ is as defined above.

In another embodiment of the present invention, compounds have formula I wherein, $R_1$ and $R_5$ together with the ring to which they are attached form a 5-membered sulfur-containing ring with 1 double bond; n is 2; A is cyano; $R_4$ is alkyl; and $R_2$ is an optionally substituted aryl group.

In another embodiment of the present invention, compounds have formula I wherein, $R_1$ and $R_5$, together with the ring to which they are attached form a 5-membered sulfur-containing ring with 1 double bond; n is 2; A is cyano; $R_4$ is alkyl; and $R_2$ is an optionally substituted heteroaryl group.

In another embodiment of the present invention, compounds have formula I wherein, A is —$XR_3$; X is C(O); $R_3$ and $R_4$ together form a 6-membered carbocyclic ring with 1 double bond and 1–2 substituents independently selected from alkyl; and R., $R_2$, $R_5$, and n are as defined above.

In another embodiment of the present invention, compounds have formula I wherein, A is —$XR_3$; X is C(O); $R_3$ and $R_4$ together form a 6-membered carbocyclic ring with 1 double bond and 1–2 substituents independently selected from alkyl; $R_1$ and $R_5$ together with the ring to which they are attached form a 5-membered sulfur-containing ring with 1 double bond; n is 2; and $R_2$ is as defined above.

In another embodiment of the present invention, compounds have formula I wherein, A is —$XR_3$; X is C(O); $R_3$ and $R_4$ together form a 6-membered carbocyclic ring with 1 double bond and 1–2 substituents independently selected from alkyl; $R_1$ and $R_5$ together with the ring to which they are attached form a 5-membered sulfur-containing ring with 1 double bond; n is 2; and $R_2$ is an optionally substituted aryl group.

In another embodiment of the present invention, compounds have formula I wherein, A is —$XR_3$; X is C(O); $R_3$ and $R_4$ together form a 6-membered carbocyclic ring with 1 double bond and 1–2 substituents independently selected from alkyl; $R_1$ and $R_5$ together with the ring to which they are attached form a 5-membered sulfur-containing ring with 1 double bond; n is 2; and $R_2$ is an optionally substituted heteroaryl group.

The present invention also relates to pharmaceutical compositions which comprise a therapeutically effective amount of a compound of formula I or a pharmaceutically acceptable salt, ester, amide, or prodrug thereof in combination with a pharmaceutically acceptable carrier.

The present invention also relates to a method of treating a disease in a mammal comprising administering an effective amount of a compound of formula I or a pharmaceutically acceptable salt, ester, amide, or prodrug thereof.

In particular, the present invention relates to a method of treating asthma, epilepsy, hypertension, Raynaud's syndrome, migraine, pain, eating disorders, urinary incontinence, functional bowel disorders, neurodegeneration, male erectile dysfunction, premature ejaculation, female anorgasmia, clitoral erectile insufficiency, vaginal engorgement, dyspareunia, vaginismus, and stroke comprising administering an effective amount of a compound of formula I or a pharmaceutically acceptable salt, ester, amide, or prodrug thereof.

Definition of Terms

The term "alkenyl," as used herein refers to a monovalent group derived from a hydrocarbon containing at least one carbon-carbon double bond by the removal of a single hydrogen atom. Alkenyl groups include, for example, vinyl (ethenyl), allyl (propenyl), butenyl, 1-methyl-2-buten-1-yl and the like.

The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkoxyalkyl," as used herein, refers to an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, 2-(2-methoxyethoxy)ethyl, and the like.

The term "alkoxyalkenyl," as used herein, refers to an alkoxy group, as defined herein, appended to the parent molecular moiety through an alkenyl group, as defined herein. Representative examples of alkoxyalkenyl include, but are not limited to, 3-methoxypropen-1-yl, 4-methoxybuten-1-yl, 5-tert-butoxypenten-1-yl, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkoxycarbonylalkenyl," as used herein, refers to an alkoxycarbonyl group, as defined herein, appended to the parent molecular moiety through an alkenyl group, as defined herein. Representative examples of alkoxycarbonylalkenyl include, but are not limited to, 3-methoxycarbonylpropen-1-yl, 4-ethoxycarbonylbuten-1-yl, and the like.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, 2-tert-butoxycarbonylethyl, and the like.

The term "alkoxycarbonyloxy," as used herein, refers to an alkoxycarbonyl group, as defined herein, appended to the parent molecular moiety through an oxy group, as defined herein. Representative examples of alkoxycarbonyloxy include, but are not limited to, 3-methoxycarbonyloxy, 4-ethoxycarbonyloxy, 2-tert-butoxycarbonyloxy, and the like.

The term "alkyl," as used herein refers to straight or branched chain alkyl radical containing from I to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl, ethylsulfinyl, and the like.

The term "alkylsulfinylalkyl," as used herein, refers to an alkylsulfinyl group, as defined herein, appended to the parent molecular moiety through an alkyl group, as defined herein. Representative examples of alkylsulfinylalkyl include, but are not limited to, methylsulfinylmethyl, ethylsulfinylmethyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl, ethylsulfonyl, and the like.

The term "alkylsulfonylalkyl," as used herein, refers to an alkylsulfonyl group, as defined herein, appended to the parent molecular moiety through an alkyl group, as defined herein. Representative examples of alkylsulfonylalkyl include, but are not limited to, methylsulfonylmethyl, ethylsulfonylmethyl, and the like.

The term "alkylthio," as used herein, refers to an alkyl group, as defined herein, appended to the parent molecular moiety through a thio group, as defined herein. Representative examples of alkylthio include, but are not limited to, methylsulfanyl, ethylsulfanyl, tert-butylsulfanyl, hexylsulfanyl, and the like.

The term "alkylthioalkyl," as used herein, refers to an alkylthio group, as defined herein, appended to the parent molecular moiety through an alkyl group, as defined herein. Representative examples of alkylthioalkyl include, but are not limited to, methylsulfanylmethyl, 2-(ethylsulfanyl)ethyl, and the like.

The term "alkynyl," as used herein, refers to a straight or branched chain hydrocarbon group containing from 2 to 10 carbon atoms and containing at least one carbon-carbon triple bond. Representative examples of alkynyl include, but are not limited to, to acetylenyl, 1-propynyl, 2-propynyl, 3-butynyl, 2-pentynyl, 1butynyl, and the like.

The term "amino," as used herein, refers to a -NR$_{65}$R$_{66}$ group, wherein R$_{65}$ and R$_{66}$ are independently selected from hydrogen, alkyl, aryl, and arylalkyl, as defined herein. Representative examples of amino include, but are not limited, to amino, ethylamino, methylamino, dimethylamino, diethylamino, benzylamino, benzylmethylamino, phenylamino (anilino), diphenylamino, phenylmethylamino, and the like.

The term "aminoalkenyl," as used herein, refers to an amino group, as defined herein, appended to the parent molecular moiety through an alkenyl group, as defined herein. Representative examples of aminoalkenyl include, but are not limited to, 3-aminopropen-1-yl, 4-ethylaminobuten-1-yl, and the like.

The term "aminoalkoxy," as used herein, refers to an amino group, as defined herein, appended to the parent molecular moiety through an alkoxy group, as defined herein. Representative examples of aminoalkoxy include, but are not limited to, aminomethoxy, ethylaminomethoxy, methylaminomethoxy, dimethylaminomethoxy, diethylaminomethoxy, benzylaminomethoxy, benzylmethylaminomethoxy, and the like.

The term "aminoalkyl," as used herein, refers to an amino group, as defined herein, appended to the parent molecular moiety through an alkyl group, as defined herein. Representative examples of aminoalkyl include, but are not limited to, aminomethyl, ethylaminomethyl, methylaminomethyl, dimethylaminomethyl, diethylaminomethyl, benzylaminomethyl, benzylmethylaminomethyl, and the like.

The term "aminoalkynyl," as used herein, refers to an amino group, as defined herein, appended to the parent molecular moiety through an alkynyl group, as defined herein. Representative examples of aminoalkynyl include, but are not limited to, 3-aminopropyn-1-yl, 4-ethylaminobutyn-1-yl, and the like.

The term "aminocarbonyl" or "amido," as used herein, refers to an amino group, as defined herein, appended to the parent molecular moiety through a carbonyl group, as defined herein. Representative examples of aminocarbonyl or amido include, but are not limited to, aminocarbonyl, ethylaminocarbonyl, methylaminocarbonyl, dimethylaminocarbonyl, diethylaminocarbonyl, benzylaminocarbonyl, benzylmethylaminocarbonyl, and the like.

The term "aminosulfonyl," as used herein, refers to an amino group, as defined herein, appended to the parent molecular moiety through a sulfonyl group, as defined herein. Representative examples of aminosulfonyl include, but are not limited to, aminosulfonyl, ethylaminosulfonyl, methylaminosulfonyl, dimethylaminosulfonyl, diethylaminosulfonyl, benzylaminosulfonyl, benzylmethylaminosulfonyl, and the like.

The term "aryl" as used herein refers to a mono- or bicyclic carbocyclic ring system having one or more aromatic rings including, but not limited to, phenyl, naphthyl, tetrahydronaphthyl, naphthyridinyl, indanyl, indenyl and the like.

The aryl groups of this invention can be optionally substituted with 1–5 substituents independently selected from alkenyl, alkoxy, alkoxyalkoxy, alkoxyalkenyl, alkoxyalkyl, alkoxycarbonylalkenyl, alkoxycarbonylalkyl, alkyl, alkylcarbonyl, alkylsulfinyl, alkylsulfonyl, alkylthio, alkylthioalkyl, alkoxycarbonyl, alkoxycarbonyloxy, alkynyl, alkylsulfonylalkyl, amino, aminoalkenyl, aminoalkyl, aminoalkynyl, aminocarbonyl, aminosulfonyl, aryl, arylalkenyl, arylalkyl, arylalkynyl, azido, carboxy, cyano, cyanoalkyl, cyanoalkenyl, cyanoalkynyl, halo, haloalkoxy, haloalkenyl, haloalkyl, haloalkylcarbonyl, haloalkynyl, heteroaryl, hydroxy, hydroxyalkyl, hydroxyalkenyl, hydroxyalkynyl, nitro, thioureido, and ureido. In addition, substituted aryl groups include tetrafluorophenyl and pentafluorophenyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxyalkyl," as used herein, refers to an arylalkoxy group, as defined herein, appended to the parent molecular moiety through an alkyl group, as defined herein. Representative examples of arylalkoxyalkyl include, but are not limited to, 2-phenylethoxymethyl, 3-naphth-2-ylpropoxymethyl, 5-phenylpentyloxymethyl, phenylmethoxymethyl, and the like.

The term "arylalkenyl," as used herein, refers to an aryl group, as defined herein, appended to the parent molecular moiety through an alkenyl group, as defined herein. Representative examples of arylalkenyl include, but are not limited to, 3-phenylpropen-1-yl, 4-phenylbuten-1-yl, 3-naphth-2-ylpropen-1-yl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "arylalkynyl," as used herein, refers to an aryl group, as defined herein, appended to the parent molecular moiety through an alkynyl group, as defined herein. Representative examples of arylalkynyl include, but are not limited to, 3-phenylpropyn-1-yl, 4-phenylbutyn-1-yl, 3-naphth-2-ylpropyn-1-yl, and the like.

The term "aryloxy," as used herein, refers to an aryl group, as defined herein, appended to the parent molecular moiety through an oxy group, as defined herein. Representative examples of aryloxy include, but are not limited to, phenoxy, naphthyloxy, 3-bromophenoxy, 4-chlorophenoxy, 4-methylphenoxy, 3,5-dimethoxyphenoxy, and the like.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl, 3-bromophenoxymethyl, and the like.

The term "azido," as defined herein, refers to -N$_3$.

The term "carbonyl," as used herein, refers to a -C(O)- group.

The term "carboxy," as used herein, refers to -CO$_2$H.

The term "cyano," as used herein, refers to -CN group.

The term "cyanoalkenyl," as used herein, refers to a cyano group, as defined herein, appended to the parent molecular moiety through an alkenyl group, as defined herein. Representative examples of cyanoalkenyl include, but are not limited to, 3-cyanopropen-1-yl, 4-cyanobuten-1-yl, and the like.

The term "cyanoalkyl," as used herein, refers to an cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, and the like.

The term "cyanoalkynyl," as used herein, refers to a cyano group, as defined herein, appended to the parent molecular moiety through an alkynyl group, as defined herein. Representative examples of cyanoalkynyl include, but are not limited to, 3-cyanopropyn-1-yl, 4-cyanobutyn-1-yl, and the like.

The term "cycloalkyl", as used herein, refers to a saturated cyclic hydrocarbon group containing from 3 to 8 carbons. Representative examples of cycloalkyl include, but are not limited to, cyclopropyl, cyclobutyl, cyclopentyl, cyclohexyl, cycloheptyl, cyclooctyl and the like.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "formyl," as used herein, refers to a -C(O)H group.

The term "halogen" or "halo" as used herein refers to I, Br, Cl or F.

The term "haloalkenyl," as used herein, refers to at least one halogen, as defined herein, appended to the parent molecular moiety through an alkenyl group, as defined herein. Representative examples of haloalkenyl include, but are not limited to, 2,2-difluoroethenyl, difluoroethenyl, and the like.

The term "haloalkoxy," as used herein, refers to at least one halogen, as defined herein, appended to the parent molecular moiety through an alkoxy group, as defined herein. Representative examples of haloalkoxy include, but are not limited to, trifluoromethoxy, 2,2,2-trifluoroethoxy, pentafluoroethoxy, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, bromodifluoromethyl, difluoromethyl, 2,2,2-trifluoroethyl, and the like.

The term "haloalkylcarbonyl," as used herein, refers to a haloalkyl group, as defined herein, appended to the parent molecular moiety through a carbonyl group, as defined herein. Representative examples of haloalkylcarbonyl include, but are not limited to, chloromethylcarbonyl, 2-fluoroethylcarbonyl, trifluoromethylcarbonyl, pentafluoroethylcarbonyl, 2,2,2-trifluoroethylcarbonyl, and the like.

The term "haloalkynyl," as used herein, refers to at least one halogen, as defined herein, appended to the parent molecular moiety through an alkynyl group, as defined herein. Representative examples of haloalkynyl include, but are not limited to, 3,3,3-trifluoropropyn-1-yl, 3-chloropropyn-3-yl, and the like.

The term "heteroaryl" as used herein represents an aromatic 5-, 6- or 7-membered ring containing one, two or three heteroatoms independently selected from the group consisting of nitrogen, oxygen and sulfur. The 5-membered ring has two double bonds and the 6- and 7-membered rings have three double bonds. The term "heteroaryl" also includes bicyclic, tricyclic and tetracyclic groups in which any of the above heteroaryl rings is fused to one or twvo rings independently selected from the group consisting of an aryl ring, a cyclohexane ring, a cyclohexene ring, a cyclopentane ring, a cyclopentene ring and another monocyclic heterocyclic ring. Examples of heteroaryl include, but are not limited to, indolyl, quinolyl, isoquinolyl, tetrahydroquinolyl, benzofuryl, benzothienyl, pyrrolyl, pyrazolyl, imidazolyl, pyridyl, pyrazinyl, pyrimidinyl, pyridazinyl, oxazolyl, isoxazolyl, thiazolyl, isothiazolyl, benzimidazolyl, benzothiazolyl, benzoxazolyl, furyl, thienyl, benzoxadiazole, and benzothiadiazole.

The heteroaryl groups of this invention can be optionally substituted with 1–4 substituents independently selected from alkenyl, alkoxy, alkoxyalkoxy, alkoxyalkenyl, alkoxyalkyl, alkoxycarbonylalkenyl, alkoxycarbonylalkyl, alkyl, alkylcarbonyl, alkylsulfinyl, alkylsulfonyl, alkylthio, alkylthioalkyl, alkoxycarbonyl, alkoxycarbonyloxy, alkynyl, alkylsulfonylalkyl, amino, aminoalkenyl, aminoalkyl, aminoalkynyl, aminocarbonyl, aminosulfonyl, aryl, arylalkenyl, arylalkyl, arylalkynyl, azido, carboxy, cyano, cyanoalkyl, cyanoalkenyl, cyanoalkynyl, halo, haloalkoxy, haloalkenyl, haloalkyl, haloalkylcarbonyl, haloalkynyl, heteroaryl, hydroxy, hydroxyalkyl, hydroxyalkenyl, hydroxyalkynyl, nitro, thioureido, and ureido.

The term "heteroarylalkoxy," as used herein, refers to a heteroaryl group, as defined herein, appended to the parent molecular moiety through an alkoxy group, as defined herein. Representative examples of heteroarylalkoxy include, but are not limited to, 2-imidazol-2-ylethoxy, 2-pyrid-3-ylethoxy, 3-quinolin-3-ylpropoxy, 5-pyrid-4-ylpentyloxy, and the like.

The term "heteroarylalkoxyalkyl," as used herein, refers to a heteroarylalkoxy group, as defined herein, appended to the parent molecular moiety through an alkyl group, as defined herein. Representative examples of heteroarylalkoxyalkyl include, but are not limited to, 2-imidazol-2-ylethoxymethyl, 2-pyrid-3-ylethoxymethyl, 3-quinolin-3-ylpropoxymethyl, 5-pyrid-4-ylpentyloxymethyl, and the like.

The term "heteroarylalkyl," as used herein, refers to a heteroaryl group, as defined herein, appended to the parent molecular moiety through an alkyl group, as defined herein. Representative examples of heteroarylalkyl include, but are not limited to, 2-imidazol-2-ylethyl, pyrid-3-ylmethyl, pyrid-3-ylhydroxymethyl, 1-hydroxy-3-pyrid-3-ylpropyl, 2-pyrimidin-2-ylpropyl, and the like.

The term "heteroaryloxy," as used herein, refers to a heteroaryl group, as defined herein, appended to the parent molecular moiety through an oxy group, as defined herein. Representative examples of heteroaryloxy include, but are not limited to, pyrid-3-yloxy, quinolin-3-yloxy, and the like.

The term "heteroaryloxyalkyl," as used herein, refers to a heteroaryloxy group, as defined herein, appended to the parent molecular moiety through an alkyl group, as defined herein. Representative examples of heteroaryloxyalkyl include, but are not limited to, pyrid-3-yloxymethyl, 2-quinolin-3-yloxyethyl, and the like.

The term "hydroxy," as used herein refers to an -OH group.

The term "hydroxyalkyl," as used herein refers to a hydroxy group, as defined herein, appended to the parent molecular moiety through an alkyl group, as defined herein. Representative examples of hydroxyalkyl include, but are not limited to, hydroxymethyl, 2-hydroxyethyl, 1-hydroxyethyl, 3-hydroxypropyl, and the like.

The term "hydroxyalkenyl," as used herein refers to a hydroxy group, as defined herein, appended to the parent molecular moiety through an alkenyl group, as defined herein. Representative examples of hydroxyalkenyl include, but are not limited to, 3-hydroxypropen-1-yl, 4-hydroxybuten-1-yl, and the like.

The term "hydroxyalkynyl," as used herein refers to a hydroxy group, as defined herein, appended to the parent molecular moiety through an alkynyl group, as defined herein. Representative examples of hydroxyalkynyl include, but are not limited to, 3-hydroxypropyn-1-yl, 4-hydroxybutyn-1-yl, 3-hydroxy-3-methylbutyn-1-yl, and the like.

The term "lower alkoxy," as used herein, refers to a lower alkyl group, as defined herein, appended to the parent molecular moiety through an oxy group, as defined herein. Representative examples of lower alkoxy include, but are not limited to, methoxy, ethoxy, propoxy, 2-propoxy, butoxy, tert-butoxy, and the like.

The term "lower alkyl," as used herein, refers to a straight or branched chain hydrocarbon group containing from 1-to-4 carbon atoms. Representative examples of lower alkyl include, but are not limited to, methyl, ethyl, n-propyl, iso-propyl, n-butyl, iso-butyl, tert-butyl, and the like.

The term "N-protecting group," as used herein, refers to those groups intended to protect an amino group against undesirable reactions during synthetic procedures. N-protecting groups comprise amides, carbamates, and sulfonamides including those containing aryl groups. Preferred N-protecting groups are formyl, acetyl, benzoyl, pivaloyl, phenylsulfonyl, t-butyloxycarbonyl (Boc), benzyloxycarbonyl (Cbz), and the like. Commonly used N-protecting groups are disclosed in T.H. Greene and P.G.M. Wuts, Protective Groups in Organic Synthesis, 2nd edition, John Wiley & Sons, New York (1991), which is hereby incorporated by reference.

The term "-$NZ^1Z^2$," as used herein, refers to two groups, $Z^1$ and $Z^2$, which are appended to the parent molecular moiety through a nitrogen atom. $Z^1$ and $Z^2$ are independently selected from hydrogen, alkoxycarbonyl, alkyl, alkylcarbonyl, alkylsulfonyl, aminocarbonyl, aryl, arylalkyl, cycloalkyl, cycloalkylalkyl, formyl, heteroaryl, and heteroarylalkyl or $Z^1$, $Z^2$ and the nitrogen atom to which they are attached form a 3, 4, 5, 6, 7, or 8 membered ring. Representative examples of-$NZ^1Z^2$ include, but are not limited to, amino, benzylamino, methylamino, acetylamino, acetylmethylamino, cyclohexylamino, and the like.

The term "($NZ^1Z^2$)alkoxy," as used herein, refers to a -$NZ^1Z^2$ group, as defined herein, appended to the parent molecular moiety through an alkoxy group, as defined herein. Representative examples of ($NZ^1Z^2$)alkoxy include, but are not limited to, 2-(methylphenylamino)ethoxy, 2-(benzylmethylamino)ethoxy, benzylaminomethoxy, (2-chlorobenzyl)methylaminomethoxy, benzylmethylaminomethoxy, and the like.

The term "($NZ^1Z^2$)alkoxyalkyl," as used herein, refers to a ($NZ^1Z^2$alkoxy) group, as defined herein, appended to the parent molecular moiety through an alkyl group, as defined herein. Representative examples of ($NZ^1Z^2$)alkoxyalkyl include, but are not limited to, 2-(methylphenylamino)ethoxymethyl, 2-(benzylmethylamino)ethoxymethyl, benzylaminomethoxymethyl, (2-chlorobenzyl)methylaminomethoxymethyl, 2-benzylmethylaminomethoxyethyl, and the like.

The term "($NZ^1Z^2$)alkyl," as used herein, refers to a -$NZ^1Z^2$ group, as defined herein, appended to the parent molecular moiety through an alkyl group, as defined herein. Representative examples of ($NZ^1Z^2$)alkyl include, but are not limited to, 2-(methylphenylamino)ethyl, 2-(benzylmethylamino)ethyl, benzylaminomethyl, (2-chlorobenzyl)methylaminomethyl, benzylmethylaminomethyl, and the like.

The term "nitro," as used herein refers to a -$NO_2$ group.

The term "oxo," refers to (=O).

The term "oxy," refers to -O-.

The term "sulfinyl," as used herein, refers to a -S(O)- group.

The term "sulfonyl," as used herein, refers to a -SO2- group.

The term "thioureido," as used herein refers to a -NHC(S)$NH_2$ group.

The term "ureido," as used herein refers to a -NHC(O)$NH_2$ group.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the invention. Prodrugs of the present invention may be rapidly transformed in vivo to the parent compound of the above formula, for example, by hydrolysis in blood, and include esters and amide analogs of the compounds of the present invention. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The present invention contemplates pharmaceutically active metabolites formed by in vivo biotransformation of compounds of formula I. The term pharmaceutically active metabolite, as used herein, refers to a compound formed by the in vivo biotransformation of compounds of formula I. The present invention contemplates compounds of formula I and metabolites thereof. A thorough discussion of biotransformation is provided in Goodman and Gilman's, The Pharmacological Basis of Therapeutics, seventh edition, hereby incorporated by reference.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Representative compounds of the present invention include, but are not limited to:

3,4,6,7,8,10-hexahydro-10-(3-nitrophenyl)-2H-thiopyrano[3,2-b]quinolin-9(5H)-one, 1,1-dioxide, 10-(3,4-dichlorophenyl)-3,4,6,7,8,10-hexahydro-2H-thiopyrano[3,2-b]quinolin-9(5H)-one, 1,1-dioxide, 10-(3-chloro-4-fluorophenyl)-3,4,6,7,8,10-hexahydro-2H-thiopyrano[3,2-b]quinolin-9(5H)-one, 1,1-dioxide, 10-(3-bromo-4-fluorophenyl)-3,4,6,7,8,10-hexahydro-2H-thiopyrano[3,2-b]quinolin-9(5H)-one, 1,1-dioxide, 10-(3-cyanophenyl)-3,4,6,7,8,10-hexahydro-2H-thiopyrano[3,2-b]quinolin-9(5H)-one, 1,1-dioxide, 3,4,6,7,8,10-hexahydro-10-[3-(trifluoromethyl)phenyl]-2H-thiopyrano[3,2-b]quinolin-9(5H)-one, 1,1-dioxide, 10-(3,4-difluorophenyl)-3,4,6,7,8,10-hexahydro-2H-thiopyrano[3,2-b]quinolin-9(5H)-one, 1,1-dioxide, 10-(3-bromophenyl)-3,4,6,7,8, 10-hexahydro-2H-thiopyrano[3,2-b]quinolin-9(5H)-one, 1,1-dioxide, 3,4,6,7,8,10-hexahydro-10-(3,4,5-trifluorophenyl)-2H-thiopyrano[3,2-b]quinolin-9(5H)-one, 1,1-dioxide, 10-[3-fluoro-5-(trifluoromethyl)phenyl]-3,4,6,7,8,10-hexahydro-2H-thiopyrano[3,2-b]quinolin-9(5H)-one, 1,1-dioxide, 10-(3-fluorophenyl)-3,4,6,7,8,10-hexahydro-2H-thiopyrano[3,2-b]quinolin-9(5H)-one, 1,1-dioxide, 3,4,6,7,8,10-hexahydro-10-phenyl-2H-thiopyrano[3,2-b]quinolin-9(5H)-one, 1,1-dioxide, 10-[4-fluoro-3-(trifluoromethyl)phenyl]-3,4,6,7,8,10-hexahydro-2H-thiopyrano[3,2-b]quinolin-9(5H)-one, 1,1-dioxide, 3,4,6,7,8,10-hexahydro-10-(4-methyl-3-nitrophenyl)2H-thiopyrano[3,2-b]quinolin-9(5H)-one, 1,1-dioxide, 10-(4-chloro-3-fluorophenyl)-3,4,6,7,8,10-hexahydro-2H-thiopyrano[3,2-b]quinolin-9(5H)-one, 1,1-dioxide, 10-(3-chlorophenyl)-3,4,6,7,8,10-hexahydro-2H-thiopyrano[3,2-b]quinolin-9(5H)-one, 1,1-dioxide, 3,4,6,7,8,10-hexahydro-10-[4-(trifluoromethyl)phenyl]-2H-thiopyrano[3,2-b]quinolin-9(5H)-one, 1,1-dioxide, 10-(4-bromophenyl)-3,4,6,7,8,10-hexahydro-2H-thiopyrano[3,2-b]quinolin-9(5H)-one, 1,1-dioxide, 10-(4-chloro-3-nitrophenyl)-3,4,6,7,8,10-hexahydro-2H-thiopyrano[3,2-b]quinolin-9(5H)-one, 1,1-dioxide, 4-(3,4-dichlorophenyl)-4,6,7,8-tetrahydro-2-methyl-3-(methylsulfonyl)-5(1H)-quinolinone, 4-(3-cyanophenyl)-4,6,7,8-tetrahydro-2-methyl-3-(methylsulfonyl)-5(1H)-quinolinone, 4-(3,4,5-trifluorophenyl)-4,6,7,8-tetrahydro-2-methyl-3-(methylsulfonyl)-5(1H)-quinolinone, 4,6,7,8-tetrahydro-2-methyl-4-(4-methyl-3-nitrophenyl)-3-(methylsulfonyl)-5(1H)-quinolinone, 4-(4-chloro-3-nitrophenyl)-4,6,7,8-tetrahydro-2-methyl-3-(methylsulfonyl)-5(1H)-quinolinone, 4-(3-bromo-4-fluorophenyl)-4,6,7,8-tetrahydro-2-methyl-3-(methylsulfonyl)-5(1H)-quinolinone, 4,6,7,8-tetrahydro-2-methyl-3-(methylsulfonyl)-4-(3-nitrophenyl)-5(1H)-quinolinone, 4-(4-chloro-3-fluorophenyl)-4,6,7,8-tetrahydro-2-methyl-3-(methylsulfonyl)-5(1H)-quinolinone, 4,6,7,8-tetrahydro-2-methyl-3-(methylsulfonyl)-4-[4-(trifluoromethyl)phenyl]-5(1H)-quinolinone, 9-(3,4-dichlorophenyl)-2,3,5,6,7,9-hexahydrothieno[3,2-b]quinolin-8(4H)-one, 1,1-dioxide, 9-(3-cyanophenyl)-2,3,5,6,7,9-hexahydrothieno[3,2-b]quinolin-8(4H)-one, 1,1-dioxide, 9-[4-fluoro-3-(trifluoromethyl)phenyl]-2,3,5,6,7,9-hexahydrothieno[3,2-b]quinolin-8(4H)-one, 1,1-dioxide, 2,3,5,6,7,9-hexahydro-9-(4-methyl-3-nitrophenyl)thieno[3,2-b]quinolin-8(4H)-one, 1,1-dioxide, 9-(3,4-difluorophenyl)-2,3,5,6,7,9-hexahydrothieno[3,2-b]quinolin-8(4H)-one, 1,1-dioxide, 9-(4-chloro-3-nitrophenyl)-2,3,5,6,7,9-hexahydrothieno[3,2-b]quinolin-8(4H)-one, 1,1-dioxide, 1-[8-(3,4-dichlorophenyl)-3,4,5,8-tetrahydro-6-methyl-1,1-dioxido-2H-thiopyrano[3,2-b]pyridin-7-yl]ethan-1-one, 1-[8-(4-chloro-3-nitrophenyl)-3,4,5,8-tetrahydro-6-methyl-1,1-dioxido-2H-thiopyrano[3,2-b]pyridin-7-yl]ethan-1-one, 9-(3,4-dichlorophenyl)-3,4,5,6,7,9-hexahydrocyclopenta[b]thiopyrano[2,3-e]pyridin-8(2H)-one, 1,1-dioxide, 9-(4-chloro-3-nitrophenyl)-3,4,5,6,7,9-hexahydrocyclopenta[b]thiopyrano[2,3-e]pyridin-8(2H)-one, 1,1-dioxide, 9-(3-chloro-4-fluorophenyl)-3,4,5,6,7,9-hexahydrocyclopenta[b]thiopyrano[2,3-e]pyridin-8(2H)-one, 1,1-dioxide, 9-(3-bromo-4-fluorophenyl)-3,4,5,6,7,9-hexahydrocyclopenta[b]thiopyrano[2,3-e]pyridin-8(2H)-one, 1,1-dioxide, 9-(3-nitrophenyl)-2,3,5,6,7,9-hexahydrothieno[3,2-b]quinolin-8(4H)-one, 1,1-dioxide, 9-(3-cyano)-3,4,5,6,7,9-hexahydrocyclopenta[b]thiopyrano[2,3-e]pyridin-8(2H)-one, 1,1-dioxide, 9-(3-bromo-4-fluorophenyl)-2,3,5,6,7,9-hexahydrothieno[3,2-b]quinolin-8(4H)-one, 1,1-dioxide, 8-(4-chloro-3-nitrophenyl)-2,3,4,5,6,8-hexahydro-7H-cyclopenta[b]thieno[2,3-e]pyridin-7-one 1,1-dioxide, 10-(4-chloro-3-nitrophenyl)-3,4,6,7,8,10-hexahydro-2H,5H-bisthiopyrano[3,2-b:2',3'-e]pyridine, 1,1,9,9-tetraoxide, 10-(3-pyridyl)-3,4,6,7,8,10-hexahydro-2H-thiopyrano[3,2-b]quinolin-9(5H)-one, 1,1-dioxide, 10-(4-pyridyl)-3,4,6,7,8,10-hexahydro-2H-thiopyrano[3,2-b]quinolin-9(5H)-one, 1,1-dioxide, 9-(4-fluoro-3-trifluoromethyl)-3,4,5,6,7,9-hexahydrocyclopenta[b]thiopyrano[2,3-e]pyridin-8(2H)-one, 1,1-dioxide, 9-(4-methyl-3-nitro)-3,4,5,6,7,9-hexahydrocyclopenta[b]thiopyrano[2,3-e]pyridin-8(2H)-one, 1,1-dioxide, 9-(3,4-difluorophenyl)-3,4,5,6,7,9-hexahydrocyclopenta[b]thiopyrano[2,3-e]pyridin-8(2H)-one, 1,1,7,7-tetraoxide, 8-(4-chloro-3-nitrophenyl)-2,3,4,5,6,8-hexahydrodithieno[3,2-b:2',3'-e]pyridine, 1,1,7,7-tetraoxide, 8-(3-cyanophenyl)-2,3,4,5,6,8-hexahydro-7H-cyclopenta[b]thieno[2,3-e]pyridin-7-one, 1,1-dioxide, 8-(3-bromo-4-fluorophenyl)-2,3,4,5,6,8-hexahydrodithieno[3,2-b:2',3'-e]pyridine, 1,1,7,7-tetraoxide, 10-(3-bromo-4-fluorophenyl)-3,4,6,7,8,10-hexahydro-2H,5H-dithiopyrano[3,2-b:2',3'-e]pyridine, 1,1,9,9-tetraoxide, 3,4,5,6,7,9-hexahydro-9-(3-nitrophenyl)cyclopenta[b]thiopyrano[2,3-e]pyridin-8(2H)-one, 1,1-dioxide, 8-(3-bromo-4-fluorophenyl)-2,3,4,5,6,8-hexahydro-7H-cyclopenta[b]thieno[2,3-e]pyridin-7-one, 1,1-dioxide, 8-(4-fluoro-3-trifluoromethylphenyl)-2,3,4,5,6,8-hexahydro-7H-cyclopenta[b]thieno[2,3-e]pyridin-7-one, 1,1-dioxide, 2,3,4,5,6,8-hexahydro-8-(3-nitrophenyl)-7H-cyclopenta[b]thieno[2,3-e]pyridin-7-one, 1,1-dioxide, 3,4,6,7,8,10-hexahydro-10-(3-nitrophenyl)-2H,5H-dithiopyrano[3,2-b:2',3'-e]pyridine, 1,1,9,9-tetraoxide, 8-(3,4-dichlorophenyl)-2,3,4,5,6,8-hexahydro-7H-cyclopenta[b]thieno[2,3-e]pyridin-7-one, 1,1-dioxide, 8-(3-chloro-4-fluorophenyl)-2,3,4,5,6,8-hexahydro-7H-cyclopenta[b]thieno[2,3-e]pyridin-7-one, 1,1-dioxide, 8-(3-cyanophenyl)-2,3,4,5,6,8-hexahydrodithieno[3,2-b:2',3'-e]pyridine, 1,1,7,7-tetraoxide, 8-(2-cyano-4-pyridinyl)-2,3,4,5,6,8-hexahydro-7H-cyclopenta[b]thieno[2,3-e]pyridin-7-one, 1,1-dioxide, 8-(3-bromophenyl)-2,3,4,5,6,8-hexahydro-7H-cyclopenta[b]thieno[2,3-e]pyridin-7-one, 1,1-dioxide, 8-(4-fluoro-3-trifluoromethylphenyl)-2,3,4,5,6,8-hexahydrodithieno[3,2-b:2',3'-e]pyridine, 1,1,7,7-tetraoxide, 1-[8-(3-bromo-4-fluorophenyl)-3,4,5,8-tetrahydro-6-methyl-1,1-dioxido-2H-thiopyrano[3,2-b]pyridin-7-yl)]ethan-1-one, 8-(4-bromo-2-thienyl)-2,3,4,5,6,8-hexahydro-7H-cyclopenta[b]thieno[2,3-e]pyridin-7-one, 1,1-dioxide, 8-(5-bromo-2-thienyl)-2,3,4,5,6,8-hexahydro-7H-cyclopenta[b]thieno[2,3-e]pyridin-7-one, 1,1-dioxide, 2,3,4,5,6,8-hexahydro-8-(5-nitro-3-thienyl)-7H-cyclopenta[b]thieno[2,3-e]pyridin-7-one, 1,1-dioxide, 2,3,4,5,6,8-hexahydro-8-(5-nitro-2-thienyl)-7H-cyclopenta[b]thieno[2,3-e]pyridin-7-one, 1,1-dioxide, 2,3,4,5,6,8-hexahydro-8-(5-nitro-2-furyl)-7H-cyclopenta[b]thieno[2,3-e]pyridin-7-one, 1,1-dioxide, 8-(3,4-dibromophenyl)-2,3,4,5,6,8-hexahydro-7H-cyclopenta[b]thieno[2,3-e]pyridin-7-one, 1,1-dioxide, 2,3,4,5,6,8-hexahydro-8-(3-nitrophenyl)dithieno[3,2-b:2',3'-e]pyridine, 1,1,7,7-tetraoxide, 8-(3-chloro-4-fluorophenyl)-2,3,4,5,6,8-hexahydrodithieno[3,2-b:2',3'-e]pyridine, 1,1,7,7-tetraoxide, 4-(3,4-dichlorophenyl)-1,4,6,7-tetrahydro-2-methyl-3-(methylsulfonyl)-5H-cyclopenta[b]pyridin-5-one, 4-(4-chloro-3-nitrophenyl)-1,4,6,7-tetrahydro-2-methyl-3-(methylsulfonyl)-5H-cyclopenta[b]pyridin-5-one, 8-(3,4-dichlorophenyl)-2,3,4,5,6,8-hexahydrodithieno[3,2-b:2',3'-e]pyridine, 1,1,7,7-tetraoxide, 8-(4-bromophenyl)-2,3,4,5,6,8-hexahydro-7H-cyclopenta[b]thieno[2,3-e]pyridin-7-one, 1,1-dioxide, 8-(3,4-difluorophenyl)-2,3,4,5,6,8-hexahydro-7H-cyclopenta[b]thieno[2,3-e]pyridin-7-one, 1,1-dioxide, 8-(4-chloro-3-fluorophenyl)-2,3,4,5,6,8-hexahydro-7H-cyclopenta[b]thieno[2,3-e]pyridin-7-one, 1,1-dioxide, 9-(3-chloro-4-fluorophenyl)-2,3,5,6,7,9-hexahydrothieno[3,2-b]quinolin-8(4H)-one, 1,1-dioxide, 8-(3-cyano-4-fluorophenyl)-2,3,4,5,6,8-hexahydrodithieno[3,2-b:2',3'-e]pyridine, 1,1,7,7-tetraoxide, (+)-9-(3-bromo-4-fluorophenyl)-2,3,5,6,7,9-hexahydrothieno[3,2-b]quinolin-8(4H)-one, 1,1-dioxide, (−)-9-(3-bromo-4-fluorophenyl)-2,3,5,6,7,9-hexahydrothieno[3,2-b]quinolin-8(4H)-one, 1,1-dioxide, 8-(2,1,3-benzoxadiazol-5-yl)-2,3,4,5,6,8-hexahydro-7H-cyclopenta[b]thieno[2,3-e]pyridin-7-one, 1,1-dioxide, (−)-8-(3-bromo-4-fluorophenyl)-2,3,4,5,6,8-hexahydro-7H-cyclopenta[b]thieno[2,3-e]pyridin-7-one, 1,1-dioxide, (+)-8-(3-bromo-4-fluorophenyl)-2,3,4,5,6,8-hexahydro-7H-cyclopenta[b]thieno[2,3-e]pyridin-7-one, 1,1-dioxide, 9-(2,1,3-benzoxadiazol-5-yl)-2,3,5,6,7,9-hexahydrothieno[3,2-b]quinolin-8(4H)-one, 1,1-dioxide, 9-(4-fluoro-3-iodophenyl)-2,3,5,6,7,9-hexahydrothieno[3,2-b]quinolin-8(4H)-one, 1,1-dioxide, 8-(4-fluoro-3-iodophenyl)-2,3,4,5,6,8-hexahydro-7H-cyclopenta[b]thieno[2,3-e]pyridin-7-one, 1,1-dioxide, (+)9-(3-bromo-4-fluorophenyl)-3,4,5,6,7,9-hexahydrocyclopenta[b]thiopyrano[2,3-e]pyridin-8(2H)-one, 1,1-dioxide, (−)-9-(3-bromo-4-fluorophenyl)-3,4,5,6,7,9-hexahydrocyclopenta[b]thiopyrano[2,3-e]pyridin-8(2H)-one, 1,1-dioxide, (+)-10-(3-bromo-4-fluorophenyl)-3,4,6,7,8,10-hexahydro-2H-thiopyrano[3,2-b]quinolin-9(5H)-one, 1,1-dioxide, (−)-10-(3-bromo-4-fluorophenyl)-3,4,6,7,8,10-hexahydro-2H-thiopyrano[3,2-b]quinolin-9(5H)-one, 1,1-dioxide, (+)-9-(3,4-dichlorophenyl)-2,3,5,6,7,9-hexahydrothieno[3,2-b]quinolin-8(4H)-one, 1,1-dioxide, (−)-9-(3,4-dichlorophenyl)-2,3,5,6,7,9-hexahydrothieno[3,2-b]quinolin-8(4H)-30 one, 1,1-dioxide, (+)-9-(2,1,3-benzoxadiazol-5-yl)-2,3,5,6,7,9-hexahydrothieno[3,2-b]quinolin-8(4H)-one, 1,1-dioxide, (−)-9-(2,1,3-benzoxadiazol-5-yl)-2,3,5,6,7,9-hexahydrothieno[3,2-b]quinolin-8(4H)-one, 1,1-dioxide, (+)-9-(4-chloro-3-nitrophenyl)-2,3,5,6,7,9-hexahydrothieno[3,2-b]quinolin-8(4H)-one, 1,1-dioxide, (−)-9-(4-chloro-3-nitrophenyl)-2,3,5,6,7,9-hexahydrothieno[3,2-b]quinolin-8(4H)-one, 1,1-dioxide, 11-(3-bromo-4-fluorophenyl)-2,3,4,5,7,8,9,11-octahydrothiepino[3,2-b]quinolin-10(6H)-one, 1,1-dioxide, 10-(3-bromo-4-fluorophenyl)-2,3,4,5,6,7,8,10-octahydro-9H-cyclopenta[b]thiepino[2,3-e]pyridin-9-one, 9-[3-(trifluoromethoxy)phenyl]-3,4,5,6,7,9-hexahydrocyclopenta[b]thiopyrano[2,3-e]pyridin-8(2H)-one, 1,1-dioxide, 9-(5-bromo-2-hydroxyphenyl)-3,4,5,6,7,9-hexahydrocyclopenta[b]thiopyrano[2,3-e]pyridin-8(2H)-one, 1,1-dioxide, 9-(5-cyano-6-methylthiopyrid-2-yl)-3,4,5,6,7,9-hexahydrocyclopenta[b]thiopyrano[2,3-e]pyridin-8(2H)-one, 1,1-dioxide, 7-(3-bromo-4-fluorophenyl)-5-methyl-2,3,4,7-tetrahydrothieno[3,2-b]pyridine-6-carboxylic acid, 1,1-dioxide, 8-(3-bromo-4-fluorophenyl)-6-methyl-5,8-dihydrothiopyrano[3,2-b]pyridine-7-carboxylic acid, 1,1-dioxide, 9-(5-bromo-2-hydroxyphenyl)-2,3,5,6,7,9-hexahydrothieno[3,2-b]quinolin-8(4H)-one, 1,1-dioxide, (+)-9-(3-chloro-4-fluorophenyl)-2,3,5,6,7,9-hexahydrothieno[3,2-b]quinolin-8(4H)-one, 1,1-dioxide, (−)-9-(3-chloro-4-fluorophenyl)-2,3,5,6,7,9-hexahydrothieno[3,2-b]quinolin-8(4H)-one, 1,1-dioxide, 9-(4-fluoro-3-methylphenyl)-2,3,5,6,7,9-hexahydrothieno[3,2-b]quinolin-8(4H)-one, 1,1-dioxide, 7-(3-bromo-4-fluorophenyl)-5-(trifluoromethyl)-2,3,4,7-tetrahydrothieno [3,2-b]pyridine, 1,1-dioxide, (+)-9-(3-cyanophenyl)-2,3,5,6,7,9-hexahydrothieno[3,2-b]quinolin-8(4H)-one, 1,1-dioxide, (−)-9-(3-cyanophenyl)-2,3,5,6,7,9-hexahydrothieno[3,2-b]quinolin-8(4H)-one, 1,1-dioxide, 9-(5-bromo-4-fluoro-2-iodophenyl)-2,3,5,6,7,9-hexahydrothieno[3,2-b]quinolin-8(4H)-one, 1,1-dioxide, 9-(3-bromo-4-fluorophenyl)-7,7-dimethyl-2,3,5,6,7,9-hexahydrothieno[3,2-b]quinolin-8(4H)-one, 1,1-dioxide, 9-(3-pyridinyl)-2,3,5,6,7,9-hexahydrothieno[3,2-b]quinolin-8(4H)-one, 1,1-dioxide, 9-(4-pyridinyl)-2,3,5,6,7,9-hexahydrothieno[3,2-b]quinolin-8(4H)-one, 1,1, dioxide, 9-(4-fluoro-2-hydroxyphenyl)-2,3,5,6,7,9-hexahydrothieno[3,2-b]quinolin-8(4H)-one, 1,1-dioxide, 9-(5-chloro-2-hydroxyphenyl)-2,3,5,6,7,9-hexahydrothieno[3,2-b]quinolin-8(4H)-one, 1,1-dioxide, 9-(5-bromo-4-fluoro-2-hydroxyphenyl)-2,3,5,6,7,9-hexahydrothieno[3,2-b]quinolin-8(4H)-one, 1,1-dioxide, 8-[4-chloro-3-(trifluoromethyl)phenyl]-2,3,4,5,6,8-hexahydrodithieno[3,2-b:2',3'-e]pyridine-1,1,7,7-tetraoxide, 8-(2,1,3-benzoxadiazol-5-yl)-2,3,4,5,6,8-hexahydrodithieno[3,2-b:2',3'-e]pyridine-1, 1,7,7-tetraoxide, 8-(3,4-dibromophenyl)-2,3,4,5,6,8-hexahydrodithieno[3,2-b:2',3'-e]pyridine-1,1,7,7-tetraoxide, 9-(3-bromo-4-fluorophenyl)-2,3,5,6,7,9-hexahydrothieno[3,2-b]quinolin-8(4H)-one, 1-oxide, (+)-9-(4-methyl-3-nitrophenyl)-2,3,5,6,7,9-hexahydro[3,2-b]quinolin-8(4H)-one, 1,1-dioxide, (−)-9-(4-methyl-3-nitrophenyl)-2,3,5,6,7,9-hexahydro[3,2-b]quinolin-8(4H)-one, 1,1-dioxide, 9-(3,4-dichlorophenyl)-7,7-dimethyl-2,3,5,6,7,9-hexahydrothieno[3,2-b]quinolin-8(4H)-one, 1,1-dioxide, 9-(5-bromo-2-thienyl)-2,3,5,6,7,9-hexahydrothieno[3,2-b]quinolin-8(4H)-one, 1,1-dioxide, 9-(4-bromo-2-thienyl)-2,3,5,6,7,9-hexahydrothieno[3,2-b]quinolin-8(4H)-one, 1,1-dioxide, 9-(4-fluoro-3-vinylphenyl)-2,3,5,6,7,9-hexahydrothieno[3,2-b]quinolin-8(4H)-one, 1,1-dioxide, 9-(3-acetyl-4-fluorophenyl)-2,3,5,6,7,9-hexahydrothieno[3,2-b]quinolin-8(4H)-one, 1,1-dioxide, 9-[4-fluoro-3-(2-furyl)phenyl]-2,3,5,6,7,9-hexahydrothieno[3,2-b]quinolin-8(4H)-one, 1,1-dioxide, 9-[6-fluoro-(1,1-biphenyl)-3-yl]-2,3,5,6,7,9-hexahydrothieno[3,2-b]quinolin-8(4H)-one, 1,1-dioxide, 9-[4-fluoro-3-(phenylethynyl)phenyl]-2,3,5,6,7,9-hexahydrothieno[3,2-b]quinolin-8(4H)-one, 1,1-dioxide, (+)-7-(3-bromo-4-fluorophenyl)-5-(trifluoromethyl)-2,3,4,7-tetrahydrothieno[3,2-b]pyridine, 1,1-dioxide, (−)-7-(3-bromo-4-fluorophenyl)-5-(trifluoromethyl)-2,3,4,7-tetrahydrothieno[3,2-b]pyridine, 1,1-dioxide, 9-(3,4-dibromophenyl)-2,3,5,6,7,9-hexahydrothieno[3,2-b]quinolin-8(4H)-one, 1,1-dioxide, (+)-9-[4-fluoro-3-(trifluoromethyl)phenyl]-2,3,5,6,7,9-hexahydrothieno[3, 2-b]quinolin-8(4H)-one, 1,1-dioxide, (−)-9-[4-fluoro-3-(trifluoromethyl)phenyl]-2,3,5,6,7,9-hexahydrothieno[3,2-b]quinolin-8(4H)-one, 1,1-dioxide, 9-[4-fluoro-3-(2-thienyl)phenyl]-2,3,5,6,7,9-hexahydrothieno[3,2-b]quinolin-8(4H)-one, 1,1-dioxide, 9-[4-fluoro-3-(3-hydroxy-3-methyl-1-butynyl)phenyl]-2,3,5,6,7,9-hexahydrothieno[3,2-b]quinolin-8(4H)-one, 1,1-dioxide, 8-(4-fluoro-3-iodophenyl)-2,3,4,5,6,8-hexahydrodithieno[3,2-b:2'3'-e]pyridine-1, 1,7,7-tetraoxide, (+)-9-(3-cyano-4-fluorophenyl)-2,3,5,6,7,9-hexahydrothieno[3,2-b]quinolin-8(4H)-one, 1,1-dioxide, (−)-9-(3-cyano-4-fluorophenyl)-2,3,5,6,7,9-hexahydrothieno[3,2-b]quinolin-8(4H)-one, 1,1-dioxide, (+)-8-(3,4-dichlorophenyl)-2,3,4,5,6,8-hexahydrocyclopenta[b]thieno[2,3-e]pyridin-7-one, 1,1-dioxide, (−)-8-(3,4-dichlorophenyl)-2,3,4,5,6,8-hexahydrocyclopenta[b]thieno[2,3-e]pyridin-7-one, 1,1-dioxide, (+)-9-(3,4-dibromophenyl)-2,3,5,6,7,9-hexahydrothieno[3,2-b]quinolin-8(4H)-one, 1,1-dioxide, (−)-9-(3,4-dibromophenyl)-2,3,5,6,7,9-hexahydrothieno[3,2-b]quinolin-8(4H)-one, 1,1-dioxide, (+)-9-(4-fluoro-3-iodophenyl)-2,3,5,6,7,9-hexahydrothieno[3,2-b]quinolin-8(4H)-one, 1,1-dioxide, (−)-9-(4-fluoro-3-iodophenyl)-2,3,5,6,7,9-hexahydrothieno[3,2-b]quinolin-8(4H)-one, 1,1-dioxide, 9-[4-chloro-3-(trifluoromethyl)phenyl]-2,3,5,6,7,9-hexahydrothieno[3,2-b]quinolin-8(4H)-one, 1,1-dioxide, (+)-9-(3-ethynyl-4-fluorophenyl)-2,3,5,6,7,9-hexahydrothieno[3,2-b]quinolin-8(4H)-one, 1,1-dioxide, (−)-9-(3-ethynyl-4-fluorophenyl)-2,3,5,6,7,9-hexahydrothieno[3,2-b]quinolin-8(4H)-one, 1,1-dioxide, 9-(3-cyano-4-methylphenyl)-2,3,5,6,7,9-hexahydrothieno[3,2-b]quinolin-8(4H)-one, 1,1-dioxide, (+)-9-(3-cyano-4-methylpheriyl)-2,3,5,6,7,9-hexahydrothieno [3,2-b]quinolin-8(4H)-one, 1,1-dioxide, (−)-9-(3-cyano-4-methylphenyl)-2,3,5,6,7,9-hexahydrothieno[3,2-b]quinolin-8(4H)-one, 1,1-dioxide, 9-[4-fluoro-3-(3-pyridinyl)phenyl]-2,3,5,6,7,9-hexahydrothieno[3,2-b]quinolin-8(4H)-one, 1,1-dioxide, 7-(3-bromo-4-fluorophenyl)-5-methyl-2,3,4,7-tetrahydrothieno[3,2-b]pyridine-6-carbonitrile, 1,1-dioxide, 8-(3-bromo-4-fluorophenyl)-6-trifluoromethyl-5,8-dihydrothiopyrano[3,2-b]pyridine, 1,1-dioxide, (+)-8-(4-chloro-3-nitrophenyl)-2,3,4,5,6,8-hexahydrocyclopenta[b]thieno [2,3-e]pyridin-7-one, 1,1-dioxide, (−)-8-(4-chloro-3-nitrophenyl)-2,3,4,5,6,8-hexahydrocyclopenta[b]thieno[2,3-e]pyridin-7-one, 1,1-dioxide, (−)-8-(3-cyanophenyl)-2,3,4,5,6,8-hexahydrocyclopenta[b]thieno[2,3-e]pyridin-7-one, 1,1-dioxide, 7-(3-chloro-4-fluorophenyl)-5-(trifluoromethyl)-2,3,4,7-tetrahydrothieno[3,2-b]pyridine, 1,1-dioxide, (+)-8-(3-cyanophenyl)-2,3,4,5,6,8-hexahydrocyclopenta[b]thieno[2,3-e]pyridin-7-one, 1,1-dioxide, (+)-9-[4-fluoro-3-(2-furyl)phenyl]-2,3,5,6,7,9-hexahydrothieno[3,2-b]quinolin-8(4H)-one, 1,1-dioxide, (−)-9-[4-fluoro-3-(2-furyl)phenyl]-2,3,5,6,7,9-hexahydrothieno[3,2-b]quinolin-8(4H)-one, 1,1-dioxide, (+)-9-(5-bromo-2-thienyl)-2,3,5,6,7,9-hexahydrothieno[3,2-b]quinolin-8(4H)-one, 1,1-dioxide, (−)-9-(5-bromo-2-thienyl)-2,3,5,6,7,9-hexahydrothieno[3,2-b]quinolin-8(4H)-one, 1,1-dioxide, 9-(3-allyl-4-fluorophenyl)-2,3,5,6,7,9-hexahydrothieno[3,2-b]quinolin-8(4H)-one, 1, 1-dioxide, 9-[3-(1-ethoxyvinyl)-4-fluorophenyl-2,3,5,6,7,9-hexahydrothieno[3,2-b]quinolin-8(4H)-one, 1, 1-dioxide, 8-(3-bromo-4-fluorophenyl)-6-methyl-3,4,5,8-tetrahydro-2H-thiopyrano[3,2-b]pyridine-7-carbonitrile, 1,1-dioxide, (−)-9-[4-chloro-3-(trifluoromethyl)phenyl]-2,3,5,6,7,9-hexahydrothieno[3,2-b]quinolin-8(4H)-one, 1,1-dioxide, (+)-9-[4-chloro-3-(trifluoromethyl)phenyl]-2,3,5,6,7,9-hexahydrothieno[3,2-b]quinolin-8(4H)-one, 1,1-dioxide, (9S)-9-(3-ethyl-4-fluorophenyl)-2,3,5,6,7,9-hexahydrothieno[3,2-b]quinolin-8(4H)-one, 1,1-dioxide, 9-(5-cyano-2-thienyl)-2,3,5,6,7,9-hexahydrothieno [3,2-b]quinolin-8(4H)-one, 1,1-dioxide, (+)-9-(3,4-difluoro)-2,3,5,6,7,9-hexahydrothieno[3,2-b]quinolin-8(4H)-one, 1,1-dioxide, (9S)-9-(3-ethenyl-4-fluorophenyl)-2,3,5,6,7,9-hexahydrothieno[3,2-b]quinolin-8(4H)-one, 1,1-dioxide, 9-(5-bromo-4-fluoro-2-nitrophenyl)-3,4,5,6,7,9-hexahydrocyclopenta[b]thiopyrano[2,3-e]pyridin-8(2H)-one, 1,1-dioxide, (−)-9-(3,4-difluorophenyl)-2,3,5,6,7,9-hexahydrothieno[3,2-b]quinolin-8(4H)-one 1,1-dioxide, (+)-9-(4-bromo-2-thienyl)-2,3,5,6,7,9-hexahydrothieno[3,2-b]quinolin-8(4H)-one 1,1-dioxide, (−)-9-(4-bromo-2-thienyl)-2,3,5,6,7,9-hexahydrothieno[3,2-b]quinolin-8(4H)-one 1, 1-dioxide, 9-(3,4-difluorophenyl)-7,7-dimethyl-2,3,5,6,7,9-hexahydrothieno[3,2-b]quinolin-8(4H)-one 1,1-dioxide, 9-(3-chloro-4-fluorophenyl)-7,7-dimethyl-2,3,5,6,7,9-hexahydrothieno[3,2-b]quinolin-8(4H)-one 1,1-dioxide, 9-[4-fluoro-3-(trifluoromethyl)phenyl]-7,7-dimethyl-2,3,5,6,7,9-hexahydrothieno[3,2-b]quinolin-8(4H)-one 1,1-dioxide, 9-(4-chloro-3-fluorophenyl)-7,7-dimethyl-2,3,5,6,7,9-hexahydrothieno[3,2-b]quinolin-8(4H)-one 1,1-dioxide, 9-(4-chloro-3-nitrophenyl)-7,7-dimethyl-2,3,5,6,7,9-hexahydrothieno[3,2-b]quinolin-8(4H)-one 1,1-dioxide, 9-(3,4-dibromophenyl)-7,7-dimethyl-2,3,5,6,7,9-hexahydrothieno[3,2-b]quinolin-8(4H)-one 1,1-dioxide, 9-[3-fluoro-4-(trifluoromethyl)phenyl]-7,7-dimethyl-2,3,5,6,7,9-hexahydrothieno[3,2-b]quinolin-8(4H)-one 1,1-dioxide, 7,7-dimethyl-9-(3-nitrophenyl)-2,3,5,6,7,9-hexahydrothieno[3,2-b]quinolin-8(4H)-one 1,1-dioxide, 9-(3-cyanophenyl)-7,7-dimethyl-2,3,5,6,7,9-hexahydrothieno[3,2-b]quinolin-8(4H)-one 1,1-dioxide, 9-(4-bromo-2-thienyl)-7,7-dimethyl-2,3,5,6,7,9-hexahydrothieno[3,2-b]quinolin-8(4H)-one 1,1-dioxide, 9-(5-chloro-2-thienyl)-7,7-dimethyl-2,3,5,6,7,9-hexahydrothieno[3,2-b]quinolin-8(4H)-one 1,1-dioxide, 9-(5-bromo-2-thienyl)-7,7-dimethyl-2,3,5,6,7,9-hexahydrothieno[3,2-b]quinolin-8(4H)-one 1,1-dioxide, 7,7-dimethyl-9-(5-nitro-3-thienyl)-2,3,5,6,7,9-hexahydrothieno[3,2-b]quinolin-8(4H)-one 1,1-dioxide, 9-(5-chloro-2-hydroxyphenyl)-7,7-dimethyl-2,3,5,6,7,9-hexahydrothieno[3,2-b]quinolin-8(4H)-one 1,1-dioxide, 9-(2-hydroxy-5-nitrophenyl)-7,7-dimethyl-2,3,5,6,7,9-hexahydrothieno[3,2-b]quinolin-8(4H)-one 1,1-dioxide, 9-(2-hydroxy-3,5-dinitrophenyl)-7,7-dimethyl-2,3,5,6,7,9-hexahydrothieno[3,2-b]quinolin-8(4H)-one 1,1-dioxide, 9-(3,5-dibromo-2-hydroxyphenyl)-7,7-dimethyl-2,3,5,6,7,9-hexahydrothieno[3,2-b]quinolin-8(4H)-one 1,1-dioxide, 9-(3-bromo-5-chloro-2-hydroxyphenyl)-7,7-dimethyl-2,3,5,6,7,9-hexahydrothieno[3,2-b]quinolin-8(4H)-one 1,1-dioxide, 9-(3-bromo-2-hydroxy-5-nitrophenyl)-7,7-dimethyl-2,3,5,6,7,9-hexahydrothieno[3,2-b]quinolin-8(4H)-one 1,1-dioxide, 9-(3,5-dichloro-2-hydroxyphenyl)-7,7-dimethyl-2,3,5,6,7,9-hexahydrothieno[3,2-b]quinolin-8(4H)-one 1,1-dioxide, 9-(2-hydroxy-3-nitrophenyl)-7,7-dimethyl-2,3,5,6,7,9-hexahydrothieno[3,2-b]quinolin-8(4H)-one 1,1-dioxide, 9-(5-bromo-2-hydroxy-3-nitrophenyl)-7,7-dimethyl-2,3,5,6,7,9-hexahydrothieno[3,2-b]quinolin-8(4H)-one 1,1-dioxide, 7,7-dimethyl-9-(2,4,5-trifluorophenyl)-2,3,5,6,7,9-hexahydrothieno[3,2-b]quinolin-8(4H)-one 1,1-dioxide, 7,7-dimethyl-9-(2,3,4-trifluorophenyl)-2,3,5,6,7,9-hexahydrothieno[3,2-b]quinolin-8(4H)-one 1,1-dioxide, 7,7-dimethyl-9-(3,4,5-trifluorophenyl)-2,3,5,6,7,9-hexahydrothieno[3,2-b]quinolin-8(4H)-one 1,1-dioxide, 9-(3,5-dibromo-4-hydroxyphenyl)-7,7-dimethyl-2,3,5,6,7,9-hexahydrothieno[3,2-b]quinolin-8(4H)-one 1,1-dioxide, 9-(4-chlorophenyl)-7,7-dimethyl-2,3,5,6,7,9-hexahydrothieno[3,2-b]quinolin-8(4H)-one 1,1-dioxide, 9-(3-chlorophenyl)-7,7-dimethyl-2,3,5,6,7,9-hexahydrothieno[3,2-b]quinolin-8(4H)-one 1,1-dioxide, 9-(4-chloro-3-fluorophenyl)-2,3,5,6,7,9-hexahydrothieno [3,2-b]quinolin-8(4H)-one 1,1-dioxide, 9-[3-(trifluoromethoxy)phenyl]-2,3,5,6,7,9-hexahydrothieno[3,2-b]quinolin-8(4H)-one 1,1-dioxide, 9-(3-bromo-4-fluorophenyl)-5,5-dimethyl-2,3,5,6,7,9-hexahydrothieno[3,2-b]quinolin-8(4H)-one 1,1-dioxide, 9-[4-(trifluoromethoxy)phenyl]-2,3,5,6,7,9-hexahydrothieno[3,2-b]quinolin-8(4H)-one 1,1-dioxide, 9-(2,1,3-benzothiadiazol-5-yl)-2,3,5,6,7,9-hexahydrothieno[3,2-b]quinolin-8(4H)-one 1,1-dioxide, 9-(4-bromo-3-nitrophenyl)-2,3,5,6,7,9-hexahydrothieno[3,2-b]quinolin-8(4H)-one 1,1-dioxide, 9-(4-ethyl-3-nitrophenyl)-2,3,5,6,7,9-hexahydrothieno[3,2-b]quinolin-8(4H)-one 11,1-dioxide, 9-[3-nitro-4-(trifluoromethoxy)phenyl]-2,3,5,6,7,9-hexahydrothieno[3,2-b]quinolin-8(4H)-one 1,1-dioxide, 9-[4-(difluoromethoxy)phenyl]-2,3,5,6,7,9-hexahydrothieno[3,2-b]quinolin-8(4H)-one 1,1-dioxide, 9-(3-methyl-4-nitrophenyl)-2,3,5,6,7,9-hexahydrothieno[3,2-b]quinolin-8(4H)-one 1,1-dioxide, 9-[3-nitro-4-(trifluoromethyl)phenyl]-2,3,5,6,7,9-hexahydrothieno[3,2-b]quinolin-8(4H)-one 1,1-dioxide, 9-[4-(difluoromethoxy)-3-nitrophenyl]-2,3,5,6,7,9-hexahydrothieno[3,2-b]quinolin-8(4H)-one 1,1-dioxide, 9-(4-chloro-3-methylphenyl)-2,3,5,6,7,9-hexahydrothieno[3,2-b]quinolin-8(4H)-one 1,1-dioxide, 9-(3-bromo-4-methylphenyl)-2,3,5,6,7,9-hexahydrothieno[3,2-b]quinolin-8(4H)-one 1,1-dioxide, (+)-9-(3-bromo-4-methylphenyl)-2,3,5,6,7,9-hexahydrothieno[3,2-b]quinolin-8(4H)-one 1,1-dioxide, (−)-9-(3-bromo-4-methylphenyl)-2,3,5,6,7,9-hexahydrothieno[3,2-b]quinolin-8(4H)-one 1,1-dioxide, 9-[4-methyl-3-(methylsulfanyl)phenyl]-2,3,5,6,7,9-hexahydrothieno[3,2-b]quinolin-8(4H)-one 1,1-dioxide, (−)-9-(4-chloro-3-fluorophenyl)-2,3,5,6,7,9-hexahydrothieno[3,2-b]quinolin-8(4H)-one 1,1-dioxide, (+)-9-(4-chloro-3-fluorophenyl)-2,3,5,6,7,9-hexahydrothieno[3,2-b]quinolin-8(4H)-one 1,1-dioxide, 9-[4-methyl-3-(methylsulfonyl)phenyl]-2,3,5,6,7,9-hexahydrothieno[3,2-b]quinolin-8(4H)-one 1,1-dioxide, (−)-9-(3-bromo-4-fluorophenyl)-5,5-dimethyl-2,3,5,6,7,9-hexahydrothieno[3,2-b]quinolin-8(4H)-one 1,1-dioxide, (+)-9-(3-bromo-4-fluorophenyl)-5,5-dimethyl-2,3,5,6,7,9-hexahydrothieno[3,2-b]quinolin-8(4H)-one 1,1-dioxide, (−)-9-(3-bromo-4-fluorophenyl)-7,7-dimethyl-2,3,5,6,7,9-hexahydrothieno [3,2-b]quinolin-8(4H)-one, 1,1-dioxide, (+)-9-(3-bromo-4-fluorophenyl)-7,7-dimethyl-2,3,5,6,7,9-hexahydrothieno[3,2-b]quinotin-8(4H)-one, 1,1-dioxide, (+)-9-(4-bromo-3-nitrophenyl)-2,3,5,6,7,9-hexahydrothieno[3,2-b]quinolin-8(4H)-one 1,1-dioxide, (−)-9-(4-bromo-3-nitrophenyl)-2,3,5,6,7,9-hexahydrothieno[3,2-b]quinolin-8(4H)-one 1,1-dioxide, 9-(3-iodo-4-methylphenyl)-2,3,5,6,7,9-hexahydrothieno[3,2-b]quinolin-8(4H)-one 1,1-dioxide, (+)-9-[3-nitro-4-(trifluoromethyl)phenyl]-2,3,5,6,7,9-hexahydrothieno[3,2-b]quinolin-8(4H)-one 1,1-dioxide, (−)-9-[3-nitro-4-(trifluoromethyl)phenyl]-2,3,5,6,7,9-hexahydrothieno[3,2-b]quinolin-8(4H)-one 1,1-dioxide, (+)-9-(2,1,3-benzothiadiazol-5-yl)-2,3,5,6,7,9-hexahydrothieno[3,2-b]quinolin-8(4H)-one 1,1-dioxide, (−)-9-(2,1,3-benzothiadiazol-5-yl)-2,3,5,6,7,9-hexahydrothieno[3,2-b]quinolin-8(4H)-one 1,1-dioxide, (+)-9-(3-iodo-4-methylphenyl)-2,3,5,6,7,9-hexahydrothieno[3,2-b]quinolin-8(4H)-one 1,1-dioxide, (−)-9-(3-iodo-4-methylphenyl)-2,3,5,6,7,9-hexahydrothieno[3,2-b]quinolin-8(4H)-one 1,1-dioxide, 9-(5-cyano-2-thienyl)-7,7-dimethyl-2,3,5,6,7,9-hexahydrothieno[3,2-b]quinolin-8(4H)-one, 1,1-dioxide, 9-(4-chloro-2-thienyl)-7,7-dimethyl-2,3,5,6,7,9-hexahydrothieno[3,2-b]quinolin-8(4H)-one, 1,1-dioxide, 9-(4-cyano-2-thienyl)-7,7-dimethyl-2,3,5,6,7,9-hexahydrothieno[3,2-b]quinolin-8(4H)-one, 1,1-dioxide, 9-(5-bromo-3-thienyl)-7,7-dimethyl-2,3,5,6,7,9-hexahydrothieno[3,2-b]quinolin-8(4H)-one, 1,1-dioxide, 9-(5-chloro-3-thienyl)-7,7-dimethyl-2,3,5,6,7,9-hexahydrothieno[3,2-b]quinolin-8(4H)-one, 1,1-dioxide, 9-(5-cyano-3-thienyl)-7,7-dimethyl-2,3,5,6,7,9-hexahydrothieno[3,2-b]quinolin-8(4H)-one, 1,1-dioxide, 7,7-dimethyl-9-(5-nitro-2-furanyl)-2,3,5,6,7,9-hexahydrothieno[3,2-b]quinolin-8(4H)-one, 1,1-dioxide, 9-(5-bromo-2-furanyl)-7,7-dimethyl-2,3,5,6,7,9-hexahydrothieno[3,2-b]quinolin-8(4H)-one, 1,1-dioxide, 9-(5-chloro-2-furanyl)-7,7-dimethyl-2,3,5,6,7,9-hexahydrothieno[3,2-b]quinolin-8(4H)-one, 1,1-dioxide, 9-(5-cyano-2-furanyl)-7,7-dimethyl-2,3,5,6,7,9-hexahydrothieno[3,2-b]quinolin-8(4H)-one, 1,1-dioxide, 9-[4-fluoro-3-(2-furanyl)phenyl]-7,7-dimethyl-2,3,5,6,7,9-hexahydrothieno[3,2-b]quinolin-8(4H)-one, 1,1-dioxide, 9-(3-ethenyl-4-fluorophenyl)-7,7-dimethyl-2,3,5,6,7,9-hexahydrothieno[3,2-b]quinolin-8(4H)-one 1,1-dioxide, 9-(3-ethynyl-4-fluorophenyl)-7,7-dimethyl-2,3,5,6,7,9-hexahydrothieno[3,2-b]quinolin-8(4H)-one, 1,1-dioxide, 9-[3-(1-ethoxyethenyl)-4-fluorophenyl]-7,7-dimethyl-2,3,5,6,7,9-hexahydrothieno[3,2-b]quinolin-8(4H)-one, 1,1-dioxide, 9-(3-fluoro-4-chlorophenyl)-7,7-dimethyl-2,3,5,6,7,9-hexahydrothieno[3,2-b]quinolin-8(4H)-one, 1,1-dioxide, 7,7-dimethyl-9-[3-(trifluoromethoxy)phenyl]-2,3,5,6,7,9-hexahydrothieno[3,2-b]quinolin-8(4H)-one, 1,1-dioxide, 9-[2-hydroxy-5-(trifluoromethoxy)phenyl]-7,7-dimethyl-2,3,5,6,7,9-hexahydrothieno[3,2-b]quinolin-8(4H)-one, 1,1-dioxide, 9-[5-chloro-2-hydroxyphenyl]-7,7-dimethyl-2,3,5,6,7,9-hexahydrothieno[3,2-b]quinolin-8(4H)-one, 1,1-dioxide, 9-(5-bromo-4-fluoro-2-hydroxyphenyl)-7,7-dimethyl-2,3,5,6,7,9-hexahydrothieno[3,2-b]quinolin-8(4H)-one, 1,1-dioxide, 9-[4-fluoro-3-(trifluoromethyl)phenyl]-7,7-dimethyl-2,3,5,6,7,9-hexahydrothieno[3,2-b]quinolin-8(4H)-one, 1,1-dioxide, 7,7-dimethyl-9-(4-methyl-3-nitrophenyl)-2,3,5,6,7,9-hexahydrothieno[3,2-b]quinolin-8(4H)-one, 1,1-dioxide, 9-(5-bromo-2-hydroxy-3-nitrophenyl)-7,7-dimethyl-2,3,5,6,7,9-hexahydrothieno[3,2-b]quinolin-8(4H)-one, 1,1-dioxide, 9-(5-bromo-2-hydroxyphenyl)-7,7-dimethyl-2,3,5,6,7,9-hexahydrothieno[3,2-b]quinolin-8(4H)-one, 1,1-dioxide, 9-(3-fluorophenyl)-7,7-dimethyl-2,3,5,6,7,9-hexahydrothieno[3,2-b]quinolin-8(4H)-one, 1,1-dioxide, 9-(3-bromophenyl)-7,7-dimethyl-2,3,5,6,7,9-hexahydrothieno[3,2-b]quinolin-8(4H)-one, 1,1-dioxide, 7,7-dimethyl-9-(4-nitrophenyl)-2,3,5,6,7,9-hexahydrothieno[3,2-b]quinolin-8(4H)-one, 1,1-dioxide, 9-(4-cyanophenyl)-7,7-dimethyl-2,3,5,6,7,9-hexahydrothieno[3,2-b]quinolin-8(4H)-one, 1,1-dioxide, 9-(4-bromophenyl)-7,7-dimethyl-2,3,5,6,7,9-hexahydrothieno[3,2-b]quinolin-8(4H)-one, 1,1-dioxide, 9-(4-fluorophenyl)-7,7-dimethyl-2,3,5,6,7,9-hexahydrothieno[3,2-b]quinolin-8(4H)-one, 1,1-dioxide, 9-(3-fluoro-2-hydroxyphenyl)-7,7-dimethyl-2,3,5,6,7,9-hexahydrothieno[3,2-b]quinolin-8(4H)-one, 1,1-dioxide, 9-(2,3,4-trifluorophenyl)-7,7-dimethyl-2,3,5,6,7,9-hexahydrothieno[3,2-b]quinolin-8(4H)-one, 1,1-dioxide, 7,7-dimethyl-9-(5-nitro-2-thienyl)-2,3,5,6,7,9-hexahydrothieno[3,2-b]quinolin-8(4H)-one, 1,1-dioxide, 7,7-dimethyl-9-(4-nitro-2-thienyl)-2,3,5,6,7,9-hexahydrothieno[3,2-b]quinolin-8(4H)-one, 1,1-dioxide, 9-(2,1,3-benzoxadiazol-5-yl)-7,7-dimethyl-2,3,5,6,7,9-hexahydrothieno [3,2-b]quinolin-8(4H)-one, 1,1-dioxide, 9-(2,1,3-benzothiadiazol-5-yl)-7,7-dimethyl-2,3 5,6,7,9-hexahydrothieno[3,2-b]quinolin-8(4H)-one, 1,1-dioxide, 9-[3-bromo-4-(trifluoromethoxy)phenyl]-2,3,5,6,7,9-hexahydrothieno[3,2-b]quinolin-8(4H)-one, 1,1-dioxide, (9S)-9-(5-bromo-4-fluoro-2-hydroxyphenyl)-2,3,5,6,7,9-hexahydrothieno[3,2-b]quinolin-8(4H)-one, 1,1-dioxide, (9R)-9-(5-bromo-4-fluoro-2-hydroxyphenyl)-2,3,5,6,7,9-hexahydrothieno[3,2-b]quinolin-8(4H)-one, 1,1-dioxide, 9-(4-fluoro-2-hydroxy-5-nitrophenyl)-2,3,5,6,7,9-hexahydrothieno[3,2-b]quinolin-8(4H)-one, 1,1-dioxide, 9-[5-bromo-4-(trifluoromethoxy)-2-hydroxyphenyl]-2,3,5,6,7,9-hexahydrothieno[3,2-b]quinolin-8(4H)-one, 1,1-dioxide, 9-(2-hydroxy-4-methyl-5-nitrophenyl)-2,3,5,6,7,9-hexahydrothieno[3,2-b]quinolin-8(4H)-one, 1,1-dioxide, 9-(4,5-dichloro-2-hydroxyphenyl)-2,3,5,6,7,9-hexahydrothieno[3,2-b]quinolin-8(4H)-one, 1,1-dioxide, 9-(5-chloro-4-fluoro-2-hydroxyphenyl)-2,3,5,6,7,9-hexahydrothieno[3,2-b]quinolin-8(4H)-one, 1,1-dioxide, 9-(3-bromophenyl)-2,3,5,6,7,9-hexahydrothieno[3,2-b]quinolin-8(4H)-one, 1,1-dioxide, 9-[3-(2-furanyl)-4-(trifluoromethoxy)phenyl]-2,3,5,6,7,9-hexahydrothieno[3,2-b]quinolin-8(4H)-one, 1,1-dioxide, 9-[4-(trifluoromethoxy)-3-[1-(trifluoromethyl)ethenyl]phenyl]-2,3,5,6,7,9-hexahydrothieno[3,2-b]quinolin-8(4H)-one, 1,1-dioxide, 9-[4-(trifluoromethoxy)-3-iodophenyl]-2,3,5,6,7,9-hexahydrothieno[3,2-b]quinolin-8(4H)-one, 1,1-dioxide, 9-(2-naphthalenyl)-2,3,5,6,7,9-hexahydrothieno[3,2-b]quinolin-8(4H)-one, 1,1-dioxide, 9-(3-methyl-5-nitro-2-thienyl)-2,3,5,6,7,9-hexahydrothieno[3,2-b]quinolin-8(4H)-one, 1,1-dioxide, 9-(5-nitro-2-thienyl)-2,3,5,6,7,9-hexahydrothieno[3,2-b]quinolin-8(4H)-one, 1,1-dioxide, 9-(4-nitro-2-thienyl)-2,3,5,6,7,9-hexahydrothieno[3,2-b]quinolin-8(4H)-one, 1,1-dioxide, 9-[4-fluoro-3-(1-methoxyethenyl)phenyl]-2,3,5,6,7,9-hexahydrothieno[3,2-b]quinolin-8(4H)-one, 1,1-dioxide, 9-[4-fluoro-3-(1H-imidazol-1-yl)phenyl]-2,3,5,6,7,9-hexahydrothieno[3,2-b]quinolin-8(4H)-one, 1,1-dioxide, 9-[4-fluoro-3-(3-furanyl)phenyl]-2,3,5,6,7,9-hexahydrothieno[3,2-b]quinolin-8(4H)-one, 1,1-dioxide, 9-[4-fluoro-3-(1-propynyl)phenyl]-2,3,5,6,7,9-hexahydrothieno[3,2-b]quinolin-8(4H)-one, 1,1-dioxide, 9-[3-(difluoromethoxy)-4-fluorophenyl]-2,3,5,6,7,9-hexahydrothieno[3,2-b]quinolin-8(4H)-one, 1,1-dioxide, 9-[3-(bromodifluoromethoxy)-4-fluorophenyl]-2,3,5,6,7,9-hexahydrothieno[3,2-b]quinolin-8(4H)-one, 1,1-dioxide, 9-[4-fluoro-3-(2-thiazolyl)phenyl]-2,3,5,6,7,9-hexahydrothieno[3,2-b]quinolin-8(4H)-one, 1,1-dioxide, 9-[4-fluoro-3-(1H-pyrazol-4-yl)phenyl]-2,3,5,6,7,9-hexahydrothieno[3,2-b]quinolin-8(4H)-one, 1,1-dioxide, 9-[4-fluoro-3-[1-(hydroxymethyl)ethenyl]phenyl]-2,3,5,6,7,9-hexahydrothieno[3,2-b]quinolin-8(4H)-one, 1,1-dioxide, 9-[4-fluoro-3-(1-methylethenyl)phenyl]-2,3,5,6,7,9-hexahydrothieno[3,2-b]quinolin-8(4H)-one, 1,1-dioxide, 9-[3-[1-[(bromodifluoromethoxy)methyl]ethenyl]-4-fluorophenyl]-2,3,5,6,7,9-hexahydrothieno[3,2-b]quinolin-8(4H)-one, 1,1-dioxide, 9-[4-fluoro-3-[1 -(trifluoromethyl)ethenyl]phenyl]-2,3,5,6,7,9-hexahydrothieno[3,2-b]quinolin-8(4H)-one, 1,1-dioxide, 9-[3-[3,5-bis(trifluoromethyl)-1H-pyrazol-1-yl]-4-fluorophenyl]-2,3,5,6,7,9-exahydrothieno[3,2-b]quinolin-8(4H)-one, 1,1-dioxide, 9-(3-chloro-4-methylphenyl)-2,3,5,6,7,9-hexahydrothieno[3,2-b]quinolin-8(4H)-one, 1,1-dioxide, 9-[4-methyl-3-(2,2,2-trifluoroethoxy)phenyl]-2,3,5,6,7,9-hexahydrothieno[3,2-b]quinolin-8(4H)-one 1,1-dioxide, 9-[4-methyl-3-(2,2,2-trifluoroethyl)phenyl]-2,3,5,6,7,9-hexahydrothieno[3,2-b]quinolin-8(4H)-one, 1,1-dioxide, 9-[4-methyl-3-[1 -(trifluoromethyl)ethenyl]phenyl]-2,3,5,6,7,9-hexahydrothieno[3,2-b]quinolin-8(4H)-one, 1,1-dioxide, 2-methyl-5-(1,1-dioxido-8-oxo-2,3,4,5,6,7,8,9-octahydrothieno[3,2-b]quinolin-9-yl)benzenesulfonamide, 9-[3-(difluoromethoxy)-4-methylphenyl]-2,3,5,6,7,9-hexahydrothieno[3,2-b]quinolin-8(4H)-one, 1,1-dioxide, 9-[3-(bromodifluoromethoxy)-4-methylphenyl]-2,3,5,6,7,9-hexahydrothieno[3,2-b]quinolin-8(4H)-one, 1,1-dioxide, 9-[4-methyl-3-(2,2,2-trifluoroacetyl)phenyl]-2,3,5,6,7,9-hexahydrothieno[3,2-b]quinotin-8(4H)-one, 1,1-dioxide, 9-(3-amino-4-methylphenyl)-2,3,5,6,7,9-hexahydrothieno[3,2-b]quinolin-8(4H)-one, 1,1-dioxide, N-[2-methyl-5-(1,1-dioxido-8-oxo-2,3,4,5,6,7,8,9-octahydrothieno[3,2-b]quinolin-9-yl)phenyl]methanesulfonamide, 9-(3-acetyl-4-methylphenyl)-2,3,5,6,7,9-hexahydrothieno[3,2-b]quinolin-8(4H)-one, 1,1-dioxide, 9-[4-(2,2,2-trifluoroethyl)-3-(trifluoromethoxy)phenyl]-2,3,5,6,7,9-hexahydrothieno[3,2-b]quinolin-8(4H)-one, 1,1-dioxide, 9-[3-(trifluoromethoxy)-4-nitrophenyl]-2,3,5,6,7,9-hexahydrothieno[3,2-b]quinolin-8(4H)-one, 1,1-dioxide, 9-[4-bromo-3-(trifluoromethoxy)phenyl]-2,3,5,6,7,9-hexahydrothieno[3,2-b]quinolin-8(4H)-one, 1,1-dioxide, 9-[3-(trifluoromethoxy)-4-methylphenyl]-2,3,5,6,7,9-hexahydrothieno[3,2b-]quinolin-8(4H)-one, 1,1-dioxide, 9-[4-ethyl-3-(trifluoromethoxy)phenyl]-2,3,5,6,7,9-hexahydrothieno[3,2b-]quinolin-8(4H)-one, 1,1-dioxide, 9-[4-ethenyl-3-(trifluoromethoxy)phenyl]-2,3,5,6,7,9-hexahydrothieno[3,2-b]quinolin-8(4H)-one, 1,1-dioxide, 9-[4-chloro-3-(trifluoromethoxy)phenyl]-2,3,5,6,7,9-hexahydrothieno[3,2-b]quinolin-8(4H)-one, 1,1-dioxide, 9-(3-bromo-4-ethylphenyl)-2,3,5,6,7,9-hexahydrothieno[3,2-b]quinolin-8(4H)-one, 1,1-dioxide, 9-[3-bromo-4-(2,2,2-trifluoroethyl)phenyl]-2,3,5,6,7,9-hexahydrothieno[3,2-b]quinolin-8(4H)-one, 1,1-dioxide, 9-[4-bromo-3-(difluoromethoxy)phenyl]-2,3,5,6,7,9-hexahydrothieno[3,2-b]quinolin-8(4H)-one, 1,1-dioxide, 9-[4-(2-furanyl)-3-(trifluoromethoxy)phenyl]-2,3,5,6,7,9-hexahydrothieno[3,2-b]quinolin-8(4H)-one, 1,1-dioxide, 9-[3-[3,5-bis(trifluoromethyl)-1H-pyrazol-1-yl]-4-methylphenyl]-2,3,5,6,7,9-hexahydrothieno[3,2-b]quinolin-8(4H)-one, 1,1-dioxide, (9S)-9-[3-(1-ethoxyethenyl)-4-fluorophenyl]-2,3,5,6,7,9-hexahydrothieno[3,2-b]quinolin-8(4H)-one, 1,1-dioxide, 9-(1,1-dioxido-2,3-dihydrobenzo[b]thiophen-6-yl)-2,3,5,6,7,9-hexahydrothieno[3,2-b]quinolin-8(4H)-one, 1,1-dioxide, 9-(2,3-dihydro-3-oxo-1H-inden-5-yl)-2,3,5,6,7,9-hexahydrothieno[3,2-b]quinolin-8(4H)-one, 1,1-dioxide, 9-(1,3-dihydro-3-oxo-5-isobenzofuranyl)-2,3,5,6,7,9-hexahydrothieno[3,2-b]quinolin-8(4H)-one, 1,1-dioxide, 9-(2,3-dihydro-3-oxo-1H-isoindol-5-yl)-2,3,5,6,7,9-hexahydrothieno[3,2-b]quinolin-8(4H)-one, 1,1-dioxide, 9-(2,3-dihydro-2-alkyl-3-oxo-1H-isoindol-5-yl)-2,3,5,6,7,9-hexahydrothieno[3,2-b]quinolin-8(4H)-one, 1,1-dioxide, 9-(2,3-dihydro-2-acyl-3-oxo-1H-isoindol-5-yl)-2,3,5,6,7,9-hexahydrothieno[3,2-b]quinolin-8(4H)-one, 1,1-dioxide, 9-(1,1-dioxido-1,3-dihydrobenzo[c]thiophen-5-yl)-2,3,5,6,7,9-hexahydrothieno[3,2-b]quinolin-8(4H)-one, 1,1-dioxide, 9-(1,3-dihydro-5-isobenzofuranyl)-2,3,5,6,7,9-hexahydrothieno[3,2-b]quinolin-8(4H)-one, 1,1-dioxide, 9-(4-ethenyl-3-nitrophenyl)-2,3,5,6,7,9-hexahydrothieno[3,2-b]quinolin-8(4H)-one 1,1-dioxide, 9-(4-ethynyl-3-nitrophenyl)-2,3,5,6,7,9-hexahydrothieno[3,2-b]quinolin-8(4H)-one, 1,1-dioxide, 9-(4-acetyl-3-nitrophenyl)-2,3,5,6,7,9-hexahydrothieno[3,2-b]quinolin-8(4H)-one, 1,1-dioxide, 9-[4-(1-methylethenyl)-3-nitrophenyl]-2,3,5,6,7,9-hexahydrothieno[3,2-b]quinolin-8(4H)-one, 1,1-dioxide, 9-[4-(1-methoxyethenyl)-3-nitrophenyl]-2,3,5,6,7,9-hexahydrothieno[3,2-b]quinolin-8(4H)-one, 1,1-dioxide, 9-[3-nitro-4-(2,2,2-trifluoroethyl)phenyl]-2,3,5,6,7,9-hexahydrothieno[3,2-b]quinolin-8(4H)-one, 1,1-dioxide, 9-[4-(1-methylethyl)-3-nitrophenyl]-2,3,5,6,7,9-hexahydrothieno[3,2-b]quinolin-8(4H)-one, 1,1-dioxide, 9-[4-(2-furanyl)-3-nitrophenyl]-2,3,5,6,7,9-hexahydrothieno[3,2-b]quinolin-8(4H)-one, 1,1-dioxide, 9-[3-nitro-4-(2-thienyl)phenyl]-2,3,5,6,7,9-hexahydrothieno[3,2-b]quinolin-8(4H)-one, 1,1-dioxide, 9-(2-nitro[1,1'-biphenyl]-4-yl)-2,3,5,6,7,9-hexahydrothieno[3,2-b]quinolin-8(4H)-one, 1,1-dioxide, 9-[3-nitro-4-(3-pyridinyl)phenyl]-2,3,5,6,7,9-hexahydrothieno[3,2-b]quinolin-8(4H)-one, 1,1-dioxide, 9-[3-bromo-4-(trifluoromethyl)phenyl]-2,3,5,6,7,9-hexahydrothieno[3,2-b]quinolin-8(4H)-one 1,1-dioxide, 9-[3-chloro-4-(trifluoromethyl)phenyl]-2,3,5,6,7,9-hexahydrothieno[3,2-b]quinolin-8(4H)-one 1,1-dioxide, 9-(3-bromo-4-chlorophenyl)-2,3,5,6,7,9-hexahydrothieno[3,2-b]quinolin-8(4H)-one 1,1-dioxide, 9-(4-bromo-3-chlorophenyl)-2,3,5,6,7,9-hexahydrothieno[3,2-b]quinolin-8(4H)-one 1,1-dioxide, 9-[4-chloro-3-(difluoromethoxy)phenyl]-2,3,5,6,7,9-hexahydrothieno[3,2-b]quinolin-8(4H)-one 1,1-dioxide, 9-[3-bromo-4-(difluoromethoxy)phenyl]-2,3,5,6,7,9-hexahydrothieno[3,2-b]quinolin-8(4H)-one 1,1-dioxide, 9-(4-bromo-3-methylphenyl)-2,3,5,6,7,9-hexahydrothieno[3,2-b]quinolin-8(4H)-one 1,1-dioxide, 9-[3-(difluoromethoxy)-4-nitrophenyl]-2,3,5,6,7,9-hexahydrothieno[3,2-b]quinolin-8(4H)-one 1,1-dioxide, 9-[3-(1-cyclopenten-1-yl)-4-fluorophenyl]-2,3,5,6,7,9-hexahydrothieno[3,2-b]quinolin-8(4H)-one 1,1-dioxide, 9-(4-fluoro-3-(1-propenyl)phenyl)-2,3,5,6,7,9-hexahydrothieno[3,2-b]quinolin-8(4H)-one 1,1-dioxide, 9-[3-(2,2-difluorovinyl)-4-fluorophenyl]-2,3,5,6,7,9-hexahydrothieno[3,2-b]quinolin-8(4H)-one 1,1-dioxide, and 9-[4-fluoro-3-(2,2,2-trifluoroethyl)phenyl]-2,3,5,6,7,9-hexahydrothieno[3,2-b]quinolin-8(4H)-one 1,1-dioxide or a pharmaceutically acceptable salt, ester, amide or prodrug thereof.

Abbreviations

Abbreviations which have been used in the descriptions of the schemes and the examples that follow are: BINAP for 2,2'-bis(diphenylphosphino)-1,1'-binaphthyl, Boc for tert-butoxycarbonyl, Boc$_2$O for di-tert-butyl dicarbonyl, BuLi for butyllithium, CS2CO$_3$ for cesium carbonate, DIBAL for diisobutylaluminum hydride, DMAP for 4-dimethylaminopyridine, DMF for N,N-dimethylformamide, Et$_3$N for triethylamine, K$_2$CO$_3$ for potassium carbonate, HCl for hydrochloric acid, LiAlH$_4$ for lithium aluminum hydride, LDA for lithium diisopropylamide, MeCN for acetonitrile, MeOH for methanol, MgSO$_4$ for magnesium sulfate, MnO$_2$ for manganese dioxide, NMO for N-methylmorpholine N-oxide, PPh$_3$ for triphenylphosphine, pyr for pyridine, Tf for triflate, TFA for trifluoroacetic acid, THF for tetrahydrofuran, and TPAP for tetrapropylammonium perruthenate.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–48.

Scheme 1

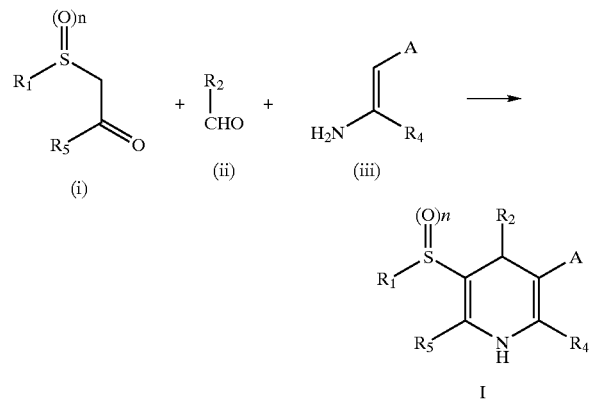

As shown in Scheme 1, the dihydropyridines of Formula I were prepared by heating ketone (i) with aldehyde (ii) and enamine (iii) in a protic solvent such as ethyl alcohol. For the case where $R_1$ and $R_5$ form a 5-membered ring, an additional heating step can be required to provide the product.

Scheme 2

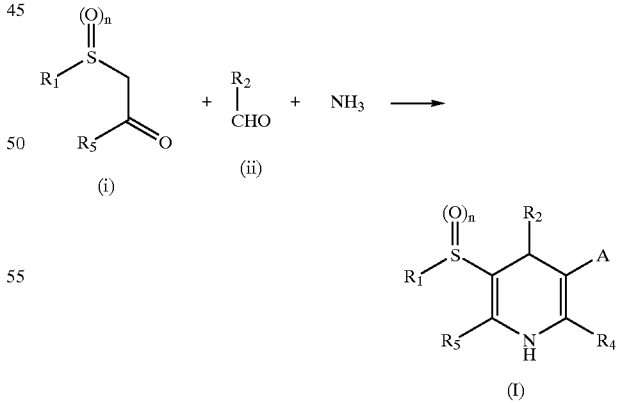

As shown in Scheme 2, for those examples wherein A=XR$_3$, X=S(O)p, p is 2, $R_1$=$R_3$, and $R_4$=$R_5$, dihydropyridines of formula I were prepared by heating 2 equivalents 5 of (i) with 1 equivalent of (ii) and concentrated ammonium hydroxide in a protic solvent such as ethyl alcohol.

Scheme 3

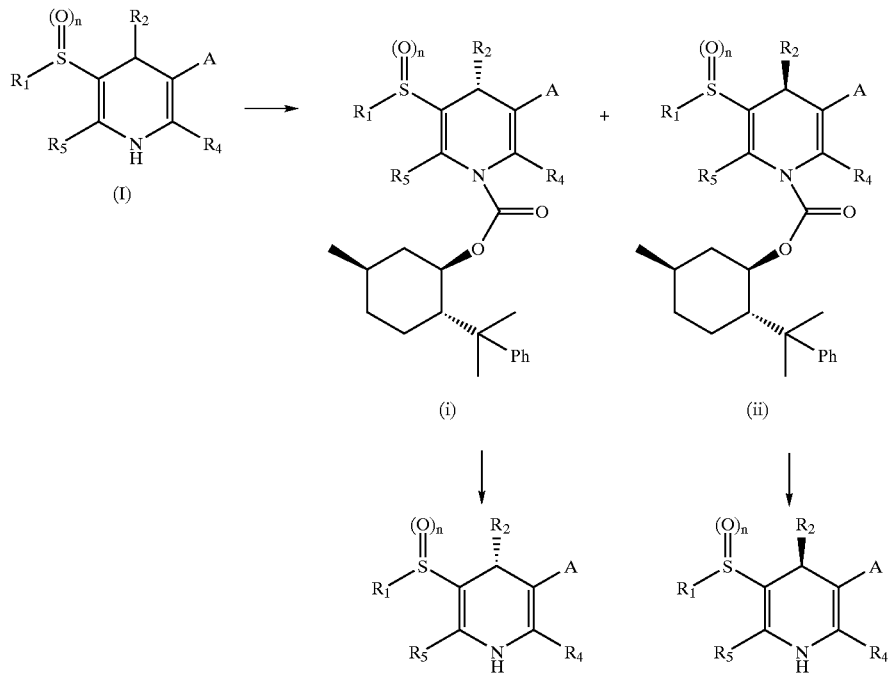

Examples of the present Invention that possess a center of chirality and thus exist in racemic form were separated into the individual enantiomers by the method shown in Scheme 33. The racemic compounds of general formula I were reacted with potassium t-butoxide (1 equivalent) in tetrahydrofuran followed by 8-phenylmenthyl chloroformate to generate a mixture of diastereomeric 8-phenylmenthyl carbamates (i) and (ii). The diastereomers (i) and (ii) were separated by column chromatography over silica gel and the 8-phenylmenthol moiety removed by reaction with sodium methoxide in methanol to provide the single enantiomers as shown.

In addition to the use of the method illustrated in Scheme 3, individual enantiomers of compounds of the Invention were also separated by chiral chromatography.

Scheme 4

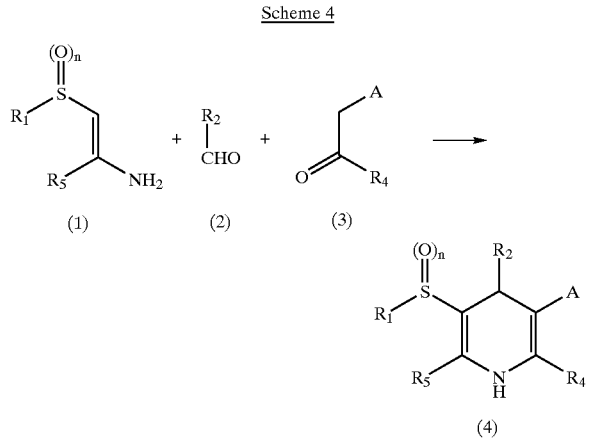

An additional method for preparing dihydropyridines of general formula (4), wherein $R_1$, $R_2$, $R_4$, $R_5$, A, and n are as defined in formula I, is shown in Scheme 4. An enamine of general formula (1) is reacted with an aldehyde of general formula (2) and a carbonyl component of general formula (3) with heating in a solvent such as ethanol, methanol or similar alcoholic solvent, acetonitrile or dimethylformamide to provide compounds of general formula (4). In certain cases an additional heating step with an acid, wherein preferred acids are hydrochloric acid, para-toluenesulfonic acid, and the like, may be required to drive the reaction to completion. This may be relevant in cases where $R_4$ is trifluoromethyl or when $R_1$ and $R_5$ form a five membered ring.

Scheme 5

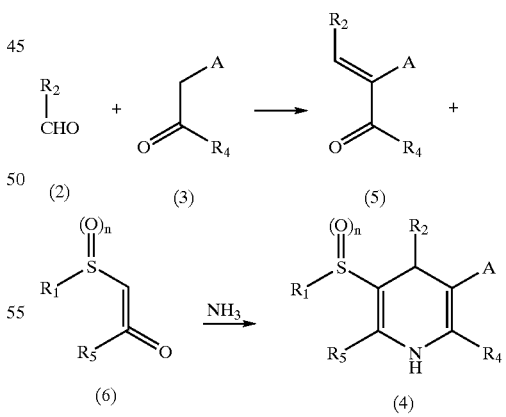

An additional method for preparing dihyropyridines of general formula (4), wherein $R_1$, $R_2$, $R_4$, $R_5$, A, and n are as defined in formula I, is shown in Scheme 5. An aldehyde of general formula (2) is first condensed in a Knoevenagel or aldol reaction with a carbonyl component of general formula (3) to produce an α,β-unsaturated carbonyl intermediate of general formula (5). Conditions for carrying out these reactions are well known to those skilled in the art of organic chemistry. The intermediate (5) is reacted with a carbonyl component of general formula (6) and ammonia or other similar reagent such as ammonium acetate or ammonium hydroxide with heating in solvents such as those described for Scheme 4 to provide compounds of general formula (4). In certain cases an additional heating step with an acid, wherein preferred acids are hydrochloric acid, para-toluenesulfonic acid, and the like, may be required to drive the reaction to completion. This may be relevant in cases where $R_4$ is trifluoromethyl or when $R_1$ and $R_5$ form a five membered ring.

Scheme 6

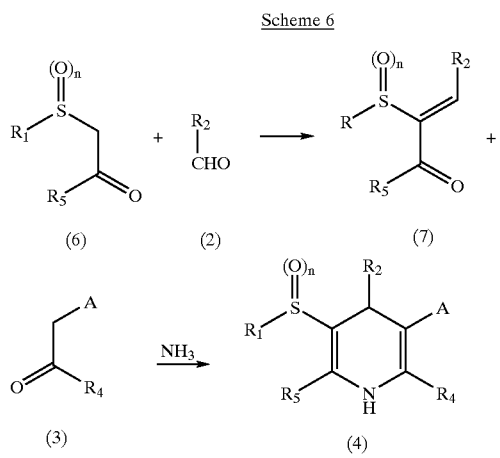

An additional method for preparing dihydropyridines of general formula (4), wherein $R_1$, $R_2$, $R_4$, $R_5$, A, and n are as defined in formula I, is shown in Scheme 6. A carbonyl component of general formula (6) is first condensed in a Knoevenagel reaction with an aldehyde component of general formula (2) to produce an α,β-unsaturated carbonyl of general formula (7). Conditions for carrying out these reactions are well known to those skilled in the art of organic chemistry. The α,β-unsaturated carbonyl of general formula (7) is reacted with a carbonyl component of general formula (3) and with ammonia or other similar reagent such as ammonium acetate or ammonium hydroxide with heating in solvents such as those described for Scheme 4 to provide compounds of general formula (4). In certain cases an additional heating step with an acid, wherein preferred acids are hydrochloric acid, para-toluenesulfonic acid, and the like, may be required to drive the reaction to completion. This may be relevant in cases where $R_4$ is trifluoromethyl or when $R_1$ and $R_5$ form a five membered ring.

Scheme 7

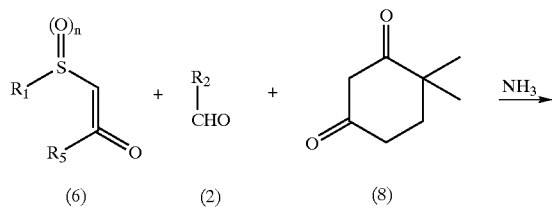

-continued

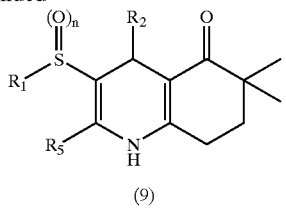

A preferred method for preparing dihydropyridines of general formula (9), wherein $R_1$, $R_2$, $R_5$, and n are as defined in formula I, is shown in Scheme 7. A carbonyl component of general formula (6), an aldehyde component of general formula (2), 4,4-dimethyl-1,3-cyclohexanedione (8), and ammonia or a similar reagent such as ammonium acetate or ammonium hydroxide are combined with heating in the solvents described for Scheme 4 to provide dihydropyridines of general formula (9). In certain cases an additional heating step with an acid, wherein preferred acids are hydrochloric acid, para-toluenesulfonic acid, and the like, may be required to drive the reaction to completion.

Scheme 8

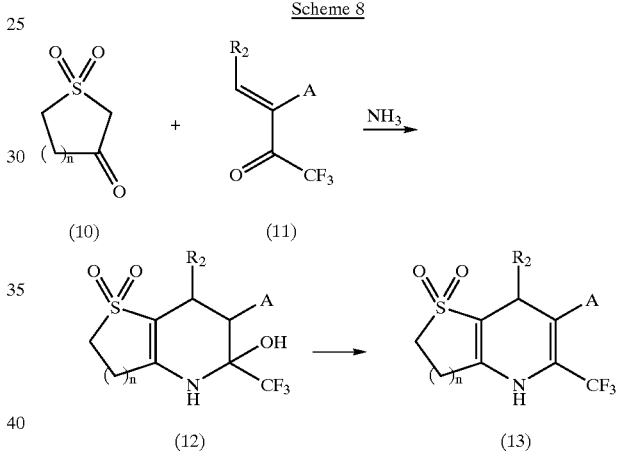

A preferred method for preparing dihydropyridines of general formula (13), wherein $R_2$ and A are as defined in formula I and n is an integer 1–3, is shown in Scheme 8. A ketosulfone of general formula (10) is reacted with a carbonyl component of general formula (11) and ammonia or a similar reagent such as ammonium hydroxide or ammonium acetate with heating in solvents such as those described in Scheme 4 to provide bicyclic compounds of general formula (12). Compounds of general formula (12) are converted to the final bicyclic products of general formula (13) by heating at levated temperature in an appropriate solvent such as ethanol or toluene in the absence r presence of an acid such as hydrochloric acid or para-toluenesulfonic acid.

Scheme 9

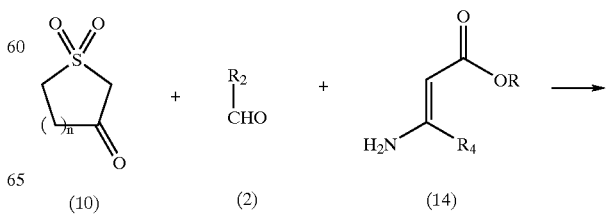

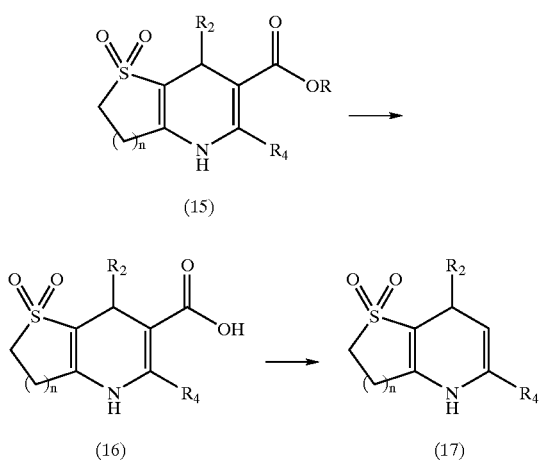

A method for preparing dihydropyridines of general formula (16) and (17), wherein $R_2$ and $R_4$ are as defined in formula I and n is an integer from 1–3, is shown in Scheme 9. A ketosulfone of general formula (10), an aldehyde component of general formula (2) and an enamine component of general formula (14), wherein R is selected from lower alkyl, benzyl, cyanoethyl, and the like, are reacted with heating in solvents such as those described in Scheme 4 to provide bicyclic compounds of general formula (15). Alternate methods for preparing (15) involve adapting Schemes 4–6. The reaction conditions and reagents employed in Schemes 4–6 are directly transferable and applicable to the preparation of compounds of general formula (15) with appropriate modifications to incorporate the ester grouping in the 3-position of the dihydropyridine ring. The ester group of compounds of general formula (15) can be cleaved to the carboxylic acid by treatment with boron trichloride or when a benzyl ester is present by hydrogenation or when R is cyanoethyl by treatment with bases such as potassium hydroxide in an alcoholic solvent such as methanol or ethanol. Such methods and conditions for converting the carboxylic ester to the carboxylic acid are well known to those skilled in the art of organic chemistry. The carboxylic acids of general formula (16) may be further reacted to provide compounds of general formula (17) by decarboxylation. Typical reaction conditions for decarboxylation involve heating at elevated temperature in solvents such as toluene, xylene, dimethylformamide, 5 diphenylether, N-methylpyrrolidinone or ethanol in the absence or presence of an acid such as hydrochloric acid or para-toluenesulfonic acid.

Scheme 10

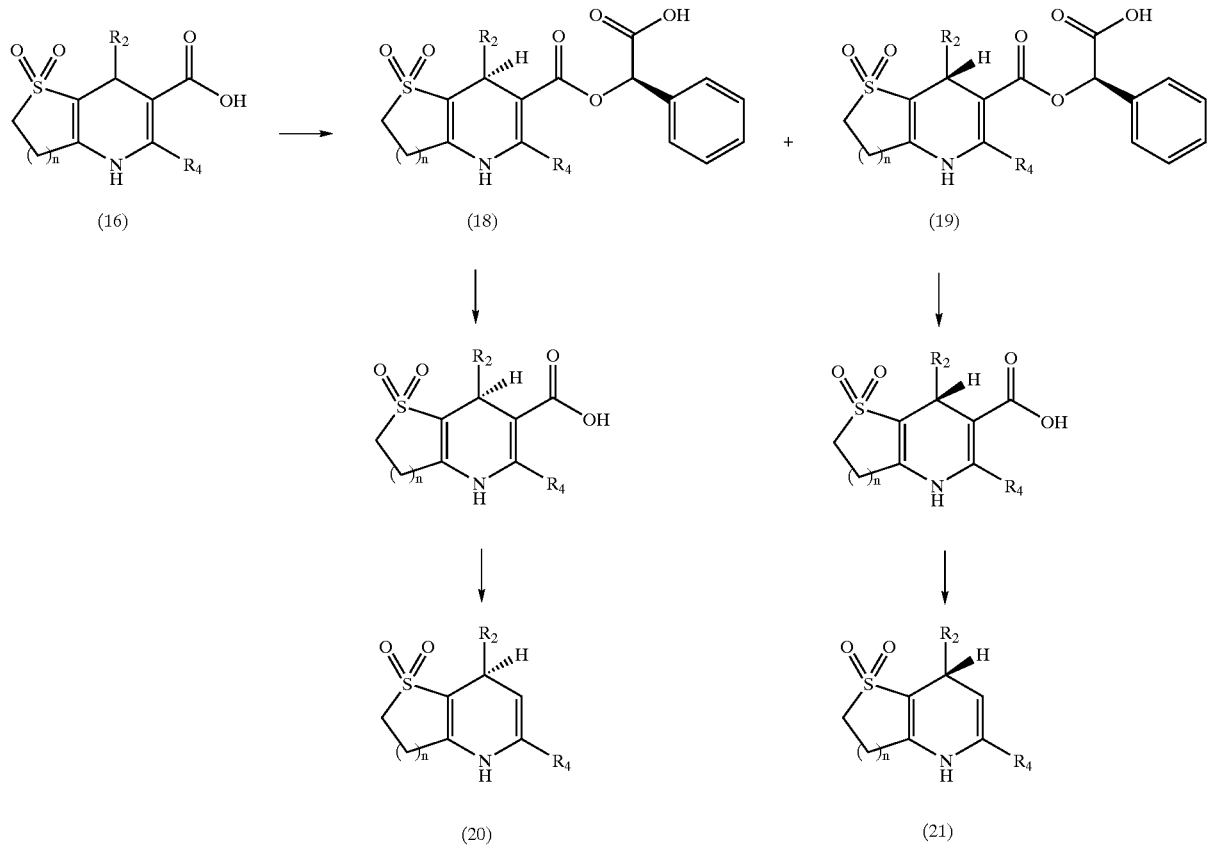

Dihydropyridines of general formula (16), wherein $R_2$ and $R_4$ are as defined in formula I and n is an integer 1–3, that exist as racemic mixtures may be separated into their R and S enantiomers by the method shown in Scheme 10. The racemic carboxylic acids of general formula (16) may be first converted to intermediate acid chlorides (not shown) by reaction with thionyichloride or oxalyl chloride and fuirther reacted without isolation with either enantiomer of mandelic acid to generate a mixture of diastereomeric esters of general formula (18) and (19). These esters (18) and (19) are separated by column chromatography and the mandelic ester group cleaved with boron trichloride or by hydrogenation. The enantiomerically pure carboxylic acids so obtained may then be further decarboxylated using the conditions described in Scheme 9 to provide the enantiomerically pure bicyclic compounds of general formula (20) and (21).

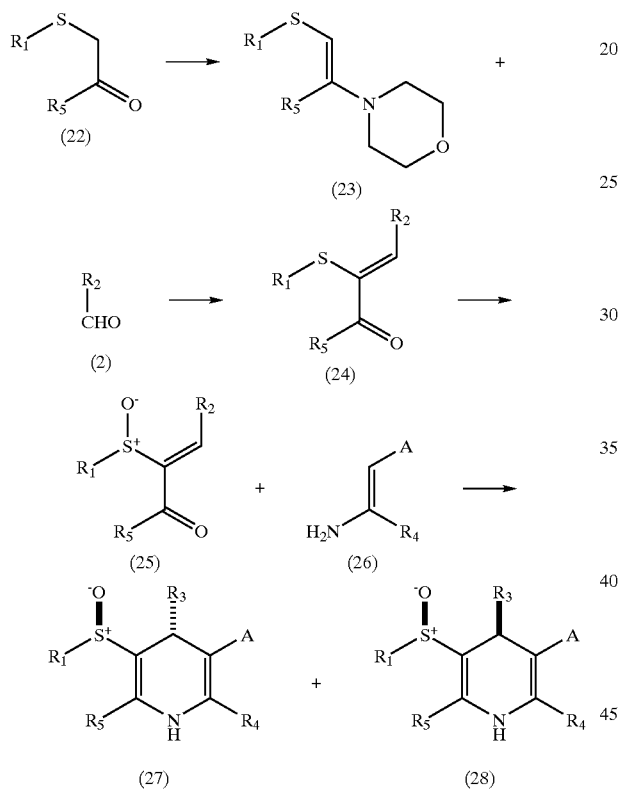

A preferred method for preparing dihydropyridines of general formula (27) and (28), wherein $R_1$, $R_2$, $R_4$, $R_5$, and A are as defined in formula I, is shown in Scheme 11. A carbonyl component of general formula (22) is converted to a morpholine enamine of general formula (23) by reaction with morpholine. Other enamines that may be used include the piperidine enamine or the pyrrolidine enamine. This conversion is well known to those skilled in the art of organic chemistry. The enamine (23) is reacted with an aldehyde component of general formula (2) to generate an intermediate α,β-unsaturated carbonyl component of general formula (24). The intermediate (24) is treated with a suitable oxidant such as meta-chloroperoxybenzoic acid or one of many other oxidants known to facilitate transformation of a sulfide to a sulfoxide. The intermediate sulfoxide of general formula (25) is reacted with an enamine of general formula (26) with heating in a solvent such as those described for Scheme 4 to provide a mixture of diastereomeric sulfoxides of general formula (27) and (28). These sulfoxides may be separated by column chromatography. An alternate method, exemplified in Scheme 6, of accomplishing the final step of the sequence involves substituting a suitable carbonyl component and ammonia or other similar reagent such as ammonium acetate or ammonium hydroxide for the enamine component (26) shown in Scheme 11. This alternate method is especially appropriate for cases where $R_1$ and $R_5$ form a five membered ring and A and $R_4$ form a five or six membered carbocyclic ring.

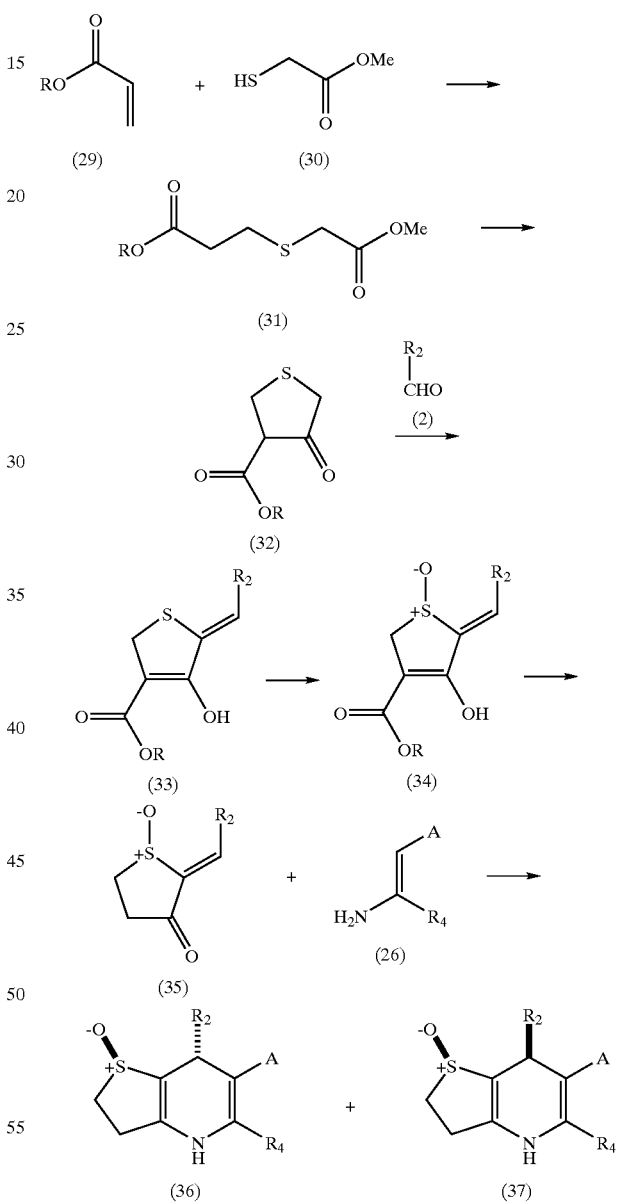

A preferred method for preparing sulfoxides of general formula (36) and (37), wherein $R_2$, $R_4$ and A are as defined in formula I, is shown in Scheme 12. A suitable acrylate component of general formula (29), wherein R is selected from lower alkyl, benzyl, and cyanoethyl, is reacted with methyl thioglycolate (30) with catalysis by piperidine to produce an intermediate sulfide of general formula (31). The intermediate (31) is cyclized by heating in methanol and toluene with sodium methoxide to provide the cyclic intermediate of general formula (32). The intermediate (32) is condensed with an aldehyde component of general formula (2) with heating and catalysis by piperidine to provide the intermediate (33). Oxidation of intermediate (33) with meta-chloroperoxybenzoic acid provides the sulfoxide of general formula (34). Cleavage of the ester functionality of (34) may be accomplished by many different methods according to the R group present. Typical conditions such as those described in Scheme 9 may also be utilized here. Decarboxylation is accomplished by heating at elevated temperature in solvents such as toluene, xylene, diphenylether, dioxane, dimethylformamide, N-methylpyrrolidinone, or dimethylacetamide in the absence or presence of acids such as hydrochloric acid, para-toluenesulfonic acid, or sulfuric acid to provide sulfoxides of general formula (35). The decarboxylated sulfoxides (35) are reacted with an enamine component of general formula (26) with heating in solvents such as those described in Scheme 4 to provide a mixture of diastereomeric sulfoxides of general formula (36) and (37). These sulfoxides may be separated by column chromatography. An alternate method, exemplified in Scheme 6, of accomplishing the final step of the sequence involves substituting a suitable carbonyl component and ammonia or other similar reagent such as ammonium acetate or ammonium hydroxide for the enarnine component (26) shown in Scheme 12.

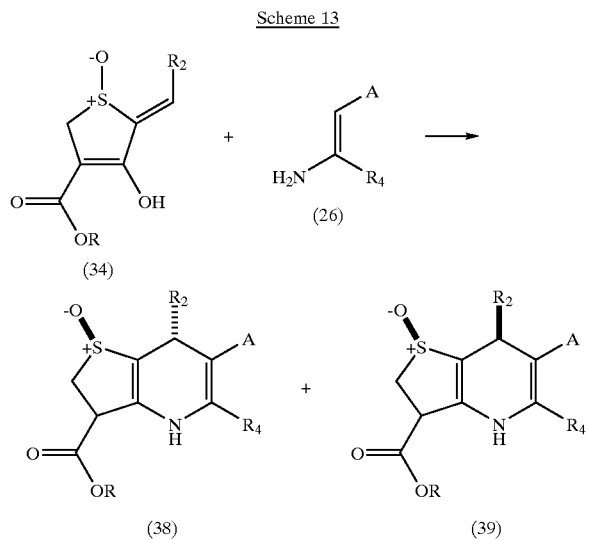

A method for preparing sulfoxide containing compounds of general formula (38) and (39), wherein $R_2$, $R_4$, and A are as defined in formula I and R is selected from lower alkyl, benzyl, and cyanoethyl, is shown in Scheme 13. A sulfoxide of general formula (34) from Scheme 12 is reacted with an enamine component of general formula (26) with heating in a solvent such as those described in Scheme 4 to provide compounds of general formula (38) and (39). An alternate method, exemplified in Scheme 6, of accomplishing this step involves substituting a suitable carbonyl component and ammonia or other similar reagent such as ammonium acetate or ammonium hydroxide for the enamine component (26) shown in Scheme 13. The sulfoxides of general formula (38) and (39) may also be further transformed by oxidation to the sulfone to provide sulfone containing compounds of the present invention with substitution on the sulfone containing ring. In addition, the ester group may be further converted to other functional groups such as amides, acids, alcohols, amines, aldehydes, cyano, or alkyl to name some representative examples. It should not be construed however that the substitutions accessible through the ester group is limited to those described here. These examples are intended only to illustrate a means of preparing examples of the present invention with substitution on the sulfone or sulfoxide ring. These transformations are well known to those skilled in the art of organic chemistry and may be accomplished either before or after the conversion of the sulfoxide to the sulfone.

Many of the starting materials necessary to carry out the methods described in the preceeding Schemes may be purchased from commercial sources whereas others are known in the chemical literature. Appropriate literature references may be found in the following section or in the Examples section for such known entities. For starting materials not previously described in the literature the following Schemes are intended to illustrate their preparation through a general method.

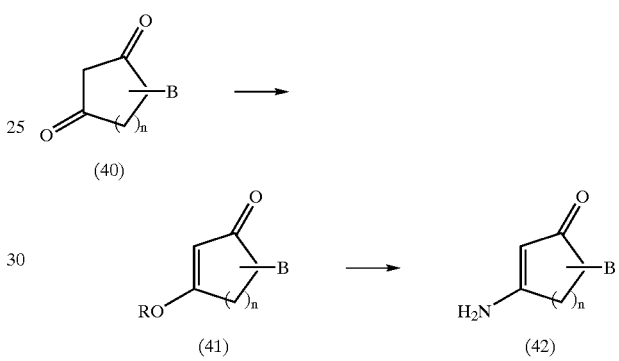

Enamines of general formula (42), wherein n is an integer 1–3 and B is absent or can be 1, 2, or 3 substituents independently selected from alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo, wherein alkyl is preferred, can be prepared according to the general method shown in Scheme 14. This method entails reaction of an appropriate cycloalkanedione of general formula (40) with an alcohol such as ethanol or methanol with catalysis by an acid such as sulfuric acid or hydrochloric acid or other similar acid to form an intermediate enol ether of general formula (41). The enol ether (41) can be converted to an enamine of general formula (42) by reaction with ammonia typically in a solvent such as methanol, ethanol or tetrahydrofuran. This method is preferred for the preparation of 3-amino-4,4-dimethyl-2-cyclohexen-1-one and 3-amino-6,6-dimethyl-2-cyclohexen-1-one.

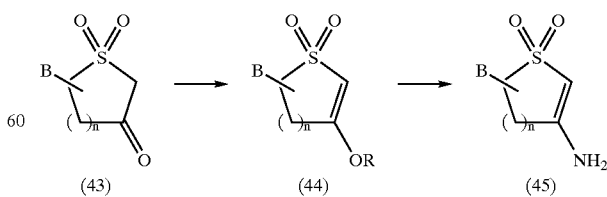

As shown in Scheme 15, enamines of general formula (45), wherein n is an integer from 1–3 and B is absent or can be 1, 2, or 3 substituents independently selected from alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo, can be prepared by procedures directly analogous to those described in Scheme 14 wherein the carbonyl compound of general formula (43) is converted to an intermediate enol ether of general formula (44) and thence to the enamine (45).

Many of the starting aryl and heteroaryl aldehydes necessary to carry out the methods described in the preceeding and following Schemes may be purchased from commercial sources or may be synthesized by known procedures found in the chemical literature. Appropriate literature references for the preparation of aryl and heteroaryl aldehydes may be found in the following section or in the Examples. For starting materials not previously described in the literature the following Schemes are intended to illustrate their preparation through a general method.

The preparation of aldehydes used to synthesize many preferred compounds of the invention may be found in the following literature references: Pearson, Org. Synth. Coll. Vol V (1973), 117; Nwaukwa, Tetrahedron Lett. (1982), 23, 3131; Badder, J. Indian Chem. Soc. (1976), 53, 1053; Khanna, J. Med. Chem. (1997), 40, 1634; Rinkes, Recl. Trav. Chim. Pays-Bas (1945), 64, 205; van der Lee, Recl. Trav. Chim. Pays-Bas (1926), 45, 687; Widman, Chem. Ber. (1882), 15, 167; Hodgson, J. Chem. Soc. (1927), 2425; Clark, J. Fluorine Chem. (1990), 50,411; Hodgson, J. Chem. Soc. (1929), 1635; Duff, J. Chem. Soc. (1951), 1512; Crawford, J. Chem. Soc. (1956), 2155; Tanouchi, J. Med. Chem. (1981), 24, 1149; Bergmann, J.Am. Chem. Soc. (1959), 81,5641; Other: Eistert, Chem. Ber. (1964), 97, 1470; Sekikawa, Bull. Chem. Soc. Jpn. (1959), 32, 551.

Scheme 16

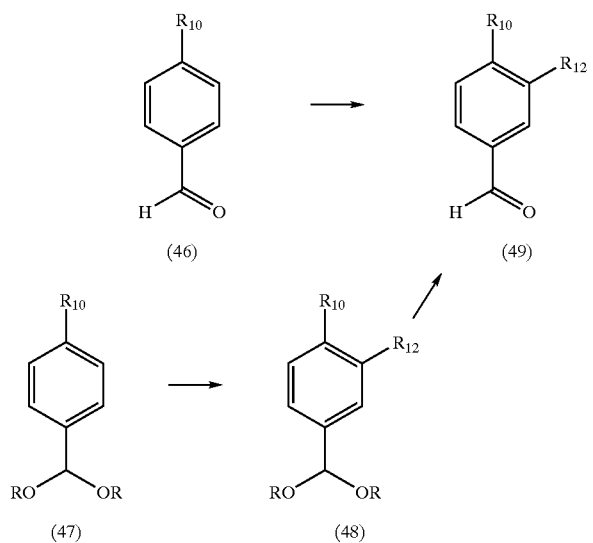

Many meta, para-disubstituted aldehydes of general formula (49), wherein $R_{10}$ is selected from alkyl, amino, amido, haloalkyl, halo, haloalkoxy, alkoxy, and thioalkoxy, and $R_{12}$ is selected from nitro, halo, and alkylcarbonyl, can be prepared according to the method illustrated in Scheme 16. A para substituted aldehyde of general formula (46) or the corresponding acetal protected aldehyde of general formula (47), wherein R is selected from alkyl or together with the oxygen atoms to which they are attached form a or 6 membered ring wherein 1,3-dioxolanes are preferred, may by subjected to conditions of an electrophilic aromatic substitution reaction to provide an aldehyde of general formula (49) or a protected aldehyde of general formula (48). Preferred protecting groups for compounds of general formula (47) and (48) include dimethyl or diethyl acetals or the 1,3-dioxolanes. These protecting groups can be introduced at the beginning and removed at the end to provide substituted aldehydes of general formula (49) using methods well known to those skilled in the art of organic chemistry.

Scheme 17

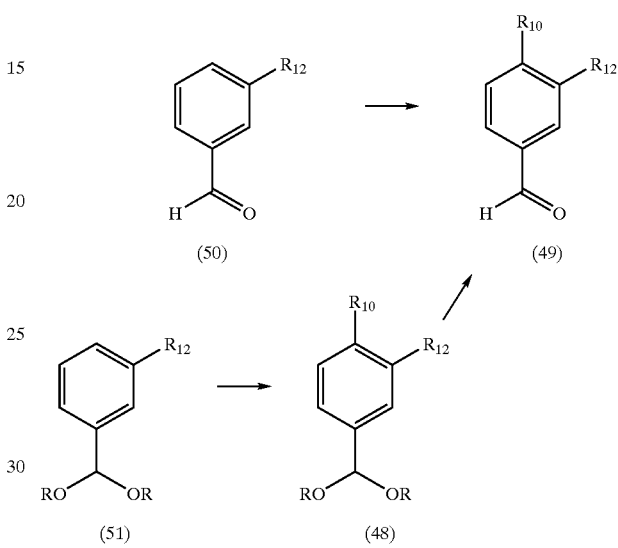

An alternative method for synthesizing meta, para disubstituted aldehydes of general formula (49), wherein $R_{10}$ is selected from nitro, halo, and alkylcarbonyl and $R_{12}$ is selected from alkyl, amino, amido, haloalkyl, halo, haloalkoxy, alkoxy, and thioalkoxy, is provided in Scheme 17. In this method a meta substituted aldehyde of general formula (50) or the corresponding acetal protected aldehyde (51), wherein R is selected from alkyl or together with the oxygen atoms to which they are attached form a 5 or 6 membered ring wherein 1,3-dioxolanes are preferred, may by subjected to conditions of an electrophilic aromatic substitution reaction to provide an aldehyde of general formula (49) or a protected aldehyde of general formula (48). Preferred protecting groups include dimethyl or diethyl acetals or the 1,3-dioxolanes. These groups can be introduced at the beginning and removed at the end to provide substituted aldehydes of general formula (49) using methods well known to those skilled in the art of organic chemistry.

Scheme 18

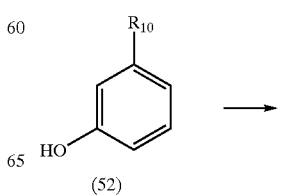

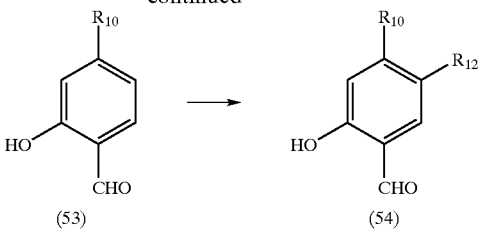

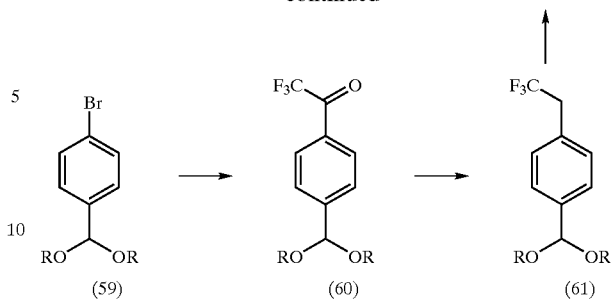

Aldehydes of general formula (54), wherein $R_{10}$ is selected from alkyl, amino, amido, haloalkyl, halo, haloalkoxy, alkoxy, and thioalkoxy, and $R_{12}$ is slected from nitro, halo, and alkylcarbonyl, can be prepared by the method shown in Scheme 18. A meta substituted phenol (52) is converted to the para substituted salicylaldehyde (53) by reaction with a base such as sodium hydroxide and a reagent such as trichloromethane or tribromomethane. This reaction is known as the Reimer-Tiemann reaction. An alternate set of reaction conditions involves reaction with magnesium methoxide and paraformaldehyde (Aldred, J. Chem. Soc. Perkin Trans. 1 (1994), 1823). The aldehyde (53) may be subjected to conditions of an electrophilic aromatic substitution reaction to provide the meta, para disubstituted salicylaldehyde of general formula (54).

Meta, para disubstituted benzaldehydes of general formula (58) wherein $R_{12}$ is selected from alkyl, amino, amido, haloalkyl, halo, haloalkoxy, alkoxy, thioalkoxy, nitro, and alkylcarbonyl, can be prepared according to one of the two methods shown in Scheme 20. A para bromo-substituted protected benzaldehyde of general formula (56) may be converted to the 4-trifluoroacetyl benzaldehyde of general formula (57) by conversion of the bromide to an anion via metal-halogen exchange wherein preferred metals are magnesium (grignards) and lithium (lithiumorganics). The anion is treated with trifluoroacetic anhydride to provide a trifluoroacetyl compound of general formula (57) which can be converted to the 4-trifluoroethyl benzaldehyde of general formula (58) by one of many methods for effecting such conversions such as the Wolff-Kishner reduction. An alternate method for preparing benzaldehydes of general formula (58) entails conversion of the protected 4-bromobenzaldehyde (59) to the protected 4-trifluoroacetylbenzaldehyde (60) using the anionic methodolgy described above followed by a Wolff-Kishner reduction to (61) and finally electrophilic aromatic substitution to (58). The choice of method between these two is guided by the nature of the $R_{12}$ substituent.

Scheme 19

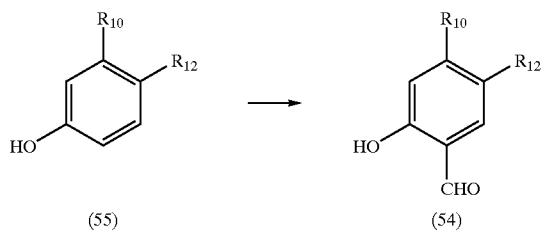

An alternative method of obtaining meta, para disubstituted salicylaldehydes of general formula (54), wherein $R_{10}$ is selected from alkyl, amino, amido, haloalkyl, halo, haloalkoxy, alkoxy, and thioalkoxy, and $R_{12}$ is selected from nitro, halo, and alkylcarbonyl, is shown in Scheme 19. A meta, para disubstituted phenol (55) is reacted with a base such as sodium hydroxide and a reagent such as trichloromethane or tribromomethane. This reaction is called the Reimer-Tiemann reaction. An alternate set of reaction conditions involves reaction with magnesium methoxide and paraformaldehyde (Aldred, J. Chem. Soc. Perkin Trans. 1 (1994), 1823).

Scheme 20

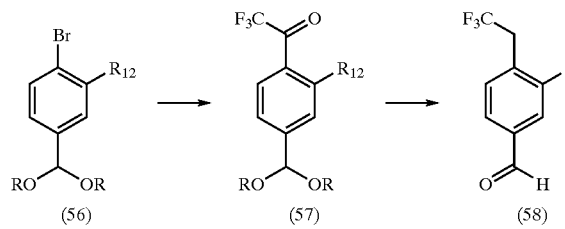

Scheme 21

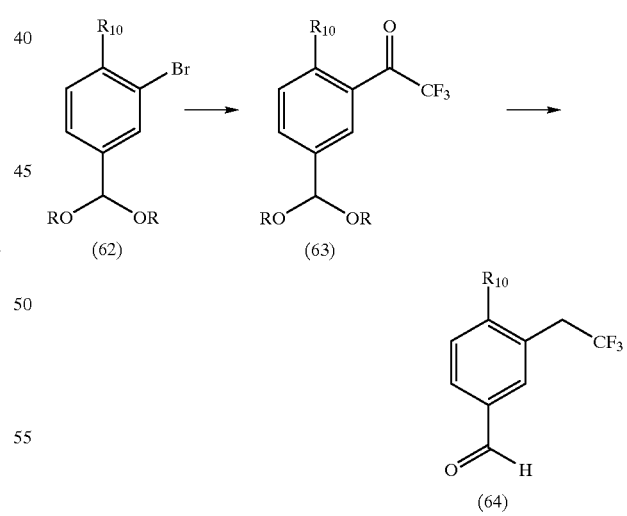

The incorporation of a trifluoroethyl group into the meta position to provide benzaldehydes of general formula (64), wherein $R_{10}$ is selected from alkyl, amino, amido, haloalkyl, halo, haloalkoxy, alkoxy, and thioalkoxy, is accomplished by a method similar to that of Scheme 20 and is shown in Scheme 21. A protected 4-substituted-3-bromobenzaldehyde of general formula (62) is converted to the protected 4-substituted-3-trifluoroacetylbenzaldehyde of general formula (63) via the anion chemistry described in Scheme 20. Wolff-Kishner reduction and deprotection provides the 4-substituted-3-trifluoroethylbernzaldehydes of general formula (64).

Scheme 22

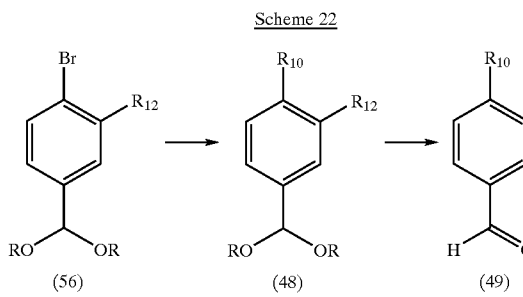

Another method for preparing 3,4-disubstituted benzaldehydes of general formula (49), wherein $R_{12}$ is selected from alkyl, amino, amido, haloalkyl, chlorine, fluorine, haloalkoxy, alkoxy, thioalkoxy, nitro, alkylcarbonyl and arylcarbonyl, $R_{10}$ is selected from alkyl, hydroxyalkyl, thioalkoxy, alkylcarbonyl, and formyl, is shown in Scheme 22. An appropriately protected 4-bromo-3-substitutedbenzaldehyde, from Scheme 20, of general formula (56), wherein R is selected from alkyl or together with the oxygen atoms to which they are attached form a 5 or 6 membered ring wherein 1,3-dioxoianes are preferred, can be converted to the 3,4-disubstituted benzaldehyde of general formula (48) by generation of an anion, as described in Scheme 20, followed by reaction with an appropriate electrophile such as an aldehyde, dialkyldisulfide, a Weinreb amide, dimethylformamide, an alkyl halide or other electrophile followed by deprotection of the acetal to provide benzaldehydes of general formula (49).

Scheme 23

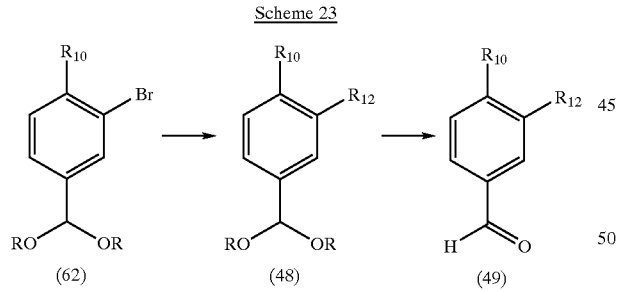

Another method directly analogous to that described in Scheme 22 may be used to provide 3,4-disubstituted benzaldehydes of general formula (49), wherein $R_{10}$ is selected from alkyl, amino, amido, haloalkyl, chlorine, fluorine, haloalkoxy, alkoxy, and thioalkoxy, $R_{12}$ is selected from alkyl, hydroxyalkyl, thioalkoxy, alkylcarbonyl, arylcarbonyl, and formyl, starting from protected benzaldehydes of general formula (62), wherein R is selected from alkyl or together with the oxygen atoms to which they are attached form a 5 or 6 membered ring wherein 1,3-dioxolanes are preferred.

Scheme 24

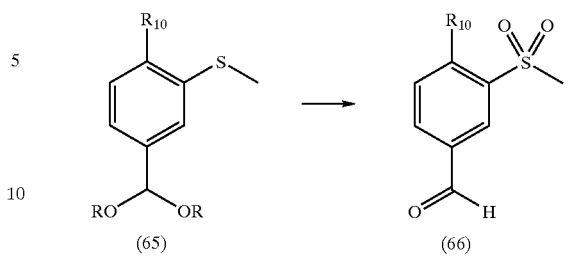

3-Methylsulfonyl-4-substituted benzaldehydes of general formula (66), wherein $R_{10}$ is selected from hydrogen, alkyl, amino, amido, haloalkyl, halo, haloalkoxy, and alkoxy, can be prepared as shown in Scheme 24. 3-Methylthio-4-substituted protected benzaldehydes of general formula (65), wherein R is selected from alkyl or together with the oxygen atoms to which they are attached form a 5 or 6 membered ring wherein 1,3-dioxolanes are preferred, prepared by the methods described in the preceeding schemes, can be oxidized with a suitable oxidant like meta-chloroperoxybenzoic acid and then deprotected to provide compounds of general formula (66). By analogy, this method can also be used to prepare benzaldehydes wherein the alkylsulfonyl group is attached at the 4-position with or without additional substitution at the 3-position.

Scheme 25

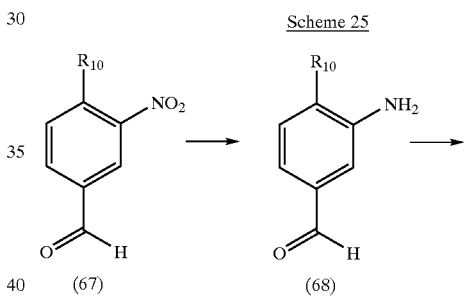

Amino and sulfonamide containing benzaldehydes of general formula (68) and (69) respectively, wherein $R_{10}$ is selected from hydrogen, alkyl, amino, amido, haloalkyl, halo, haloalkoxy, alkoxy, and thioalkoxy and R is selected from alkyl and haloalkyl, can be prepared as shown in Scheme 25. Reduction of an aromatic nitro compound of general formula (67) provides the corresponding aniline of general formula (68). This transformation can be accomplished using many different methods which are well known to those skilled in the art of organic chemistry. The sulfonamide of general formula (69) is prepared from the aniline (68) by reaction with an alkylsulfonylchloride or haloalkylsulfonylchloride and is usually mediated by a base such as pyridine. Although this sequence is shown specifically for the case wherein the amino or sulfonamide groups are attached at the 3-position of the benzaldehyde, this method

Scheme 26

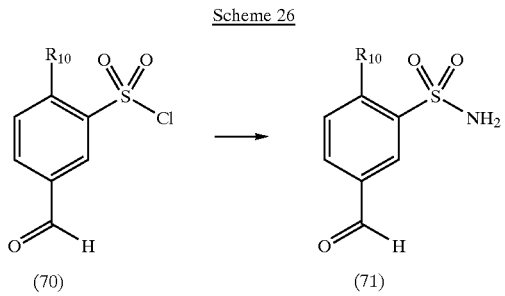

A method for preparing benzaldehydes of general formula (71), wherein $R_{10}$ is selected from hydrogen, alkyl, amino, amido, haloalkyl, halo, haloalkoxy, alkoxy, and thioalkoxy, is shown in Scheme 26. A chlorosulfonyl benzaldehyde of general formula (70), prepared by chlorosulfonation of the corresponding benzaldehyde, is reacted with ammonia to provide the sulfonamide substituted benzaldehyde of general formula (71). Although this sequence is shown specifically for the case wherein the sulfonamide group is attached at the 3-position of the benzaldehyde, this method can also be used to prepare the analogous benzaldehydes wherein the sulfonamide group is attached at the 4-position with or without additional substitution at the 3-position.

Scheme 27

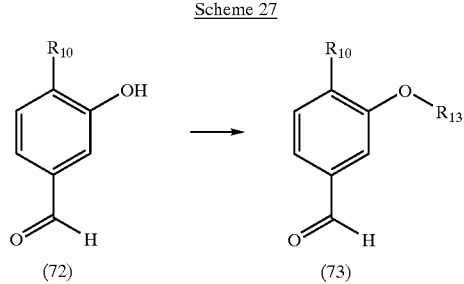

The preparation of benzaldehydes of general formula (73), wherein $R_{10}$ is selected from hydrogen, alkyl, alkylsulfonyl, amino, amido, aryl, heteroaryl, cyano, haloalkyl, halo, haloalkoxy, nitro, alkoxy, and thioalkoxy, and $R_{13}$ is selected from hydrogen, alkyl, arylalkyl, and haloalkyl wherein preferred haloalkyl groups are selected from difluoromethyl, 2,2,2-trifluoroethyl and bromodifluoromethyl, is shown in Scheme 27. A 3-hydroxybenzaldehyde of general formula (72) is reacted with a suitable alkylating reagent such as benzylbromide, iodomethane, 2-iodo-1,1,1-trifluoroethane, chlorodifluoromethane, or dibromodifluoromethane in the presence of a base such as potassium carbonate, potassium tert-butoxide or sodium tert-butoxide, to provide benzaldehydes of general formula (73). The synthesis of useful 3-hydroxybenzaldehydes of general formula (72) may be found in the following literature references: J. Chem. Soc. (1923), 2820; J. Med Chem. (1986), 29, 1982; Monatsh. Chem. (1963), 94, 1262; Justus Liebigs Ann. Chem. (1 897), 294, 381; J. Chem. Soc. Perkin Trans. 1 (1990), 315; Tetrahedron Lett. (1990), 5495; J. Chem. Soc. Perkin Trans. 1 (1981), 2677.

Scheme 28

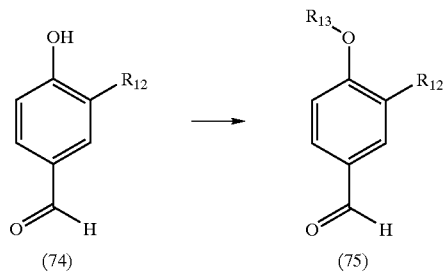

The preparation of benzaldehydes of general formula (75), wherein $R_{12}$ is selected from hydrogen, alkyl, alkylsulfonyl, amino, amido, aryl, heteroaryl, cyano, haloalkyl, halo, haloalkoxy, nitro, alkoxy, and thioalkoxy, and $R_{13}$ is selected from hydrogen, alkyl, arylalkyl, and haloalkyl wherein preferred haloalkyl groups are selected from difluoromethyl, 2,2,2-trifluoroethyl, and bromodifluoromethyl, is shown in Scheme 28. A 4-hydroxybenzaldehyde of general formula (74) is reacted with a suitable alkylating reagent such as benzylbromide, iodomethane, 2-iodo-1,1,1-trifluoroethane, chlorodifluoromethane, or dibromodifluoromethane, in the presence of a base such as potassium carbonate, potassium tert-butoxide or sodium tert-butoxide to provide a benzaldehyde of general formula (75). The synthesis of useful 4-hydroxybenzaldehydes of general formula (74) may be found in the following literature references: Angyal, J. Chem. Soc. (1950), 2141; Ginsburg, J. Am. Chem. Soc. (1951), 73, 702; Claisen, Justus Liebigs Ann. Chem. (1913), 401, 107; Nagao, Tetrahedron Lett. (1980), 21, 4931; Ferguson, J. Am. Chem. Soc. (1950), 72, 4324; Barnes, J. Chem. Soc. (1950), 2824; Villagomez-Ibarra, Tetrahedron (1995), 51, 9285; Komiyama, J. Am. Chem. Soc. (1983), 105, 2018; DE 87255; Hodgson, J. Chem. Soc. (1929), 469; Hodgson, J. Chem. Soc. (1929), 1641.

Scheme 29

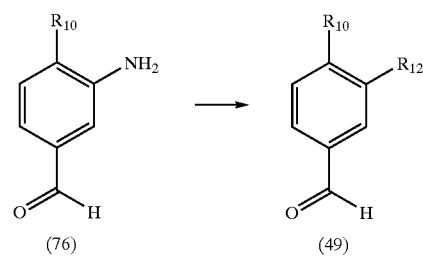

An alternate method for introduction of substituents at the 3-position of benzaldehydes of general formula (49), wherein $R_{10}$ is selected from hydrogen, alkyl, alkylsulfonyl, amido, aryl, heteroaryl, cyano, haloalkyl, halo, haloalkoxy, nitro, alkoxy, and thioalkoxy, is shown in Scheme 29. This method, also known as the Sandmeyer reaction, involves converting 3-amino benzaldehydes of general formula (76) to an intermediate diazonium salt with sodium nitrite that is further reacted with appropriate reagents to give the desired $R_{12}$ groups. The types of $R_{12}$ substituents that may be introduced in this fashion include cyano, hydroxy, or halo. The Sandmeyer reaction and conditions for effecting the transformation are well known to those skilled in the art of organic chemistry. In order to successfully carry out this transformation it may in certain circumstances be advantageous to perform the Sandmeyer reaction on a protected aldehyde.

Scheme 30

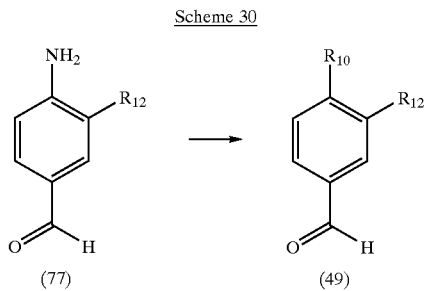

(77) (49)

An alternate method for introduction of substituents at the 4-position of benzaldehydes of general formula (49), wherein $R_{12}$ is selected from hydrogen, alkyl, alkylsulfonyl, amido, aryl, heteroaryl, cyano, haloalkyl, halo, haloalkoxy, nitro, alkoxy, and thioalkoxy, is shown in Scheme 30. This method, also known as the Sandmeyer reaction, involves converting 4-amino benzaldehydes of general formula (77) to an intermediate diazonium salt with sodium nitrite that is further reacted with appropriate reagents to give the desired $R_{10}$ group. The types of $R_{10}$ substituents that may be introduced in this fashion include cyano, hydroxy, or halo. The Sandmeyer reaction and conditions for effecting the transformation are well known to those skilled in the art of organic chemistry. In order to successfully carry out this transformation it may in certain circumstances be advantageous to perform the Sandmeyer reaction on a protected aldehyde.

Scheme 31

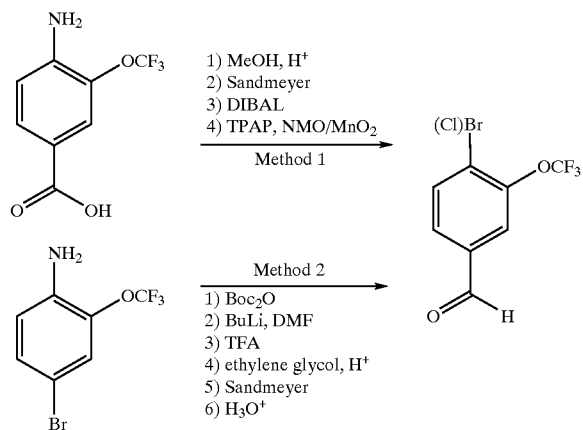

In Scheme 31 are shown 2 methods that may be used for the synthesis of 4-bromo-3-(trifluoromethoxy)benzaldehyde or 4-chloro-3-(trifluoromethoxy)benzaldehyde. Method 1: Commercially available 4-amino-3-(trifluoromethoxy) benzoic acid can be converted into the ester followed by a Sandmeyer reaction, described in Scheme 30, to provide the bromide or chloride. Reduction of the ester provides 4-bromo-3-(trifluoromethoxy)benzyl alcohol. The alcohol can be oxidized to the aldehyde to give the desired substituted benzaldehyde. Method 2: Commercially available 4-bromo-2-(trifluoromethoxy)aniline can be protected on the amino group with a suitable amino protecting groups well known to those skilled in the art of organic chemistry. The bromine can then be converted to the lithio or magnesio derivative and reacted directly with dimethylformamide to provide the 4-aminoprotected-3-(trifluoromethoxy) benzaldehyde derivative. Removal of the N-protecting group followed by protection of the aldehyde provides 4-(1,3-dioxolan-2-yl)-2-(trifluoromethoxy)aniline. Conversion of the amine to a bromide via the Sandmeyer method of Scheme 30 followed by hydrolysis of the dioxolane provides 4-bromo-3-(trifluoromethoxy)benzaldehyde.

Scheme 32

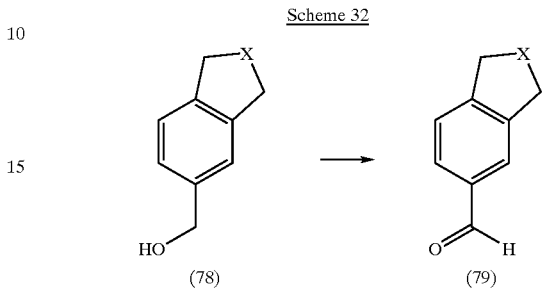

(78) (79)

Another method for synthesizing aldehydes useful for the present invention is shown in Scheme 32. This method involves reacting a benzylic alcohol of general formula (78), wherein X is selected from O and $SO_2$, with a suitable oxidant such as manganese dioxide or other similar oxidant to provide the benzaldehyde of general formula (79). Althought this method is shown for the specific case of (78) to (79), this general method may also be utilized to transform other benzylic alcohols to benzaldehydes. Benzylic alcohols useful for the present invention may be synthesized in accordance with the procedures found in the following reference: Grigg, J. Chem. Soc. Perkin Trans. 1 (1988), 1357.

Scheme 33

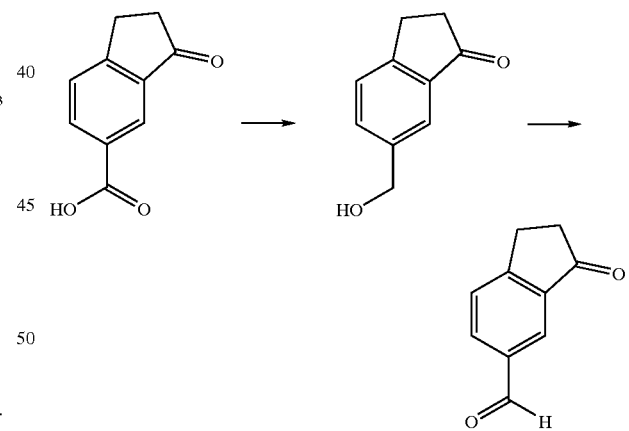

Another general method for synthesizing aldehydes useful for the present invention is shown in Scheme 33. This method involves reducing a benzoic acid to the benzylic alcohol preferrably with borane then oxidation of the benzylic alcohol to the benzaldehyde with manganese dioxide or other similar oxidant. Althought this method is shown for the specific case of 3-oxo-5-indanecarboxylic acid to 3-oxo-5-indanecarbaldehyde, this general method may also be utilized to transform other benzoic acids to benzaldehydes. Benzoic acids useful for the present invention may be synthesized in accordance with the procedures found in the following reference: Baddeley, J. Chem. Soc. (1956), 4647.

Scheme 34

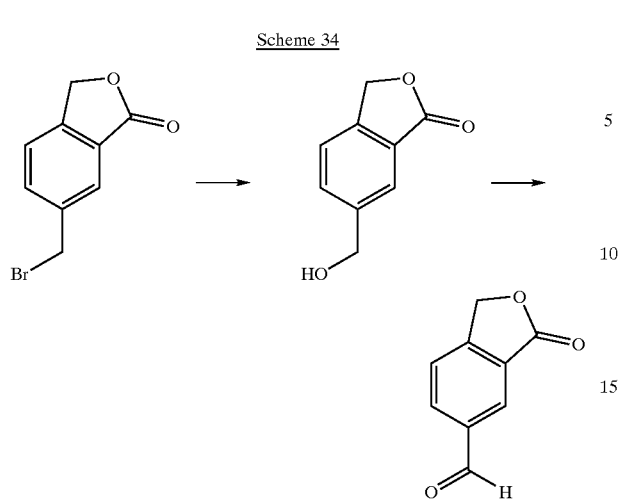

Another method for synthesizing aldehydes useful for the present invention is shown in Scheme 34. This method involves converting a benzylbromide to the benzylic alcohol, a standard transformation in organic chemistry, and then oxidation of the benzylic alcohol to the benzaldehyde with manganese dioxide or other similar oxidant. Althought this method is shown for the specific case of 6-(bromomethyl)-2-benzofuran-1(3H)-one to 3-oxo-1,3-dihydro-2-benzofuran-5-carbaldehyde, this general method may also be utilized to transform other benzylbromides to benzaldehydes. Benzylbromides useful for the present invention may be synthesized in accordance with the procedures found in the following reference: Neudeck, Monatsh. Chem. (1996), 127, 201.

Scheme 35

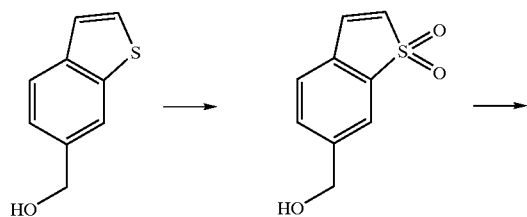

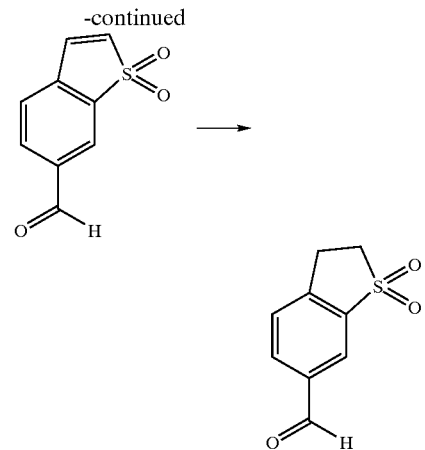

Another method for synthesizing benzaldehydes useful for the present invention is shown in Scheme 35. 1-Benzothiophen-6-ylmethanol can be oxidized to the correponding sulfone with oxidants such as meta-chloroperoxybenzoic acid or other similar oxidant, then further oxidized to benzo[b]thiophene-6-carboxaldehyde, 1,1-dioxide using manganese dioxide or other related oxidant for transforming a benzylic alcohol to a benzaldehyde. Benzo[b]thiophene-6-carboxaldehyde, 1,1-dioxide itself is useful for preparing compounds of the present invention but also can be further transformed by hydrogenation to 2,3-dihydrobenzo[b]thiophene-6-carboxaldehyde, 1,1-dioxide. The order of reactions described for this sequence is given simply to illustrate the method, being that it is also possible to effect the transformation of 1-benzothiophen-6-ylmethanol to 2,3-dihydrobenzo[b]thiophene-6-carboxaldehyde, 1,1-dioxide by changing the order of one or more of the reaction transformations. An alternative to this sequence preferable for the synthesis of 2,3-dihydrobenzo[b]thiophene-6-carboxaldehyde, 1,1-dioxide involves hydrogenation of benzo[b]thiophene-6-methanol, 1,1-dioxide to 2,3-dihydrobenzo[b]thiophene-6-methanol, 1,1-dioxide followed by oxidation of the alcohol to the aldehyde to provide 2,3-dihydrobenzo[b]thiophene-6-carboxaldehyde, 1,1-dioxide.

Scheme 36

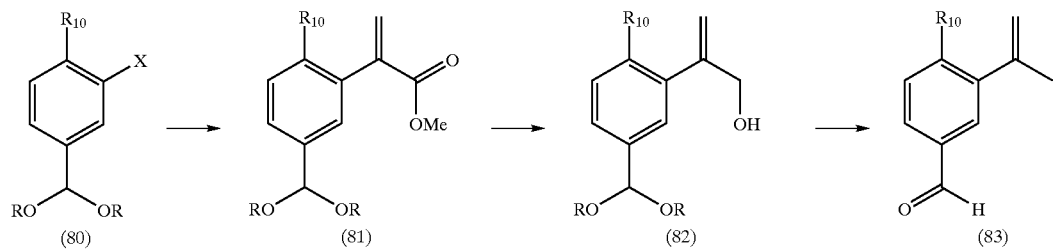

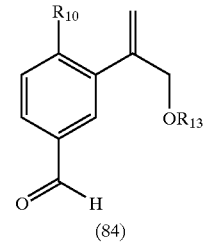

(84)

Methods for the preparation of benzaldehydes of general formula (83) and (84), wherein $R_{13}$ is selected from hydrogen, alkyl, arylalkyl, and haloalkyl, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, are shown in Scheme 36. A protected benzaldehyde of general formula (80), wherein X is selected from bromine, iodine, and triflate, and R is selected from alkyl or together with the oxygen atoms to which they are attached form a 5 or 6 membered ring wherein 1,3-dioxolanes are preferred, may be reacted with a suitable vinyl tin reagent in a Stille coupling to provide a protected benzaldehyde of general formula (81). This protected benzaldehyde (81) may be deprotected and used directly to synthesize compounds of the present invention or further transformed to the protected benzaldehyde of general formula (82) by reduction with reagents such as diisobutylaluminum hydride, lithium aluminum hydride and the like. Deprotection of (82) provides aldehydes useful for the direct preparation of compounds of the present invention. Further transformation of (82) to (83) involves conversion of (82) to an intermediate methanesulfonate ester, reductive removal of the methanesulfonate group, and finally deprotection to provide benzaldehydes of general formula (83). Alternatively, the intermediate (82) may transformed to (84) by alkylation or haloalkylation with a base such as potassium carbonate, potassium tert-butoxide or sodium tert-butoxide followed by reaction with an appropriate alkylating agent such as benzylbromide, methyl iodide, 2-iodo-1,1,1-trifluoroethane, chlorodifluoromethane, or dibromodifluoromethane. Although this sequence is shown specifically for the case wherein a Stille coupling is effected at the 3-position of the protected benzaldehyde and the resultant product then further transformed, this method can also be used to prepare the analogous benzaldehydes wherein the Stille coupling and subsequent transformations occur at the 4-position of the protected benzaldehyde with or without additional substitution at the 3-position.

For certain aromatic ring substitutions of $R_2$ for compounds of the present invention it is preferable to effect transformations of the aromatic ring substitutions after the aldehyde has been incorporated into the core structure of the present invention. As such, compounds of the present invention may be further transformed to other distinct compounds of the present invention. These transformations involve Stille, Suzuki and Heck coupling reactions all of which are well known to those skilled in the art of organic chemistry. Shown below are some representative methods of such transformations of compounds of the present invention to other compounds of the present invention.

Scheme 37

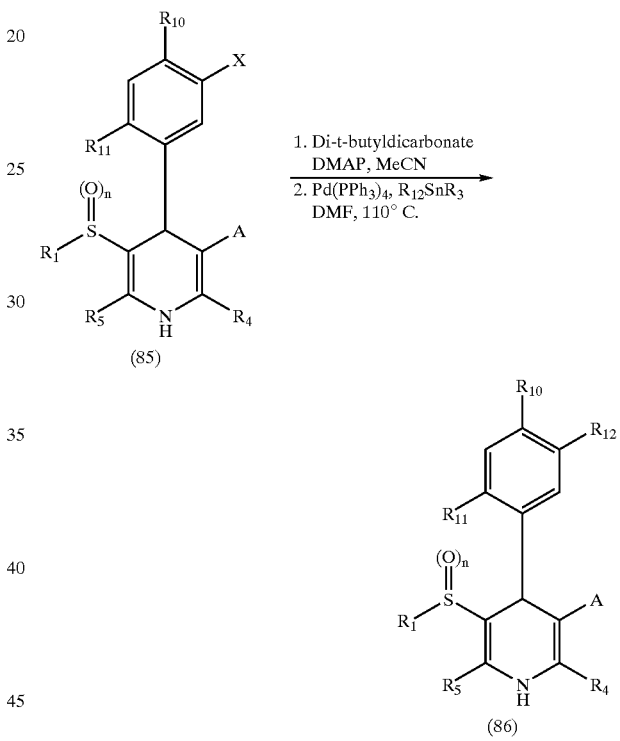

A method for preparing dihydropyridines of general formula (86), wherein $R_1$, $R_4$, $R_5$, and A are as defined in formula I, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, $R_{12}$ is selected from alkyl, vinyl, aryl, heteroaryl, cyano and the like, and n is an integer 0–2, is shown in Scheme 37. Compounds of general formula (85), wherein X is selected from bromine, iodine, and triflate, are protected with a tert-butoxycarbonyl (Boc) group using standard procedures. The aromatic bromide, iodide, or triflate X is reacted with a suitable tin or boronic acid reagent in the presence of a palladium catalyst with heating in a solvent such as dimethylformamide to effect a coupling reaction that affords a new substituent $R_{12}$. The conditions for this transformation also effect the removal of the Boc protecting group.

Scheme 38

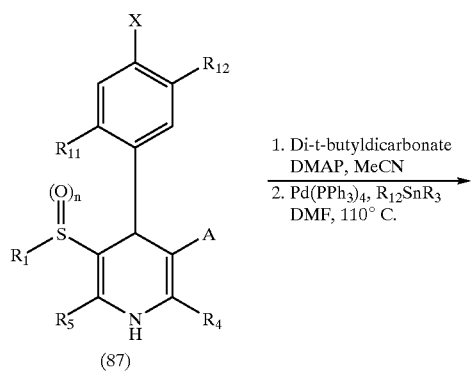

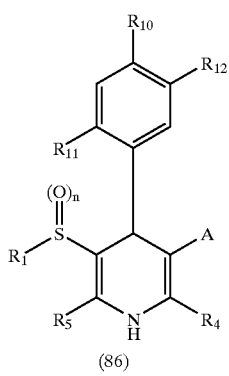

Another method for preparing dihydropyridines of general formula (86), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$ is selected from hydrogen, hydroxy, alkoxy, haloalkoxy, and arylalkoxy, $R_{10}$ is selected from alkyl, vinyl, aryl, heteroaryl, cyano and the like, and n is an integer 0–2, is shown in Scheme 37. Compounds of general formula (87), wherein X is selected from bromine, iodine, and triflate, are protected with a tert-butoxycarbonyl (Boc) group using standard procedures. The aromatic bromide, iodide, or triflate X is reacted with a suitable tin or boronic acid reagent in the presence of a palladium catalyst with heating in a solvent such as dimethylformamide to effect a coupling reaction that affords a new substituent $R_{10}$. The conditions for this transformation also effect the removal of the Boc protecting group.

Scheme 39

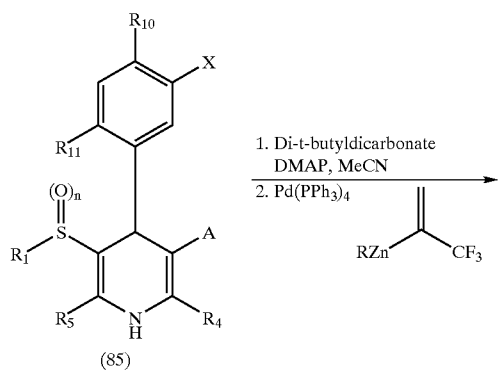

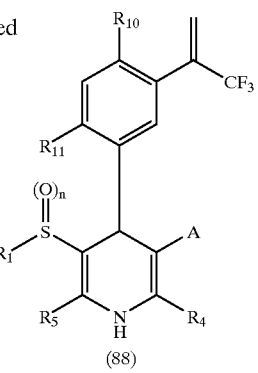

A method for preparing dihydropyridines of general formula (88), wherein $R_1$, $R_4$, $R_5$, and A are as defined in formula I, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, and n is an integer 0–2, is shown in Scheme 39. Dihydropyridines of general formula (85), wherein X is selected from bromine, iodine, and triflate are protected with a tert-butoxycarbonyl (Boc) group using standard procedures. The aromatic bromide, iodide, or triflate X is reacted with a suitable halozinc reagent in the presence of a palladium catalyst with heating in a solvent such as dimethylformamide to effect a coupling reaction that affords a new substituent at the meta position. The conditions for this transformation also effect the removal of the Boc protecting group. The types of meta substituents that may be introduced in this fashion include trihalopropenyl and more specifically the trifluoropropenyl group.

Scheme 40

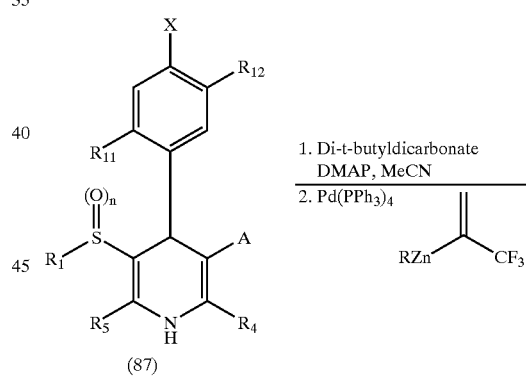

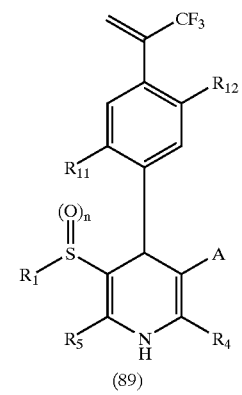

A method for preparing dihydropyridines of general formula (89), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$ is selected from hydrogen, hydroxy, alkoxy, haloalkoxy, and arylalkoxy, and n is an integer 0–2, is shown in Scheme 40. Dihydropyridines of general formula (87), wherein X is selected from bromine, iodine, and triflate are protected with a tert-butoxycarbonyl (Boc) group using standard procedures. The aromatic bromide, iodide, or triflate X is reacted with a suitable halozinc reagent in the presence of a palladium catalyst with heating in a solvent such as dimethylformamide to effect a coupling reaction that affords a new substituent at the para position. The conditions for this transformation also effect the removal of the Boc protecting group. The types of para substituents that may be introduced in this fashion include trihalopropenyl and more specifically the trifluoropropenyl group.

the meta position. The conditions for this transformation may also effect the removal of the Boc protecting group. In cases where the Boc group remains in place, the Boc protecting group may be removed using chemistry well known to those skilled in the art.

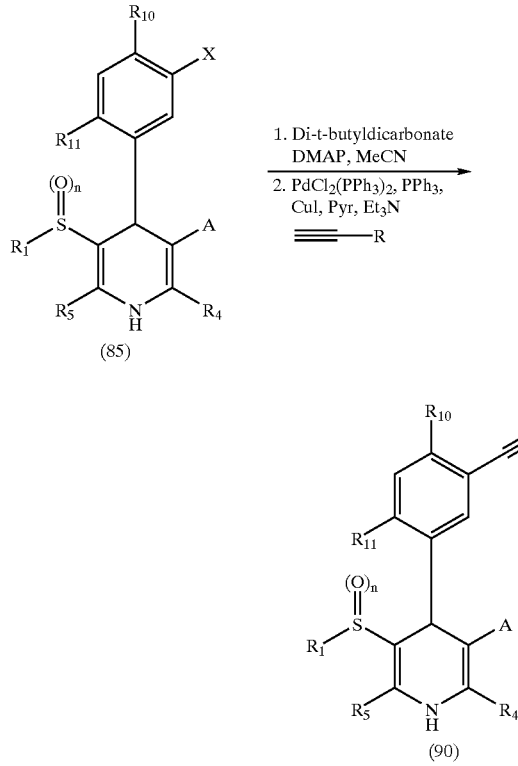

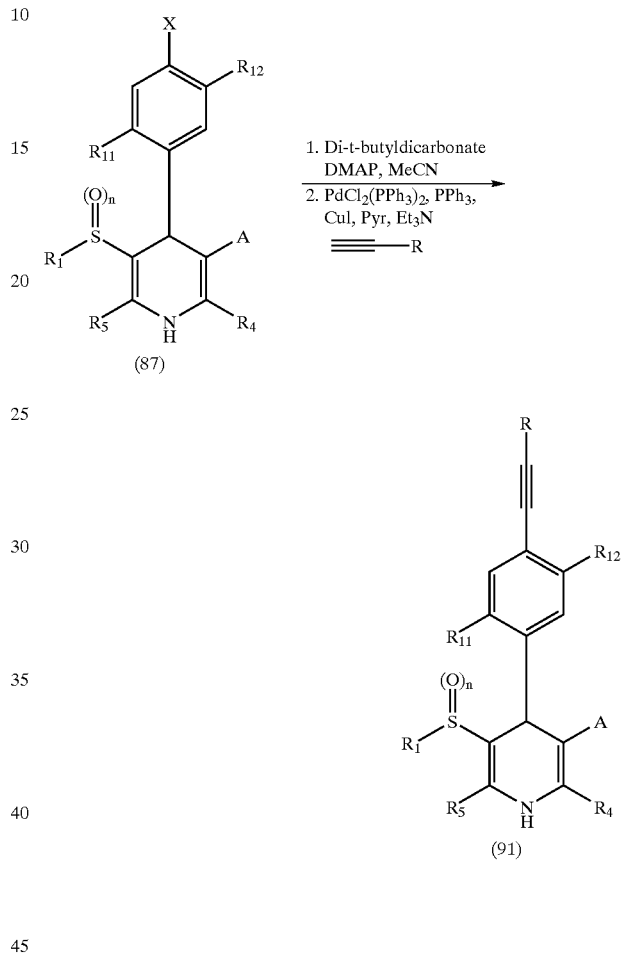

A method for preparing dihydropyridines of general formula (90), wherein $R_1$, $R_4$, $R_5$, and A are as defined in formula I, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$ is selected from hydrogen, hydroxy, alkoxy, haloalkoxy, and arylalkoxy, R is selected from hydrogen, alkyl, haloalkyl, hydroxyalkyl, and n is an integer 0–2, is shown in Scheme 41. Dihydropyridines of general formula (85), wherein X is selected from bromine, iodine, and triflate are protected with a tert-butoxycarbonyl (Boc) group using standard procedures. The aromatic bromide, iodide, or triflate X is reacted with a terminal alkyne in the presence of a palladium catalyst, copper iodide, triphenylphosphine and triethylamine with heating in a solvent such as pyridine to effect a coupling reaction that affords a new substituent at A method for preparing dihydropyridines of general formula (91), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, R is selected from hydrogen, alkyl, haloalkyl, hydroxyalkyl, and n is an integer 0–2, is shown in Scheme 42. Dihydropyridines of general formula (87), wherein X is selected from bromine, iodine, and triflate, are protected with a tert-butoxycarbonyl (Boc) group using standard procedures. The aromatic bromide, iodide, or triflate X is reacted with a terminal alkyne in the presence of a palladium catalyst, copper iodide, triphenylphosphine and triethylamine with heating in a solvent such as pyridine to effect a coupling reaction that affords a new substituent at the meta position. The conditions for this transformation may also effect the removal of the Boc protecting group. In cases where the Boc group remains in place, the Boc protecting group may be removed using chemistry well known to those skilled in the art.

Scheme 43

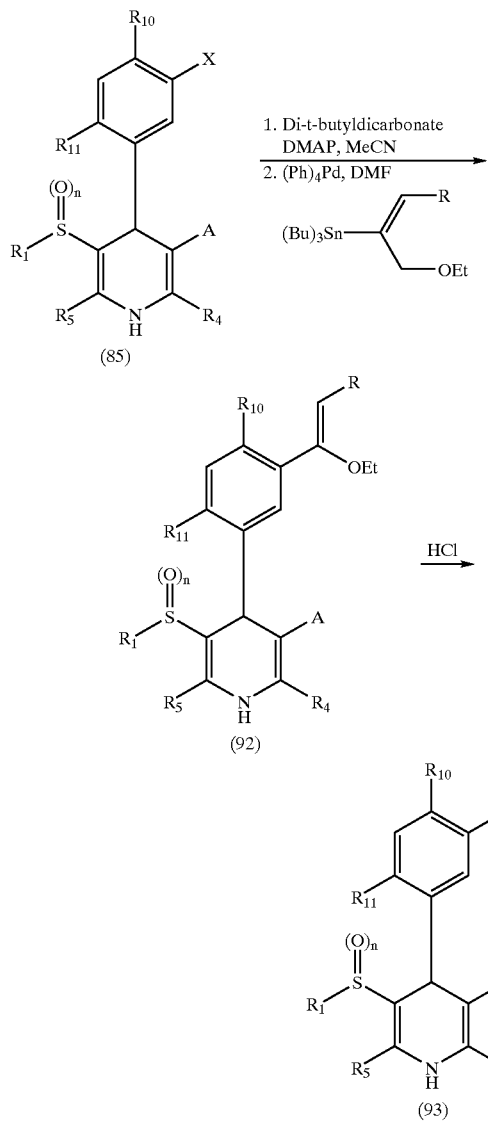

Scheme 44

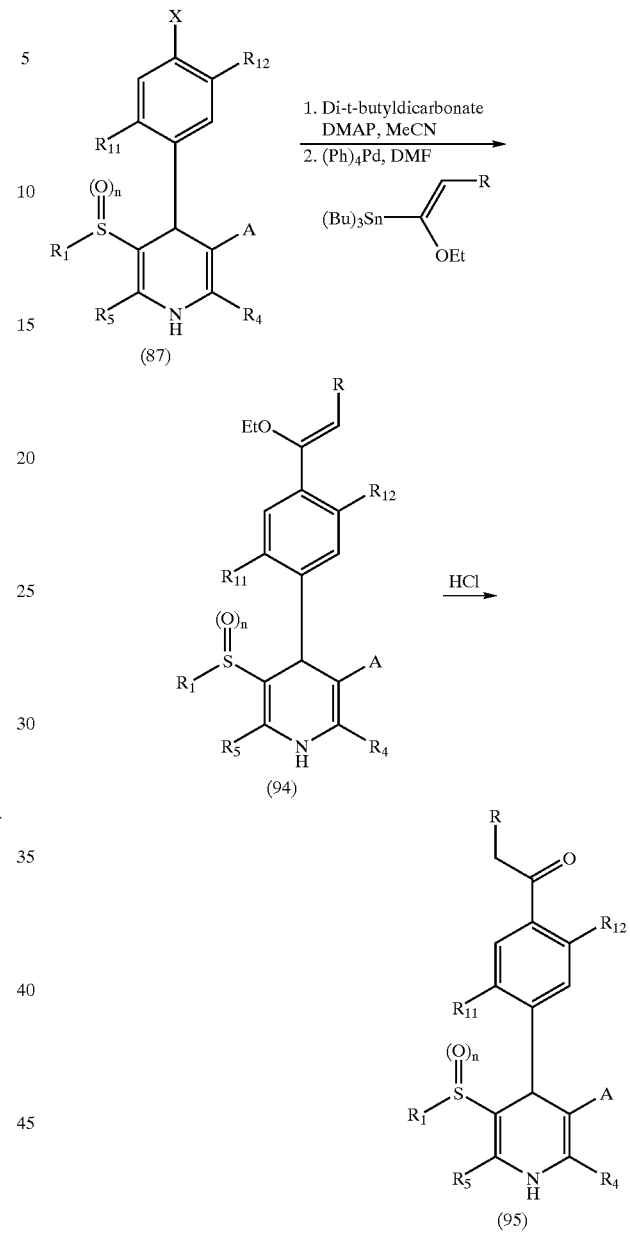

A method for preparing dihydropyridines of general formula (93), wherein $R_1$, $R_4$, $R_5$, and A are as defined in formula I, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, R is selected from hydrogen and alkyl, and n is an integer 0–2, is shown in Scheme 43. Dihydropyridines of general formula (85), wherein X is selected from bromine, iodine, and triflate, are protected with a tert-butoxycarbonyl (Boc) group using standard procedures. The aromatic bromide, iodide, or triflate X is reacted with a suitable vinyl tin reagent in a Stille coupling to provide dihydropyridines of general formula (92). The conditions for this transformation may also effect the removal of the Boc protecting group. Hydrolysis of (92) provides dihyropridines of general formula (93).

A method for preparing dihydropyridines of general formula (95), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, R is selected from hydrogen and alkyl, and n is an integer 0–2, is shown in Scheme 44. Dihydropyridines of general formula (87), wherein X is selected from bromine, iodine, and triflate, are protected with a tert-butoxycarbonyl (Boc) group using standard procedures. The aromatic bromide, iodide, or triflate X is reacted with a suitable vinyl tin reagent in a Stille coupling to provide dihydropyridines of general formula (94). The conditions for this transformation may also effect the removal of the Boc protecting group. Hydrolysis of (94) provides dihydropyridines of general formula (95).

Scheme 45

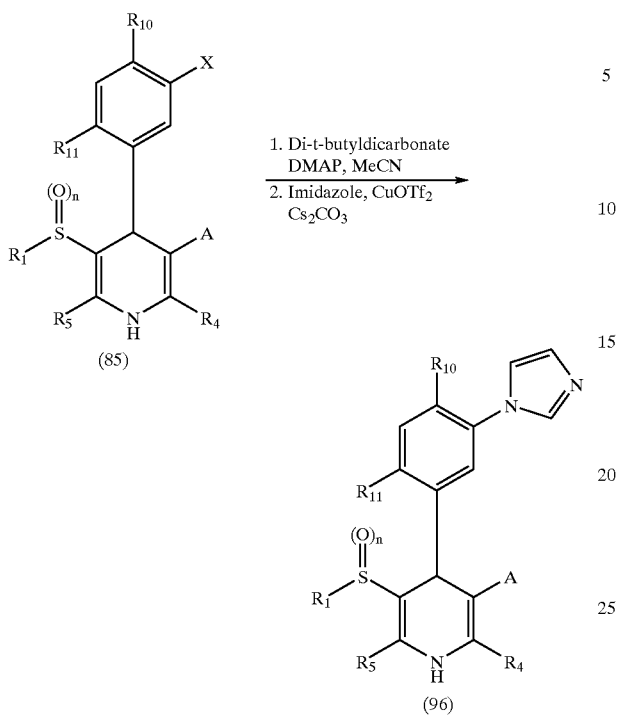

A method for preparing dihydropyridines of general formula (96), wherein $R_1$, $R_4$, $R_5$, and A are as defined in formula 1, $R_{10}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, and n is an integer 0–2, is shown in Scheme 45. Dihydropyridines of general formula (85), wherein X is selected from bromine, iodine, and triflate, are protected with a tert-butoxycarbonyl (Boc) group using standard procedures and then reacted with an optionally substituted imidazole in the presence of copper triflate, cesium carbonate, dibenzylideneacetone and 1,10-phenanthroline in a suitable solvent to effect a coupling reaction that affords an optionally substituted imidazole at the meta position. The conditions for this transformation may also effect the removal of the Boc protecting group. The types of meta substituents that may be introduced in this fashion include imidazole and substituted imidazole.

Scheme 46

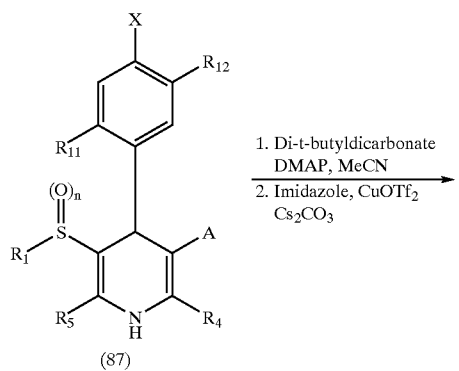

A method for preparing dihydropyridines of general formula (97), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$ is selected from hydrogen, hydroxy, alkoxy, haloalkoxy, and arylalkoxy, and n is an integer 0–2, is shown in Scheme 46. Dihydropyridines of general formula (87), wherein X is selected from bromine, iodine, and triflate, are protected with a tert-butoxycarbonyl (Boc) group using standard procedures and then reacted with an optionally substituted imidazole in the presence of copper triflate, cesium carbonate, dibenzylideneacetone and 1,10-phenanthroline in a suitable solvent to effect a coupling reaction that affords an optionally substituted imidazole at the para position. The conditions for this transformation may also effect the removal of the Boc protecting group. The types of para substituents that may be introduced in this fashion include imidazole and substituted imidazole.

Scheme 47

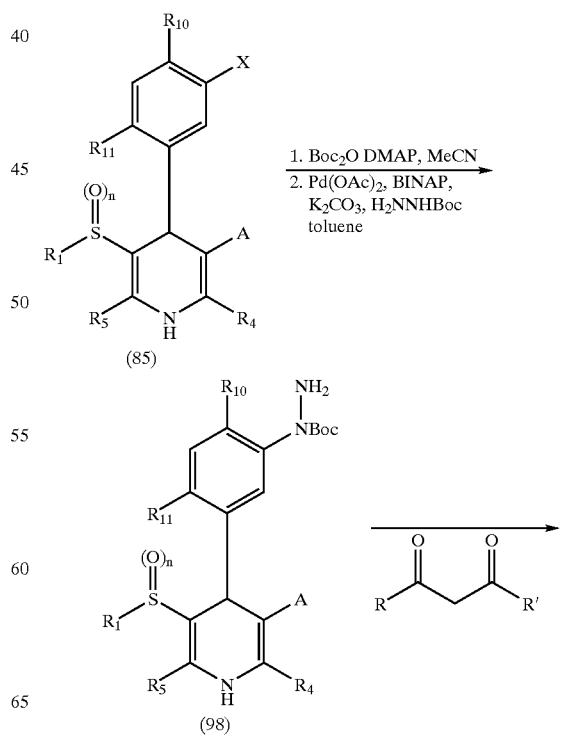

-continued

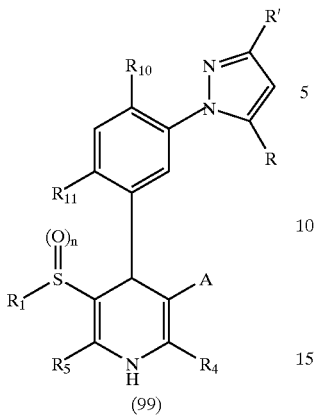

(99)

-continued

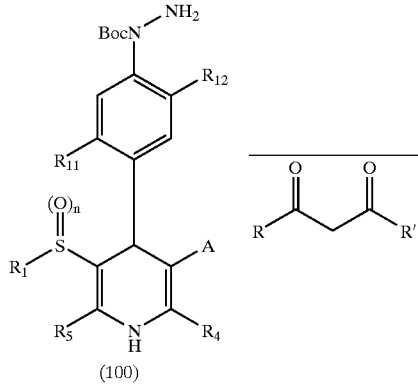

(100)

A method for preparing dihydropyridines of general formula (99), wherein $R_1$, $R_4$, $R_5$, and A are as defined in formula I, $R_{10}$ is selected from hydrogen, alkyl, alkylcarbonfyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, R is selected from hydrogen, alkyl, and haloakyl, R' is selected from hydrogen, alkyl, and haloalkyl, and n is an integer 0–2, is shown in Scheme 47. Dihydropyridines of general formula (85), wherein X is selected from bromine, iodine, and triflate, are protected with a tert-butoxycarbonyl (Boc) group using standard procedures. The aromatic bromide, iodide, or triflate X is reacted with mono Boc-protected hydrazine in the presence of a palladium catalyst, BINAP and potassium carbonate with heating in a solvent to effect a coupling reaction that affords a protected hydrazine substituent at the meta position. Dihydropyridines of general formula (98) may be further transformed by reaction with 1,3-dicarbonyls to afford pyrazole and substituted pyrazole compounds. The conditions for this transformation also effect the removal of the Boc protecting group. The types of meta substituents that may be introduced in this fashion include pyrazole and substituted pyrazoles.

Scheme 48

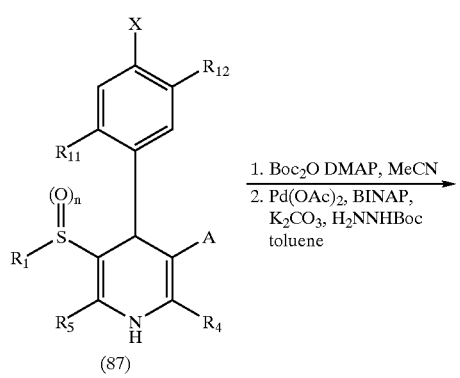

(87)

1. Boc₂O DMAP, MeCN
2. Pd(OAc)₂, BINAP, K₂CO₃, H₂NNHBoc toluene

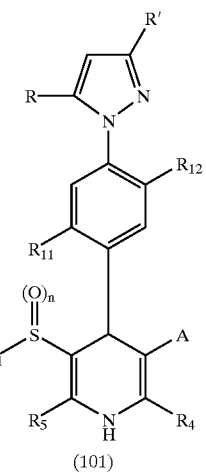

(101)

A method for preparing dihydropyridines of general formula (101), wherein $R_1$, $R_4$, $R_5$, and A are as defined in formula I, $R_{12}$ is selected from hydrogen, alkyl, alkylcarbonyl, alkylsulfonyl, amido, aryl, heteroaryl, cyano, haloalkyl, chlorine, fluorine, haloalkoxy, nitro, alkoxy, and thioalkoxy, $R_{11}$, is selected from hydrogen, hydroxy, alkoxy, haloalkoxy, and arylalkoxy, R is selected from hydrogen, alkyl, and haloakyl, R' is selected from hydrogen, alkyl, and haloalkyl, and n is an integer 0–2, is shown in Scheme 48. Dihydropyridines of general formula (87), wherein X is selected from bromine, iodine, and triflate, are protected with a tert-butoxycarbonyl (Boc) group using standard procedures. The aromatic bromide, iodide, or triflate X is reacted with mono Boc-protected hydrazine in the presence of a palladium catalyst, BINAP and potassium carbonate with heating in a solvent to effect a coupling reaction that affords a protected hydrazine substituent at the para position. Dihydropyridines of general formula (100) may be further transformed by reaction with 1,3-dicarbonyls to afford pyrazole and substituted pyrazole compounds. The conditions for this transformation also effect the removal of the Boc protecting group. The types of para substituents that may be introduced in this fashion include pyrazole and substituted pyrazoles.

Examples of the present Invention that possess a center of chirality and thus exist in racemic form were separated into the individual enantiomers by the method shown in Scheme 3. The racemic compounds of general formula I were reacted with potassium t-butoxide (1 equivalent) in tetrahydrofuran followed by 8-phenylmenthyl chloroformate to generate a mixture of diastereomeric 8-phenylmenthyl carbamates (i) and (ii). The diastereomers (i) and (ii) were separated by column chromatography over silica gel and the 8-phenylmenthol moiety removed by reaction with sodium methoxide in methanol to provide the single enantiomers as shown.

In addition to the use of the method illustrated in Scheme 3, individual enantiomers of compounds of the Invention were also separated by chiral chromatography.

EXAMPLE 1

3,4,6,7,8,10-hexahydro-10-(3-nitrophenyl)-2H-thiopyrano[3,2-b]quinolin-9(5H)-one, 1,1-dioxide A solution of 3-nitrobenzaldehyde (151 mg, 1.00 mmol), tetrahydrothiopyran-3-one-1,1-dioxide (148 mg, 1.00 mmol), prepared according to the method described in J. Heterocycl. Chem. (1990), 27, 1453, and 3-amino-2-cyclohexen-1-one (111 mg, 1.00 mmol) in ethanol (7 mL) was heated at reflux for 24 hours and cooled. The solid that precipitated was washed with ethanol, dried, and triturated with hot methanol to provide the title compound.
MS (APCI) m/e 375 (M+H)$^+$;
$^1$H NMR (DMSO-d$_6$) δ 1.75 (m, 1H), 1.90 (m, 1H), 2.22 (m, 4H), 2.55 (m, 4H), 3.22 (m, 2H), 5.15 (s, 1H), 7.55 (t, 1H), 7.65 (d, 1H), 8.00 (m, 1H), 9.48 (br s, 1H);
Anal. Calcd for $C_{18}H_{18}N_2O_5S$: C, 57.74; H, 4.85; N, 7.48. Found: C, 57.41; H, 4.75; N, 7.39.

EXAMPLE 2

10-(3,4-dichlorophenyl)-3,4,6,7,8,10-hexahydro-2H-thiopyrano[3.2-b)]quinolin-9(5H)-one, 1,1-dioxide 3,4-Dichlorobenzaldehyde (175 mg, 1.00 mmol) was processed as in Example 1 to provide the title compound.
MS(APCI) m/e 398 (M+H)$^+$, 400 (M+H)$^+$;
$^1$H NMR (DMSO-d$_6$) δ 1.75 (m, 1H), 1.90 (m, 1H), 2.22 (m, 4H), 2.55 (m, 4H), 3.20 (m, 2H), 5.01 (s, 1H), 7.06 (dd, 1H), 7.32 (d, 1H), 7.50 (d, 1H), 9.40 (br s, 1H);
Anal. Calcd for $C_{18}H_{17}Cl_2NO_3S$: C, 54.28; H, 4.30; N, 3.52. Found: C, 54.13; H, 4.18; N, 3.46.

EXAMPLE 3

10-(3-chloro-4-fluorophenyl)-3,4,6,7,8,10-hexahydro-2H-thiopyrano [3,2-b]quinolin-9(5H)-one, 1,1-dioxide 3-Chloro-4-fluorobenzaldehyde (159 mg, 1.00 mmol) was processed as in Example 1 to provide the title compound.
MS (APCI) m/e 382 (M+H)$^+$, 384 (M+H)$^+$;
$^1$H NMR (DMSO-d$_6$) δ 1.75 (m, 1H), 1.88 (m, 1H), 2.20 (m, 4H), 2.50 (m, 4H), 3.20 (m, 2H), 5.01 (s, 1H), 7.15 (ddd, 1H), 7.26 (m, 3H), 9.38 (br s, 1H);
Anal. Calcd for $C_{18}H_{17}ClFNO_3S$: C, 56.62; H, 4.49; N, 3.67. Found: C, 56.64; H, 4.43; N, 3.57.

EXAMPLE 4

10-(3-bromo-4-fluorophenyl)-3,4,6,7,8,10-hexahydro-2H-thiopyrano [3,2-b]quinolin-9(5H)-one, 1,1-dioxide 3-Bromo-4-fluorobenzaldehyde (203 mg, 1.00 mmol) was processed as in Example 1 to provide the title compound.
MS(APCI) m/e 426 (M+H)$^+$, 428 (M+H)$^+$;
$^1$H NMR (DMSO-d$_6$) δ 1.75 (m, 1H), 1.90 (m, 1H), 2.20 (m, 4H), 2.55 (m, 4H), 3.20 (m, 2H), 5.01 (s, 1H), 7.20 (m, 2H), 7.40 (dd, 1H), 9.35 (br s, 1H);
Anal. Calcd for $C_{18}H_{17}BrFNO_3S$: C, 50.71; H, 4.02; N, 3.29. Found: C, 50.69;H, 3.99; N, 3.16.

EXAMPLE 5

10-(3-cyanophenyl)-3,4,6,7,8,10-hexahydro-2H-thiopyrano [3,2-b]quinolin-9(5H)-one, 1,1-dioxide 3-Cyanobenzaldehyde (131 mg, 1.00 mmol) was processed as in Example 1 to provide the title compound.
MS(APCI) m/e 355 (M+H)$^+$;
$^1$H NMR (DMSO-d$_6$) δ 1.75 (m, 1H), 1.88 (m, 1H), 2.20 (m, 4H), 2.55 (m, 4H), 3.20 (m, 2H), 5.07 (s, 1H), 7.45 (t, 1H), 7.52 (s, 1H), 7.54 (dt, 1H), 7.60 (dt, 1H), 9.40 (br s, 1H);
Anal. Calcd for $C_{19}H_{18}N_2O_3S$: C, 64.39; H, 5.12; N, 7.90. Found: C, 64.18; H, 5.15; N, 7.83.

EXAMPLE 6

3,4,6,7,8,10-hexahydro-10-[3-(trifluoromethyl) phenyl]-2H-thiopyrano [3 2-b]quinolin-9(5H)-one, 1,1-dioxide 3-Trifluoromethylbenzaldehyde (134 μL, 1.00 mmol) was processed as in Example 1 to provide the title compound.
MS(APCI) m/e 398 (M+H)$^+$;
$^1$H NMR (DMSO-d$_6$) δ 1.74 (m, 1H), 1.90 (m, 1H), 2.20 (m, 4H), 2.55 (m, 4H), 3.18 (m, 2H), 5.11 (s, 1H), 7.48 (br s, 4H), 9.40 (br s, 1H);
Anal. Calcd for $C_{19}H_{18}F_3NO_3S$: C, 57.42; H, 4.57; N, 3.52. Found: C, 57.12; H, 4.67; N, 3.39.

EXAMPLE 7

10-(3,4-difluorophenyl)-3,4 6,7,8,10-hexahydro-2H-thiopyrano [3,2-b]quinolin-9(5H)-one, 1,1-dioxide 3,4-Difluorobenzaldehyde (110 μL, 1.00 mmol) was processed as in Example 1 to provide the title compound.
MS(APCI) m/e 366 (M+H)$^+$;
$^1$H NMR (DMSO-d$_6$) δ 1.75 (m, 1H), 1.88 (m, 1H), 2.20 (m, 4H), 2.50 (m, 4H), 3.20 (m, 2H), 5.02 (s, 1H), 7.02 (m, 1H), 7.10 (m, 1H), 7.26 (dt, 1H), 9.37 (br s, 1H);
Anal. Calcd for $C_{18}H_{17}F_2NO_3S$: C, 59.17; H, 4.69; N, 3.83. Found: C, 58.91; H, 4.70; N, 3.69.

EXAMPLE 8

10-(3-bromophenyl)-3,4,6,7,8,10-hexahydro-2H-thiopyrano [3,2-b]quinolin-9(5H)-one, 1,1-dioxide 3-Bromobenzaldehyde (117 μL, 1.00 mmol) was processed as in Example 1 to provide the title compound.
MS(APCI) m/e 408 (M+H)$^+$, 410 (M+H)$^+$;
$^1$H NMR (DMSO-d$_6$) δ 1.75 (m, 1H), 1.90 (m, 1H), 2.20 (m, 4H), 2.55 (m, 4H), 3.20 (m, 2H), 5.01 (s, 1H), 7.20 (m, 2H), 7.30 (m, 2H), 9.40 (br s, 1H);
Anal. Calcd for $C_{18}H_{18}BrNO_3S$: C, 52.95; H, 4.44; N, 3.43. Found: C, 52.91; H, 4.53; N, 3.37.

EXAMPLE 9

3,4,7,8,10-hexahydro-10-(3,4,5-trifluorophenyl)-2H-thiopyrano 3,2-b]quinolin-9(5H)-one, 1,1-dioxide 3,4,5-Trifluorobenzaldehyde (160 mg, 1.00 mmol) was processed as in Example 1 to provide the title compound.
MS(APCI) m/e 384 (M+H)$^+$;
$^1$H NMR (DMSO-d$_6$) δ 1.75 (m, 1H), 1.88 (m, 1H), 2.20 (m, 4H), 2.50 (m, 4H), 3.20 (m, 2H), 5.02 (s, 1H), 7.00 (m, 2H), 9.41 (br s, 1H);

EXAMPLE 10

10-[3-fluoro-5-(trifluoromethyl)phenyl-3,4,6,7,8,10-hexahydro-2H-thiopyrano [3.2-b]quinolin-9(5H)-one, 1,1-dioxide 3-Fluoro-5-trifluoromethylbenzaldehyde (192 mg, 1.00 mmol) was processed as in Example 1 to provide the title compound.
MS(APCI) m/e 416 (M+H)$^+$;
$^1$H NMR (DMSO-d$_6$) δ 1.75 (m, 1H), 1.90 (m, 1H), 2.20 (m, 4H), 2.55 (m, 4H), 3.20 (m, 2H), 5.14 (s, 1H), 7.23 (d, 1H), 7.36 (s, 1H), 7.44 (d, 1H), 9.45 (br s, 1H);
Anal. Calcd for C$_{19}$H$_{17}$F$_4$NO$_3$S: C, 54.94; H, 4.12; N, 3.37. Found: C, 54.84; H, 4.20; N, 3.26.

EXAMPLE 10

10-(3-fluorophenyl)-3,4,6,7,8,10-hexahydro-2H-thionyrano [3,2-b]quinolin-9(5H)-one, 1,1-dioxide 3-Fluorobenzaldehyde (106 μL, 1.00 mmol) was processed as in Example 1 to provide the title compound.
MS(APCI) m/e 348 (M+H)$^+$;
$^1$H NMR (DMSO-d$_6$) δ 1.75 (m, 1H), 1.88 (m, 1H), 2.20 (m, 4H), 2.55 (m, 4H), 3.20 (m, 2H), 5.05 (s, 1H), 6.93 (m, 2H), 7.04 (d, 1H), 7.25 (dt, 1H), 9.35 (br s, 1H);
Anal. Calcd for C$_{18}$H$_{18}$FNO$_3$S: C, 62.23; H, 5.22; N, 4.03. Found: C, 61.95; H, 5.03; N, 3.89.

EXAMPLE 12

3,4,6,7,8,10-hexahydro-10-phenyl-2H-thiopyrano [3.2-b]quinolin-9(5H)-one, 1,1-dioxide Benzaldehyde (102 μL, 1.00 mmol) was processed as in Example 1 to provide the title compound.
MS(APCI) m/e 330 (M+H)$^+$;
$^1$H NMR (DMSO-d$_6$) δ 1.73 (m, 1H), 1.90 (m, 1H), 2.20 (m, 4H), 2.50 (m, 4H), 3.18 (m, 2H), 5.03 (s, 1H), 7.10 (m, 1H), 7.20 (m, 4H), 9.28 (br s, 1H);
Anal. Calcd for C$_{18}$H$_{19}$NO$_3$S: C, 65.63; H, 5.81; N, 4.25. Found: C, 65.57; H, 5.99; N, 4.12.

EXAMPLE 13

10-[4-fluoro-3-(trifluoromethyl)phenyl]-3,4,6,7,8,10-hexahydro-2H-thiopyrano [3,2-b]quinolin-9(5H)-one, 1,1-dioxide 4-Fluoro-3-trifluoromethylbenzaldehyde (194 mg, 1.01 mmol) was processed as in Example 1 to provide the title compound.
MS(APCI) m/e 416 (M+H)$^+$;
$^1$H NMR (DMSO-d$_6$) δ 1.75 (m, 1H), 1.90 (m, 1H), 2.22 (mn, 4H), 2.52 (m, 4H), 3.20 (m, 2H), 5.09 (s, 1H), 7.38 (dd, 1H), 7.50 (m, 2H), 9.42 (br s, 1H);
Anal. Calcd for C$_{19}$H$_{17}$F$_4$NO$_3$S: C, 54.93; H, 4.12; N, 3.37. Found: C, 54.77; H, 4.16; N, 3.26.

EXAMPLE 14

3,4,6,7,8,10-hexahydro-10-(4-methyl-3-nitrophenyl) 2H-thiopyrano [3,2-b]quinolin-9(5H)-one, 1,1-dioxide 4-Methyl-3-nitrobenzaldehyde (165 mg, 1.00 mmol) was processed as in Example 1 to provide the title compound.
MS(APCI) m/e 389 (M+H)$^+$;
$^1$H NMR (DMSO-d$_6$) δ 1.75 (m, 1H), 1.88 (m, 1H), 2.22 (m, 4H), 2.45 (s, 3H), 2.55 (m, 4H), 3.20 (m, 2H), 5.09 (s, 1H), 7.35 (d, 1H), 7.43 (dd, 1H), 7.72 (d, 1H), 9.42 (br s, 1H);
Anal. Calcd for C$_{19}$H$_{20}$N$_2$O$_5$S0.25H$_2$O: C, 58.07; H, 5.25; N, 7.12. Found: C, 58.21;H, 5.36; N, 6.95.

EXAMPLE 15

10-(4-chloro-3-fluorophenyl)-3,4,6,7,8,10-hexahydro-2H-thiopyrano [3.2-b]quinolin-9(5H)-one, 1,1-dioxide 4-Chloro-3-fluorobenzaldehyde (159 mg, 1.00 mmol) was processed as in Example 1 to provide the title compound.
MS(APCI) m/e 382 (M+H)$^+$, 384 (M+H)$^+$;
$^1$H NMR (DMSO-d$_6$) δ 1.75 (m, 1H), 1.90 (m, 1H), 2.20 (m, 4H), 2.55 (m, 4H), 3.20 (m, 2H), 5.03 (s, 1H), 7.07 (m, 2H), 7.42 (t, 1H), 9.37 (br s, 1H);
Anal. Calcd for C$_{18}$H$_{17}$ClFNO$_3$S: C, 56.62; H, 4.49; N, 3.67. Found: C, 56.36; H, 4.53; N, 3.59.

EXAMPLE 16

10-(3-chlorophenyl)-3,4,6,7,8,10-hexahydro-2H-thiopyrano [3.2-b]quinolin-9(5H)-one, 1,1-dioxide 3-Chlorobenzaldehyde (113 μL, 1.00 mmol) was processed as in Example 1 to provide the title compound.
MS(APCI) m/e 364 (M+H)$^+$, 366 (M+H)$^+$;
$^1$H NMR (DMSO-d$_6$) δ 1.75 (m, 1H), 1.90 (m, 1H), 2.20 (m, 4H), 2.50 (m, 4H), 3.18 (m, 2H), 5.02 (s, 1H), 7.15 (m, 3H), 7.25 (m, 1H), 9.35 (br s, 1H);
Anal. Calcd for C$_{18}$H$_{18}$ClNO$_3$S: C, 59.42; H, 4.99; N, 3.85. Found: C, 59.16; H, 5.13; N, 3.71.

EXAMPLE 17

3,4,6,7,8,10-hexahydro-10-[4-(trifluoromethyl) phenyl]-2H-thiopyrano [3.2-b]quinolin-9(5H)-one 1, 1-dioxide 4-Trifluoromethylbenzaldehyde (137 μL, 1.00 mmol) was processed as in Example 1 to provide the title compound.
MS(APCI) m/e 398 (M+H)$^+$;
$^1$H NMR (DMSO-d$_6$) δ 1.75 (m, 1H), 1.89 (m, 1H), 2.20 (m, 4H), 2.50 (m, 4H), 3.19 (m, 2H), 5.10 (s, 1H), 7.38 (d, 2H), 7.58 (d, 2H), 9.37 (br s, 1H);
Anal. Calcd for C$_{19}$H$_{18}$F$_3$NO$_3$S: C, 57.42; H, 4.56; N, 3.52. Found: C, 57.28; H, 4.58; N, 3.32.

EXAMPLE 18

10-(4-bromophenyl)-3,4,6,7,8,10-hexahydro-2H-thiopyrano [3,2-b]quinolin-9(5H)-one, 1,1-dioxide 4-Bromobenzaldehyde (185 mg, 1.00 mmol) was processed as in Example 1 to provide the title compound.
MS(APCI) m/e 408 (M+H)$^+$, 410 (M+H)$^+$;
$^1$H NMR (DMSO-d$_6$) δ 1.75 (m, 1H), 1.90 (m, 1H), 2.20 (m, 4H), 2.50 (m, 4H), 3.20 (m, 2H), 5.00 (s, 1H), 7.12 (d, 2H), 7.40 (d, 2H), 9.32 (br s, 1H);
Anal. Calcd for C$_{18}$H$_{18}$BrNO$_3$S: C, 52.95; H, 4.44; N, 3.43. Found: C, 52.76; H, 4.34; N, 3.40.

EXAMPLE 19

10-(4-chloro-3-nitrolphenyl)-3,4,6,7,8,10-hexahydro-2H-thiopyrano [3,2-b]quinolin-9(5H)-one, 1,1-dioxide 4-Chloro-3-nitrobenzaldehyde (185 mg, 1.00 mmol) was processed as in Example 1 to provide the title compound.

Anal. Calcd for C$_{18}$H$_{16}$F$_3$NO$_3$S: C, 56.39; H, 4.21; N, 3.65. Found: C, 56.26; H, 4.27; N, 3.55.

MS(APCI) m/e 409 (M+H)$^+$, 411 (M+H)$^+$;
$^1$H NMR (DMSO-d$_6$) δ 1.75 (m, 1H), 1.90 (m, 1H), 2.21 (m, 4H), 2.55 (m, 4H), 3.20 (m, 2H), 5.10 (s, 1H), 7.50 (dd, 1H), 7.63 (d, 1H), 7.75 (d, 1H), 9.45 (br s, 1H);
Anal. Calcd for C$_{18}$H$_{17}$ClN$_2$O$_5$S: C, 52.88; H, 4.19; N, 6.85. Found: C, 52.59; H, 4.11; N, 6.72.

EXAMPLE 20

4-(3,4-dichlorophenyl)-4,6,7,8-tetrahydro-2-methyl-3-(methylsulfonyl)-5(1H)-quinolinone A solution of methanesulfonylacetone (135 mg, 1.00 mmol), 3,4-dichlorobenzaldehyde (175 mg, 1.00 mmol) and 3-amino-2-cyclohexen-1-one (111 mg, 1.00 mmol) in ethanol (7 mL) was heated to reflux for 24 hours and cooled. The solid that precipitated was collected, washed with ethanol, dried, and triturated with methanol to provide the title compound.
MS(APCI) m/e 386 (M+H)$^+$, 388 (M+H)$^+$;
$^1$H NMR (DMSO-d$_6$) δ 1.75 (m, 1H), 1.90 (m, 1H), 2.21 (m, 2H), 2.32 (s, 3H), 2.50 (m, 2H), 2.73 (s, 3H), 4.94 (s, 1H), 7.18 (dd, 1H), 7.34 (d, 1H), 7.53 (d, 1H), 9.48 (br s, 1H);
Anal. Calcd for C$_{17}$H$_{17}$Cl$_2$NO$_3$S: C, 52.86; H, 4.44; N, 3.63. Found: C, 52.91; H, 4.31; N, 3.55.

EXAMPLE 21

4-(3-cyanophenyl)-4,6,7,8-tetrahydro-2-methyl-3-(methylsulfonyl)-5(1H)-quinolinone 3-Cyanobenzaldehyde (131 mg, 1.00 mmol) was processed as in Example 20 to provide the title compound.
MS(APCI) m/e 343 (M+H)$^+$;
$^1$H NMR (DMSO-d$_6$) δ 1.75 (m, 1H), 1.90 (m, 1H), 2.22 (m, 2H), 2.32 (s, 3H), 2.50 (m, 2H), 2.68 (s, 3H), 4.99 (s, 1H), 7.50 (m, 3H), 7.63 (dt, 1H), 9.48 (br s, 1H);
Anal. Calcd for C$_{18}$H$_{18}$N$_2$O$_3$S: C, 63.14; H, 5.30; N, 8.18. Found: C, 63.15; H, 5.35; N, 8.11.

EXAMPLE 22

4-(3,4,5-trifluorophenyl)-4,6,7,8-tetrahydro-2-methyl-3-(methylsulfonyl)-5(1H)-quinolinone 3,4,5-Trifluoromethylbenzaldehyde (160 mg, 1.00 mmol) was processed as in Example 20 to provide the title compound.
MS(APCI) m/e 370 (M-H)–, 406 (M+Cl)–;
$^1$H NMR (DMSO-d$_6$) δ 1.75 (m, 1H), 1.90 (m, 1H), 2.22 (m, 2H), 2.33 (s, 3H), 2.52 (m, 2H), 2.76 (s, 3H), 4.97 (s, 1H), 7.00 (m, 2H), 9.51 (br s, 1H);
Anal. Calcd for C$_{17}$H$_{16}$F$_3$NO$_3$S: C, 54.98; H, 4.34; N, 3.77. Found: C, 55.14; H, 4.16; N, 3.76.

EXAMPLE 23

4,6,7,8-tetrahydro-2-methyl-4-(4-methyl-3-nitrophenyl)-3-(methylsulfonyl)-5(1H)-quinolinone 4-Methyl-3-nitrobenzaldehyde (165 mg, 1.00 mmol) was processed as in Example 20 to provide the title compound.
MS(APCI) m/e 377 (M+H)$^+$;
$^1$H NMR (DMSO-d$_6$) δ 1.73 (m, 1H), 1.90 (m, 1H), 2.20 (m, 2H), 2.32 (s, 3H), 2.45 (s, 3H), 2.50 (m, 2H), 2.70 (s, 3H), 5.00 (s, 1H), 7.39 (d, 1H), 7.43 (dd, 1H), 7.75 (d, 1H), 9.48 (br s, 1H);
Anal. Calcd for C$_{18}$H$_2$ON$_2$O$_5$S: C, 57.43; H, 5.36; N, 7.44. Found: C, 57.41; H, 5.28; N, 7.48.

EXAMPLE 24

4-(4-chloro-3-nitrophenyl)-4,6,7,8-tetrahydro-2-methyl-3-(methylsulfonyl)-5(1H)-quinolinone 4-Chloro-3-nitrobenzaldehyde (185 mg, 1.00 mmol) was processed as in Example 20 to provide the title compound.
MS(APCI) m/e 397 (M+H)$^+$;
$^1$H NMR (DMSO-d$_6$) δ 1.75 (m, 1H), 1.90 (m, 1H), 2.22 (m, 2H), 2.33 (s, 3H), 2.50 (m, 2H), 2.78 (s, 3H), 5.02 (s, 1H), 7.50 (dd, 1H), 7.67 (d, 1H), 7.76 (d, 1H), 9.51 (br s, 1H);
Anal. Calcd for C$_{17}$H$_{17}$ClN$_2$O$_5$S: C, 51.45; H, 4.32; N, 7.06. Found: C, 51.50; H, 4.26; N, 7.10.

EXAMPLE 25

4-(3-bromo-4-fluorophenyl)-4,6,7,8-tetrahydro-2-methyl-3-(methylsulfonyl)-5(1H)-quinolinone 3-Bromo-4-fluorobenzaldehyde (203 mg, 1.00 mmol) was processed as in Example 20 to provide the title compound.
MS(APCI) m/e 414 (M+H)$^+$;
$^1$H NMR (DMSO-d$_6$) δ 1.75 (m, 1H), 1.90 (m, 1H), 2.22 (m, 2H), 2.31 (s, 3H), 2.50 (m, 2H), 2.70 (s, 3H), 4.94 (s, 1H), 7.25 (m, 2H), 7.40 (dd, 1H), 9.47 (br s, 1H);
Anal. Calcd for C$_{17}$H$_{17}$BrFNO$_3$S: C, 49.29; H, 4.14; N, 3.38. Found: C, 49.57; H, 3.93; N, 3.39.

EXAMPLE 26

4,6,7,8-tetrahydro-2-methyl-3-(methylsulfonyl)-4-(3-nitrophenyl)-5(1H)-quinolinone 3-Nitrobenzaldehyde (151 mg, 1.00 mmol) was processed as in Example 20 to provide the title compound.
MS(APCI) m/e 363 (M+H)$^+$;
$^1$H NMR (DMSO-d$_6$) δ 1.70 (m, 1H), 1.90 (m,1H), 2.32 (s, 3H), 2.50 (m, 2H), 2.70 (s, 3H), 5.07 (s, 1H), 7.57 (t, 1H), 7.65 (dt, 1H), 8.00 (m, 2H), 9.50 (br s, 1H);
Anal. Calcd for C$_{17}$H$_{18}$N$_2$O$_5$S: C, 56.34; H, 5.01; N, 7.73. Found: C, 56.39; H, 4.92; N, 7.75.

EXAMPLE 27

4-(4-chloro-3-fluorophenyl)-4,6,7,8-tetrahydro-2-methyl-3-(methylsulfonyl)-5(1H)-quinolinone 4-Chloro-3-fluorobenzaldehyde (159 mg, 1.00 mmol) was processed as in Example 20 to provide the title compound.
MS(APCI) m/e 370 (M+H)$^+$;
$^1$H NMR (DMSO-d$_6$) δ 1.73 (m, 1H), 1.90 (m, 1H), 2.21 (m, 2H), 2.31 (s, 3H), 2.50 (m, 2H), 2.70 (s, 3H), 4.96 (s, 1H), 7.10 (m, 2H), 7.46 (t, 1H), 9.46 (br s, 1H);
Anal. Calcd for C$_{17}$H$_{17}$ClFNO$_3$S: C, 55.21; H, 4.63; N, 3.79. Found: C, 55.07; H, 4.50; N, 3.67.

EXAMPLE 28

4,6,7,8-tetrahydro-2-methyl-3-(methylsulfonyl)-4-[4-(trifluoromethyl)phenyl]-5(1H)-quinolinone 4-Trifluoromethylbenzaldehyde (137 μL, 1.00 mmol) was processed as in Example 20 to provide the title compound.
MS(APCI) m/e 386 (M+H)$^+$;
$^1$H NMR (DMSO-d$_6$) δ 1.72 (m, 1H), 1.90 (m, 1H), 2.21 (m, 1H), 2.31 (s, 3H), 2.50 (m, 3H), 2.63 (s, 3H), 5.02 (s, 1H), 7.41 (d, 2H), 7.61 (d, 2H), 9.65 (br s, 1H);
Anal. Calcd for C$_{18}$H$_{18}$F$_3$NO$_3$S: C, 56.10; H, 4.71; N, 3.63. Found: C, 56.13; H, 4.61; N, 3.56.

EXAMPLE 29

9-(3,4-dichlorophenyl)-2,3,5,6,7,9-hexahydrothieno [3,2-b]quinolin-8(4H)-one, 1,1-dioxide A solution of tetrahydrothiophene-3-oxo-1,1-dioxide (144 mg, 1.07 mmol) prepared according to the method in J.

Heterocycl. Chem., v. 27 pp. 1453 (1990), 3,4-dichlorobenzaldehyde (175 mg, 1.00 mmol) and 3-amino-2-cyclohexen-1-one (111 mg, 1.00 mmol) in ethanol (7 mL) was heated to reflux for 24 hours. The precipitate was isolated, heated to reflux in toluene (5 mL) for 24 hours, and cooled. The solid that precipitated was collected, washed with toluene and ethanol and triturated to provide the title compound.
MS(APCI) m/e 384 (M+H)$^+$;
$^1$H NMR (DMSO-d$_6$) δ 1.75–2.0 (m, 2H), 2.23 (m, 2H), 2.57 (m, 2H), 2.85 (dt, 1H), 3.03 (dt, 1H), 3.38 (m, 2H), 4.84 (s, 1H), 7.17 (dd, 1H), 7.35 (d, 1H), 7.50 (d, 1H), 9.85 (br s, 1H);
Anal. Calcd for C$_{17}$H$_{15}$Cl$_2$NO$_3$S: C, 53.14; H, 3.93; N, 3.64. Found: C, 52.97; H, 3.90; N, 3.56.

EXAMPLE 30

9-(3-cyanophenyl)-2,3,5,6,7,9-hexahydrothieno [3.2-b]quinolin-8(4H)-one, 1,1-dioxide 3-Cyanobenzaldehyde (136 mg, 1.04 mmol) was processed as in Example 29 to provide the title compound.
MS(APCI) m/e 341 (M+H)$^+$;
$^1$HNMR (DMSO-d$_6$) δ 1.88 (m, 2H), 2.22 (m, 2H), 2.56 (m, 2H), 2.85 (dtd, 1H), 3.03 (dt, 1H), 3.36 (m, 2H), 4.90 (s, 1H), 7.45 (td, 1H), 7.54 (dd, 1H), 7.56 (d, 1H), 7.61 (dd, 1H), 9.81 (br s, 1H);
Anal. Calcd for C$_{18}$H$_{16}$N$_2$O$_3$S: C, 63.51; H, 4.73; N, 8.22. Found: C, 63.31;H, 4.61; N, 8.19.

EXAMPLE 31

9-[4-fluoro-3-(trifluoromethyl)phenyl]-2,3,5,6,7,9-hexahydrothieno[3,2-b]quinolin-8(4H)-one, 1,1-dioxide 4-Fluoro-3-trifluoromethylbenzaldehyde (130, μL) was processed as in Example 29 to provide the title compound.
MS(APCI) m/e 402 (M+H)$^+$;
$^1$HNMR (DMSO-d$_6$) δ 1.88 (m, 2H), 2.23 (m, 2H), 2.55 (m, 2H), 2.85 (dtd, 1H), 3.03 (dt, 1H), 3.35 (m, 2H), 4.95 (s, 1H), 7.40 (dd, 1H), 7.52 (m, 2H), 9.60 (br s, 1H);
Anal. Calcd for C$_{18}$H$_{15}$F$_4$NO$_3$S.0.25H$_2$O: C, 53.27; H, 3.85; N, 3.49. Found: C, 53.29; H, 3.74; N, 3.55.

EXAMPLE 32

2,3,5,6,7,9-hexahydro-9-(4-methyl-3-nitrophenyl) thieno [3,2-b]quinolin-8(4H)-one, 1,1-dioxide 4-Methyl-3-nitrobenzaldehyde (165 mg, 1.00 mmol) was processed as in Example 29 to provide the title compound.
MS(APCI) m/e 375 (M+H)$^+$;
$^1$H NMR (DMSO-d$_6$) δ 1.88 (m, 2H), 2.23 (m, 2H), 2.45 (s, 3H), 2.56 (m, 2H), 2.85 (dtd, 1H), 3.03 (dt, 1H), 3.35 (m, 2H), 4.93 (s, 1H), 7.36 (d, 1H), 7.45 (dd, 1H), 7.72 (d, 1H), 9.83 (br s, 1H);
Anal. Calcd for C$_{18}$H$_{18}$N$_2$O$_5$S.0.25H$_2$O: C, 57.06; H, 4.92; N, 7.39. Found: C, 57.24; H, 4.77; N, 7.23.

EXAMPLE 33

9-(3.4-difluorophenyl)-2,3,5,6,7,9-hexahydrothieno [3,2-b]quinolin-8(4H)-one, 1,1-dioxide 3,4-Difluorobenzaldehyde (110 μL, 1.00 mmol) was processed as in Example 29 to provide the title compound.
MS(APCI) m/e 352 (M+H)$^+$;
$^1$H NMR (DMSO-d$_6$) δ 1.90 (m, 2H), 2.23 (m, 2H), 2.55 (m, 2H), 2.82 (dt, 1H), 3.02 (dt, 1H), 3.35 (m, 2H), 4.86 (s, 1H), 7.02 (m, 1H), 7.15 (ddd, 1H), 7.29 (dt, 1H), 9.79 (br s, 1H);
Anal. Calcd for C$_{17}$H$_{15}$F$_2$NO$_3$S: C, 58.11; H, 4.30; N, 3.99. Found: C, 57.90; H, 3.96; N, 3.88.

EXAMPLE 34

9-(4-chloro-3-nitrophenyl)-2,3,5,6,7,9-hexahydrothieno [3,2-b]quinolin-8(4H)-one, 1,1-dioxide 4-Chloro-3-nitrobenzaldehyde (185 mg, 1.00 mmol) was processed as in Example 29 to provide the title compound.
MS(APCI) m/e 393 (M-H)$^-$, 395 (M-H)$^-$;
$^1$H NMR (DMSO-d$_6$) δ 1.90 (m, 2H), 2.23 (m, 2H), 2.55 (m, 2H), 2.85 (dtd, 1H), 3.01 (dt, 1H), 3.35 (m, 2H), 4.95 (s, 1H), 7.51 (dd, 1H), 7.64 (d, 1H), 7.79 (d, 1H), 9.88 (br s, 1H);
Anal. Calcd for C$_{17}$H$_{15}$ClN$_2$O$_5$S: C, 51.71; H, 3.38; N, 7.09. Found: C, 51.46; H, 3.86; N, 6.95.

EXAMPLE 35

1-[8-(3,4-dichlorophenyl)-3,4,5,8-tetrahydro-6-methyl-1,1-dioxido-2H-thiopyrano [3,2-b]pyridin-7-yl]ethan-1-one A solution of tetrahydrothiopyran-3-one-1,1-dioxide (255 mg, 1.72 mmol), 3,4-dichlorobenzaldehyde (250 mg, 1.43 mmol) and 4-amino-3-penten-2-one (140 mg, 1.41 mmol) in ethanol (5 mL) was heated to reflux for 24 hours and cooled. The solid that precipitated was collected, washed with ethanol, and dried to provide the title compound.
MS(APCI) m/e 386 (M+H)$^+$, 388 (M+H)$^+$;
$^1$H NMR (DMSO-d$_6$) δ 2.19 (m, 2H), 2.20 (s, 3H), 2.30 (s, 3H), 2.50 (m, 2H), 3.20 (m, 2H), 5.07 (s, 1H), 7.15 (dd, 1H), 7.34 (d, 1H), 7.51 (d, 1H), 9.15 (br s, 1H);
Anal. Calcd for C$_{17}$H$_{17}$Cl$_2$NO$_3$S: C, 52.86; H, 4.44; N, 3.63. Found: C, 52.74; H, 4.39; N, 3.64.

EXAMPLE 36

1-[8-(4-chloro-3-nitrophenyl)-3,4,5,8-tetrahydro-6-methyl-1,1-dioxido-2H-thiopyrano [3.2-pyridin-7-yl]ethan-1-one 4-Chloro-3-nitrobenzaldehyde (220 mg, 1,19 mmol) was processed as in Example 35 to provide the title compound.
MS(APCI) m/e 397 (M+H)$^+$;
$^1$H NMR (DMSO-d$_6$) δ 2.19 (m, 2H), 2.23 (s, 3H), 2.31 (s, 3H), 2.4–2.6 (m, 2H), 3.1–3.3 (m, 2H), 5.15 (s, 1H), 7.49 (dd, 1H), 7.64 (d, 1H), 7.76 (d, 1H), 9.19 (br s, 1H);
Anal. Calcd for C$_{17}$H$_{17}$ClN$_2$O$_5$S: C, 51.45; H, 4.32; N, 7.06. Found: C, 51,18; H, 4.12; N, 7.03.

EXAMPLE 37

9-(3,4-dichlorophenyl)-3,4,5,6,7,9-hexahydrocyclopenta[b]thiopyrano [2,3-e]pyridin-8(2H)-one, 1,1-dioxide A solution of tetrahydrothiopyran-3-one-1,1-dioxide (175 mg, 1.20 mmol), 3,4-dichlorobenzaldehyde (175 mg, 1.00 mmol) and 3-amino-2-cyclopenten-1-one, prepared by the method described in Synthesis, p. 176 (1990)(101 mg, 1.05 mmol) in ethanol (5 mL) was heated to reflux for 24 hours, and cooled. The solid that precipitated was collected, washed with ethanol and dried to provide the title compound.
MS(APCI) m/e 384 (M+H)$^+$;
$^1$H NMR (DMSO-d$_6$) δ 2.25 (m, 4H), 2.60 (m, 4H), 3.20 (m, 2H), 4.82 (s, 1H), 7.20 (dd, 1H), 7.36 (d, 1H), 7.52 (d, 1H), 9.98 (br s, 1H);

EXAMPLE 38

9-(4-chloro-3-nitrophenyl)-3,4,5,6,7,9-hexahydrocyclopenta[b]thiopyrano [2.3-e]pyridin-8(2H)-one, 1,1-dioxide 4-Chloro-3-nitrobenzaldehyde (187 mg, 1.01 mmol) was processed as in Example 37 to provide the title compound.
MS(APCI) m/e 395 (M+H)$^+$;
$^1$H NMR (DMSO-d$_6$) δ 2.25 (m, 4H), 2.60 (m, 4H), 3.24 (m, 2H), 4.93 (s, 1H), 7.55 (dd, 1H), 7.67 (d, 1H), 7.80 (d, 1H), 10.03 (br s, 1H);
Anal. Calcd for $C_{17}H_{15}ClN_2O_5S.0.25H_2O$: C, 51.13; H, 3.91; N, 7.01. Found: C, 50.96; H, 4.02; N, 6.79.

EXAMPLE 39

9-(3-chloro-4-fluorophenyl)-3,4,5,6,7,9-hexahydrocyclopenta[b]thiopyrano [2,3-e]pyridin-8(2H)-one, 1,1-dioxide 3-Chloro-4-fluorobenzaldehyde (158 mg, 1.00 mmol) was processed as in Example 37 and recrystallized from methanol/ethyl acetate to provide the title compound.
MS(APCI) m/e 368 (M+H)$^+$, 370 (M+H)$^+$;
$^1$H NMR (DMSO-d$_6$) δ 2.25 (m, 4H), 2.62 (m, 4H), 3.20 (m, 2H), 4.93 (s, 1H), 7.20 (ddd, 1H), 7.30 (m, 2H), 9.96 (br s, 1H);
Anal. Calcd for $C_{17}H_{15}ClFNO_3S$: C, 55.51; H, 4.11; N, 3.81. Found: C, 55.24; H, 3.85; N,3.67.

EXAMPLE 40

9-(3-bromo-4-fluorophenyl)-3,4,5,6,7,9-hexahydrocyclopenta[b]thiopyrano [2.3-e]pyridin-8(2H)-one, 1,1-dioxide 3-Bromo-4-fluorobenzaldehyde (212 mg, 1.04 mmol) was processed as in Example 37 to provide the title compound.
MS(APCI) m/e 412 (M+H)$^+$, 414 (M+H)$^+$;
$^1$H NMR (DMSO-d$_6$) δ 2.25 (m, 4H), 2.60 (m, 4H), 3.20 (m, 2H), 4.83 (s, 1H), 7.25 (m, 2H), 7.41 (dd, 1H), 9.96 (br s, 1H);
Anal. Calcd for $C_{17}H_{15}BrFNO_3S.0.25H_2O$: C, 48.99; H, 3.75; N, 3.36. Found: C, 48.98; H, 3.63; N, 3.28.

EXAMPLE 41

9-(3-nitrophenyl)-2,3,5,6,7,9-hexahydrothieno[3,2-b]quinolin-8(4H)-one, 1,1-dioxide 3-Nitrobenzaldehyde (153 mg, 1.01 mmol) was processed as in Example 29 to provide the title compound.
MS(APCI) m/e 359 (M-H)−;
$^1$H NMR (DMSO-d$_6$) δ 1.83 (m, 1H), 1.92 (m, 1H), 2.24 (m, 2H), 2.57 (m, 2H), 2.85 (dtd, 1H), 3.05 (dt, 1H), 3.35 (m, 2H), 4.99 (s, 1H), 7.55 (t, 1H), 7.67 (dt, 1H), 7.98 (t, 1H), 8.03 (ddd, 1H), 9.91 (s, 1H);
Anal. Calcd for $C_{17}H_{16}N_2O_5S$: C, 56.65; H, 4.47; N, 7.77. Found: C, 56.67; H, 4.35; N, 7.59.

EXAMPLE 42

9-(3-cyano)-3,4,5,6,7,9-hexahydrocyclopenta[b]thiopyrano [2,3-e[pyridin-8(2H)-one, 1,1-dioxide 3-Cyanobenzaldehyde (131 mg, 1.0 mmol) was processed as in Example 37 to provide the title compound.
MS(APCI); m/e 339 (M-H)−;
$^1$H NMR (DMSO-d$_6$) δ 2.25 (m, 4H), 2.60 (m, 4H), 3.21 (m, 2H), 4.89 (s, 1H), 7.47 (t, 1H), 7.57 (dd, 1H), 7.59 (d, 1H), 7.64 (dt, 1H), 9.98 (br s, 1H);
Anal. Calcd for $C_{18}H_{16}N_2O_3S.0.25H_2O$: C, 62.68; H, 4.82; N, 8.12. Found: C, 62.53; H, 4.53; N, 8.08.

EXAMPLE 43

9-(3-bromo-4-fluoronhenyl)-2,3,5,6,7,9-hexahydrothieno [3,2-b]quinolin-8(4H)-one, 1,1-dioxide 3-Bromo-4-fluorobenzaldehyde (201 mg, 0.99 mmol) was processed as in Example 29 and recrystallized from methanol/chloroform to provide the title compound.
MS(APCI); m/e 410 (M-H)−, 412 (M-H)−;
$^1$H NMR (DMSO-d$_6$) δ 1.88 (m, 2H), 2.23 (m, 2H), 2.56 (m, 2H), 2.83 (dtd, 1H), 3.03 (dt, 1H), 3.33 (t, 2H), 4.85 (s, 1H), 7.22 (m, 2H), 7.40 (dd, 1H), 9.78 (br s, 1H);
Anal. Calcd for $C_{17}H_{15}BrFNO_3S$: C, 49.52; H, 3.66; N, 3.39. Found: C, 49.19; H, 3.59; N, 3.24.

EXAMPLE 44

8-(4-chloro-3-nitrophenyl)-2,3,4,5,6,8-hexahydro-7H-cyclopenta[b]thieno[2,3-e]pyridin-7-one 1,1-dioxide A solution of tetrahydrothiophene-3-oxo-1,1-dioxide (171 mg, 1.28 mmol), 4-chloro-3-nitrobenzaldehyde (210 mg, 1.13 mmol) and 3-amino-2-cyclopenten-1-one (110 mg, 1.13 mmol) in ethanol (3 mL) was heated to reflux for 24 hours and cooled. The precipitate was collected, washed with ethanol, dried and recrystallized from methanol/ chloroform to provide the title compound.
MS(APCI); m/e 379 (M-H)−;
$^1$H NMR (DMSO-d$_6$) δ 2.30 (t, 2H), 2.65 (m, 2H), 2.89 (dt, 1H), 3.05 (dt, 1H), 3.40 (t, 2H), 4.87 (s, 1H), 7.58 (dd, 1H), 7.68 (d, 1H), 7.88 (d, 1H), 10.4 (s, 1H);
Anal. Calcd for $C_{16}H_{13}ClN_2O_5S$ .0.25 $CH_3OH$: C, 50.19; H, 3.62; N, 7.20. Found: C, 49.87; H, 3.26; N, 7.07.

EXAMPLE 45

10-(4-chloro-3-nitrolphenyl)-3,4,6,7,8,10-hexahydro-2H,5H-bisthiopyrano [3,2-b:2',3'-e] pyridine 1,1,9,9-tetraoxide A solution of tetrahydrothiopyran-3-one, 1,1-dioxide (150 mg, 1.01 mmol), 4-chloro-3-nitrobenzaldehyde (95 mg, 0.51 mmol) and concentrated ammonium hydroxide (0.5 mL) was heated to 78° C. in ethanol (1 mL) for 24 hours in a sealed tube and cooled. The solid that precipitated was washed with ethanol, dried and triturated with hot acetone to provide the title compound.
MS(APCI); m/e 443 (M-H)−;
$^1$H NMR (DMSO-d$_6$) δ 2.18 (m, 4H), 2.50 (m, 4H), 3.20 (m, 4H), 5.18 (s, 1H), 7.51 (dd, 1H), 7.69 (d, 1H), 7.76 (d, 1H), 9.24 (s, 1H);
Anal. Calcd for $C_{17}H_{17}ClN_2O_6S_2.0.15$ $NH_4OH$: C, 45.36; H, 3.99; N, 6.72. Found: C, 45.71; H, 3.85; N, 7.02.

EXAMPLE 46

10-(3-pyridyl)-3 4,6,7,8,10-hexahydro-2H-thiopyrano [3,2-b]quinolin-9(5H)-one, 1,1-dioxide 3-Pyridinecarboxaldehyde (94 μL, 1.0 mmol) was processed as in Example 1 with recrystallization from methanol to provide the title compound.

MS(APCI); m/e 331 (M+H)+;
¹H NMR (DMSO-d₆) δ 1.75 (m, 1H), 1.90 (m, 1H), 2.20 (m, 4H), 2.53 (m, 4H), 3.20 (m, 2H), 5.03 (s, 1H), 7.25 (dd, 1H), 7.52 (dt, 1H), 8.31 (dd, 1H), 8.38 (d, 1H), 9.40 (br s, 1H);
Anal. Calcd for C₁₇H₁₈N₂O₃S·H₂O:C, 58.60; H, 5.79; N, 8.04. Found: C, 58.79; H, 5.81; N, 7.63.

EXAMPLE 47

10-(4-pyridyl)-3,4,6,7,8,10-hexahydro-2H-thiopyrano [3,2-b]quinolin-9(5H)-one, 1,1-dioxide 4-Pyridinecarboxaldehyde (95 μL, 1.0 mmol) was processed as in Example 1 and recrystallized from methanol to provide the title compound.
MS(APCI); m/e 331 (M+H)+;
¹H NMR (DMSO-d₆) δ 1.75 (m, 1H), 1.90 (m, 1H), 2.20 (m, 4H), 2.53 (m, 4H), 3.20 (m, 2H), 5.03 (s, 1H), 7.20 (d, 2H), 8.41 (d, 2H), 9.44 (br s, 1H);
Anal. Calcd for C₁₇H₁₈N₂O₃S: C, 61.80; H, 5.49; N, 8.48. Found: C, 61.71; H, 5.40; N, 8.42.

EXAMPLE 48

9-(4-fluoro-3-trifluoromethyl)-3,4,5,6,7,9-hexahydrocyclopenta[b]thiopyrano [2,3-e]pyridin-8(2H)-one, 1,1-dioxide 4-Fluoro-3-trifluoromethylbenzaldehyde (130 μL) was processed as in Example 37 to provide the title compound.
MS(APCI); m/e 400 (M-H)−;
¹H NMR (DMSO-d₆) δ 2.25 (m, 4H), 2.58 (m, 4H), 3.20 (m, 2H), 4.92 (s, 1H), 7.40 (dd, 1H), 7.54 (m, 2H), 9.96 (br s, 1H);
Anal. Calcd for C₁₈H₁₅F₄NO₃S: C, 53.86; H, 3.77; N, 3.49. Found: C, 53.60; H, 3.82; N, 3.38.

EXAMPLE 49

9-(4-methyl-3-nitro)-3,4,5,6,7,9-hexahydrocyclopenta[b]thiopyrano [2,3-e]pyridin-8(2H)-one, 1,1-dioxide 4-Methyl-3-nitrobenzaldehyde (165 mg, 1.00 mmol) was processed as in Example 37 to provide the title compound.
MS(APCI); m/e 373 (M-H)−;
¹H NMR (DMSO-d₆) δ 2.24 (m, 4H), 2.45 (s, 3H), 2.60 (m, 4H), 3.20 (m, 2H), 4.90 (s, 1H), 7.38 (d, 1H), 7.46 (dd, 1H), 7.73 (d, 1H), 9.97 (br s, 1H);
Anal. Calcd for C₁₈H₁₈N₂O₅S: C, 57.74; H, 4.85; N, 7.48. Found: C, 57.43; H, 4.72; N, 7.34.

EXAMPLE 50

9-(3.4-difluorophenyl)-3,4,5,6,7,9-hexahydrocyclopenta[b]thiopyrano [2,3-e]pyridin-8(2H)-one, 1,1-dioxide 3,4-Difluorobenzaldehyde (110 μL) was treated according to the procedure described in Example 37 to provide 107 mg of the title compound as a white solid.
¹H NMR (DMSO-d₆) δ 2.25 (m, 4H), 2.60 (m, 4H), 3.20 (m, 2H), 4.83 (s, 1H), 7.05 (m, 1H), 7.16 (ddd, 1H), 7.30 (dt, 1H), 9.95 (br s, 1H);
MS(APCI-) m/z 350 (M-H)−;
Anal. Calcd for C₁₇H₁₅F₂NO₃S: C, 58.11; H, 4.30; N, 3.98. Found: C, 58.10; H, 4.32; N, 3.94.

EXAMPLE 51

8-(4-chloro-3-nitrophenyl)-2,3,4,5,6,8-hexahydrodithieno [3,2-b:2',3'-e]pyridine, 1,1 7,7-tetraoxide 4-Chloro-3-nitrobenzaldehyde (215 mg, 1.16 mmol), tetrahydrothiophene-3-oxo-1,1-dioxide (310 mg, 2.32 mmol) and 2.0 M NH₃ in ethyl alcohol (0.75 mL, 1.5 mmol) were heated in ethyl alcohol (4 mL) for 3 days at 80° C. in a sealed tube, cooled, the solid precipitate collected, and washed with ethyl alcohol. The solid was then heated to reflux in toluene with catalytic para-toluenesulfonic acid, cooled, the solid collected, washed with toluene, ethyl alcohol, methyl alcohol and dried. Trituration with hot methyl alcohol/chloroform (1:1) gave 184 mg of off-white solid.
¹H NMR (DMSO-d₆) δ 2.85 (m, 2H), 3.00 (dt, 2H), 3.40 (m, 4H), 5.12 (s, 1H), 7.63 (dd, 1H), 7.72 (d, 1H), 7.97 (d, 1H), 10.11 (br s, 1H);
MS(APCI-) m/z 415 (M-H)−;
Anal. Calcd for C₁₅H₁₃ClN₂O₆S₂·0.1 toluene: C, 44.26; H, 3.26; N, 6.57. Found: C, 44.63; H, 3.06; N, 6.53.

EXAMPLE 52

8-(3-cyanophenyl)-2,3,4,5,6,8-hexahydro-7H-cyclopenta[b]thieno [2,3-e]pyridin-7-one, 1,1-dioxide 3-Cyanobenzaldehyde (206 mg, 1.57 mmol), tetrahydrothiophene-3-oxo-1,1-dioxide (212 mg, 1.58 mmol), and 3-amino-2-cyclopenten-1-one (150 mg, 1.55 mmol) were heated in ethanol (4 mL) to 80° C. for 3 days in a sealed tube, cooled, the solid precipitate collected and washed with ethanol. The solid was then heated to reflux in ethanol (10 mL) with 1N HCl in ether (0.5 mL) for 2 hours, cooled and the solvent evaporated. The crude oil was triturated with ethyl acetate, and the resultant solid collected, washed with ethyl acetate and dried to provide 252 mg of a tan solid.
mp 156–176° C.;
¹H NMR (DMSO-d₆) δ 2.30 (t, 2H), 2.63 (m, 2H), 2.88 (dt, 1H), 3.07 (dt, 1H), 3.40 (t, 2H), 4.70 (s, 1H), 7.49 (t, 1H), 7.60 (d, 1H), 7.64 (s, 1H), 7.66 (dd, 1H), 10.38 (s, 1H);
MS(APCI-) m/z 325 (M-H)−;
Anal. Calcd for C₁₇H₁₄N₂O₃S·0.33 EtOAc·0.75H₂O:C, 59.64; H, 4.95; N, 7.59. Found: C, 59.32;H, 4.77; N, 7.41.

EXAMPLE 53

8-(3-bromo-4-fluorophenyl)-2,3,4,5,6,8-hexahydrodithieno [3,2-b:2',3'-e]pyridine, 1,1,7,7-tetraoxide 3-Bromo-4-fluorobenzaldehyde (305 mg, 1.5 mmol), tetrahydrothiophene-3-oxo-1,1-dioxide (402 mg, 3.00 mmol), and 2.0 M NH₃ in ethanol (1,1 mL, 2.2 mmol) in ethanol (3 mL) were heated to 80° C. for 3 days in a sealed tube, cooled, the solid precipitate collected, and washed with ethanol. The solid was heated to reflux overnight in ethanol with 1.0 M HCl in ether (1 mL), cooled, the solid collected, washed with ethanol and dried to provide 185 mg of the title compound as an off-white solid.
¹H NMR (DMSO-d₆) δ2.80 (m, 2H), 3.01 (dt, 2H), 3.35 (m, 4H), 4.97 (s, 1H), 7.30 (m, 2H), 7.53 (dd, 1H), 9.19 (br s, 1H);
MS(APCI) m/z 432 (M-H)−;
Anal. Calcd for C₁₅H₁₃BrFNO₄S₂: C, 41.48; H, 3.01; N, 3.22. Found: C, 41.61; H, 2.76; N, 3.14.

EXAMPLE 54

10-(3-bromo-4-fluorophenyl)-3,4,6,7,8,10-hexahydro-2H,5H-dithiopyrano [3,2-b:2',3'-e] pyridine, 1,1,9,9-tetraoxide 3-Bromo-4-fluorobenzaldehyde (202 mg, 1.0 mmol), tetrahydrothiopyran-3-one-1,1-dioxide (305 mg, 2.06 mmol) and 2.0 M NH₃ in ethanol (0.70 mL, 1.4 mmol) were heated in ethanol (3 mL) to 80° C. for 5 days in a sealed tube, cooled, the solid precipitate collected and washed with ethanol. The solid in toluene (10 mL) was then heated to reflux overnight, cooled, the solid collected, washed with ethanol and dried to provide 129 mg of the title compound as a white solid.
$^1$H NMR (DMSO-d$_6$) δ2.17 (m, 4H), 2.50 (m, 4H), 3.18 (m, 4H), 5.09 (s, 1H), 7.24 (m, 2H), 7.38 (dd, 1H), 9.11 (s, 1H);
MS(APCI-) m/z 460 (M-H)⁻;
Anal. Calcd for C$_{17}$H$_{17}$BrFNO$_4$S$_2$: C, 44.16; H, 3.70; N, 3.02. Found: C, 43.97; H, 3.80; N, 2.95.

EXAMPLE 55

3,4,5,6,7,9-hexahydro-9-(3-nitrophenyl)cyclopenta[b]thiopyrano[2,3-e]pyridin-8(2H)-one, 1,1-dioxide 3-Nitrobenzaldehyde (153 mg, 1.0 mmol), tetrahydrothiopyran-3-one-1,1-dioxide (148 mg, 1.00 mmol) and 3-amino-2-cyclopenten-1-one (97 mg, 1.00 mmol) were heated in ethanol (3 mL) to 80° C. for 5 days in a sealed tube, cooled, the solid precipitate collected, washed with ethanol and dried to provide 145 mg of the title compound as a tan solid.
mp>260° C.;
$^1$H NMR (DMSO-d$_6$) δ 2.25 (m, 4H), 2.60 (m, 4H), 3.23 (m, 2H), 4.98 (s, 1H), 7.57 (t, 1H), 7.69 (d, 1H), 8.00 (s, 1H), 8.04 (d, 1H), 10.03 (br s, 1H);
MS(APCI-) m/z 359 (M-H)⁻;
Anal. Calcd for C$_{17}$H$_{16}$N$_2$O$_5$S: C, 56.65; H, 4.47; N, 7.77. Found: C, 56.34; H, 4.44; N, 7.50.

EXAMPLE 56

8-(3-bromo-4-fluorophenyl)-2,3,4,5,6,8-hexahydro-7H-cyclopenta[b]thieno[2,3-e]pyridin-7-one, 1,1-dioxide 3-Bromo-4-fluorobenzaldehyde (250 mg, 1.23 mmol) was treated according to the procedure described in Example 44, except that the heating phase was for 3 days and no recrystallization was necessary, to provide 241 mg of the title compound as an off-white solid.
mp >260° C.;
$^1$H NMR (DMSO-d$_6$) δ 2.30 (t, 2H), 2.63 (m, 2H), 2.85 (dt, 1H), 3.06 (dt, 1H), 3.40 (t, 2H), 4.72 (s, 1H), 7.27 (m, 2H), 7.47 (d, 1H), 10.33 (br s, 1H);
MS(APCI-) m/z 396 (M-H)⁻;
Anal. Calcd for C$_{16}$H$_{13}$BrFNO$_3$S: C, 48.25; H, 3.29; N, 3.52. Found: C, 48.26; H, 3.17; N, 3.34.

EXAMPLE 57

8-(4-fluoro-3-trifluoromethylphenyl)-2,3,4,5,6,8-hexahydro-7H-cyclopenta[b]thieno[2.3-e]pyridin-7-one, 1,1-dioxide 4-Fluoro-3-trifluoromethylbenzaldehyde (0.20 mL), tetrahydrothiophene-3-oxo-1,1-dioxide (136 mg, 1.01 mmol) and 3-amino-2-cyclopenten-1-one (97 mg, 1.00 mmol) were heated in ethanol (4 mL) to 80° C. in a sealed tube for 3 days, cooled and the solvent evaporated. Flash chromatography over silica gel (10% methanol/chloroform) followed by trituration of the product with ethyl acetate provided the title compound as a white solid.
mp 254° C.;
$^1$H NMR (DMSO-d$_6$) δ 2.30 (t, 2H), 2.65 (m, 2H), 2.88 (dt, 1H), 3.06 (dt, 1H), 3.40 (t, 2H), 4.85 (s, 1H), 7.41 (dd, 1H), 7.58 (m, 2H), 10.38 (s, 1H);

MS(APCI-) m/z 386 (M-H)⁻;
Anal. Calcd for C$_{17}$H$_{13}$F$_4$NO$_3$S0.25H$_2$O: C, 52.10; H, 3.47; N, 3.57. Found: C, 52.13; H, 3.31; N, 3.47.

EXAMPLE 58

2,3,4,5,6,8-hexahydro-8-(3-nitrophenyl)-7H-cyclopenta[b]thieno[2.3-e]pyridin-7-one, 1,1-dioxide 3-Nitrobenzaldehyde (225 mg, 1.49 mmol), tetrahydrothiophene-3-oxo-1,1-dioxide (202 mg, 1.51 mmol) and 3-amino-2-cyclopenten-1-one (144 mg, 1.48 mmol) were heated in ethanol (5 mL) to 80° C. in a sealed tube for 3 days, cooled, and the solid precipitate filtered off. The filtrate was treated with 1.0M HCl in ether (0.1 mL), heated to reflux for 1.5 hours, cooled and solvent evaporated. Recrystallization from ethanol provided 130 mg of the title compound as a light yellow solid.
$^1$H NMR (DMSO-d$_6$) δ 2.31 (t, 2H), 2.65 (m, 2H), 2.90 (dt, 1H), 3.08 (dt, 1H), 3.40 (t, 2H), 4.90 (s, 1H), 7.58 (t, 1H), 7.73 (dt, 1H), 8.05 (m, 2H), 10.41 (s, 1H);
MS(APCI-) m/z 345 (M-H)⁻;
Anal. Calcd for C$_{16}$H$_{14}$N$_2$O$_5$S: C, 55.48; H, 4.07; N, 8.08. Found: C, 55.37; H, 4.02; N, 7.88.

EXAMPLE 59

3,4,6,7,8,10-hexahydro-10-(3-nitrophenyl)-2H,5H-dithiopyrano[3.2-b:2',3'-e]pyridine, 1,1,9,9-tetraoxide 3-Nitrobenzaldehyde (153 mg, 1.0 mmol) was treated according to the procedure described in Example 54 to provide 188 mg of the title compound as a white solid.
mp >260° C.;
$^1$H NMR (DMSO-d$_6$) δ 2.19 (m, 4H), 2.52 (m, 4H), 3.20 (m, 4H), 5.23 (s, 1H), 7.60 (t, 1H), 7.68 (d, 1H), 7.98 (s, 1H), 8.08 (d, 1H), 9.23 (br s, 1H);
MS(APCI-) m/z 409 (M-H)⁻;
Anal. Calcd for C$_{17}$H$_{18}$N$_2$O$_6$S$_2$: C, 49.75; H, 4.42; N, 6.82. Found: C, 49.58; H, 4.34; N, 6.79.

EXAMPLE 60

8-(3 4-dichlorophenyl)-2,3 4,5,6,8-hexahydro-7H-cyclopenta[b]thieno[2,3-e]pyridin-7-one, 1,1-dioxide 3,4-Dichlorobenzaldehyde (175 mg, 1.0 mmol) was treated according to the procedure described in Example 52 to provide 204 mg of the title compound as a white solid.
mp >260° C.;
$^1$H NMR (DMSO-d$_6$) δ 2.30 (t, 2H), 2.63 (m, 2H), 2.87 (dt, 1H), 3.05 (dt, 1H), 3.40 (t, 2H), 4.72 (s, 1H), 7.22 (dd, 1H), 7.41 (d, 1H), 7.52 (d, 1H), 10.36 (br s, 1H);
MS(APCI-) m/z 368 (M-H)⁻;
Anal. Calcd for C$_{16}$H$_{13}$Cl$_2$NO$_3$S: C, 51.90; H, 3.54; N, 3.78. Found: C, 51.93; H, 3.59; N, 3.53.

EXAMPLE 61

8-(3-chloro-4-fluorophenyl)-2,3,4,5,6,8-hexahydro-7H-cyclopenta[b]thieno[2,3-e]pyridin-7-one, 1,1-dioxide 3-Chloro-4-fluorobenzaldehyde (0.16 mL) was treated according to the procedure described in Example 56 to provide 107 mg of the title compound as a white solid.
$^1$H NMR (DMSO-d$_6$) δ 2.30 (t, 2H), 2.64 (m, 2H), 2.85 (dt, 1H), 3.05 (dt, 1H), 3.39 (t, 2H), 4.72 (s, 1H), 7.23 (m, 1H), 7.28 (m, 1H), 7.37 (d, 1H), 10.31 (br s, 1H);

MS(APCI-) m/z 352 (M-H)⁻;
Anal. Calcd for $C_{16}H_{13}ClFNO_3S$: C, 54.32; H, 3.70; N, 3.96. Found: C, 54.34; H, 3.68; N, 3.85.

EXAMPLE 62

8-(3-cyanophenyl)-2,3,4,5,6,8-hexahydrodithieno [3.2-b:2',3'-e]pyridine. 1,1,7,7-tetraoxide 3-Cyanobenzaldehyde (132 mg, 1.01 mmol), tetrahydrothiophene-3-oxo-1,1-dioxide (272 mg, 2.03 mmol) and 2.0 M $NH_3$ in ethanol (0.75 mL, 1.5 mmol) were heated to 80° C. in ethanol (4 mL) in a sealed tube for 3 days, cooled, treated with 1.0 M HCl in ether (1 mL), heated to reflux for 1 hour, cooled and solvent evaporated. The crude was flash chromatographed over silica gel (15% methanol/chloroform), and the product triturated with ethyl acetate to provide 87 mg of the title compound as an off-white solid.
mp 248° C.;
¹H NMR (DMSO-$d_6$) δ 2.83 (dt, 2H), 3.02 (dt, 2H), 3.40 (m, 4H), 5.03 (s, 1H), 7.50 (t, 1H), 7.61 (d, 1H), 7.70 (d, 1H), 7.73 (s, 1H), 10.07 (br s, 1H);
MS(APCI-) m/z 361 (M-H)–;
Anal. Calcd for $C_{16}H_{14}N_2O_4S_2 \cdot 0.33$ EtOAc$\cdot 0.6H_2O$: C, 51.71;H, 4.47; N, 6.96. Found: C, 51.84; H, 4.21; N, 6.61.

EXAMPLE 63

8-(2-cyano-4-pyridinyl)-2,3,4,5,6,8-hexahydro-7H-cyclopenta[b]thieno [2,3-e]pyridin-7-one, 1,1-dioxide 2-Cyanopyridine-4-carboxaldehyde (0.20 g, 1.52 mmrol), prepared according to the method of Ashimori (Chem Pharm Bull 1990, 38, 2446), tetrahydrothiophene-3-oxo-1,1-dioxide (241 mg, 1.8 mmol) and 3-amino-2-cyclopenten-1-one (0.146 g, 1.5 mmol) were heated to 40–50° C. in isopropanol for 3 days, cooled, solvent evaporated and flash chromatographed (10% methanol/methylene chloride). The product was dissolved in isopropanol, treated with 1.0M HCl in ether (1.5 mL), heated to 50° C. for 10 minutes, cooled and solvent evaporated. The residue was triturated with ether, collected, washed with ether and dried to provided 63.5 mg of the title compound as a light-yellow powder.
¹H NMR (DMSO-$d_6$) δ 2.30 (t, 2H), 2.65 (m, 2H), 3.02 (m, 2H), 3.45 (t, 2H), 4.85 (s, 1H), 7.64 (d, 1H), 7.94 (s, 1H), 8.65 (d, 1H), 10.48 (s, 1H); MS(APCI-) m/z 326 (M-H)⁻;
Anal. Calcd for $C_{16}H_{13}N_3O_3S \cdot 0.42$ $C_2H_6O \cdot 0.25H_2O \cdot 0.115HCl$: C, 57.31; H, 4.48; N, 11.62; Cl, 1.47. Found: C,57.63; H, 4.74; N, 11.22; Cl, 1.37.

EXAMPLE 64

8-(3-bromophenyl)-2,3,4,5,6,8-hexahydro-7H-cyclopenta[b]thieno [2,3-e]pyridin-7-one, 1,1-dioxide 3-Bromobenzaldehyde (0.12 mL, 1.0 mmol), tetrahydrothiophene-3-oxo-1,1-dioxide (137 mg, 1.02 mmol) and 3-amino-2-cyclopenten-1-one (98 mg, 1.0 mmol) were heated in ethanol (4 mL) to 80° C. in a sealed tube for 3 days, then treated with 1.0 M HCl in ether (0.5 mL), heated to reflux for 3 hours, cooled and solvent evaporated. The crude was flash chromatographed over silica gel (10% methanol/chloroform) and the product triturated with ethyl acetate to provide 147 mg of the title compound as an off-white solid.
mp 246° C.;
¹H NMR (DMSO-$d_6$) δ 2.32 (t, 2H), 2.65 (m, 2H), 2.85 (dt, 1H), 3.07 (dt, 1H), 3.40 (t, 2H), 4.69 (s, 1H), 7.22 (m, 2H), 7.36 (m, 2H), 10.33 (br s, 1H);
MS(APCI-) m/z 378 (M-H)⁻;
Anal. Calcd for $C_{16}H_{14}BrNO_3S$: C, 50.54; H, 3.71; N, 3.68. Found: C, 50.62; H, 3.63; N, 3.54.

EXAMPLE 65

8-(4-fluoro-3-trifluoromethylphenyl)-2,3,4,5,6,8-hexahydrodithieno [3,2-b:2',3'-elpyridine, 1,1,7,7-tetraoxide 4-Fluoro-3-trifluoromethylbenzaldehyde (0.19 mL) was treated according to the procedure described in Example 62 to provide 35 mg of the title compound as a white solid.
mp >260 ° C.;
¹H NMR (DMSO-$d_6$) o 2.83 (dtd, 2H), 3.02 (dt, 2H), 3.39 (m, 4H), 5.11 (s, 1H), 7.45 (dd, 1H), 7.62 (d, 1H), 7.67 (m, 1H), 10.07 (br s, 1H); MS(APC1-) m/z 422 (M-H)⁻;
Anal. Calcd for $C_{16}H_{13}F_4NO_4S_2$: C, 45.39;H, 3.09; N, 3.31. Found: C, 45.23;H, 2.87; N, 3.12.

EXAMPLE 66

1-[8-(3-bromo-4-fluorophenyl)-3,4,5,8-tetrahydro-6-methyl-1.-dioxido-2H-thiopyrano[3,2-b]pyridin-7-yl)lethan-1-one 3-Bromo-4-fluorobenzaldehyde (246 mg, 1.21 mmol) was treated according to the procedure described in Example 35 to provide 325 mg of the title compound as a white solid.
mp >260 ° C.;
¹H NMR (DMSO-$d_6$) δ 2.17 (m, 2H), 2.20 (s, 3H), 2.30 (s, 3H), 2.50 (m, 2H), 3.20 (m, 2H), 5.06 (s, 1H), 7.20 (m, 2H), 7.40 (dd, 1H), 9.11 (s, 1H); MS(APC1-) m/z 412 (M-H)⁻;
Anal. Calcd for $C_{17}H_{17}BrFNO_3S$: C, 49.28;H, 4.13; N, 3.38. Found: C, 49.06;H, 4.10; N, 3.28.

EXAMPLE 67

8-(4-bromo-2-thienyl)-2,3,4,5,6,8-hexahydro-7H-cyclopentafblthieno [2,3-elpyridin-7-one, 1,1-dioxide 4-Bromothiophene-2-carboxaldehyde (500 mg, 2.6 mmol), tetrahydrothiophene-3-oxo-1,1-dioxide (295 mg, 2.2 mmol) and 3-amino-2-cyclopenten-1-one (215 mg, 2.2 mmol) were heated in ethyl alcohol (5 mL) to 80 ° C. in a sealed tube for 2 days, cooled, the solid precipitate collected, washed with ethanol, dissolved in a solution of methanol/methylene chloride 1:3, filtered through cotton, concentrated on a steam bath and allowed to crystallize to provide 0.34 g of the title compound as a light brown solid.
mp 254–255 ° C.; ¹HNMR (DMSO-$d_6$) δ 2.35 (t, 2H), 2.53–2.75 (m, 2H), 2.78–2.91 (m, 1H), 2.97–3.10 (m, 1H), 3.42 (t, 2H), 4.95 (s, 1H), 6.88 (d, 1H), 7.46 (d, 1H), 10.43 (bs, 1H); MS(APCI+) m/z 386 (M+H)⁺, 403 (M+NH$_4$)⁺, MS(APC1-) m/z 384 (M-H)⁻;
Anal. Calcd for $C_{14}H_{12}NO_3S_2Br$: C, 43.53;H, 3.13; N, 3.63. Found: C, 43.39;H, 2.84; N, 3.41.

EXAMPLE 68

8-(5-bromo-2-thienyl)-2,3,4,5,6,8-hexahydro-7H-cyclopenta[b]thieno [2,3-elpyridin-7-one 11-dioxide 5-Bromothiophene-2-carboxaldehyde (500 mg, 2.6 mmol), was treated according to the procedure described in Example 67 to provide 0.297 g of the title compound as a brown solid.

mp 246–247 ° C.;
$^1$H NMR (DMSO-d$_6$) δ 2.35 (t, 2H), 2.52–2.73 (m, 2H), 2.78–2.90 (m, 1H), 2.95–3.08 (m, 1H), 3.41 (t, 2H), 4.92 (s, 1H), 6.73 (d, 1H), 6.97 (d, 1H), 10.39 (s, 1H); MS(APC1-) m/z 384 (M-H)$^-$;
Anal. Calcd for C$_{14}$H$_2$NO$_3$S$_2$Br: C, 43.53;H, 3.13; N, 3.63. Found: C, 43.19;H, 3.16; N, 3.31.

EXAMPLE 69

2,3,4,5,6,8-hexahydro-8-(5-nitro-3-thienyl)-7H-cyclopenta[b]thieno [2,3-e]pyridin-7-one,1-dioxide 2-Nitrothiophene-4-carboxaldehyde (0.41 g, 2.6 mmol) was treated according to the procedure described in Example 67 to provide 0.423 g of the title compound as a brown powder.
$^1$H NMR (DMSO-d$_6$) δ 2.34 (t, 2H), 2.52–2.74 (m, 2H), 2.80–2.92 (m, 1H), 2.98–3.11 (m, 1H), 3.43 (t, 2H), 4.84 (s, 1H), 7.78 (d, 1H), 7.94 (d, 1H), 10.39 (s, 1H); MS(APCl+) m/z 353 (M+H)$^+$, 370 (M+NH$_4$)$^+$, MS(APC1-) m/z 351 (M-H)$^-$;
Anal. Calcd for C$_{14}$H$_2$N$_2$O$_5$S$_2$: C, 47.72;H, 3.43; N, 7.95. Found: C, 47.43;H, 3.22; N, 7.65.

EXAMPLE 70

2,3,4,5,6,8-hexahydro-8-(5-nitro-2-thienyl)-7H-cyclopenta[b]thieno [2,3-e]pyridin-7-one, 1,1-dioxide 5-Nitrothiophene-2-carboxaldehyde (205 mg, 1.30 mmol) was treated according to the procedure described in Example 67 to provide 238 mg of the title compound as a brown solid. mp 251–254 ° C.;
$^1$H NMR (DMSO-d$_6$) δ 2.37 (t, 2H), 2.56–2.78 (m, 2H), 2.83–2.96 (m, 1H), 3.01–3.14 (m, j H), 3.46 (t, 2H), 5.07 (s, 1H), 7.10 (d, 1H), 7.97 (d, 1H), 10.59 (s, 1H); MS(APCl+) rn/z 353 (M+H)$^+$, 370 (M+NH$_4$)$^+$, (APC1-) m/z 351 (M-H)$^-$;
Anal. Calcd for C$_{14}$H$_2$N$_2$O$_5$S$_2$: C, 47.72;H, 3.43; N, 7.95. Found: C, 47.39;H, 3.39; N, 7.67.

EXAMPLE 71

2,3,4,5,6,8-hexahydro-8-(5-nitro-2-furyl)-7H-cyclopenta[b]thieno [2.3-e]pyridin-7-one, 1,1-dioxide 5-Nitro-2-furaldehyde (185 mg, 1.30 mmol) was treated according to the procedure described in Example 67 to provide 117 mg of the title compound as a brown solid.
$^1$H NMR (DMSO-d$_6$) δ 2.38 (t, 2H), 2.57–2.79 (m, 2H), 2.83–2.96 (m, 1H), 2.96–3.09 (m, 1H), 3.43 (t, 2H), 4.96 (s, 1H), 6.71 (d, 1H), 7.65 (d, 1H), 10.52 (s, 1H); MS(APCl+) m/z 337 (M+H)$^+$, 354 (M+NH$_4$)$^+$, MS(APC1-) m/z 335 (M-H)$^-$;
Anal. Calcd for C$_{14}$H$_2$N$_2$O$_6$S: C, 50.00;H, 3.60; N, 8.33. Found: C, 49.80;H, 3.42; N, 8.14.

EXAMPLE 72

8-(3,4-dibromophenyl)-2,3,4,5,6 8-hexahydro-7H-cyclopenta[b]thieno [2.3-e]pyridin-7-one, 1,1-dioxide 3,4-Dibromobenzaldehyde (293 mg, 1,11 mmol), tetrahydrothiophene-3-oxo-1,1-dioxide (146 mg, 1.09 mmol) and 3-amino-2-cyclopenten-1-one (107 mg, 1,10 mmol) were heated in ethanol (4 mL) to 80 ° C. in a sealed tube for 3 days, cooled, the solid precipitate collected, washed with ethanol and dried to provide 211 mg of the title compound. The filtrate was treated with 1.0 M HCl in ether (1 mL), heated to reflux for 2 hours, cooled and solvent evaporated. The residue was treated with ethanol, heated and the resultant solid collected, washed with ethanol and dried to provide an additional 29 mg of the title compound. The two lots of material were combined, triturated with hot ethyl acetate, collected, washed with ethyl acetate and dried to provide 197 mg of the title compound as a tansolid.
mp >260 ° C.; $^1$HNMR (DMSO-d$_6$) δ 2.30 (t, 2H), 2.55–2.75 (m, 4H), 2.85 (dt, 1H), 3.05 (dt, 1H), 3.40 (t, 2H), 4.71 (s, 1H), 7.17 (dd, 1H), 7.54 (d, 1H), 7.65 (d, 1H), 10.36 (br s, 1H); MS(APC1-) m/z 458 (M-H)$^-$;
Anal. Calcd for C$_{16}$H$_{13}$Br$_2$NO$_3$S: C, 41.85;H, 2.85; N, 3.05. Found: C, 41.79;H, 2.75; N, 2.78.

EXAMPLE 73

2,3,4,5,6,8-hexahydro-8-(3-nitrophenyl)dithieno[3,2-b:2',3'-e]pyridine, 1..7.7-tetraoxide 3-Nitrobenzaldehyde (155 mg, 1.03 mmol), tetrahydrothiophene-3-oxo-1,1-dioxide (273 mg, 2.04 mmol) and 2.0 M NH$_3$ in ethanol (0.7 mL, 1.4 mmol) were heated to 80 ° C. in ethanol (4 mL) for 3 days in a sealed tube, cooled, treated with 1.0 M HCl in ether (1 mL), heated to reflux for 15 minutes, cooled, the solid precipitate collected, washed with ethanol and dried. The solid was triturated with hot ethyl acetate, collected, washed with ethyl acetate and dried to provide 174 mg of the title compound as an orange-yellow solid. mp 248–252 ° C.;
$^1$H NMR (DMSO-d$_6$) 62.85 (m, 2H), 3.05 (m, 2H), 3.40 (m, 4H), 5.15 (s, 1H), 7.61 (t, 1H), 7.77 (dt, 1H), 8.10 (m, 2H), 10.09 (br s, 1H); MS(APC1-) m/z 381 (M-H)$^-$;
Anal. Calcd for C$_{15}$H$_{14}$N$_2$O$_6$S$_2$: C, 47.1 1;H, 3.68; N, 7.32. Found: C, 47.47;H, 3.68; N, 7.29.

EXAMPLE 74

8-(3-chloro-4-fluorophenyl)-2,3,4,5,6,8-hexahydrodithieno [3,2-b:2',3'-e]pyridine, 1,1,7,7-tetraoxide 3-Chloro-4-fluorobenzaldehyde (160 mg, 1.0 mmol), tetrahydrothiophene-3-oxo-1,1-dioxide (273 mg, 2.04 mmol) and 2.OM NH$_3$ in ethanol (0.7 mL, 1.4 mmol) were heated to 80 ° C. in ethanol (4 mL) for 3 days in a sealed tube, cooled, the solid precipitate collected, washed with ethanol and dried to provide 146 mg of the title compound as a light-yellow solid.
mp>260 ° C.
$^1$H NMR (DMSO-d$_6$) δ 2.82 (dt, 2H), 3.02 (dt, 2H), 3.38 (m, 4H), 4.97 (s, 1H), 7.24–7.38 (m, 2H), 7.43 (dd, 1H), 9.35 (br s, 1H); MS(APC1-) m/z 388 (M-H)$^-$;
Anal. Calcd for C$_{15}$H$_{13}$ClFNO$_4$S$_2$: C, 46.09;H, 3.61; N, 3.58. Found: C, 45.91;H, 3.40; N, 3.63.

EXAMPLE 75

4-(3,4-dichlorophenyl)- 1,4,6,7-tetrahydro-2-methyl-3-(methylsulfonyl)-5H-cyclopenta[b]pyridin-5-one 3,4-Dichlorobenzaldehyde (175 mg, 1.0 mmol), methanesulfonylacetone (137 mg, 1.01 mmol) and 3-aminocyclopentenone (95 mg, 0.98 mmol) were heated to 80 ° C. in ethanol (4 mL) in a sealed tube for 3 days, cooled and the solvent evaporated. The crude material was flash chromatographed on silica gel (5% methanol/chloroform) to provide 80 mg of the title compound as a tan solid.

mp 218–220 °C.;
$^1$H NMR (CDCl$_3$) δ 2.48–2.50 (br s, 5H), 2.59 (s, 3H), 2.63 (m, 2H), 5.01 (s, 1H), 6.53 (br s, 1H), 7.25 (m, 1H), 7.48 (m, 2H); MS(APCl-) m/z 370 (M-H)$^-$;
Anal. Calcd for C$_{16}$H$_{15}$Cl$_2$NO$_3$S: C, 51.62;H, 4.06; N, 3.76. Found: C, 51.36;H, 3.99; N, 3.83.

EXAMPLE 76

4-(4-chloro-3-nitrophenyl)-1,4,6,7-tetrahydro-2-methyl-3-,(methylsulfonyl)-5H-cyclopenta[b]pyridin-5-one 4-Chloro-3-nitrobenzaldehyde (186 mg, 1.0 mmol) was treated according to the procedure described in Example 75 to provide 105 mg of the title compound as an off-white solid.
mp 232 °C.;
$^1$H NMR (DMSO-d$_6$) δ 2.27 (m, 2H), 2.36 (s, 3H), 2.58 (m, 2H), 2.83 (s, 3H), 4.87 (s, 1H), 7.53 (dd, 1H), 7.70 (d, 1H), 7.80 (d, 1H), 10.10 (s, 1H); MS(APCl-) m/z 381 (M-H)$^-$;
Anal. Calcd for C$_{16}$H$_5$ClN$_2$O$_5$S: C, 51.62;H, 4.06; N, 3.76. Found: C, 51.36;H, 3.99; N, 3.83.

EXAMPLE 77

8-(3.4-dichlorophenyl)-2,3,4,5,6,8-hexahydrodithieno [3,2-b:2',3'-e1pyridine. 1,1,7,7-tetraoxide 3,4-Dichlorobenzaldehyde (196 mg) ) was treated according to the procedure described in Example 74 to provide 165 mg of the title compound as a light-yellow solid.
mp>260 °C.;
$^1$H NMR (DMSO-d$_6$) δ 2.82 (m, 2H), 3.00 (dt, 2H), 3.39 (m, 4H), 4.97 (s, 1H), 7.26 (dd, 1H), 7.49 (d, 1H), 7.55 (d, 1H), 9.53 (br s, 1H); MS(APCl-) m/z 404 (M-H)$^-$;
Anal. Calcd for C$_{15}$H$_{13}$Cl$_2$NO$_4$S$_2$: C, 44.34;H, 3.22; N, 3.44. Found: C, 43.99;H. 3.11; N, 3.68.

EXAMPLE 78

8-(4-bromophenyl)-2,3,4,5,6,8-hexahydro-7H-cyclopenta[b]thieno [2,3-e]pyridin-7-one, 1,1-dioxide 4-Bromobenzaldehyde (377 mg, 2.00 mmol) tetrahydrothiophene-3-oxo-1,1-dioxide (230 mg, 1.7 mmol) and 3-amino-2-cyclopenten-1-one (165 mg, 1.7 mmol) were heated to 80 °C. in a sealed tube for 2 days, cooled, the solid precipitate collected, and washed with ethanol. The filtrate was treated with 1.0 M HCl/diethyl ether (4 mL), heated to reflux for 15 minutes, cooled, concentrated, combined with the solid precipitate and purified by flash chromatography over silica gel (5 % methanol/methylene chloride). The product was crystallized from ethanol to provide 218 mg of the title compound.
mp 253–256 °C.;
$^1$H NMR (DMSO-d$_6$) δ 2.30 (t, 2H), 2.51–2.72 (m, 2H), 2.79–2.91 (m, 1H), 2.97–3.09 (m, 1H), 3.34–3.42 (m, 2H), 4.66 (s, 1H), 7.17 (d, 2H), 7.43 (d, 2H), 10.27 (s, 1H); MS(APCl+) m/z 380 (M+H)$^+$, MS(APCl-) m/z 378 (M-H)$^-$;
Anal. Calcd for C$_{16}$H$_{14}$BrNO$_3$S: C, 50.54;H, 3.71; N, 3.68. Found: C, 50.50;H, 3.74; N, 3.52.

EXAMPLE 79

8-(3,4-difluorophenyl)-2,3,4,5,6,8-hexahydro-7H-cyclopenta[b]thieno [2,3-e]pyridin-7-one, 1,1-dioxide 3,4-Difluorobenzaldehyde (162 mg) was treated according to the procedure described in Example 56 to provide 169 mg of the title compound as a white powder.
mp >260 °C.
$^1$H NMR (DMSO-d$_6$) δ 2.30 (t, 2H), 2.5–2.75 (m, 2H), 2.86 (dt, 1H), 3.07 (dt, 1H), 3.40 (t, 2H), 4.72 (s, 1H), 7.08 (m, 1H), 7.18–7.36 (m, 2H), 10.32 (br s, 1H); MS(APCl-) m/z 336 (M-H)$^-$;
Anal. Calcd for C$_{16}$H$_{13}$F$_2$NO$_3$S: C, 56.96;H, 3.88; N, 4.15. Found: C, 57.01;H, 3.78; N, 4.08.

EXAMPLE 80

8-(4-chloro-3-fluorophenyl)-2,3,4,5,6,8-hexahydro-7H-cyclopenta[b]thieno [2.3-e]pyridin-7-one, 1 1-dioxide 4-Chloro-3-fluorobenzaldehyde (180 mg, 1,13 mmol) was treated according to the procedure described in Example 56 to provide 135 mg of the title compound as a tan solid.
mp >260 °C.
$^1$H NMR (DMSO-d$_6$) δ 2.30 (t, 2H), 2.50–2.75 (m, 2H), 2.87 (dt, 1H), 3.05 (dt, 1H), 3.40 (t, 2H), 4.73 (s, 1H), 7.10 (dd, 1H), 7.21 (dd, 1H), 7.45 (t, 1H), 10.32 (br s, 1H); MS(APCl-) m/z 352 (M-H)$^-$;
Anal. Calcd for C$_{16}$H$_{13}$ClFNO$_3$S: C, 54.31;H, 3.70; N, 3.95. Found: C, 54.08;H, 3.65; N, 3.88.

EXAMPLE 81

9-(3-chloro-4-fluorophenyl)-2,3,5,6,7,9-hexahydrothieno [3.2-b]quinolin-8(4H)-one, 1 1-dioxide 3-Chloro-4-fluorobenzaldehyde (264 mg, 1.66 mmol) was treated according to the procedure described in Example 43 to provide 317 mg of the title compound as a white solid.
mp >260 °C.
$^1$H NMR (DMSO-d$_6$) δ 1.73–1.96 (m, 2H), 2.23 (m, 2H), 2.55 (m, 2H), 2.82 (dt, 1H), 3.02 (dt, 1H), 3.46 (m, 2H), 4.85 (s, 1H), 7.17 (m, 1H), 7.28 (m, 2H), 9.75 (br s, 1H); MS(APCl-) m/z 366 (M-H)$^-$;
Anal. Calcd for C$_{17}$H$_{15}$ClFNO$_3$S: C, 55.51;H, 4.1 1; N, 3.80. Found: C, 55.24;H, 3.97; N, 3.85.

EXAMPLE 82

8-(3-cyano-4-fluorophenyl)-2,3,4,5,6,8-hexahydrodithieno [3.2-b:2',3'-e]pyridine. 1,1,7,7-tetraoxide

EXAMPLE 82A 3-cyano-4-fluorobenzyl bromide

A solution of 3-Cyano-4-fluorotoluene (1.0 g, 7.4 mmol), N-bromosuccinimide (1.3 g, 7.4 mmol) and catalytic 2,2'-azobisisobutyronitrile (AIBN) in benzene was heated to reflux for 16 hours, evaporated to dryness and flash chromatographed over silica gel eluting with 10% ethyl acetate/hexane to provide 1.0 g of 3-cyano-4-fluorobenzyl bromide.
$^1$H NMR (CDCl$_3$) δ 4.45 (s, 2H), 7.21 (t, 1H), 7.65 (m, 2H).

EXAMPLE 82B 3-cyano-4-fluorobenzyl alcohol

A solution of 85% formic acid (0.63 mL) and triethylamine (2.32 mL, 16.7 mmol) in acetonitrile at 0 °C. was treated with the product from Example 82A (1.3 g, 5.6 mmol), stirred at room temperature for 3 hours, the reaction evaporated to dryness partitioned between ethyl acetate/water, the organic layer dried with sodium sulfate, filtered and solvent evaporated to provide a crude formate ester. This residue was dissolved in methanol:water (5:1), treated with a catalytic amount of concentrated hydrochloric acid, stirred at room temperature overnight, evaporated to dryness, and flash chromatographed over silica gel eluting with ethyl acetate:hexane (1:1) to provide 0.40 g 3-cyano-4-fluorobenzyl alcohol. $^1$HNMR (CDCl$_3$) δ 1.81 (t, 1H), 4.72 (d, 2H), 7.21 (t, 1H), 7.62 (m, 2H).

EXAMPLE 82C 3-cyano-4-fluorobenzaldehyde

A solution of the product from Example 82B (0.40 g, 2.6 mmol) in chloroform (50 mL) was treated with manganese dioxide (0.55 g, 7.8 mmol), stirred at room temperature overnight, filtered, solvent evaporated and the residue flash chromatographed over silica gel eluting with ethyl acetate-:hexane (1:1) to provide 0.21 g 3-cyano-4-fluorobenzaldehyde.
$^1$H NMR (CDC$_3$) δ 7.43 (t, 1H), 8.17 (m, 2H), 9.99 (s, 1H).

EXAMPLE 82D 8-(3-cyano-4-fluorophenyl)-2,3 4,5,6,8-hexahydrodithieno

[3,2-b:2',3'-e]pyridine. 1,1,7,7-tetraoxide 3-Cyano-4-fluorobenzaldehyde (0.21 g, 1.4 mmol) was treated according to the procedure described in Example 62 to provide 0.20 g of the title compound as a tan solid.
mp 275–280 ° C. (dec);
$^1$H NMR (DMSO-d$_6$) δ 2.82 (m, 2H), 3.0 (m, 2H), 3.4 (m, 4H), 5.06 (s, 1H), 7.48 (t, 1H), 7.7 (m, 1H), 7.86 (dd, 1H) 10.1 (s, 1H); MS(ESI+) m/z 398 (M+NH$_4$)$^+$, MS(ES1-) m/z 379 (M-H)$^-$;
Anal. Calcd for C$_{16}$H$_3$FN$_2$O$_4$S$_2$: C, 50.52;H, 3.44; N, 7.36. Found: C, 50.47;H, 3.52; N, 7.26.

EXAMPLE 83

(+)-(9R)-9-(3-bromo-4-fluorophenyl)-2,3,5,6,7,9-hexahydrothieno [3.2-b]quinolin-8(4H)-one, 1,1-dioxide The product from Example 43 (0.50 g) was chromatographed on a 5×25 cm Regis WhelkO2 chiral column with 280 g of packing, eluting with hexane:methanol:methylene chloride (77.5/15/7.5) as the mobile phase with a flow rate of 117 mL/minute to provide 220 mg of the title compound as the more polar enantiomer. [a]23D +50.240 (CH$_3$CN);
$^1$H NMR (DMSO-d$_6$) δ 1.72–1.98 (m, 2H), 2.22 (m, 2H), 2.55 (m, 2H), 2.8 (m, 1H), 3.1 (m, 1H), 3.32 (m, 2H), 4.82 (s, 1H), 7.2 (m, 2H), 7.4 (m, 1H), 9.8 (s, 1H); MS(APCI+) m/z 414 (M+H)$^+$;
Anal. Calcd for C$_{17}$H$_{15}$BrFNO$_3$S: C, 49.52;H, 3.66; N, 3.39. Found: C, 49.56;H, 3.86; N, 3.33.

EXAMPLE 84

(−)-(9S)-9-(3-bromo-4-fluorophenyl)-2,3,5,6,7,9-hexahydrothieno [3,2-b]quinolin-8(4H)-one, 1,1-dioxide From the chiral chromatography described in Example 83 was obtained 210 mg of the title compound as the less polar enantiomer. [a]23D -48.8 (CH$_3$CN);
$^1$H NMR (DMSO-d$_6$) δ 1.72–1.98 (m, 2H), 2.22 (m, 2H), 2.52 (m, 2H), 2.8 (m, 1H), 3.1 (m, 1H), 3.31 (m, 2H), 4.82 (s, 1H), 7.2 (m, 2H), 7.4 (m, 1H), 9.8 (s, 1H); MS(APCI+) m/z 414 (M+H)$^+$;

Anal. Calcd for C$_{17}$H$_{15}$BrFNO$_3$S: C, 49.52;H, 3.66; N, 3.39. Found: C, 49.54;H, 3.76; N,3.41.

EXAMPLE 85

8-(2.1.3-benzoxadiazol-5-yl)-2,3,4,5,6,8-hexahydro-7H-cyclopenta[b]thieno [2,3-e]pyridin-7-one, 1.1-dioxide 2,1,3-Benzoxadiazole-5-carboxaldehyde (0.296 g, 2.00 mmol), prepared according to the method of Gasco (Eur. J. Med. Chem. 1996, 31, 3), tetrahydrothiophene-3-oxo-1,1-dioxide (0.27 g, 2.0 mmol), and 3-amino-2-cyclopenten-1-one (0.194 g, 2.00 mmol) were heated in ethanol (4 mL) to 80° C. for 2 days in a sealed tube, treated with 1.0 M HCl in ether (1 mL), heated to reflux for 3 hours, cooled, the solid precipitate collected, washed with ethanol and dried to provide 0.27 g of the title compound.
$^1$H NMR (DMSO-d$_6$) δ 2.31 (t, 2H), 2.65 (m, 2H), 2.9 (m, 1H), 3.05 (m, 1H), 3.42 (m, 2H), 4.92 (s, 1H), 7.55 (d, 1H), 7.82 (s, 1H), 7.96 (d, 1H), 10.42 (s, 1H); MS(CI/NH3) m/z 361 (M+NH$_4$)$^+$;
Anal. Calcd for C1$_6$H$_{13}$N$_3$O$_4$S: C, 55.96;H, 3.81; N, 12.23. Found: C, 55.80;H, 3.73; N, 12.18.

EXAMPLE 86

(−)-8-(3-bromo-4-fluorophenyl)-2,3,4,5,6,8-hexahydro-7H-cyclopentafblthieno [2.3-e]pyridin-7-one, 1,1-dioxide The product from Example 56 (0.80 g) was chromatographed on a 5×25 cm Regis WhelkO 2 chiral column with 280 g of packing, eluting with hexane:methanol:methylene chloride (70/15/15) as the mobile phase at a flow rate of 117 mL/minute to provide 250 mg of the title compound as the less polar enantiomer. [a]23D-4.50 (CH$_3$CN);
$^1$H NMR (DMSO-d$_6$) δ 2.3 (t, 2H), 2.63 (m, 2H), 2.85 (m, 1H), 3.06 (m, 1H), 3.4 (m, 2H), 4.71 (s, 1H), 7.25 (d, 2H), 7.47 (d, 1H) 10.35 (s, 1H); MS(ESI+) m/z 400 (M+H)$^+$;
Anal. Calcd for C$_{16}$H$_{13}$BrFNO$_3$S: C, 48.25;H, 3.29; N, 3.52. Found: C, 48.14;H, 3.42; .N,3.42.

EXAMPLE 87

(+)-8-(3-bromo-4-fluorophenyl)-2,3,4,5,6,8-hexahydro-7H-cyclopentafblthieno[2,3-e]pyridin-7-one, 1,1-dioxide From the chiral chromatography described in Example 86 was obtained 264 mg of the title compound as the more polar enantiomer. [a]$^{23}$D+4.8° (CH$_3$CN);
$^1$H NMR (DMSO-d$_6$) δ 2.3 (m, 2H), 2.62 (m, 2H), 2.85 (m, 1H), 3.05 (m, 1H), 3.4 (m, 2H), 4.72 (s, 1H), 7.25 (m, 2H), 7.48 (d, 1H), 10.35 (s, 1H); MS(ESI+) m/z 400 (M+H)$^+$;
Anal. Calcd for C$_{16}$H$_{13}$BrFNO$_3$S: C, 48.25;H, 3.29; N, 3.52. Found: C, 48.14;H, 3.52; N, 3.42.

EXAMPLE 88

9-(2,1.3-benzoxadiazol-5-yl)-2,3,5,6,7,9-hexahydrothieno [3,2-b]quinolin-8(4H)-one, 1,1-dioxide 2,1,3-Benzoxadiazole-5-carboxaldehyde (0.296 g, 2.00 mmol) was treated according to the procedure described in Example 89 to provide 0.42 g of the title compound.
$^1$H NMR (DMSO-d$_6$) δ 1.9 (m, 2H), 2.25 (m, 2H), 2.55 (m, 2H), 2.88 (m, 1H), 3.05 (m, 1H), 3.4 (m, 2H), 5.0 (s, 1H), 7.51 (d, 1H), 7.7 (s, 1H), 7.95 (d, 1H), 9.96 (s, 1H); MS(ESI+) m/z 358 (M+H)$^+$;

Anal. Calcd for $C_{17}H_{15}N_3O_4S$: C, 57.13;H, 4.23; N, 11.75. Found: C, 57.05;H, 4.31; N, 11.73.

EXAMPLE 89

9-(4-fluoro-3-iodophenyl)-2,3,5,6,7,9-hexahydrothieno [3.2-b]quinolin-8(4H)-one, 1,1-dioxide

EXAMPLE 89A

3-Amino-4-fluorobenzyl alcohol

3-Amino-4-fluorobenzoic acid (15 g, 97 mmol) in THF at 0 ° C. was treated with ] .OM $BH_3THF$ (50 mL), stirred overnight at room temperature, treated with an additional 130 mL 1.0 M $BH_3THF$, stirred 10 hours, quenched by the addition of methanol, stirred 3 hours at room temperature, solvent evaporated, the product partitioned between aqueous sodium bicarbonate/methylene chloride, the organic layer dried (sodium sulfate), filtered and solvent evaporated. The product was purified by flash chromatography over silica gel (ethyl acetate/hexane 1:1) to provide 7.0 g of the title compound.
$^1$H NMR ($CDCl_3$) δ 4.58 (s, 2H), 6.67 (br m, 1H), 6.81 (d, 1H), 6.95 (t, 1H).

EXAMPLE 89B

4-fluoro-3-iodobenzylalcohol

The product from Example 89A (7.0 g, 50 mmol) in water (100 mL) at 0 ° C. was treated slowly with concentrated sulfuric acid (30 mL) at a rate to maintain the temperature below 10 ° C., then treated dropwise with an aqueous solution of sodium nitrite (3.45 g, 50 mmol). This solution was then added to a solution of potassium iodide (8.13 g, 50 mmol) in water (15 mL), heated to 60 ° C. for 2 hours, cooled, extracted with methylene chloride, the organics washed with 10% sodium hydroxide, 1M sodium thiosulfate, 10% hydrochloric acid, aqueous sodium bicarbonate, dried (sodium sulfate), filtered and solvent evaporated. The material was purified by flash chromatography over silica gel (ethyl acetate/hexane 7:3) to provide 6.4 g of the title compound. $^1$HNMR ($CDCl_3$) δ 1.69 (t, 1H), 4.66 (d, 2H), 7.05 (t, 1H), 7.60 (d, 1H), 7.78 (dd, 1H).

EXAMPLE 89C

4-fluoro-3-iodobenzaldehyde

The product from Example 89B (6.4 g, 26 mmol) in chloroform (300 mL) was treated with manganese dioxide (4.5 g, 50 mmol), stirred overnight, treated with an additional portion of manganese dioxide (2.25 g), stirred overnight, filtered and solvent evaporated. The material was purified by flash chromatography over silica gel (ethyl acetate/hexane 1:4) to provide 1.9 g of the title compound.
$^1$HNMR ($CDCl_3$) δ 7.23 (t, 1H), 7.89 (m, 1H), 8.32 (dd, 1H), 9.91 (s, 1H).

EXAMPLE 89D

9-(4-fluoro-3-iodophenyl)-2,3,5,6,7,9-hexahydrothieno

[3.2-b]quinolin-8(4H)-one, 1,1-dioxide 4-Fluoro-3-iodobenzaldehyde (0.25 g, 1.0 mmol), tetrahydrothiophene-3-oxo-1,1-dioxide (0.13 g, 1.0 mmol), 3-amino-2-cyclohexen-1-one (0.11 g, 1.0 mmol) and triethylamine (0.07 mL) were heated in ethanol (2 mL) to 80 ° C. in a sealed tube for 96 hours, cooled, solvent evaporated, flash chromatographed on silica gel (10% ethanol/methylene chloride), the product dissolved in ethanol, treated with 1.0 M HCl in ether (1 mL), heated to reflux for 2 hours, cooled, the solid precipitate collected, washed with ethanol and dried to provide 0.20 g of the title compound.
mp >250 ° C.; $^1$HNMR (DMSO-$d_6$) δ 1.88 (m, 2H), 2.22 (m, 2H), 2.62 (m, 2H), 2.7 (m, 1H), 3.02 (m, 1H), 3.45 (m, 2H), 4.81 (s, 1H), 7.12 (m, 1H), 7.18 (m, 1H), 7.55 (dd, 1H), 9.81 (s, 1H); MS(ESI+) m/z 460 (M+H)$^+$;
Anal. Calcd for $C_{17}Hl_5FINO_3S$: C, 44.45;H, 3.29; N, 3.04. Found: C, 44.51;H, 3.31; N, 2.97.

EXAMPLE 90

8-(4-fluoro-3-iodophenyl)-2,3,4,5,6,8-hexahydro-7H-cyclopenta[b]thieno[2,3-e]pyridin-7-one, 1,1-dioxide 4-Fluoro-3-iodobenzaldehyde (0.25 g, 1.0 mmol), tetrahydrothiophene-3-oxo-1,1-dioxide (0.13 g, 1.0 mmol) and 3-amino-2-cyclopenten-1-one (97 mg, 1.0 mmol) were heated in ethanol (2 mL) to 80 ° C. in a sealed tube for 96 hours, cooled, solvent evaporated, flash chromatographed on silica gel (10% ethanol/methylene chloride), the product dissolved in ethanol, treated with 1.0 M HCl in ether (1 mL), heated to reflux for 2 hours, cooled, the solid precipitate collected, washed with ethanol and dried to provide 0.10 g of the title compound.
mp>250 ° C.; $^1$HNMR (DMSO-$d_6$) 62.3 (t, 2H), 2.62 (m, 2H), 2.85 (m, 1H), 3.08 (m, 1H), 3.4 (m, 2H), 4.68 (s, 1H), 7.13 (t, 1H), 7.24 (m, 1H), 7.6 (dd, 1H), 10.33 (s, 1H); MS(ESI+) m/z 446 (M+H)$^+$;
Anal. Calcd for $C_{16}Hl_3FINO_3S$: C, 43.16;H, 2.94; N, 3.14. Found: C, 42.91;H, 2.94; N, 3.00.

EXAMPLE 91

(+)-9-(3-bromo-4-fluorophenyl)-3,4,5,6,7,9-hexahydrocyclopenta[rbthiopyrano[2,3-e]pyridin-8 (2H)-one, 1,1-dioxide The product from Example 40 (1.476 g, 3.58 mmol) as a slurry in THF (20 mL) under nitrogen at 5 ° C. was treated dropwise with a solution of 1.0 M potassium tert-butoxide in THF (3.9 mL), allowed to warm to room temperature over 20 minutes, treated with a solution of (−)-8-phenylmenthylchloroformate (1,17 g, 3.97 mmol) in THF (5 mL), stirred at room temperature overnight, quenched in aqueous sodium bicarbonate, extracted with diethyl ether (2x), the organics dried with sodium sulfate, filtered and solvent evaporated to provide a mixture of diastereomeric carbamates. This mixture was flash chromatographed over a 6×36 cm column of silica gel, eluting with ether:hexane (85/15) to provide 746 mg of the less polar diastereomer. This material, as a slurry in methanol (10 mL) under nitrogen, was treated with catalytic sodium methoxide, stirred at room temperature for 24 hours, treated with glacial acetic acid (3 drops), the solid precipitate collected, washed with ethyl alcohol and dried to provide 227 mg of the title compound as a white solid. [c]23D +63.9 (MeCN);
$^1$H NMR (DMSO-$d_6$) δ 2.15–2.35 (m, 4H), 2.46–2.70 (m, 4H), 3.23 (m, 2H), 4.83 (s, 1H), 7.25 (m, 2H), 7.42 (dd, 1H), 9.96 (br s, 1H); MS(APC1-) m/z 410 (M-H)$^-$;
Anal. Calcd for $C_{18}H_{15}BrFNO_3S$: C, 49.53;H, 3.67; N, 3.40. Found: C, 49.47;H, 3.53; N, 3.37.

EXAMPLE 92

(−)-9-(3-bromo-4-fluoronhenyl)-3,4,5,6,7,9-hexahydrocyclopenta[b]thiopyranor[2,3-e]pyridin-8 (2H)-one,1,1-dioxide From the chromatography of diastereomers described in Example 91 was obtained 824 mg of the impure more polar diastereomer. This material was flash chromatographed over a 6×36 cm column of silica gel, eluting with ether:hexane (9/1) to provide 695 mg of the more polar diastereomer. This diastereomer, as a slurry in methanol (10 mL) under nitrogen, was treated with catalytic sodium methoxide, stirred at room temperature for 5 days, treated with glacial acetic acid (3 drops), the solid precipitate collected, washed with ethyl alcohol and dried to provide 120 mg of the title compound as a white solid. The filtrate was flash chromatographed (5–15% ethanol/methylene chloride) and the product triturated with ethyl acetate to provide an additional 186 mg of the title compound. [o]123D -60.8 (MeCN);
$^1$H NMR (DMSO-$d_6$) 62.15–2.30 (m, 4H), 2.47–2.70 (m, 4H), 3.20 (m, 2H), 4.83 (s, 1H), 7.25 (m, 2H), 7.41 (dd, 1H), 9.96 (br s, 1H); MS(APC1-) m/z 410 (M-H)$^-$;
Anal. Calcd for $C_{18}H_{15}BrFNO_3S$: C, 49.53;H, 3.67; N, 3.40. Found: C, 49.61;H, 3.58; N, 3.34.

EXAMPLE 93

(+)-10-(3-bromo-4-fluorophenyl)-3,4,6,7,8,10-hexahydro-2H-thiopyrano[3,2-b]quinolin-9(5H)-one, 1,1-dioxide The product from Example 4 (1.646 g, 3.86 mmol) was processed by the method described in Example 91 to provide 223 mg of the title compound as a white solid. [a]23D +7.3 (DMSO); $^1$HNMR (DMSO-$d_6$) δ 1.75 (m, 1H), 1.88 (m, 1H), 2.20 (m, 4H), 2.50 (m, 4H), 3.20 (m, 2H), 5.01 (s, 1H), 7.15–7.28 (m, 2H), 7.88 (dd, 1H), 9.39 (br s, 1H); MS(APC1-) m/z 424 (M-H)$^-$;
Anal. Calcd for $C_{18}H_{17}BrFNO_3S$: C, 50.71;H, 4.02; N, 3.29. Found: C, 50.73;H, 4.24; N, 3.26.

EXAMPLE 94

(−)-10-(3-bromo-4-fluorophenyl)-3,4,6,7,8,10-hexahydro-2H-thiopyrano[3,2-b]quinolin-9(5H)-one 1,1-dioxide The product from Example 4 (1.646 g, 3.86 mmol) was processed by the methods described in Example 91 and Example 92 to provide 148 mg of the title compound as a white solid. [cc]$^{23}$D -5.2 (DMSO); $^1$HNMR (DMSO-$d_6$) δ 1.73 (m, 1H), 1.88 (m, 1H), 2.20 (m, 4H), 2.50 (m, 4H), 3.20 (m, 2H), 5.01 (s, 1H), 7.15–7.27 (m, 2H), 7.38 (dd, 1H), 9.40 (br s, 1H); MS(APC1-) m/z 424 (M-H)$^-$;
Anal. Calcd for $C,,H_1,BrFNO_3S$: C, 50.71;H, 4.02; N, 3.29. Found: C, 50.68;H, 4.17; N, 3.22.

EXAMPLE 95

(+)-9-(3,4-dichlorophenyl)-2,3,5,6,7,9-hexahydrothieno[3,2-b]quinolin-8(4H)-one, 1,1-dioxide The title compound from Example 29 (1.65 g, 4.30 mmol) as a slurry in THF (20 mL) under nitrogen at 5 ° C. was treated dropwise with a solution of 1.0 M potassium tert-butoxide in THF (3.9 mL), allowed to warm to room temperature over 20 minutes, treated with a solution of (−)-8-phenylmenthylchloroformate (4.3 mmol) in THF (5 mL), stirred at room temperature overnight, quenched in aqueous sodium bicarbonate, extracted with diethyl ether (3x), the organics dried with sodium sulfate, filtered and solvent evaporated to provide a mixture of diastereomeric carbamates. This mixture was flash chromatographed over a 6×40 cm column of silica gel, eluting with chloroform:hexane:ether (7:2: 1) to provide 664 mg of the less polar diastereomer. This material, as a slurry in methanol (10 mL) under nitrogen, was treated with catalytic sodium methoxide, stirred at room temperature overnight, treated with glacial acetic acid (2 drops), the solid precipitate collected, washed with ethyl alcohol and dried to provide 295 mg of the title compound as a white solid. [x]23D +70.90 (DMSO);
$^1$H NMR (DMSO-$d_6$) δ 1.75–1.95 (m, 2H), 2.23 (m, 2H), 2.54 (m, 2H), 2.83 (dt, 1H), 3.02 (dt, 1H), 3.45 (m, 2H), 4.84 (s, 1H), 7.16 (dd, 1H), 7.34 (d, 1H), 7.49 (d, 1H), 9.82 (br s, 1H); MS(APC1-) m/z 382 (M-H)$^-$;
Anal. Calcd for $C_{17}H_{15}Cl_2NO_3S$: C, 53.14;H, 3.93; N, 3.64. Found: C, 53.38;H, 4.19; N, 3.61.

EXAMPLE 96

(−)-9-(3,4-dichlorophenyl)-2,3,5,6,7,9-hexahydrothieno[3,2-b]quinolin-8(4H)-one, 1,1-dioxide From the chromatography of the diastereomers described in Example 95 was obtained the impure more polar diastereomer. This material was flash chromatographed over a 6×40 cm column of silica gel, eluting with chloroform:hexane:ether (7:2:1) to provide 628 mg of the more polar diastereomer. This diastereomer, as a slurry in methanol (10 mL) under nitrogen, was treated with catalytic sodium methoxide, stirred at room temperature overnight, treated with glacial acetic acid (2 drops), the solid precipitate collected, washed with ethyl alcohol and dried to provide 228 mg of the title compound as a white solid. [C]23D -68.80 (DMSO);
$^1$H NMR (DMSO-$d_6$) 8 1.75–1.95 (m, 2H), 2.23 (m, 2H), 2.55 (m, 2H), 2.73 (dt, 1H), 3.03 (dt, 1H), 3.35 (m, 2H), 4.84 (s, 1H), 7.17 (dd, 1H), 7.35 (d, 1H), 7.50 (d, 1H), 9.85 (brs, 1H); MS(APC1-) m/z 382 (M-H)$^-$;
Anal. Calcd for $C_{17}H_{15}Cl_2NO_3S$: C, 53.14;H, 3.93; N, 3.64. Found: C, 53.11;H, 4.01; N, 3.59.

EXAMPLE 97

(+)-9-(2. 1,3-benzoxadiazol-5-yl)-2,3,5,6,7,9-hexahydrothieno[3.2-b]quinolin-8(4H)-one, 11-dioxide The product from Example 88 (1.34 g) was processed using the method described in Example 95 to provide 120 mg of the title compound as a white solid. [a]23D +43.30 (DMSO); $^1$HNMR (DMSO-$d_6$) δ 1.9 (m, 2H), 2.23 (m, 2H), 2.56 (m, 2H), 2.88 (m, 1H), 3.05 (m, 1H), 3.4 (m, 2H), 5.0 (s, 1H), 7.51 (d, 1H), 7.7 (s, 1H), 7.95 (d, 1H), 9.95 (s, 1H); MS(ES1-) m/z 356 (M-H)$^-$;
Anal. Calcd for $C_{17}H_{15}N_3O_4S$: C, 57.13;H, 4.23; N, 11.75. Found: C, 56.98;H, 4.28; N, 11.76.

EXAMPLE 98

(−)-9-(2.1 .3-benzoxadiazol-5-yl)-2,3,5,6,7,9-hexahydrothieno[3.2-b]quinolin-8(4H)-one, 1,1-dioxide The product from Example 88 (1.34 g) was processed using the methods of Examples 95 and 96 to provide I 10 mg of the title compound as a white solid. [oJ$^{23}$D-41.70 (DMSO);
$^1$H NMR (DMSO-$d_6$) δ 1.9 (m, 2H), 2.25 (m, 2H), 2.57 (m, 2H), 2.9 (m, 1H), 3.05 (m, 1H), 3.4 (m, 2H), 5.0 (s, 1H), 7.51 (d, 1H), 7.7 (s, 1H), 7.95 (d, 1H), 9.95 (s, 1H); MS(ES1-) m/z 356 (M-H)$^-$;

Anal. Calcd for $C_{17}H_{15}N_3O_4S$: C, 57.13;H, 4.23; N, 11.75. Found: C, 56.97;H, 4.43; N, 11.71.

EXAMPLE 99

(+)-9-(4-chloro-3-nitrophenyl)-2,3,5,6,7,9-hexahydrothieno[3.2-b]quinolin-8(4H)-one, 1,1-dioxide The product from Example 34 (1.64 g) was processed according to the method described in Example 95 to provide 300 mg of the title compound. [aJ23D +41.040 (DMSO); $^1$HNMR (DMSO-$d_6$) δ 1.90 (m, 2H), 2.25 (m, 2H), 2.52 (m, 2H), 2.85 (m, 1H), 3.02 (m, 1H), 3.35 (m, 2H), 4.95 (s, 1H), 7.54 (dd, 1H, J=3Hz), 7.65 (d, 1H, J=9Hz), 7.80 (d, 1H, J=3Hz), 9.90 (s, 1H); MS(ES1-) m/z 393 (M-H)$^-$;
Anal. Calcd for $C_{17}H_{15}ClN_2O_5S$: C, 51.71;H, 3,83; N, 7.10. Found: C, 51.72;H, 3.85; N, 7.10.

EXAMPLE 100

(−)-9-(4-chloro-3-nitrophenyl)-2,3,5,6,7,9-hexahydrothieno[3,2-b]quinolin-8(4H)-one, 1,1-dioxide The product from Example 34 (1.64 g) was processed using the methods described in Examples 95 and 96 to provide 424 mg of the title compound as a white solid. [o]23D -31.740 (DMSO);
$^1$H NMR (DMSO-$d_6$) δ 1.92 (m, 2H), 2.24 (m, 2H), 2.52 (m, 2H), 2.86 (m, 1H), 3.02 (m, H), 3.38 (m, 2H), 4.95 (s, 1H), 7.54 (dd, 1H, J=3Hz), 7.66 (d, 1H, J=9Hz), 7.79 (d, 1H, J=3Hz), 9.89 (s, 1H); MS(ES1-) m/z 393 (M-H)$^-$;
Anal. Calcd for $C_{17}H_{15}ClN_2O_5S$: C, 7.10;H, 3.83; N, 7.10. Found: C, 51.70;H, 3.83; N, 7.08.

EXAMPLE 101

1-(3-bromo-4-fluorophenyl)-2,3,4,5,7,8,9,11-octahydrothiepino[3.2-b]quinolin-10(6H)-one, 1,1-dioxide A solution of 3-bromo-4-fluorobenzaldehyde (1.22 g, 6.00 mmol), 3-amino-2-cyclohexen-1-one (667 mg, 6.00 mmol) and thiacycloheptan-3-one 1,1-dioxide (973 mg, 6.00 mmol) (prepared according to the method described in J. Heterocycl. Chem. (1990), 27, 1453) in ethyl alcohol (10 mL) with triethylamine (0.4 mL) was heated to 80 ° C. in a sealed tube for 3 days, cooled, the solid precipitate collected, washed with ethyl alcohol and dried to provide 1.8 g of the title compound as a white solid.
$^1$H NMR (DMSO-$d_6$) δ 1.65 (m, 1H), 1.75 (m, 2H), 1.90 (m, 1H), 2.02 (m, 2H), 2.52 (m, 2H), 2.75 (m, 3H), 3.15 (m, 1H), 4.95 (s, 1H), 7.20 (m, 1H), 7.25 (m, 1H), 7.40 (dd, 1H, J=3Hz), 9.44 (s, 1H);
MS(ESI+) m/z 441 (M+H)$^+$;
Anal. Calcd for $C_{19}H_{19}BrFNO_3S$: C, 51.83;H, 4.35; N, 3.18. Found: C, 51.59;H, 4.35; N, 3.18.

EXAMPLE 102

10-(3-bromo-4-fluorophenyl)-2,3,4,5,6,7,8,10-octahydro-9H-cyclopenta[b]thiepino[2,3-e]pyridin-9-one A solution of 3-bromo-4-fluorobenzaldehyde (639 mg, 3.14 mmol), 3-amino-2-cyclopenten-1-one (305 mg, 3.14 mmol) and thiacycloheptan-3-one 1,1-dioxide (510 mg, 3.14 mmol) in ethyl alcohol (10 mL) was heated to 80 ° C. in a sealed tube for 3 days, cooled, the solid precipitate collected, washed with ethyl alcohol and dried to provide 15 700 mg of the title compound as a white solid.
mp21$^{0°}$ C.;
$^1$H NMR (DMSO-$d_6$) δ 1.60 (m, 1H), 1.82 (m, 1H), 2.05 (m, 2H), 2.32 (m, 2H), 2.62 (m, 3H), 2.92 (m, 2H), 3.20 (m, 1H), 4.75 (s, 1H), 7.25 (dd, 1H, J=3Hz), 7.32 (m, 1H), 7.45 (dd, 1H, J=3Hz), 10.02 (s, 1H); MS(ESI+) m/z 427 (M+H)$^+$;
Anal. Calcd for $C_{18}H_{17}BrFNO_3S$: C, 50.71;H, 4.02; N, 3.29. Found: C, 50.71;H, 4.10; N, 3.20.

EXAMPLE 103

9-[3-(trifluoromethoxy)phenyl]-3,4,5,6,7,9-hexahydrocyclopenta[b]thiopyrano[2,3-e]pyridine-8(2H)-one, 1,1-dioxide 3-(Trifluoromethoxy)benzaldehyde (38 mg, 0.2 mmol) was processed according to the method of Example 37 to provide 36 mg of the title compound.
MS (APC1-) m/z: 398 (M-H)$^-$;
$^1$H NMR (DMSO-$d_6$) δ 2.22 (m, 4H), 2.55 (m, 4H), 3.20 (m, 2H), 4.87 (s, 1H), 7.10 (m, 2H), 7.20 (d, 1H), 7.37 (m, 1H), 9.94 (br s, 1H);
Anal. calcd for $C_{18}H_{16}F_3NO_4S$: C, 54.13;H, 4.04; N, 3.51. Found: C, 54.15;H, 4.13; N, 3.44.

EXAMPLE 104

9-(5-bromo-2-hydroxyphenyl)-3,4,5,6,7,9-hexahydrocyclopenta[b]thiopyrano[2.3-e]pyridine-8(2H)-one, 1,1-dioxide 5-Bromosalicylaldehyde (40 mg, 0.2 mmol) was processed according to the method of Example 37 to provide 33 mg of the title compound.
MS (APCI+) m/z: 410 (M+H)$^+$;
$^1$H NMR (DMSO-$d_6$) 62.20 (m, 4H), 2.58 (m, 4H), 3.18 (m, 2H), 5.04 (s, 1H), 6.63 (d, 1H), 7.02 (d, 1H), 7.10 (dd, 1H), 9.60 (br s, 1H), 9.90 (br s, 1H);
Anal. calcd for $C_{17}H_{16}BrNO_4S$: C, 49.77;H, 3.93; N, 3.41. Found: C, 49.75;H, 4.11; N, 3.48.

EXAMPLE 105

9-(5-cyano-6-methylthiopyrid-2-yl)-3,4,5,6,7,9-hexahydrocyclopenta[rbthiopyrano[2,3-e]pyridine-8(2H)-one, 1,1-dioxide A solution of 3-amino-2-cyclopenten-1-one (38.8 mg, 0.4 mmol), tetrahydrothiopyrane-3-one-1, 1-dioxide (59.2 mg, 0.40 mmol) and 3-cyano-2-(methylthio)pyridine (71.2 mg, 0.40 mmol) in absolute ethanol (3 mL) was heated at 80 ° C. for 3 days in a sealed tube. Solvent was evaporated, and the residue purified by preparative TLC to provide 85 mg of the title compound.
MS (APCI+) m/z: 388 (M+H)$^+$; $^1$HNMR (DMSO-$d_6$) δ 2.21 (m, 4H), 2.50 (s, 3H), 2.58 (m, 4H), 3.20 (m, 2H), 4.92 (s, 1H), 7.11 (d, 1H), 8.08 (d, 1H), 10.01 (s, 1H);
Anal. calcd for $C_{18}H_{17}N_3O_3S_2$: C, 55.79;H, 4.42; N, 10.84; S, 16.55; Found: C, 55.62;H, 4.45; N, 10.81; S, 16.42.

EXAMPLE 106

7-(3-bromo-4-fluorophenyl)-5-methyl-2,3,4,7-tetrahydrothieno[3.2-b]pyridine-6-carboxylic acid, 1,1-dioxide

EXAMPLE 106A methyl 7-(3-bromo-4-fluorophenyl)-5-methyl-2.3 4.7-tetrahydrothieno [3,2-b]pyridine-6-carboxylate. 1,1-dioxide 3-Bromo-4-fluorobenzaldehyde (2.03 g, 10.0 mmol), methyl 3-aminocrotonate (1,15 g, 10.0 mmol) and tetrahydrothiophene-3-oxo-1,1-dioxide (1.29 g, 9.60 mmol) in methanol (30 mL) were heated at 65 °C. overnight. The white precipitate, was collected, washed with acetone, dried, then heated to reflux in methanol (30 mL) with 1.0 M HCl in ether (10 mL) for 2 hours. The reaction was cooled, solvent evaporated, the solid triturated with ether, collected washed with ether and dried to provide 2.88 g of the title compound as a white solid.
mp 232–234 °C.;
MS (ES1-) m/z: 416 (M-H)⁻;
$^1$H NMR (DMSO-d$_6$) δ 2.28 (s, 3H), 2.75–3.05 (m, 2H), 3.28–3.35 (m, 2H), 3.52 (s, 3H), 4.87 (s, 1H), 7.19 (m, 1H), 7.26 (t, 1H), 7.48 (d, 1H), 9.50 (s, 1H);
Anal. calcd for $C_{16}H_{15}BrFNO_4S$: C, 46.17;H, 3.63; N, 3.36. Found: C, 46.13;H, 3.78; N, 3.27.

EXAMPLE 106B 7-(3-bromo-4-fluorophenyl)-5-methyl-2,3,4,7-tetrahydrothieno [3,2-b]pyridine-6-carboxylic acid, 1,11-dioxide The ester from Example 106A (416 mg, 1.00 mmol) in methylene chloride (4 mL) at 0 °C., was treated 1.0 M BCl$_3$ in methylene chloride (6 mL), allowed to warm to room temperature, stirred 4 hours, diluted with ice-water (50 mL) and extracted with ethyl acetate (4x). The organic extracts were dried over magnesiumn sulfate, filtered and solvent evaporated. The crude material was triturated with small amount of ethyl acetate, the solid precipitate collected, washed with ethyl acetate and dried to provide 271 mg of the title compound as a yellow solid.
mp 220–223 °C.;
MS (ES1-) m/z: 400 (M-H)⁻;
$^1$H NMR (DMSO-d$_6$) δ 2.28 (s, 3H), 2.23–3.02 (m, 2H), 3.30–3.40 (m, 2H), 4.84 (s, 1H), 7.18 (m, 1H), 7.28 (t, 1H), 7.37 (d, 1H), 9.39 (s, 1H), 11.97 (s, 1H);
Anal. calcd for $C_{15}H_{13}BrFNO_4S$: C, 45.92;H, 3.94; N, 3.08. Found: C, 46.31;H, 4.34; N, 2.84.

EXAMPLE 107

8-(3-bromo-4-fluorophenyl)-6-methyl-5,8-dihydrothiopyrano[3.2-b]pyridine-7-carboxylic acid, 1,1-dioxide

EXAMPLE 107A methyl 8-(3-bromo-4-fluorophenyl)-6-methyl-5,8-dihydrothiopyrano[3 2-b]pyridine-7-carboxylate. 1,1-dioxide 3-Bromo-4-fluorobenzaldehyde (2.03 g, 10.0 mmol), methyl 3-aminocrotonate (1,15 g, 10.0 mmol) and tetrahydrothiopyran-3-one-1, 1-dioxide (1.48 g, 10.0 mmol) in methanol (30 mL) were heated at 65 °C. overnight. The white precipitate, was collected, washed with acetone and dried to provide 3.1 1 g of the title compound as a white solid.
mp 255 °C.;
MS (ES1-) m/z: 430 (M-H)⁻;
$^1$H NMR (DMSO-d$_6$) o2.18 (m, 2H), 2.27 (s, 3H), 2.43–2.55 (m, 2H), 3.14–3.22 (m, 2H), 3.58 (s, 3H), 4.97 (s, 1H), 7.19 (m, 1H), 7.25 (t, 1H), 7.36 (d, 1H), 9.12 (s, 1H);
Anal. calcd for $C_{17}H_{17}BrFNO_4S$: C, 47.45;H, 3.98; N, 3.26. Found: C, 47.40;H, 4.11; N, 3.2 1.

EXAMPLE 107B 8-(3-bromo-4-fluorophenyl)-6-methyl-5,8-dihydrothiopyrano [32-b]pyridine-7-carboxylic acid, 1,1-dioxide The ester from Example 107A (430 mg, 1.00 mmol) in methylene chloride (4 mL) at 0 °C., was treated 1.0 M BCl$_3$ in methylene chloride (6 mL), allowed to warm to room temperature, stirred 4 hours, diluted with ice-water (50 mL) and extracted with ethyl acetate (4x). The organic extracts were dried (MgSO$_4$), filtered, and solvent evaporated. The crude material was triturated with small amount of ethyl acetate, the solid precipitate collected, washed with ethyl acetate and dried to provide 180 mg of the title compound as a yellow solid.
mp 208–210 °C.;
MS (ES1-) m/z: 414 (M-H)⁻;
$^1$H NMR (DMSO-d$_6$) 82.15–2.18 (m, 2H), 2.24 (s, 3H), 2.52–2.60 (m, 2H), 3.14–3.22 (m, 2H), 4.96 (s, 1H), 7.18 (m, 1H), 7.25 (t, 1H), 7.37 (d, 1H), 8.95 (S, 1H), 11.88 (S, 1H);
Anal. calcd for $C_{16}H_{15}BrFNO_4S$ 0.5 $CH_2Cl_2$: C, 43.20;H, 3.52; N, 3.05. Found: C, 42.72; H, 3.88; N, 2.99.

EXAMPLE 108

9-(5-bromo-2-hydroxyphenyl)-2,3,5,6,7,9-hexahydrothieno[3,2-b]quinolin-8(4H)-one 1,1-dioxide 5-Bromosalicylaldehyde (0.201 g, 1.0 mmol), tetrahydrothiophene-3-oxo-1,1-dioxide (0.13 g, 1.0 mmol), 3-amino-2-cyclohexen-1-one (0.11 g, 1.0 mmol) and triethylamine (0.85 mL) were heated in ethanol (4 mL) to 80 °C. in a sealed tube for 72 hours, cooled, and solvent evaporated. The crude intermediate in ethanol (5 mL) was treated with 1.0 M HCl in ether (1 mL), heated to reflux for 1 hour, cooled, the solid precipitate collected, washed with ethanol and dried to provide 0.13 g of the title compound as an orange-yellow solid.
MS (APC1-) m/z: 408 (M-H)⁻;
$^1$H NMR (DMSO-d$_6$) δ 1.74–2.0 (m, 2H), 2.23 (m, 2H), 2.56 (m, 2H), 2.78 (dt, 1H), 2.95 (dt, 1H), 3.28 (t, 2H), 5.11 (s, 1H), 6.63 (d, 1H), 6.97 (d, 1H), 7.07 (dd, 1H), 9.70 (s, 1H), 9.73 (s, 1H);
Anal. calcd for $C_{17}H_{16}BrNO_4S$: C, 49.77;H, 3.93; N, 3.41. Found: C, 49.89;H, 4.12; N, 3.31.

EXAMPLE 109

(+)-9-(3-chloro-4-fluorophenyl)-2,3,5,6,7,9-hexahydrothieno[3,2-b]quinolin-8(4H)-one, 1,1-dioxide Example 81 was processed according to the method of Example 95 to provide the title compound.
mp >250 °C.; [c]$^{23}$D +50.34 (c 0.58, DMSO);
MS (ESI+) m/z: 368 (M+H)⁺;
$^1$H NMR (DMSO-d$_6$) δ 1.90 (M, 2H), 2.25 (M, 2H), 2.55 (M, 2H), 2.85 (M, 1H), 3.04 (M, 1H), 3.35 (M, 2H), 4.85 (S, 1H), 7.18 (M, 1H), 7.28 (M, 2H), 9.86 (S, 1H);
Anal. calcd for $C_{17}H_{15}ClFNO_3S$: C, 55.51;H, 4.11; N, 3.81. Found: C, 55.20;H, 4.16; N, 3.80.

EXAMPLE 110

(-)-9-(3-chloro-4-fluorophenyl)-2,3,5,6,7,9-hexahydrothieno[3.2-b]quinolin-8(4H)-one, 1,1-dioxide Example 81 was processed according to the method of Example 96 to provide the title compound.
mp >250 °C.; [a]$^{23}$D -49.57 (c 0.56, DMSO);
MS (ESI+) m/z: 368 (M+H)⁺;
$^1$H NMR (DMSO-d$_6$) δ 1.86 (m, 2H), 2.22 (m, 2H), 2.56 (m, 2H), 2.85 (m, 1H), 3.05 (m, 1H), 3.35 (m, 2H), 4.85 (s, 1H), 7.18 (m, 1H), 7.28 (m, 2H), 9.88 (s, 1H);

Anal. calcd for $C_{17}H_{15}ClFNO_3S$: C, 55.51;H, 4.11; N, 3.81. Found: C, 55.76;H, 4.12; N, 3.78.

EXAMPLE 111

9-(4-fluoro-3-methylphenyl)-2,3,5,6,7,9-hexahydrothieno[3,2-b]quinolin-8(4H)-one, 1,1-dioxide 3-Methyl-4-fluorobenzaldehyde (77 mg, 0.56 mmol) (Khanna J. Med Chem. (1997), 40, 1634), tetrahydrothiophene-3-oxo-1,1-dioxide (68 mg, 0.51 mmol), 3-amino-2-cyclohexen-1-one (55 mg, 0.50 mmol) and triethylamine (35 µL) were heated in ethanol (2 mL) to 80° C. in a sealed tube for 48 hours, cooled, and solvent evaporated. The crude reaction product was flash chromatographed over silica gel eluting with methanol:methylene chloride (7:93) to provide 92 mg of an intermediate hemiaminal that was heated to reflux in ethanol (6 mL), treated with 1.0 M HCl in ether (0.5 mL), heated for 1 hour, cooled, the solid precipitate collected, washed with ethanol and dried to provide 55 mg of the title compound as a white solid.
mp >260° C.;
MS (APCl-) m/z: 346 (M-H)$^-$; H NMR (DMSO-d$_6$) δ 1.70–1.98 (m, 2H), 2.22 (m, 2H), 2.54 (m, 2H), 2.80 (dt, 1H), 2.99 (dt, 1H), 3.33 (t, 2H), 4.80 (s, 1H), 6.91–7.07 (m, 3H), 9.74 (br s, 1H);
Anal. calcd for $C_{18}H_{1}FNO_3S$: C, 62.23;H, 5.22; N, 4.03. Found: C, 62.29;H, 5.30; N, 3.90.

EXAMPLE 112

7-(3-bromo-4-fluorophenyl)-5-(trifluoromethyl)-2,3,4,7-tetrahydrothieno[3,2-b]pyridine. 1,1-dioxide

EXAMPLE 112A 4-(3-bromo-4-fluorophenyl)-1 I1,1-trifluoro-3-buten-2-one

To 3-bromo-4-fluorobenzaldehyde (406 mg, 2.0 mmol) in benzene (10 mL) with piperidine (0.08 mL), and acetic acid (0.01 mL) was added 1,1,1-trifluoroacetone (1.8 mL, 20 mmol) to the bottom of the vessel by syringe. The reaction vessel was sealed and heated to 50° C. overnight. The solvents were evaporated, the residue was flash chromatographed over silica gel eluting with hexane:ethyl acetate (4:1) to provide 226 mg of the title compound.
$^1$H NMR (CDCl$_3$) δ 6.95 (d, 1H), 7.21 (t, 1H), 7.58 (m, 1H), 7.85 (d, 1H), 7.87 (dd, 1H).

EXAMPLE 112B 7-(3-bromo-4-fluorophenyl)-5-(trifluoromethyl)-2,3,4,7-tetrahydrothieno[3,2-b]pyridine 1,1-dioxide Example 112A (800 mg, 2.69 mmol), tetrahydrothiophene-3-oxo-1,1-dioxide (361 mg, 2.69 mmol) and 2.0 M NH$_3$ in ethanol (2.1 mL) in EtOH (5 mL) were heated to reflux overnight. The solvent was evaporated, the residue dissolved in toluene, treated with para-toluenesulfonic acid (catalytic amount) and heated to reflux for 0.5 to 1.5 hours. The solvent was evaporated, and the crude product flash chromatographed over silica gel eluting with methanol:methylene chloride (5:95) to provide 630 mg of the title compound as'a white solid.
MS (APCl+) m/z: 429 (M+NH$_4$)$^+$;
$^1$H NMR (DMSO-d$_6$) δ 2.84 (m, 1H), 2.98 (m, 1H), 3.3 (m, 2H), 4.81 (s, 1H), 5.42 (s, 1H), 7.33 (m, 2H), 7.56 (d, 1H), 9.57 (br s, 1H);

Anal. calcd for $C_{14}HI_0BrF_4NO_2S$: C, 40.79;H, 2.45; N, 3.40. Found: C, 40.72;H, 2.53; N, 3.54.

EXAMPLE 113

(+)-9-(3-cyanophenyl)-2,3,5,6,7,9-hexahydrothieno[3,2-b]quinolin-8(4H)-one, 1,1-dioxide Example 30 (1.27 g, 3.70 mmol) was processed according to the method of Example 95 to provide 245 mg of the title compound.
mp >250° C.; [a]23D +34.38, (c 0.48, DMSO);
MS (ESI+) m/z: 341 (M+H)$^+$;
$^1$H NMR (DMSO-d$_6$) δ 1.85 (m, 2H), 2.20 (m, 2H), 2.60 (m, 2H), 2.85 (m, 1H), 3.05 (m, 1H), 3.35 (m, 2H), 4.90 (s, 1H), 7.45 (t, 1H, J=7.5Hz), 7.55 (d, 2H, J=9Hz), 7.62 (d, 1H, J=7.5Hz), 10.45 (s, 1H);
Anal. calcd for $C_{18}H_{16}N_2O_3S$: C, 63.51;H, 4.74; N, 8.23. Found: C, 63.38;H, 4.59; N, 8.26.

EXAMPLE 114

(−)-9-(3-cyanophenyl)-2,3,5,6,7,9-hexahydrothieno[3,2-b]quinolin-8(4H)-one, 1,1-dioxide Example 30 (1.27 g) was processed according to the method of Example 96 to provide 280 mg of the title compound.
mp >250° C.; [a23D -33.77, (c=0.53, DMSO);
MS (ESI+) m/z: 341 (M+H)$^+$;
$^1$H NMR (DMSO-d$_6$) δ 1.85 (m, 2H), 2.20 (m, mH, J=2Hz), 2.55 (m, 2H), 2.85 (m, 1H), 3.05 (m, 1H), 3.32 (m, 2H), 4.90 (s, 1H), 7.45 (t, 1H, J=7.5Hz), 7.55 (d, 2H, J=9Hz), 7.62 (d, 1H, J=7.5Hz), 10.45 (s, 1H);
Anal. calcd for $C_{18}H_{16}N_2O_3S$: C, 63.51;H, 4.74; N, 8.23. Found: C, 63.59;H, 4.61; N, 8.28.

EXAMPLE 115

9-(5-bromo-4-fluoro-2-iodophenyl)-2,3,5,6,7,9-hexahydrothienof3,2-b]quinolin-8(4H)-one, 1,1-dioxide

EXAMPLE 115A

5-Bromo-4-fluoro-2-nitrobenzaldehyde.

To a solution of 3-bromo-4-fluorobenzaldehyde (5.00 g, 24.6 mmol) in sulfuric acid (25 mL) at 0° C. was added dropwise fuming nitric acid (3 mL) in sulfuric acid (30 mL), stirred at room temperature overnight, poured onto ice, the precipitate collected, washed with water, and dried. The crude product was purified by flash chromatography over silica gel eluting with ethylacetate/hexane (3:7) to provide 3.9 g of the title compound as yellow crystals.
$^1$H NMR (CDCl$_3$) 8 7.92 (d, 1H), 8.23 (d, 1H), 10.4 (s, 1H).

EXAMPLE 115B

5-Bromo-4-fluoro-2-iodobenzaldehyde.

To a solution of Example 115A (1.0 g, 4.0 mmol) in 1: 1 ethanol-water (50 mL), was added iron-powder (0.6 g) then 6 N hydrochloric acid (1 mL). The reaction mixture was heated to reflux overnight, cooled, neutralized with I N sodium hydroxide, filtered, and the filtrate extracted with ethyl acetate (3x). The organic extracts were dried over magnesium sulfate, filtered and solvent evaporated to provide 0.68 g of 5-bromo-4-fluoro-2-aminobenzaldehyde. To a solution of 2-amino-5-bromo-4-fluorobenzaldehyde (0.68 g, 3.1 mmol) in water (10 mL) at 0 ° C. was added sulfuric acid (2 mL) then slowly a solution of sodium nitrite (0.23 g, 3.4 mmol) in water (10 mL) keeping the temperature below 10 ° C.. After stirring at this temperature for 1 hour this suspension was added to a solution of potassium iodide (0.50 g, 3.1 mmol) in water (20 mL), the reaction mixture stirred at room temperature overnight, extracted with ethyl acetate (3x). The organic extracts were washed with aqueous sodium thiosulfate, 5% sodium bicarbonate solution and water, then dried over magnesium sulfate, filtered and solvent evaporated. The crude residue was purified by flash chromatography over silica gel eluting with ethyl acetate- :hexane (1:9) to provide 0.16 g of the title compound as a tan solid.

$^1$H NMR (CDCl$_3$) δ 7.72 (d, 1H), 8.1 (d, 1H), 9.92 (s, 1H) Example 115C 9-(5-bromo-4-fluoro-2-iodophenyl)-2,3,5, 6,7,9-hexahydrothieno[3,2-b]quinolin-8(4H)-one, 1,1- dioxide Example 1I5B (0.14 g, 0.43 mmol), tetrahydrothiophene-3-oxo-1, 1-dioxide (0.058 g, 0.43 mmol), 3-amino-2-cyclohexene-1-one (0.048 g, 0.43 mmol), and triethylamine (0.1 mL) in ethanol (2 mL) were heated at reflux for 48 hours, cooled, and the precipitate collected (0.11 g). The precipitate was suspended in ethanol (5 mL), treated with 1.0 M HCl in ether (1.0 mL) heated to reflux for 2 hours, the solid precipitate collected, washed with ethanol and dried to provide 0.08 g of the title compound.

MS (ES1-) m/z: 536 (M-H)$^-$;
$^1$H NMR (DMSO-d$_6$) δ 1.9 (m, 2H), 2.2 (m, 2H), 2.58 (m, 2H), 2.7–3.0 (m, 2H), 3.28 (m, 2H), 5.12 (s, 1H), 7.35 (d, 1H), 7.75 (d, 1H), 9.81 (s, 1H);
Anal. calcd for C,,H$_{15}$NBrFIO$_3$S: C, 37.87;H, 2.80; N, 2.60. Found: C, 38.05;H, 2.75; N, 2.53.

EXAMPLE 116

9-(3-bromo-4-fluorophenyl)-7,7-dimethyl-2,3,5,6,7, 9-hexahydrothieno[3.2-b]quinolin-8(4H)-one, 1,1- dioxide A stirred solution of 3-bromo-4-fluorobenzaldehyde (725 mg, 3.57 mmol), 4,4-dimethyl-1,3-cyclohexanedione (500 mg, 3.57 mmol), and tetrahydrothiophene-3-oxo-1, 1-dioxide (479 mg, 3.57 mmol) in ethanol (40 mL) was treated with anhydrous ammonium acetate (330 mg, 4.29 mmol), and the mixture was heated at reflux for 60 hours. The reaction mixture was cooled to ambient temperature, and the white solid that precipitated was isolated by filtration. The solid was triturated sequentially with 10% ethyl acetate/ethanol, diethyl ether, then 25% diethyl ether/ethanol to provide 543 mg of the title compound as a white solid. mp >270 ° C.;

MS (DCI/NH$_3$) m/z: 457 (M+NH$_4$)$^+$;
$^1$H NMR (DMSO-d$_6$) 60.89 (s, 3H), 0.98 (s, 3H), 1.75 (t, 2H, J=6.1Hz), 2.50–2.640 (m, 2H), 2.68–3.07 (m, 3H), 3.29–3.41 (m, 1H), 4.80 (s, 1H), 7.13–7.32 (m, 2H), 7.38 (dd, 1H, J=6.7, 2.0Hz), 9.69 (br s, 1H);
Anal. calcd for C$_{19}$Hg$_9$BrFNO$_3$S: C, 51.83;H, 4.35; N, 3.18. Found: C, 51.58;H, 4.09; N, 3.25.

EXAMPLE 117

9-(3-pyridinyl)-2,3,5,6,7,9-hexahydrothieno[3,2-b] quinolin-8(4H)-one, 1,1-dioxide 3-Pyridinecarboxaldehyde (214 mg, 2.00 mmol) was processed according to the method of Example 11 5C to provide 500 mg of the title compound.
mp >250 ° C.;
MS (ESI+) m/z: 317 (M+H)$^+$;
$^1$H NMR (DMSO-d$_6$) 6 1.90 (m, 2H), 2.25 (m, 2H), 2.55 (m, 2H), 3.02 (m, 2H),,3.35 (m, 2H), 5.10 (s, 1H), 7.92 (dd, 1H, J=9Hz), 8.40 (d, 1H, J=9Hz), 8.70 (d, 1H, J=6Hz), 8.82 (s, 1H), 10.25 (s, 1H);
Anal. calcd for C$_{16}$H$_{16}$N$_2$O$_3$S: C, 60.74;H, 5.10; N, 8.85. Found: C, 60.67;H, 5.19; N, 8.87.

EXAMPLE 118

9-(4-pyridinyl)-2,3,5,6,7,9-hexahydrothieno[3,2-b] quinolin-8(4H)-one, 1,1-dioxide 4-Pyridinecarboxaldehyde (214 mg, 2.00 mol) was processed according to the method of Example 115C to provide 550 mg of the title compound.
mp >250 ° C.;
MS (ESI+) rn/z: 317 (M+H)$^+$;
$^1$H NMR (DMSO-d$_6$) δ 1.90 (m, 2H), 2.25 (m, 2H), 2.55 (m, 2H), 2.95 (m, 1H), 3.05 (m, 1H), 3.35 (m, 2H), 5.08 (s, 1H), 7.85 (d, 2H, J=6Hz), 8.78 (d, 2H, J=6Hz), 10.18 (s, 1H);
Anal. calcd for C$_{16}$H$_{16}$N$_2$O$_3$S: C, 60.74;H, 5.10; N, 8.85. Found: C, 60.56;H, 5.16; N, 8.61.

EXAMPLE 119

9-(4-fluoro-2-hydroxyphenyl)-2,3,5,6,7,9- hexahydrothieno[3,2-b]quinolin-8(4H)-one, 1,1- dioxide

EXAMPLE 119A 4-fluoro-2-hydroxybenzaldehyde

To a stirred solution of magnesium methoxide (13 g, 150 mmol, 6% in methanol) in methanol (50 mL) was added 3-fluorophenol (22.4 g, 200 mmol). The solution was heated to reflux, approximately half the methanol distilled off, toluene (300 mL) added, and the reaction heated with azeotropic removal of solvent until the temperature of the distillate reached 95 ° C.. A slurry of paraformaldehyde powder (22 g, 720 mmol) in toluene (20 mL) was added in small portions over 1 hour to the reaction with concurrent removal of volatile materials by distillation. Stirring was continued at 95 ° C. for 1 hour, cooled to 25 ° C., the reaction quenched by slow addition to 10% sulfuric acid and stirred at 30–40 ° C. for 2 hours. The layers were separated and the aqueous portion extracted with toluene (2x50 mL). The combined organic layers were washed with 10% sulfuric acid, water, dried with sodium sulfate, filtered and solvent evaporated. The resulting yellow oil was purified by flash chromatography over silica gel eluting with hexane:ethyl acetate (5: 1) to provide 9.7 g of the title compound as a white solid.

$^1$H NMR (CDCl$_3$) δ 6.70 (m, 2H), 7.58 (m, 1H), 9.85 (s, 1H), 11.35 9s, 1H);
MS (APC1-) m/z: 139 (M-H)$^-$

EXAMPLE 119B 9-(4-fluoro-2-hydroxyphenyl)-2,3,5,6,7,9- hexahydrothieno[3,2-b]quinolin-8(4H)-one, 1,1- dioxide Example 119A (280 mg, 2.00 mmol) was processed according to the method of Example 115C to provide 620 mg of the title compound.
mp >250 ° C.;

MS (ESI+) m/z: 350 (M+H)+;
$^1$H NMR (DMSO-d$_6$) δ 1.90 (m, 2H), 2.25 (m, 2H), 2.54 (m, 2H), 3.25 (t, 2H, J=7.5Hz), 5.08 (s, 1H), 6.45 (m, 2H), 6.92 (dd, 1H, J=9Hz), 9.68 (s, 1H), 9.85 (s, 1H);
Anal. calcd for C$_{17}$H$_{16}$FNO$_4$S: C, 58.44;H, 4.62; N, 4.01. Found: C, 58.12;H, 4.77; N, 3.87.

EXAMPLE 120

9-(5-chloro-2-hydroxyphenyl)-2,3,5,6,7,9-hexahydrothieno[3.2-b]quinolin-8(4H)-one, 1,1-dioxide 5-Chloro-2-hydroxybenzaldehyde (940 mg, 6.00 mmol) was processed according to the method of Example 115C to provide 1.7 g of the title compound.
mp >250 ° C.;
MS (ESI+) m/z: 366 (M+H)+;
$^1$H NMR (DMSO-d$_6$) δ 1.90 (m, 2H), 2.25 (m, 2H), 2.55 (m, 2H), 2.80 (m, 1H), 2.92 (m, 1H), 3.26 (t, 2H, J=7.5Hz), 5.12 (s, 1H), 6.68 (d, 1H, J=9Hz), 6.84 (d, 1H, J=3Hz), 6.95 (dd, 1H, J=3, 9Hz), 9.66 (s, 1H), 9.70 (s, 1H);
Anal. calcd for C$_{17}$H$_{16}$ClNO$_4$S: C, 55.81;H, 4.41; N, 3.83. Found: C, 55.54;H, 4.51;N, 3.77.

EXAMPLE 121

9-(5-bromo-4-fluoro-2-hydroxyphenyl)-2.35,6,7,9-hexahydrothieno[3.2-b]quinolin-8(4H)-one, 1,1-dioxide

EXAMPLE 121A 4-fluoro-5-bromo-2-hydroxybenzaldehyde

Example 119A (2.00 g, 14.3 mmol) in chloroform (10 mL) was treated slowly with a solution of bromine (0.70 mL, 13 mmol) in chloroform (6 mL) at room temperature. After the free bromine had disappeared, the mixture was refluxed with 20% sodium hydroxide (20 mL) for 4 hours, cooled, the chloroform evaporated, the solid dissolved in ethyl acetate, acidified with I N hydrochloric acid (pH=5), and the solvents evaporated. The crude product was purified by flash chromatography over silica gel eluting with hexane:ethyl acetate (6:1) to provide 1.95 g of the title compound.
MS (ESI+) m/z: 219 (M+H)'; $^1$HNMR (CDCl$_3$) δ 6.78 (d, 1H, J=9Hz), 7.75 (d, 1H, J=9Hz), 9.80 (s, 1H), 11.25 (s, H).

EXAMPLE 121B 9-(5-bromo-4-fluoro-2-hydroxyphenyl)-2,3,5,6,7,9-hexahydrothieno[3,2-b]quinolin-8(4H)-one, 1 1-dioxide Example 121B (657 mg, 3.00 mmol) was processed according to the method of 115C to provide 1,1 g of the title compound.
mp >250 ° C.;
MS (ESI+) m/z: 429 (M+H)+;
$^1$H NMR (DMSO-d$_6$) δ 1.90 (m, 2H), 2.25 (m, 2H), 2.55 (m, 2H), 2.80 (m, 1H), 2.92 (m, 1H), 3.26 (t, 2H, J=7.5Hz), 5.10 (s, 1H), 6.6 (d, 1H, J=12Hz), 7.05 (d, 1H, J=9Hz), 9.70 (s, 1H), 10.25 (s, 1H);
Anal. calcd for C$_{17}$H$_{15}$BrFNO$_4$S: C, 47.68;H, 3.53; N, 3.27. Found: C, 48.00;H, 3.78; N, 3.24.

EXAMPLE 122

8-[4-chloro-3-(trifluoromethyl)phenyl]-2,3,4,5,6,8-hexahydrodithieno[3,2-b:2',3'-e]pyridine-1,1,7,7-tetraoxide 4-Chloro-3-trifluoromethylbenzaldehyde (210 mg, 1.00 mmol) was processed as in Example 53 to provide 185 mg of the title compound as a white solid.
mp >260 ° C.;
MS (APC1-) m/z: 438 (M-H)−;
$^1$H NMR (DMSO-d$_6$) δ 2.83 (m, 2H), 3.02 (m, 2H), 3.40 (m, 4H), 5.12 (s, 1H), 7.60 (dd, 1H), 7.67 (d, 1H), 7.70 (s, 1H), 10.1 (br s, 1H);
Anal. calcd for C$_{16}$H$_{13}$ClF$_3$NO$_4$S$_2$: C, 43.69;H, 2.98; N, 3.18. Found: C, 43.79;H, 3.05; N,3.04.

EXAMPLE 123

8-(2,1,3-benzoxadiazol-5-yl)-2,3,4,5,6,8-hexahydrodithieno[3,2-b:2',3'-e]pyridine-1,1,7,7-tetraoxide 2,1,3-Benzoxadiazole-5-carboxaldehyde (0.148 g, 1.00 mmol) was processed as in Example 53 to provide 175 mg of the title compound as a tan solid.
mp >260 ° C.;
MS (APC1-) m/z: 378 (M-H)−;
$^1$H NMR (DMSO-d$_6$) δ 2.86 (m, 2H), 3.03 (m, 2H), 3.40 (m, 4H), 5.20 (s, 1H), 7.58 (d, 1H), 7.94 (s, 1H), 8.01 (d, 1H), 10.12 (s, 1H);
Anal. calcd for C$_{15}$H$_{13}$N$_3$O$_5$S$_2$: C, 47.49;H, 3.45; N, 11.07. Found: C, 47.57;H, 3.53; N, 10.89.

EXAMPLE 124

8-(3.4-dibromophenyl)-2,3,4,5,6,8-hexahydrodithieno[3.2-b:2',3 '-e]pyridine-1,1,7,7-tetraoxide 3,4-Dibromobenzaldehyde (263 mg, 1.00 mmol) was processed as in Example 53 to provide 150 mg of the title compound as a white solid.
mp >260 ° C.;
MS (APC1-) ni/z: 494 (M-H)−;
$^1$H NMR (DMSO-d$_6$) δ 2.82 (m, 2H), 3.01 (m, 2H), 3.39 (m, 4H), 4.94 (s, 1H), 7.21 (dd, 1H), 7.60 (d, 1H), 7.68 (d, 1H), 10.02 (br s, 1H);
Anal. calcd for C$_{15}$H$_{13}$Br$_2$NO$_4$S$_2$: C, 36.38;H, 2.65; N, 2.83. Found: C, 36.55;H, 2.75; N, 2.66.

EXAMPLE 125

9-(3-bromo-4-fluorophenyl)-2,3,5,6,7,9-hexahydrothieno[3.2-b]quinolin-8(4H)-one, 1-oxide (Two different diastereomers isolated; see below)

EXAMPLE 125A

2-[(3-bromo-4-fluorophenyl)methylideneldihydro-3-thiophenone

A solution of 4-(4,5-dihydro-3-thiophenyl)morpholine (2.0 g, 11.6 mmol) (Buiter, Rec. Trav. Chim. (1964), 83, 1160) and 3-bromo-4-fluorobenzaldehyde (2.38 g, 11.6 mmol) were stirred in toluene at room temperature for 5 days, treated with saturated ammonium chloride, and extracted with ethyl acetate. The ethyl acetate extract was washed with brine, dried with sodium sulfate, filtered, and concentrated. The residue was purified by flash chromatography on silica gel eluting with ethyl acetate:hexanes (1:5) to provide 350 mg of the title compound.
MS (DCI/NH$_3$) m/z: 287 (M+H)+;
$^1$H NMR (DMSO-d$_6$) δ 2.81 (t, J=7.0Hz, 2H), 3.33 (t, J=7.0Hz, 2H), 7.32 (s, 1H), 7.52 (t, J=8.8Hz, 1H), 7.73 (ddd, J=8.8, 7.0, 2.2Hz, 1H), 8.0 (dd, J=7.0, 2.2Hz, 1H).

EXAMPLE 125B

2-[(3-bromo-4-fluorophenyl)methylideneldihydro-3-thiophenone, 1-oxide

A solution of Example 125A (306 mg, 1.07 mmol) and meta-chloroperoxybenzoicacid (242 mg of 77%, 1.07 mmol) were stirred in methylene chloride at 0 °C. for 1 hour, treated with saturated sodium bicarbonate, and extracted with ethyl acetate. The extract was washed with brine, dried with sodium sulfate, filtered, and concentrated. The residue was purified by flash chromatography on silica gel eluting with methanol:dichloromethane (5:95) to provide 234 mg of the desired compound.
MS (DCI/NH$_3$) m/z: 320 (M+NH$_4$)$^+$;
$^1$H NMR (DMSO-d$_6$) δ 2.76–2.85 (m, 2H), 3.10–3.30 (m, 2H), 7.65 (t, J=8.6Hz, 1H), 8.01 (s, 1H), 8.06 (ddd, J=8.6, 6.6, 2.2Hz, 1H), 8.35 (dd, J=6.6, 2.2Hz, 1H).

EXAMPLE 125C 9-(3-bromo-4-fluorophenyl)-2,3,5,6,7,9-hexahydrothieno[3,2-b]quinolin-8(4H)-one, 1,1-oxide A solution of Example 125B (110 mg, 0.36 mmol) and 3-amino-2-cyclohexen-1-one (61 mg, 0.55 mmol) were stirred in ethanol at 90 °C. in a sealed tube for 3 days, cooled to room temperature, treated with saturated sodium bicarbonate, and extracted with ethyl acetate. The extract was washed with brine, dried with sodium sulfate, filtered, and concentrated. The residue was purified by flash chromatography on silica gel eluting with 5%-15% methanol/dichloromethane to provide the diastereomeric dihydropyridines (25 mg, 17%) and (5.0 mg, 3.4%).

The major diastereomer was eluted off the column as the more polar diastereomer.
MS (DCI+) m/z: 413 (M+NH$_4$)$^+$;
$^1$H NMR (CDCl$_3$) δ 2.02–2.05 (m, 2H), 2.33–2.40 (m, 2H), 2.51 (t, 2H, J=6.6Hz), 2.81-2.95 (m, 2H), 3.26–3.40 (m, 2H), 5.10 (s, 1H), 6.62 (s, 1H), 7.03 (dd, 1H, J=8.5, 8.3Hz), 7.26–7.31 (m, 1H), 7.39 (dd, 1H, J=6.6, 2.0Hz);
Anal. calcd for C$_{17}$H$_{15}$BrFNO$_2$S0.25H$_2$0: C, 50.94;H, 3.89; N, 3.49. Found: C, 50.83; H, 4.01; N, 3.09.

The minor diastereomer was eluted off the column as the less polar diastereomer.
MS (DCI+) m/z: 413 (M+NH$_4$)$^+$;
$^1$H NMR (CDCl$_3$) δ 2.00–2.03 (m, 2H), 2.30–2.40 (m, 2H), 2.43–2.49 (m, 2H), 2.65-2.77 (m, 1H), 2.83–2.91 (m, 1H), 3.35–3.56 (m, 2H), 5.14 (s, 1H), 6.56 (s, 1H), 6.99 (t, J=8.5Hz, 1H), 7.31 (ddd, J=8.5, 6.8, 2.3Hz, 1H), 7.48 (dd, J=6.8, 2.3Hz, 1H).

EXAMPLE 126

9-(4-methyl-3-nitrophenyl)-2,3 5,6,7,9-hexahydro[3.2-b]quinolin-8(4H)-one, 1,1-dioxide The title compound of Example 32 (1.24 g, 3.32 mmol) was processed as in Example 96 to provide 63 mg of the title compound as a white solid.
MS (APC1-) m/z: 373 (M-H)$^-$;
$^1$H NMR (DMSO-d$_6$) δ 1.82 (m, 1H), 1.90 (m, 1H), 2.23 (m, 2H), 2.45 (s, 3H), 2.54 (m, 2H), 2.84 (dt, 1H), 3.03 (dt, 1H), 3.35 (m, 2H), 4.91 (s, 1H), 7.37 (d, 1H), 7.45 (dd, 1H), 7.71 (d, 1H), 9.87 (br s, 1H);
Anal. calcd for C$_{18}$H$_{18}$N$_2$O$_5$S: C, 57.74;H, 4.85; N, 7.48. Found: C, 57.51;H, 4.72; N, 7.29.

EXAMPLE 127

9-(3,4-dichlorophenyl)-7,7-dimethyl-2,3,5,6,7,9-hexahydrothieno[3,2-b Iquinolin-8(4H)-one, 1,1-dioxide 3,4-Dichlorobenzaldehyde, 4,4-dimethyl-1,3-cyclohexanedione, and tetrahydrothiophene-3-oxo-1,1-dioxide, were processed as in Example 1 16 to provide the title compound as a white solid.
mp 262–265 °C. (dec);
MS (DCI/NH$_3$) m/z: 429 (M+NH$_4$)$^+$;
$^1$H NMR (DMSO-d$_6$) 60.90 (s, 3H), 0.98 (s, 3H), 1.75 (t, 2H, J=6.1Hz), 2.48–2.61 (m, 2H), 2.77–3.06 (m, 3H), 3.29–3.44 (m, 1H), 4.80 (s, 1H), 7.16 (dd, 1H, J=8.4, 2.0Hz), 7.33 (d, 1H, J=2.1Hz), 7.49 (d, 1H, J=8.1Hz), 9.71 (br s, 1H);
Anal. calcd for C$_{19}$Hl$_9$Cl$_2$NO$_3$S: C, 55.34;H, 4.64; N, 3.40. Found: C, 55.03;H, 4.54; N, 3.24.

EXAMPLE 128

9-(5-bromo-2-thienyl)-2,3,5,6,7,9-hexahydrothieno[3,2-b]quinolin-8(4H)-one, 1,1-dioxide 5-Bromo-2-thiophenecarboxaldehyde (1,1 g, 6.0 mmol) was processed according to the method of Example 115C to provide 1.9 g of the title compound.
mp >250 °C.;
MS (ESI+) m/z: 401 (M+H)$^+$; .
$^1$H NMR (DMSO-d$_6$) δ 1.92 (m, 2H), 2.30 (t, 2H, J=7.5Hz), 2.55 (m, 2H), 2.85 (m, 1H), 3.00 (m, 1H), 3.42 (m, 2H), 5.08 (s, 1H), 6.65 (d, 1H, J=3Hz), 6.95 (d, 1H, J=3Hz), 9.94 (s, 1H);
Anal. calcd for C$_{15}$H$_{14}$BrNO$_3$S$_2$: C, 45.01;H, 3.52; N, 3.50. Found: C, 44.78;H, 3.61; N, 3.35.

EXAMPLE 129

9-(4-bromo-2-thienyl)-2,3,5,6,7,9-hexahydrothieno[3,2-b]quinolin-8(4H)-one, 1,1-dioxide 4-Bromo-2-thiophenecarboxaldehyde (1,1 g, 6.0 mmol) was processed according to the method of Example 115C to provide 1.85 g of the title compound.
mp >250 °C.;
MS (ESI+) m/z: 401 (M+H)$^+$;
$^1$H NMR (DMSO-d$_6$) δ 1.82 (m, 1H), 1.94 (m, 1H), 2.30 (m, 2H), 2.55 (m, 2H), 2.84 (m, 1H), 3.05 (m, 1H), 3.42 (m, 2H), 5.12 (s, 1H), 6.80 (s, 1H), 7.40 (s, 1H), 9.95 (s, 1H);
Anal. calcd for C$_{15}$H$_{14}$BrNO$_3$S$_2$: C, 45.01;H, 3.52; N, 3.50. Found: C, 44.80;H, 3.57; N, 3.34.

EXAMPLE 130

9-(4-fluoro-3-vinylphenyl)-2,3,5,6,7,9-hexahydrothieno[3,2-b]quinolin-8(4H)-one, 1,1-dioxide

EXAMPLE 130A 1,1-dimethylethyl 9-(3-bromo-4-fluorophenyl)-8-oxo-3,5,6,7,8,9-hexahydrothienor3,2-b]quinoline-4(2H)-carboxylate, 1,1-dioxide A solution of Example 43 (1.0 g, 2.4 mmol) and di-tert-butyldicarbonate (1.0 g, 24 mmol) in acetonitrile was treated with 4-dimethylaminopyridine (29 mg, 0.1 mmol), heated to reflux for 1 hour, cooled to room temperature and concentrated. The residue was purified by flash chromatography on silica gel with 50% ethyl acetate/hexanes to provide 900 mg of the title compound.
$^1$H NMR (DMSO-d$_6$) δ 1.57 (s, 9H), 1.90–2.00 (m, 2H), 2.3–2.5 (m, 2H), 3.00 (m, 2H), 3.45 (m, 2H), 3.50 (m, 2H), 4.83 (s, 1H), 7.20 (m, 1H), 7.32 (t, 1H), 7.37 (dd, 1H).

EXAMPLE 130B 9-(4-fluoro-3-vinylphenyl)-2,3,5,6,7,9-hexahydrothieno[3,2-b]quinolin-8(4H)-one, 1,1-dioxide A solution of Example 130A (200 mg, 0.39 mmol) and tetrakis(triphenylphoshine)-palladium(0) (10 mol%) in dimethylformamide (0.1 M) was treated with vinyl tributylstannane (0.6 mL, 1.85 mmol), heated to 110 °C. for 24 hours, cooled to room temperature, treated with saturated potassium fluoride, and extracted with ethyl acetate. The extract was washed with brine, dried with sodium sulfate, filtered, and concentrated. The residue was purified by flash chromatography on silica gel eluting with 5% methanol/dichloromethane, followed by recrystallization from ethanol to provide 100 mg of the title compound as an off white solid.

MS (ES1-) m/z: 358 (M-H)$^-$;

$^1$H NMR (DMSO-d$_6$) δ 1.99–1.82 (m, 2H), 2.25–2.20 (m, 2H), 2.5 (m, 2H), 2.79–2.73 (m, 1H), 3.32–3.30 (m, 4H), 3.25–2.81 (m, 1H), 4.86 (s, 1H), 5.40 (dd, 1H, J=1 1.53, 1.35 Hz), 5.80 (dd, 1H, J=18.0, 1.35Hz), 6.77 (dd, 1H, J=17.63, 11.20Hz), 7.08–7.01 (m, 2H), 7.35 (dd, 1H, J=7.46, 2.04Hz), 9.74 (S, 1H); Anal. calcd for CgHl$_8$FNO$_3$S 0.3H$_2$0: C, 63.49;H, 5.05; N, 3.90. Found: C, 62.27;H, 5.20; N, 3.56.

EXAMPLE 131

9-(3-acetyl-4-fluorophenyl)-2,3 5,6,7,9-hexahydrothieno[3,2-b]quinolin-8(4H)-one, 1,1-dioxide Example 130 (108 mg, 0.27 mmol) in ether at 0 °C. was treated with hydrochloric acid/ether (1 mL, 1 mmol), stirred for 2 hours, treated with saturated sodium bicarbonate, and extracted with ethyl acetate. The residue was purified by flash chromatography on silica gel eluting with 5% methanol/dichloromethane, followed by recrystallization from ethanol to provide 93 mg of the title compound.

MS (ESI+) m/z: 376 (M+H)$^+$;

$^1$H NMR (DMSO-d$_6$) δ 1.8 (M, 2H), 2.2 (M, 2H), 2.5 (m, 2H), 2.55 (s, 3H), 2.8 (m, 2H), 3.0 (m, 2H), 4.89 (s, 1H), 7.21 (dd, 1H, J=8.5, 2.94Hz), 7.48 (m, 1H), 7.60 (m, 1H), 9.82 (s, 1H);

Anal. calcd for C$_{19}$H,8FNO$_4$S: C, 60.79;H, 4.83; N, 3.73. Found: C, 60.02;H, 4.92; N, 3.46.

EXAMPLE 132

9-[4-fluoro-3-(2-furyl)phenyl]-2,3,5,6,7,9-hexahydrothieno[3,2-b]quinolin-8(4H)-one, 1,1-dioxide Example 130A (200 mg, 0.39 mmol) and 2-(tributylstannyl)furan were processed as in Example 130 to provide 64 mg of the title compound.

MS (ESI+) m/z: 400 (M+H)$^+$;

$^1$H NMR (DMSO-d$_6$) δ 1.96 (m, 2H), 2.2 (m, 2H), 2.5 (m, 2H), 2.8 (m, 2H), 3.0 (m, 2H), 4.88 (s, 1H), 6.6 (dd, 1H, J=3.31, 1.47Hz), 6.81 (t, 1H, J=3.68Hz), 7.15 (m, 2H), 7.58 (dd, 1H, J=7.19, 2.21Hz), 7.85 (d, 1H, J=1.8Hz), 9.80 (s, 1H);

Anal. calcd for C$_2$,H$_{18}$FNO$_4$S: C, 63.15;H, 4.54; N, 3.51. Found: C, 61.85;H, 4.78; N, 3.47.

EXAMPLE 133

9-[6-fluoro-(1,1'-biphenyl)-3-vyl-2.3 5,6,7,9-hexahydrothienor3,2-b]quinolin-8(4H)-one, 1,1-dioxide Example 130A (200 mg, 0.39 mmol) and tetraphenyltin were processed as in Example 130 to provide 95 mg of the title compound.

MS (ESI+) m/z: 410 (M+H)$^+$;

$^1$H NMR (DMSO-d$_6$) δ 1.90 (m, 2H), 2.25 (M, 2H), 2.5 (M, 2H), 2.8 (M, 2H), 3.0 (M, 2H), 4.92 (S, 1H), 7.16 (M, 1H), 7.18 (S, 1H), 7.27 (d, 1H, J=6.6Hz), 7.40 (m, 1H), 7.48 (s, 2H), 7.49 (s, 2H), 9.77 (s, 1H);

Anal. calcd for C$_{23}$H$_{20}$FN0$_3$S: C, 67.46;H, 4.92; N, 3, 42. Found: C, 64.87;H, 4.76; N, 3.23.

EXAMPLE 134

9-[4-fluoro-3-(phenylethynyl)Dhenyl]-2,3,5,6,7,9-hexahydrothieno[3,2-b]quinolin-8(4H)-one, 1,1-dioxide Example 130A (200 mg, 0.39 mmol) and tributyl (phenylethynyl)tin were processed as in Example 130 to provide 118 mg of the title compound.

MS (ESI+) m/z: 434 (M+H)$^+$;

$^1$H NMR (DMSO-d$_6$) δ 1.86 (m, 2H), 2.22 (m, 2H), 2.5 (m, 2H), 2.85 (m, 2H), 3.0 (m, 2H), 4.86 (s, 1H), 7.25 (m, 2H), 7.35 (d, 1H, J=6.99Hz), 7.48 (m, 3H), 7.59 (m, 2H);

Anal. calcd for C$_{25}$H$_{20}$FN0$_3$S: C, 69.27;H, 4.65; N, 3.23. Found: C, 68.72;H, 4.54; N, 3.03.

EXAMPLE 135

7-(3-bromo-4-fluorophenyl)-5-(trifluoromethyl)-2,3,4,7-tetrahydrothieno[3,2-b]pyridine, 1,1-dioxide The racemic compound from Example 112 (0.7 g) was chromatographed using a 4.6×250 cm Chiralcel OJ chiral column eluting with hexane:ethanol (8:2) to provide 0.28 g of the title compound as the less polar enantiomer as a white solid.

MS (ES1-) m/z: 412 (M-H)$^-$;

$^1$H NMR (CD$_3$OD) δ 2.80–3.07 (m, 2H), 3.32–3.38 (m, 2H), 4.80 (br s, 1H), 5.39 (d, 1H), 7.18 (t, 1H), 7.28 (m, 1H), 7.51 (d, 1H);

Anal. calcd for C$_{14}$HIOBrF$_4$NO$_2$S: C, 40.79;H, 2.45; N, 3.40. Found: C, 40.95;H, 2.58; N, 3.34.

EXAMPLE 136

7-(3-bromo-4-fluorophenyl)-5-(trifluoromethyl)-2, 3 4 7-tetrahydrothieno[3 2-b]pyridine, 1,1-dioxide From the chiral chromatography described in Example 135 was obtained 0.26 g of the title compound as the more polar enantiomer as a white solid.

MS (ES1-) m/z: 412 (M-H)$^-$;

$^1$H NMR (CD$_3$OD) δ 2.80–3.07 (m, 2H), 3.32–3.38 (m, 2H), 4.80 (br s, 1H), 5.39 (d, 1H), 7.18 (t, 1H), 7.28 (m, 1H), 7.51 (d, 1H);

Anal. calcd for C$_{14}$H,oBrF$_4$NO$_2$S: C, 40.79;H, 2.45; N, 3.40. Found: C, 41.00;H, 2.55; N, 3.37.

EXAMPLE 137

9-(3 4-dibromophenyl)-2,3,5,6,7,9-hexahydrothieno [3,2-b]quinolin-8(4H)-one 1 1-dioxide 3,4-Dibromobenzaldehyde (1.58 g, 6.00 mmol) was processed according to the method of Example 11 5C to provide 1.8 g of the title compound.

mp >250 °C.;

MS (ESI+) m/z: 474 (M+H)$^+$;

$^1$H NMR (DMSO-d$_6$) δ 1.90 (m, 2H), 2.25 (m, 2H), 2.60 (m, 2H), 2.85 (m, 1H), 3.02 (m, 1H), 3.38 (m, 2H), 4.80 (s, 1H), 7.12 (dd, 1H, J=3, 9Hz), 7.48 (d, 1H, J=3Hz), 7.62 (d, 1H, J=9Hz), 9.85 (s, 1H);

Anal. calcd for C$_{17}$H$_{15}$Br$_2$NO$_3$S: C, 43.15;H, 3.20; N, 2.96. Found: C, 43.10;H, 3.29; N, 2.88.

EXAMPLE 138

(+)-9-[4-fluoro-3-(trifluoromethyl)phenyl]-2,3,5,6,7,9-hexahydrothieno[3,2-b]quinolin-8(4H)-one, 1,1-dioxide 4-Fluoro-3-trifluoromethylbenzaldehyde (1.9 g, 5.4 mmol) was processed according to the methods of Examples 11 5 C and 95 to provide 300 mg of the title compound.
mp >250 °C.; [a]23D +48.21, (c=0.59, DMSO)
MS (ESI+) m/z: 402 (M+H)$^+$;
$^1$H NMR (DMSO-d$_6$) δ 1.90 (m, 2H), 2.23 (m, 2H), 2.56 (m, 2H), 2.88 (m, 1H), 3.05 (m, H), 3.35 (t, 2H, J=9Hz), 4.92 (s, 1H), 7.38 (m, 1H), 7.51 (m, 2H), 9.95 (s, 1H);
Anal. calcd for C$_{18}$H$_{15}$F$_4$NO$_3$S: C, 53.86;H, 3.77; N, 3.49. Found: C, 53.56;H, 3.67; N, 3.68.

EXAMPLE 139

(−)-9-r4-fluoro-3-(trifluoromethyl)phenyl]-2,3,5,6,7,9-hexahydrothieno[3.2-b]quinolin-8(4H)-one, 1,1-dioxide 4-Fluoro-3-trifluoromethylbenzaldehyde (1.9 g, 5.4 mmol) was processed according to the methods of Examples 115C and 96 to provide 312 mg of the title compound.
mp >250 °C.; [a]23D -50.26 (c=0.59, DMSO);
MS (ESI+) m/z: 402 (M+H)$^+$;
$^1$H NMR (DMSO-d$_6$) o 1.90 (m, 2H), 2.23 (m, 2H), 2.56 (m, 2H), 2.88 (m, 1H), 3.05 (m, 1H), 3.35 (t, 2H, J=9Hz), 4.92 (s, 1H), 7.38 (m, 1H), 7.51 (mn, 2H), 9.95 (s, 1H);
Anal. calcd for C$_{18}$H$_{15}$F$_4$NO$_3$S: C, 53.86;H, 3.77; N, 3.49. Found: C, 53.85;H, 3.56; N, 3.50.

EXAMPLE 140

9-[4-fluoro-3-(2-thienyl)phenyl]-2,3,5,6,7,9-hexahydrothieno[3, 2-b]quinolin-8(4H)-one, 1,1-dioxide Example 130A (200 mg, 0.39 mmol) and 2-(tributylstannyl)thiophene were processed as in Example 130 to provide 119 mg of the title compound as a white solid.
MS (ESI+) m/z: 333 (M +H)$^+$;
$^1$H NMR (DMSO-d$_6$) δ 1.9 (m, 2H), 2.22 (m, 2H), 2.52 (m, 2H), 2.86 (m, 2H), 3.00 (m, 2H), 4.90 (s, 1H), 7.08–7.21 (m, 4H), 7.48–7.51 (m, 2H), 7.66 (d, 1H, J=5.15Hz), 9.81 (s, 1H);
Anal. calcd for C$_2$Hl$_8$FN0$_3$S$_2$: C, 60.70;H, 4.37; N, 3.09. Found: C, 60.51;H, 4.25; N, 3.09.

EXAMPLE 141

9-[4-fluoro-3-(3-hydroxy-3-methyl-1-butynyl)phenyl]-2,3,5,6,7,9-hexahydrothieno[3,2-b]quinolin-8(4H)-one, 1,1-dioxide To a slurry of Example 130A (400 mg, 0.78 mmol) in 10 mL triethylamine:pyridine (3:7) was added triphenylphosphine (21 mg, 0.08 mmol), PdCl$_2$(Ph$_3$P)$_2$ (5.5 mg, 0.008 mmol) and copper iodide (21 mg, 0.028 mmol). 2-Methyl-3-butyn-2-ol (98 µL, 1.014 mmol) was then syringed in and this mixture was heated under reflux for 40 minutes, cooled to room temperature, and concentrated. The resulting residue was purified by flash chromatography over silica gel eluting with methylene chloride:methanol (19:1) to provide 28 mg of the title compound as an off white solid.
MS (ESI+) m/z: 416 (M+H)$^+$;
$^1$H NMR (DMSO-d$_6$) δ 1.46 (s, 6H), 1.7–1.9 (m, 2H), 2.20 (m, 2H), 2.50 (m, 2H), 2.83 (m, 2H), 3.02 (m, 2H), 4.80 (s, 1H), 5.56 (s, 1H), 7.08–7.21 (m, 3H), 9.81 (s, 1H);
Anal. calcd for C$_{22}$H$_{22}$FN0$_4$S: C, 63.60;H, 5.34; N, 3.37. Found: C, 62.83;H, 5.44; N, 3.2.

EXAMPLE 142

8-(4-fluoro-3-iodophenyl)-2,3,4.5,6.8-hexahydrodithieno[3,2-b:2',3'-e]pyridine-1,1,7,7-tetraoxide 4-Fluoro-3-iodobenzaldehyde (250 mg, 1.00 mmol) was processed according to the method of Example 53 to provide 150 mg of the title compound as a white solid.
MS (APC1-) m/z: 480 (M-H)$^−$;
$^1$H NMR (DMSO-d$_6$) δ 2.81 (m, 2H), 3.02 (dt, 2H), 3.48 (m, 4H), 4.93 (s, 1H), 7.18 (t, 1H), 7.29 (ddd, 1H), 7.65 (dd, 1H), 10.0 (br s, 1H);
Anal. calcd for C$_{15}$Hl$_3$FINO$_4$S$_2$: C, 37.43;H, 2.72; N, 2.91. Found: C, 37.66;H, 2.96; N, 2.64.

EXAMPLE 143

9-(3-cyano-4-fluorophenyl)-2,3,5,6,7,9-hexahydrothieno[3,2-b]quinolin-8(4H)-one, 1,1-dioxide Example 130A (200 mg, 0.390 mmol) and zinc cyanide were processed as in Example 130 to provide the desired racemate. The racemate (2 x 30 mg) was chromatographed on a 2×25 cm Regis Whelk-O1 column, eluting with hexane:methanol:methylene chloride (60:27:13) as the mobile phase at a flow rate of 10 mL/min to provide 18 mg of the less polar enantiomer of the title compound as a white solid.
MS (ESI+) m/z: 359 (M+H)$^+$;
$^1$H NMR (DMSO-d$_6$) δ 1.8–2.0 (m, 2H), 2.19–2.30 (m, 2H), 2.51 (m, 2H), 2.85 (m, 2H), 2.9–3.1 (m, 2H), 4.91 (s, 1H), 7.40 (t, 1H, J=8.83Hz), 7.60–7.76 (m, 2H), 9.98 (s, 1H);
Anal. calcd for C$_{18}$Hl$_5$FN$_2$O$_3$S: C, 60.32;H, 4.22; N, 7.82. Found: C, 58.83;H, 4.05; N, 7.46.

EXAMPLE 144

9-(3-cyano-4-fluorophenyl)-2,3,5,6,7,9-hexahydrothieno[3,2-b]quinolin-8(4H)-one, 1,1-dioxide The product from Example 143 (2×30 mg) was chromatographed on a 2×25 cm Regis Whelk-O1 column, eluting with hexane:methanol:methylene chloride (60:27:13) as the mobile phase at a flow rate of 10 mL/min to provide 24 mg of the more polar enantiomer of the title compound as a white solid.
MS (ESI+) m/z: 359 (M+H)$^+$;
$^1$H NMR (DMSO-d$_6$) δ 1.8–2.0 (m, 2H), 2.19–2.30 (m, 2H), 2.51 (m, 2H), 2.78 (m, 2H), 2.9–3.1 (m, 2H), 4.91 (s, 1H), 7.38 (t, 1H, J=8.83Hz), 7.60–7.76 (m, 2H), 9.88 (s, 1H);
Anal. calcd for C$_{18}$H$_{15}$FN$_2$O$_3$S: C, 60.32;H, 4.22; N, 7.82. Found: C, 58.86;H, 4.15; N, 7.56.

EXAMPLE 145

8-(3,4-dichlorophenyl)-2,3,4,5,6,8-hexahydrocyclopenta[b]thieno[2.3-e]pyridin-7-one, 1,1-dioxide The product from Example 60 (150 mg) was processed according to the method of Example 143 to provide 37 mg of the less polar enantiomer of the title compound.
mp >250 °C.;
MS (ESI+) m/z: 371 (M+H)$^+$;
$^1$H NMR (DMSO-d$_6$) δ 2.30 (t, 2H, J=4.5Hz), 2.63 (m, 2H), 2.87 (m, 1H), 3.06 (m, 1H), 3.42 (t, 2H, J=7.5Hz), 4.72 (s, 1H), 7.22 (dd, 1H, J=3, 9Hz), 7.42 (d, 3H), 7.52 (d, 1H, J=12Hz), 10.35 (s, 1H);
Anal. calcd for $C_{16}Hl_3Cl_2NO_3S \cdot 0.2H_2O$: C, 51.40;H, 3.61; N, 3.75. Found: C, 51,16;H, 3.63; N, 3.37.

EXAMPLE 146

8-(3,4-dichlorophenyl)-2,3,4,5,6,8-hexahydrocyclonenta[b]thieno[2.3-e]pyridin-7-one, 1,1-dioxide The product from Example 60 (150 mg) was processed according to the method of Example 144 to provide the more polar enantiomer of the title compound.
mp >250 ° C.;
MS (ESI+) m/z: 371 (M+H)$^+$;
$^1$H NMR (DMSO-d$_6$) δ 2.30 (t, 2H, J=4.5Hz), 2.63 (m, 2H), 2.87 (m, 1H), 3.06 (m, 1H), 3.42 (t, 2H, J=7.5Hz), 4.72 (s, 1H), 7.22 (dd, 1H, J=3, 9Hz), 7.42 (d, 3H), 7.52 (d, 1H, J=12Hz), 10.35 (s, 1H);
Anal. calcd for $C_{16}Hl_3Cl_2NO_3S$: C, 51.90;H, 3.54; N, 3.78. Found: C, 51.80;H, 3.42; N, 3.44.

EXAMPLE 147

9-(3,4-dibromophenyl)-2,3,5,6,7,9-hexahydrothieno[3.2-b]quinolin-8(4H)-one, 1,1-dioxide Example 137 (180 mg) was processed according to the method of Example 143 to provide 44 mg of the less polar enantiomer of the title compound.
mp >250 ° C.;
MS (ESI+) m/z: 474 (M+H)$^+$;
$^1$H NMR (DMSO-d$_6$) δ 1.90 (m, 2H), 2.25 (m, 2H), 2.60 (m, 2H), 2.86 (m, 1H), 3.02 (m, 1H), 3.38 (m, 2H), 4.80 (s, 1H), 7.12 (dd, 1H, J=3, 9Hz), 7.48 (d, 1H, J=3Hz), 7.62 (d, 1H, J=9Hz), 9.85 (br, s, 1H);
Anal. calcd for $C_{17}H_{15}Br_2NO_3S$: C, 43.15;H, 3.20; N, 2.96. Found: C, 43.48;H, 3.50; N, 2.71.

EXAMPLE 148

9-(3,4-dibromophenyl)-2,3,5,6,7,9-hexahydrothieno[3,2-b]quinolin-8(4H)-one,1,1-dioxide Example 137 (180 mg) was processed according to the method of Example 144 to provide 45 mg of the more polar enantiomer of the title compound.
mp >250 ° C.;
MS (ESI+) m/z: 474 (M+H)$^+$;
$^1$H NMR (DMSO-d$_6$) δ 1.90 (m, 2H), 2.25 (m, 2H), 2.60 (m, 2H), 2.86 (m, 1H), 3.02 (m, 1H), 3.38 (m, 2H), 4.80 (s, 1H), 7.12 (dd, 1H, J=3, 9Hz), 7.48 (d, 1H, J=3Hz), 7.62 (d, 1H, J=9Hz), 9.85 (br, s, 1H);
Anal. calcd for $C,,H_{15}Br_2NO_3S$: C, 43.15;H, 3.20; N, 2.96. Found: C, 43.25;H, 3.05; N, 2.75.

EXAMPLE 149

9-(4-fluoro-3-iodophenyl)-2,3,5,6,7,9-hexahydrothieno[3 2-b]quinolin-8(4H)-one, 1,1-dioxide Example 89D (110 mg) was chromatographed over a Regis Whelko-1 2×25 cm chiral column eluting with hexane:methanol:methylene chloride (60:27:13) at a flow rate of 10 mL/minute to provide 45 mg of the less polar enantiomer of the title compound as an off white solid.
MS (ESI+) m/z: 460 (M +H)$^+$; MS (ES1-) m/z: 458 (M-H)$^-$;
$^1$H NMR (DMSO-d$_6$) δ 1.80–1.95 (m, 2H), 2.23 (m, 2H), 2.55 (m, 2H), 2.75–3.08 (m, 2H), 3.30–3.35 (m, 2H), 4.81 (s, 1H), 7.12 (t, 1H), 7.18 (m, 1H), 7.54 (d, 1H), 9.79 (s, 1H);

Anal. calcd for $C,,H_{15}FINO_3S \cdot 0.1 C_6H_{14}$: C, 45.18;H, 3.53; N, 2.99. Found: C, 45.17;H, 3.64; N, 2.93.

EXAMPLE 150

9-(4-fluoro-3-iodophenyl)-2,3,5,6,7,9-hexahydrothieno[3,2-b]quinolin-8(4H)-one, 1,1-dioxide From the chiral chromatography of Example 149 was obtained 45 mg of the more polar enantiomer of the title compound as an off white solid.
MS (ESI+) m/z: 460 (M +H)$^+$; MS (ES1-) m/z: 458 (M-H)$^-$;
$^1$H NMR (DMSO-d$_6$) δ 1.80–1.95 (m, 2H), 2.23 (m, 2H), 2.55 (m, 2H), 2.75–3.08 (m, 2H), 3.30–3.35 (m, 2H), 4.81 (s, 1H), 7.12 (t, 1H), 7.18 (m, 1H), 7.54 (d, 1H), 9.82 (s, 1H);
Anal. calcd for $C_{17}H_{15}FINO_3S$: C, 44.46;H, 3.29; N, 3.05. Found: C, 44.63;H, 3.37; N, 2.95.

EXAMPLE 151

9-[4-chloro-3-(trifluoromethyl)phenyl]-2,3,5,6,7,9-hexahydrothieno [32-b]quinolin-8(4H)-one, 1,1-dioxide 4-Chloro-3-trifluoromethylbenzaldehyde (1,16 g, 6.00 mmol) was processed according to the method of Example 11 5C to provide 1.6 g of the title compound.
mp >250 ° C.;
MS (ESI+) m/z: 418 (M+H)$^+$;
$^1$H NMR (DMSO-d$_6$) δ 1.82 (m, 1H), 1.94 (m, 1H), 2.25 (t, 1H, J=6Hz), 2.55 (m, 2H), 2.85 (m, 1H), 3.02 (m, 1H), 3.35 (m, 2H), 4.94 (s, 1H), 7.48 (dd, 1H, J=3Hz), 7.60 (d, 2H, J=12Hz), 9.88 (s, 1H);
Anal. calcd for $C_{18}H_{15}ClF_3NO_3S$: C, 51.74;H, 3.62; N, 3.35. Found: C, 51.96;H, 3.74; N, 3.36.

EXAMPLE 152

9-(3-ethynyl-4-fluorophenyl)-2,3,5,6,7,9-hexahydrothieno[3,2-biquinolin-8(4H)-one, 1,1-dioxide

EXAMPLE 152A 1,1-dimethylethyl 9-[4-fluoro-3-(3-hydroxy-3-methyl-1-butynyl)phenyl]-8-oxo-3,5,6,7,8,9-hexahydrothieno[3,2-b]quinoline-4(2H)-carboxylate, 1,1-dioxide To a slurry of Example 130A (400 mg, 0.78 mmol) in 10 mL triethylamine:pyridine (3:7) was added triphenylphosphine (21 mg, 0.08 mmol), PdCl$_2$(Ph$_3$P)$_2$ (5.5 mg, 0.008 mmol) and copper iodide (21 mg, 0.028 mmol). 2-Methyl-3-butyn-2-ol (98 ul, 1.014 mmol) was then syringed in and this mixture was heated under reflux for 40 minutes, cooled to room temperature, and concentrated. The resulting residue was purified by flash chromatography over silica gel eluting with methylene chloride:methanol (19:1) to provide 110 mg of the desird compound as an off white solid.
$^1$H NMR (DMSO-d$_6$) δ 1.45 (s, 6H), 1.57 (s, 9H), 1.90 (m, 2H), 2.35 (m, 2H), 2.60 (m, 2H), 3.0–3.1 (m, 2H), 3.4–3.5 (m, 4H), 4.80 (s, 1H), 5.56 (s, 1H), 7.11 (m, 1H), 7.21 (m, 2H).

EXAMPLE 152B 9-(3-ethynyl-4-fluorophenyl)-2,3,5,6,7,9-hexahydrothieno[3,2-b]quinolin-8(4H)-one, 1,1-dioxide To Example 152A (110.4 mg, 0.2 mmol) in n-butanol (48 mg, 0.85 mmol) was added 48 mg of potassium hydroxide, the reaction heated to reflux for 20 minutes, cooled to room temperature, diluted with ethyl acetate, washed with saturated sodium bicarbonate, brine, dried with sodium sulfate, filtered and solvent evaporated. The crude residue was purified by flash chromatography over silica gel eluting with methylene chloride:methanol (19:1) to yield 50 mg of the title compound as a racemic mixture as a white solid. The racemic mixture (50 mg) was chromatographed on a Regis Whelk-O1 2×25 cm chiral column with hexane:methanol:methylene chloride (5:2:1) as the mobile phase at a rate of 10 mL/minute to provide 14 mg of the less polar enantiomer of the title compound as a white solid.
MS (ESI+) m/z: 358 (M+H)$^+$;
$^1$H NMR (DMSO-d$_6$) δ 1.70–1.92 (m, 2H), 2.19–2.30 (m, 2H), 2.51 (m, 2H), 2.8 (m, 2H), 3.01 (m, 2H), 4.48 (s, 1H), 4.83 (s, 1H), 7.10–7.30 (m, 3H), 9.81 (s, 1H);
Anal. calcd for C$_9$H$_{16}$FN0$_3$S: C, 63.85;H, 4.5 1; N, 3.92. Found: C, 62.54;H, 4.80; N, 3.65.

EXAMPLE 153

9-(3-ethynyl-4-fluorophenyl)-2,3,5,6,7,9-hexahydrothieno[3.2-b]quinolin-8(4H)-one, 1,1-dioxide The chiral chromatography described in Example 152B also provided the more polar enantiomer as a white solid (15 mg, 30%).
MS (ESI+) m/z: 358 (M+H)$^+$;
$^1$H NMR (DMSO-d$_6$) δ 1.70–1.92 (m, 2H), 2.19–2.30 (m, 2H), 2.51 (m, 2H), 2.8 (m, 2H), 3.01 (m, 2H), 4.48 (s, 1H), 4.82 (s, 1H), 7.10–7.30 (m, 3H), 9.81 (s, 1H);
Anal. calcd for C$_{19}$H$_{16}$FN0$_3$S: C, 63.85;H, 4.51; N, 3.92. Found: C, 62.54;H, 4.80; N, 3.65.

EXAMPLE 154

9-(3-cyano-4-methylphenyl)-2,3,5,6,7,9-hexahydrothieno[3.2-b]quinolin-8(4H)-one, 1,1-dioxide

EXAMPLE 154A 3-amino-4-methylbenzylalcohol

4-Methyl-3-nitro benzylalcohol (9.7 g, 58 mmol) in ethanol (200 mL) was reduced under 4 atmospheres of hydrogen gas for 4 hours in the presence of 10% Pd/C (0.5 g) to yield after a standard workup 7.54 g (93%) of the title compound.
MS (DCI+) m/z: 138 (M+H)$^+$.

EXAMPLE 154B 3-cyano-4-methylbenzylalcohol

To Example 154A (7.54 g, 55 mmol) in 2 N hydrochloric acid (200 mL) was added dropwise a solution of sodium nitrite (5.67 g, 82 mmol) in water (65 mL), keeping the temperature below 10 ° C.. After stirring for 2 hours the solution of the diazonium salt was added to a suspension of copper cyanide (9.4 g, 0.1 mole) and sodium cyanide (3.0 g, 61 mmol) in water (75 mL) keeping the temperature below 10 ° C.. The reaction mixture was allowed to warm to room temperature, stirred overnight, filtered through Celites and extracted with ethyl acetate (3x). The organic extracts were washed with I N hydrochloric acid, brine, 5% sodium bicarbonate, water, dried (MgSO$_4$), filtered and solvent evaporated. The crude residue was purified by flash chromatography over silica gel eluting with ethyl acetate:hexane (3:7) to provide 1.4 g of the title compound.
$^1$H NMR (CDCl$_3$) 6 1.52 (s, 1H), 2.57 (s, 3H), 4.72 (d, 2H), 7.32 (d, 1H), 7.49 (d, 1H), 7.62 (s, 1H).

EXAMPLE 154C 3-cyano-4-methylbenzaldehyde

Example 154B (1.4 g, 10 mmol) in chloroform (30 mL) was treated with manganese dioxide (3.3 g, 40 mmol). The reaction mixture was stirred at room temperature for 12 hours, filtered, the solvent evaporated and the crude residue purified by flash chromatography over silica gel eluting with ethyl acetate:hexane (5:95) to provide 0.9 g of the title compound.
$^1$H NMR (CDCl$_3$) 6 2.67 (s, 3H), 7.48 (dd, 1H), 8.0 (dd, 1H), 10.0 (s, 1H).

EXAMPLE 154D 9-(3-cyano-4-methylphenyl)-2,3,5,6,7,9-hexahydrothieno[3,2-b]quinolin-8(4H)-one, 1,1-dioxide Example 154C (0.87 g, 6 mmol) was processed according to the method of Example 111 to provide 0.68 g of the title compound.
MS (ES1-) m/z: 353 (M-H)$^-$;
$^1$H NMR (DMSO-d$_6$) 6 1.72–1,1.95 (m, 2H), 2.22 (m, 2H), 2.41 (s, 3H), 2.55 (m, 2H), 2.82 (m, 1H), 3.0 (m, 1H), 4.88 (s, 1H), 7.31 (d, 1H), 7.41 (dd, 1H), 7.49 (s, 1H), 9.82 (s, 1H);
Anal. calcd for C$_9$H$_{18}$N$_2$O$_3$S0.25H$_2$O: C, 63.58;H, 5.20; N, 7.80. Found: C, 63.57;H, 5.27; N, 7.35.

EXAMPLE 155

9-(3-cvano-4-methylphenyl)-2,3 5,6,7,9-hexahydrothieno[3,2-b]quinolin-8(4H)-one, 1,1-dioxide The racemic compound from Example 154D (0.11 g) was chromatographed over a Regis WhelkO-1 2×25 cm chiral column eluting with hexane:methanol:methylene chloride (70:20: 10) at a flow rate of 10 mL/minute to provide 0.030 g of the less polar enantiomer of the title compound.
MS (ES1-) m/z: 353 (M-H)$^-$;
$^1$H NMR (DMSO-d$_6$) δ 1.72–1,1.95 (m, 2H), 2.22 (m, 2H), 2.41 (s, 3H), 2.55 (m, 2H), 2.82 (m, 1H), 3.0 (m, 1H), 4.88 (s, 1H), 7.31 (d, 1H), 7.41 (dd, 1H), 7.49 (s, 1H), 9.82 (s, 1H);
Anal. calcd for C$_{19}$H$_{18}$N$_2$O$_3$S: C, 64.39;H, 5.12; N, 7.90. Found: C, 64.20;H, 5.24; N, 7.56.

EXAMPLE 156

9-(3-cyano-4-methylphenyl)-2,3,5,6,7,9-hexahydrothieno[3,2-b]quinolin-8(4H)-one, 1,1-dioxide From the chiral chromatography described in Example 155 was obtained 0.047 g of the more polar enantiomer of the title compound:
MS (ES1-) m/z: 353 (M-H)$^-$;
$^1$H NMR (DMSO-d$_6$) δ 1.72–1,1.95 (m, 2H), 2.22 (m, 2H), 2.41 (s, 3H), 2.55 (m, 2H), 2.82 (m, 1H), 3.0 (m, 1H), 4.88 (s, 1H), 7.31 (d, 1H), 7.41 (dd, 1H), 7.49 (s, 1H), 9.82 (s, 1H);
Anal. calcd for C$_{19}$H$_{18}$N$_2$O$_3$S0.25H$_2$O: C, 63.58;H, 5.20; N, 7.80. Found: C, 63.1 1;H, 5.20; N, 7.56.

EXAMPLE 157

9-[4-fluoro-3-(3-pyridinyl)phenyl]-2,3,5,6,7,9-hexahydrothieno[3,2-biquinolin-8(4H)-one, 1,1-dioxide Example 130A (200 mg, 0.390 mmol) and 3-(tributylstannyl)pyridine were processed as in Example 130 to provide 89 mg of the title compound as a white solid.

MS (ESI+) m/z: 411 (M+H)+;
$^1$H NMR (DMSO-d$_6$) δ 1.8–1.95 (m, 2H), 2.20–2.30 (m, 2H), 2.8 (m, 1H), 3.0 (m, 1H), 4.95 (s, 1H), 7.20–7.30 (m, 2H), 7.34 (d, 1H, J=7.5Hz), 7.52 (d, 1H, J=7.5Hz), 7.92 (m, 1H), 8.61 (m, 1H), 8.68 (s, 1H), 9.79 (s, 1H);
Anal. calcd for C$_{22}$H$_{19}$FN$_2$O$_3$S: C, 64.38;H, 4.67; N, 6.82. Found: C, 62.19;H, 5.10; N, 6.45.

EXAMPLE 158

7-(3-bromo-4-fluorophenyl)-5-methyl-2,3,4,7-tetrahydrothieno[3,2-b]pyridine-6-carbonitrile. 1,1-dioxide 3-Bromo-4-fluorobenzaldehyde (1.02 g, 5.00 mmol), tetrahydrothiophene-3-oxo-1,1-dioxide (0.67 g, 5.0 mmol) and 3-aminocrotononitrile (0.41 g, 5.0 nimol) in methanol (10 mL) were heated at 65 ° C. for 2 days, cooled, solvent evaporated and the crude product purified by flash chromatography over silica gel eluting with methanol:methylene chloride (5:95) to provide 520 mg of the title compound as a white solid.
MS (ES1-) m/z: 383 (M-H)-;
$^1$H NMR (DMSO-d$_6$) δ 2.07 (s, 3H), 2.72–3.04 (m, 2H), 3.31–3.40 (m, 2H), 4.78 (s, 1H), 7.34 (m, 2H), 7.59 (d, 1H), 9.84 (s, 1H);
Anal. calcd for C$_{15}$H$_{12}$BrFN$_2$O$_2$S: C, 47.01;H, 3.16; N, 7.31. Found: C, 47.32;H, 3.40; N, 7.19.

EXAMPLE 159

8-(3-bromo-4-fluorophenyl)-6-trifluoromethyl-5,8-dihydrothiopyrano[3 .2-b]pyridine, 1,1-dioxide Example 112A (226 mg, 0.76 mmol) and tetrahydrothiopyran-3-one-1,1-dioxide (112 mg, 0.76 mmol) were processed as in Example 112 to provide 187 mg of the title compound as an off-white solid.
mp 195–198 ° C.;
MS (ES1-) m/z: 426 (M-H)-;
$^1$H NMR (CD$_3$OD) δ 2.30–2.38 (m, 2H), 2.52–2.60 (m, 2H), 3.15–3.20 (m, 2H), 4.80 (d, 1H), 5.44 (d, 1H), 7.14 (t, 1H), 7.27 (m, 1H), 7.50 (d, 1H);
Anal. calcd for C$_{15}$H$_{12}$BrF$_4$NO$_2$S: C, 42.27;H, 2.84; N, 3.29. Found: C, 42.43;H, 3.02; N, 2.96.

EXAMPLE 160

8-(4-chloro-3-nitrophenyl)-2,3,4,5,6,8-hexahydrocyclopenta[b]thieno[2.3-e]pyridin-7-one, 1,1-dioxide Example 44 (200 mg) was chromatographed over a Regis Whelk 0–1 2×25 cm chiral column eluting with hexane:methanol:methylene chloride (50:33:17) at a flow rate of 10 mL/minute to provide 60 mg of the less polar enantiomer of the title compound.
mp >250 ° C.;
MS (ESI+) m/z: 381 (M+H)+;
$^1$H NMR (DMSO-d$_6$) δ 2.30 (t, 2H, J=4.5Hz), 2.65 (m, 2H), 2.90 (m, 1H), 3.06 (m, 1H), 3.4 (t, 2H, J=6Hz), 4.86 (s, 1H), 7.58 (dd, 1H, J=3, 4.5Hz), 7.68 (d, 1H, J=9Hz), 7.88 (d, 1H, J=3Hz), 10.42 (br, s, 1H);
Anal. calcd for C$_{16}$H$_{13}$ClN$_2$O$_5$S: C, 50.46;H, 3.44; N, 7.36. Found: C, 50.37;H, 3.67; N, 7.28.

EXAMPLE 161

8-(4-chloro-3-nitrophenyl)-2,3,4,5,6,8-hexahydrocyclopenta[b]thieno[2.3-e]pyridin-7-one, 1,1-dioxide From the chiral chromatography described in Example 160 was obtained 48 mg of the more polar enantiomer of the title compound as an off white solid.
mp >250 ° C.;
MS (ESI+) m/z: 381 (M+H)+;
$^1$H NMR (DMSO-d$_6$) δ 2.30 (t, 2H, J=4.5Hz), 2.65 (m, 2H), 2.90 (m, 1H), 3.06 (m, 1H), 3.4 (t, 2H, J=6Hz), 4.86 (s, 1H), 7.58 (dd, 1H, J=3, 4.5Hz), 7.68 (d, 1H, J=9Hz), 7.88 (d, 1H, J=3Hz), 10.42 (br, s, 1H);
Anal. calcd for C$_{16}$H$_{13}$ClN$_2$O,S: C, 50.46;H, 3.44; N, 7.36. Found: C, 50.45;H, 3.56; N, 7.30.

EXAMPLE 162

(−)-8-(3-cyanophenyl)-2,3,4,5,6,8-hexahydrocyclopenta[fbthieno[2.3-e]pyridin-7-one, 1,1-dioxide Example 52 (300 mg) was processed according to the method of Example 86 to provide 95 mg of the title compound as the less polar enantiomer.
mp >250 ° C.; [a]73D -32.0 (c 0.53, DMSO);
MS (ESI+) m/z: 327 (M+H)+;
$^1$H NMR (DMSO-d$_6$) δ 2.30 (t, 2H), 2.63 (m, 2H), 2.88 (dt, 1H), 3.07 (dt, 1H), 3.40 (t, 2H), 4.70 (s, 1H), 7.49 (t, 1H), 7.60 (d, 1H), 7.64 (s, 1H), 7.66 (dd, 1H), 10.38 (s, 1H);
Anal. calcd for C$_{17}$H$_{14}$N$_2$O$_3$S: C, 62.56;H, 4.32; N, 8.58. Found: C, 62.24;H, 4.48; N, 8.41.

EXAMPLE 163

7-(3-chloro-4-fluorophenyl)-5-(trifluoromethyl)-2,3,4,7-tetrahydrothieno[3,2-b]pyridine, 1,1-dioxide 3-Chloro-4-fluorobenzaldehyde (317 mg) was processed according to the method of Example 112 to provide 162 mg of the title compound as a white solid.
mp 180–183 ° C.;
MS (ES1-) m/z: 366 (M-H)-;
$^1$H NMR (CD$_3$OD) δ 2.80–3.07 (m, 2H), 3.33–3.38 (m, 2H), 4.80 (br s, 1H), 5.39 (d, 1H), 7.19 (t, 1H), 7.25 (m, 1H), 7.37 (d, 1H);
Anal. calcd for C$_{14}$H,OClF$_4$NO$_2$S: C, 45.72;H, 2.74; N, 3.81. Found: C, 45.92;H, 2.83; N,3.64.

EXAMPLE 164

(+)-8-(3-cyanophenyl)-2,3,4,5,68-hexahydrocyclopenta[rbthieno[2,3-e]pyridin-7-one 1,1-dioxide Example 52 (300 mg) was processed according to the method of Example 87 to provide 102 mg of the title compound as the more polar enantiomer.
mp >250 ° C.; [a]23D +31.61 (c 0.47, DMSO);
MS (ESI+) m/z: 327 (M+H)+;
$^1$H NMR (DMSO-d$_6$) δ 2.30 (t, 2H), 2.63 (m, 2H), 2.88 (dt, 1H), 3.07 (dt, 1H), 3.40 (t, 2H), 4.70 (s, 1H), 7.49 (t, 1H), 7.60 (d, 1H), 7.64 (s, 1H), 7.66 (dd, 1H), 10.38 (s, 1H);
Anal. calcd for C$_{17}$H$_{14}$N$_2$O$_3$S0.2H$_2$0: C, 61.88;H, 4.40; N, 8.48. Found: C, 61.63;H, 4.41; N, 8.45.

EXAMPLE 165

9-[4-fluoro-3-(2-furyl)phenyl]-2,3,5,6,7,9-hexahydrothieno[3,2-b]quinolin-8(4H)-one, 1,1-dioxide The racemic furan from Example 132 was chromatographed on a 2×25 cm Regis Whelk-Ol column, eluting with hexane:methanol:methylene chloride (78:14:8) as the I ; mobile phase at a flow rate of 10 mL/min to provide 40 mg of the less polar enantiomer of the title compound as a white solid.

MS (ESI+) m/z: 400 (M+H)+;
$^1$H NMR (DMSO-d$_6$) δ 1.96 (m, 2H), 2.2 (m, 2H), 2.51 (m, 2H), 2.82 (m, 2H), 3.03 (m, 2H), 4.88 (s, 1H), 6.6 (dd, 1H, J=3.31, 1.47Hz), 6.81 (t, 1H, J=3.68Hz), 7.15 (m, 2H), 7.58 (dd, 1H, J=7.19, 2.21Hz), 7.85 (d, 1H, J=1.8Hz), 9.80 (s, 1H);
Anal. calcd for C$_2$Hl$_8$FNO$_4$S: C, 63.15;H, 4.54; N, 3.51. Found: C, 61.54;H, 4.73; N, 3.43.

EXAMPLE 166

9-[4-fluoro-3-(2-furyl)phenyl]-2,3,5,6,7,9-hexahydrothieno[3.2-b]quinolin-8(4H)-one, 1,1-dioxide The racemic furan from Example 132 was chromatographed on a 2×25 cm Regis Whelk-O1 column, eluting with hexane:methanol:methylene chloride (78:14:8) as the mobile phase at a flow rate of 10 mL/min to provide 21 mg of the more polar enantiomer of the title compound as a white solid.
MS (ESI+) m/z: 400 (M+H)+;
$^1$H NMR (DMSO-d$_6$) δ 1.96 (m, 2H), 2.2 (m, 2H), 2.51 (m, 2H), 2.82 (m, 2H), 3.03 (m, 2H), 4.88 (s, 1H), 6.6 (dd, 1H, J=3.31, 1.47Hz), 6.81 (t, 1H, J=3.68Hz), 7.15 (m, 2H), 7.58 (dd, 1H, J=7.19, 2.21Hz), 7.85 (d, 1H, J=1.8Hz), 9.80 (s, 1H);
Anal. calcd for C$_2$H$_{18}$FNO$_4$S: C, 63.15;H, 4.54; N, 3.51. Found: C, 61.54;H, 4.73; N, 3.43.

EXAMPLE 167

9-(5-bromo-2-thienyl)-2,3,5,6,7,9-hexahydrothieno[3,2-b]quinolin-8(4H)-one, 1,1-dioxide The product from Example 128 (150 mg) was chromatographed on a 2×25 cm Regis Whelk-O1 chiral column, eluting with hexane:methanol:methylene chloride (50:33:17) as the mobile phase at a flow rate of 10 mL/min to provide 37 mg of the less polar enantiomer of the title compound as a white solid.
mp >250° C.;
MS (ESI+) m/z: 401 (M+H)+;
$^1$H NMR (DMSO-d$_6$) δ 1.92 (m, 2H), 2.30 (t, 2H, J=7.5Hz), 2.55 (m, 2H), 2.85 (m, 1H), 3.00 (m, 1H), 3.42 (m, 2H), 5.08 (s, 1H), 6.65 (d, 1H, J=3Hz), 6.95 (d, 1H, J=3Hz), 9.94 (s, 1H);
Anal. calcd for C$_{15}$H$_{14}$BrNO$_3$S$_2$: C, 45.00;H, 3.53; N, 3.50. Found: C, 44.77;H, 3.20; N, 3.65.

EXAMPLE 168

9-(5-bromo-2-thienyl)-2,3,5,6,7,9-hexahydrothieno[3,2-b]quinolin-8(4H)-one, 1,1-dioxide From the chiral chromatography described in Example 167 was obtained 49 mg of the more polar enantiomer of the title compound as a white solid.
mp >250° C.;
MS (ESI+) m/z: 401 (M+H)+;
$^1$H NMR (DMSO-d$_6$) δ 1.92 (m, 2H), 2.30 (t, 2H, J=7.5Hz), 2.55 (m, 2H), 2.85 (m, 1H), 3.00 (m, 1H), 3.42 (m, 2H), 5.08 (s, 1H), 6.65 (d, 1H, J=3Hz), 6.95 (d, 1H, J=3Hz), 9.94 (s, 1H);
Anal. calcd for C$_{15}$H$_{14}$BrNO$_3$S$_2$: C, 45.00;H, 3.53; N, 3.50. Found: C, 44.87;H, 3.43; N, 3.45.

EXAMPLE 169

9-(3-allyl-4-fluorophenyl)-2,3,5,6,7,9-hexahydrothieno[3,2-b]quinolin-8(4H)-one, 1,1-dioxide Example 130A (100 mg, 0.195 mmol) and allyltributyltin were processed as in Example 130 to provide 36.5 mg of the title compound as a white solid.

MS (ESI+) m/z: 374 (M+H)+;
$^1$H NMR (DMSO-d$_6$) δ 1.72–1.98 (m, 2H), 2.23 (m, 2H), 2.51 (m, 2H), 2.80 (m, 1H), 2.98 (m, 1H), 3.35 (m, 2H), 4.81 (s, 1H), 4.99–5.07 (m, 2H), 5.83–5.96 (m, 1H), 6.91-7.09 (m, 3H), 9.75 (s, 1H);
Anal. calcd for C$_{20}$H$_{20}$FNO$_3$S: C, 64.32;H, 5.40; N, 3.75. Found: C, 62.83;H, 5.27; N, 3.34.

EXAMPLE 170

9-[3-(1-ethoxyvinyl)-4-fluorolphenyl]-23.5,6,7,9-hexahydrothieno[3.2-b]quinolin-8(4H)-one, 1,1-dioxide Example 130A (100 mg, 0.195 mmol) and tributyl(1-ethoxyvinyl)tin were processed as in Example 130 to provide 54.2 mg of the title compound as a white solid.
MS (ESI+) m/z: 404 (M+H)+;
$^1$H NMR (DMSO-d$_6$) δ 1,10 (m, 2H), 1.32 (t, 3H, J=7.01Hz), 1.60 (m, 2H), 1.80–1.99 (m, 2H), 2.2 (m, 2H), 2.80 (m, 1H), 3.00 (m, 1H), 3.86 (q, 2H, J=7.01Hz), 4.48 (d, 1H, J=2.5Hz), 4.55 (d, 1H, J=2.5Hz), 4.83 (s, 1H), 7.03–7.20 (m, 2H), 7.41 (dd, 1H, J=7.31, 1.90Hz), 9.78 (s, 1H);
Anal. calcd for C$_{21}$H$_{22}$FNO$_4$S: C, 62.51;H, 5.50; N, 3.47. Found: C, 59.95;H, 5.28; N, 3.13.

EXAMPLE 171

8-(3-bromo-4-fluorophenyl)-6-methyl-3,4,5,8-tetrahydro-2H-thiopyrano[3.2-b1lyridine-7-carbonitrile. 1,1-dioxide 3-Bromo-4-fluorobenzaldehyde (1.02 g, 5.00 mmol), tetrahydrothiopyran-3-one-1, 1-dioxide (0.74 g, 5.0 mmol) and 3-aminocrotononitrile (0.41 g, 5.0 mmol) in methanol (10 mL) were heated at 65° C. for 2 days, cooled, solvent evaporated and the crude product purified by flash chromatography over silica gel eluting with methanol:methylene chloride (5:95) to provide 780 mg of the title compound as a white solid.
MS (ES1-) m/z: 397 (M-H)-;
$^1$H NMR (DMSO-d$_6$) δ 2.03 (s, 3H), 2.18 (m, 2H), 2.42–2.58 (m, 2H), 3.17–3.24 (m, 2H), 4.66 (s, 1H), 7.28 (m, 1H), 7.35 (t, 1H), 7.50 (d, 1H), 9.41 (s, 1H);
Anal. calcd for C$_{16}$H$_{14}$BrFN$_2$O$_2$S 0.1H$_2$O: C, 48.16;H, 3.59; N, 7.02. Found: C, 48.21; H, 3.86; N, 6.64.

EXAMPLE 172

(−)-9-[4-chloro-3-(trifluoromethyl)vhenyl]-2,3,5,6,7,9-hexahydrothieno[3,2-b]quinolin-8(4H)-one, 1,1-dioxide Example 151 (200 mg) was processed according to the method of Example 149 to provide 57 mg of the title compound as the less polar enantiomer.
mp >250° C.; [a]23D -59.78, (c 0.47, DMSO);
MS (ESI+) m/z: 418 (M+H)+;
$^1$H NMR (DMSO-d$_6$) δ 1.82 (m, 1H), 1.94 (m, 1H), 2.25 (t, 1H, J=6Hz), 2.85 (m, 1H), 3.02 (m, 1H), 3.35 (m, 2H), 4.94 (s, 1H), 7.48 (d, 1H, J=6Hz), 7.6 (d, 1H, J=6Hz);
Anal. calcd for C$_8$H$_{15}$ClF$_3$NO$_3$S: C, 51.74;H, 3.62; N, 3.35. Found: C, 51.65;H, 3.87; N, 3.23.

EXAMPLE 173

(+)-9-[4-chloro-3-(trifluoromethyl)phenyl]-2,3,5,6,7,9-hexahydrothieno[3,2-b]quinolin-8(4H)-one, 1,1-dioxide From the chiral chromatography described in Example 172 was obtained 76 mg of the title compound as the more polar enantiomer.

mp >250 ° C.; [oC]23D +59.58, (c 0.48, DMSO);
MS (ESI+) m/z: 418 (M+H)+;
1H NMR (DMSO-d6) δ 1.82 (m, 1H), 1.94 (m, 1H), 2.25 (t, 1H, J=6Hz), 2.85 (m, 1H), 3.02 (m, 1H), 3.35 (m, 2H), 4.94 (s, 1H), 7.48 (d, 1H, J=6Hz), 7.6 (d, 1H, J=6Hz);
Anal. calcd for $C_{18}H_{15}ClF_3NO_3S$: C, 51.74;H, 3.62; N, 3.35. Found: C, 51.61;H, 3.75; N, 3.17.

EXAMPLE 174

(9S)-9-(3-ethyl-4-fluorophenyl)-2,3,5,6,7,9-hexahydrothieno[3,2-b]quinolin-8(4H)-one, 1,1-dioxide Example 177A (32 mg, 0.06 mmol) and tetraethyltin were processed as in Example 177B to provide the title compound as a white solid.
MS (ESI+) m/z: 362 (M+H)+;
1H NMR (DMSO-d6) δ 1,12 (t, 3H, J=7.36Hz), 1.70–2.00 (m, 2H), 2.19–2.22 (m, 2H), 2.55 (m, 2H), 2.56 (m, 2H), 2.71–2.85 (m, 1H), 3.02 (m, 1H), 4.82 (s, 1H), 6.90 (m, 2H), 7.06 (d, 1H, J=8.09Hz), 9.74 (s, 1H);
Anal. calcd for $C_{19}H_{20}FNO_3S$: C, 63.14;H, 5.58; N, 3.88. Found: C, 64.10;H, 5.68; N, 3.70.

EXAMPLE 175

9-(5-cyano-2-thienyl)-2,3,5,6,7,9-hexahydrothieno[3,2-b]quinolin-8(4H)-one, 1,1-dioxide To a stirred solution of Example 128 (1.00 g, 2.50 mmol) in dimethylformamide (10 mL), was added copper cyanide (694 mg, 7.74 mmol), the reaction heated to reflux for 3 hours, cooled to room temperature, then poured into a solution of potassium cyanide (732 mg) in water (10 mL), stirred for 40 minutes and filtered. The resulting solution was extracted with methylene chloride (3x), the combined organic extracts washed with water and brine, dried ($MgSO_4$), filtered, and evaporated. The crude product was purified by flash chromatography over silica gel eluting with methanol:chloroform (3:97) to provide 750 mg of the title compound.
mp >250 ° C.;
MS (ESI+) m/z: 347 (M+H)+;
1H NMR (DMSO-d6) δ 1.90 (m, 2H), 2.30 (t, 2H, J=6Hz), 2.55 (m, 2H), 2.85 (m, 1H), 3.05 (m, 1H), 3.4 (m, 2H), 5.2 (s, 1H), 7.0 (d, 1H, J=4.5Hz), 7.74 (d, 1H, J=4.5Hz), 10.08 (s, 1H);
Anal. calcd for $C_{16}H_{14}N_2O_3S_2$: C, 55.47;H, 4.07; N, 8.09. Found: C, 55.31;H, 4.12; N, 8.06.

EXAMPLE 176

(+)-9-(3,4-difluoro)-2,3,5,6,7,9-hexahydrothieno[3,2-b]quinolin-8(4H)-one 1,1-dioxide Example 33 (1.2 g, 3.4 mmol) was processed according to the method of Example 95 to provide 105 mg of the title compound.
mp >250 ° C.; [a]23D +34.4 (c 0.63, DMSO);
MS (ESI+) m/z: 352 (M+H)+; =
1H NMR (DMSO-d6) δ 1.88 (m, 2H), 2.25 (m, 2H), 2.55 (m, 2H), 2.82 (m, 1H), 3.02 (m, . H), 3.35 (m, 2H), 4.85 (s, 1H), 7.03 (m, 1H), 7.15 (m, 1H), 7.28 (m, 1H), 9.82 (s, 1H);
Anal. calcd for $C_{17}H_{15}F_2NO_3S$: C, 58.1 1;H, 4.30; N, 3.99. Found: C, 58.42;H, 4.1 1; N, 3.61.

EXAMPLE 177

(9S)-9-(3-ethenyt-4-fluorophenyl)-2,3,5,6,7,9-hexahydrothieno[3,2-b]quinolin-8(4H)-one 1,1-dioxide

EXAMPLE 177A (9S)-I 1-dimethylethyl 9-(3-bromo-4-fluorophenyl)-8-oxo-3,5,6,7,8,9-hexahydrothieno[3,2-b]quinoline-4(2H)-carboxylate, 1,1-dioxide A solution of Example 84 (1.0 g, 2.4 mmol) and di-tert-butyldicarbonate (1.0 g, 24 mmol) in acetonitrile was treated with 4-dimethylaminopyridine (29 mg, 0.1 mmol), heated to reflux for 1 hour, cooled to room temperature, and concentrated. The residue was purified by flash chromatography on silica gel eluting with ethyl acetate:hexane (1:1) to provide 900 mg of the title compound.
1H NMR (DMSO-d6) δ 1.56 (s, 9H), 1.90–2.02 (m, 2H), 2.3–2.5 (m, 2H), 3.00 (m, 2H), 3.45 (m, 2H), 3.50 (m, 2H), 4.83 (s, 1H), 7.20 (m, 1H), 7.32 (t, 1H), 7.37 (dd, 1H).

EXAMPLE 177B (9S)-9-(3-ethenyl-4-fluoronhenyl)-2,3,5,6,7,9-hexahydrothieno[3,2-b]quinolin-8(4H)-one, 1,1-dioxide A solution of Example 177A (150 mg, 0.29 mmol) and tetrakis(triphenylphoshine)-palladium(0) (10 mol%) in dimethylformamide (0.1 M) was treated with vinyl tributylstannane (0.45 mL, 1.4 mmol), heated to 110 IC for 24 hours, cooled to room temperature, treated with saturated potassium fluoride, and extracted with ethyl acetate. The extract was washed with brine, dried over sodium sulfate, filtered, and concentrated. The residue was purified by flash chromatography on silica gel eluting with methanol:dichloromethane (5:95), followed by recrystallization from ethanol to _provide 82 of the title compound as a white solid.
MS (ES1-) m/z: 358 (M-H)-;
1H NMR (DMSO-d6) δ 1.99–1.82 (m, 2H), 2.25–2.20 (m, 2H), 2.5 (m, 2H), 2.79–2.73 (m, 1H), 3.32–3.30 (m, 4H), 3.25–2.81 (m, 1H), 4.86 (s, 1H), 5.40 (dd, 1H, J=1 1.53, 1.35 Hz), 5.80 (dd, 1H, J=18.0, 1.35Hz), 6.77 (dd, 1H, J=i7.63, 11.20Hz), 7.08–7.01 (m, 2H), 7.35 (dd, 1H, J=7.46, 2.04Hz), 9.74 (S, 1H);
Anal. calcd for $C_{19}H_{18}FNO_3S0.3H_2O$: C, 63.49;H, 5.05; N, 3.90. Found: C, 63.27;H, 5.10; N, 3.66.

EXAMPLE 178

9-(5-bromo-4-fluoro-2-nitrophenyl)-3 .4,5,6,7,9-hexahydrocyclopenta[b]thiopyrano[2,3-e]pyridin-8(2H)-one, 1,1-dioxide Example 115A (0.249 g, 1.00 mmol) was processed according to the method of Example 37. The crude product was purified by flash chromatography over silica gel eluting with ethanol/methylene chloride (5:95) to provide 0.17 g of the title compound.
MS (ESI+) m/z: 459 (M+H)+;
1H NMR (DMSO-d6) δ 2.2 (m, 4H), 2.6 (m, 4H), 3.22 (m, 2H), 5.76 (s, 1H), 7.67 (d, 1H), 7.97 (d, 1H), 10.02 (s, 1H);
Anal. calcd for $Cl_7H_5N_2BrFO_5S$: C, 44.54;H, 3.27; N, 6.11. Found: C, 44.84;H, 3.57; N, 5.9 1.

EXAMPLE 179

(−)-9-(3,4-difluorophenyl)-2,3,5,6,7,9-hexahydrothieno[3,2-b]quinolin-8(4H)-one 1,1-dioxide The product from Example 33 (1.2 g, 3.4 mmol) was processed according to the method of Example 96 to provide 200 mg of the title compound.
mp >250; [a]23D -34.0 (c 0.70, DMSO);
1H NMR (DMSO-d6) δ 1.88 (m, 2H), 2.25 (m, 2H), 2.55 (m, 2H), 2.82 (m, 1H), 3.02 (m, 1H), 3.35 (m, 2H), 4.85 (s, 1H), 7.03 (m, 1H), 7.15 (m, 1H), 7.28 (m, 1H), 9.82 (s, 1H);

MS (ESI+) m/z 352 (M+H)+;
Anal. Calcd for $C_{17}H_{15}F_2NO_3S$: C, 58.11;H, 4.30; N, 3.99. Found: C, 58.05;H, 4.32; N, 4.02.

EXAMPLE 180

9-(4-bromo-2-thienyl)-2,3,5,6,7,9-hexahydrothieno[3,2-b]quinolin-8(4H)-one 1,1-dioxide Example 129 was chromatographed over a 2×25 cm Regis Whelk-O1 chiral column eluting with hexane:methanol:methylene chloride (50:34:16) as the mobile phase at a flow rate of 10 mL/minute to provide the title compound as the less polar enantiomer.
mp >250;
$^1$H NMR (DMSO-$d_6$) δ 1.81 (m, 1H), 1.94 (m, 1H), 2.55 (m, 2H), 2.84 (m, 1H), 3.05 (m, 1H), 3.42 (m, 2H), 5.12 (s, 1H), 6.80 (s, 1H), 7.40 (s, 1H), 9.95 (br s, 1H);
MS (ESI+) m/z 400 (M+H)+;
Anal. Calcd for $C_{15}H_{14}BrNO_3S_2$: C, 45.01;H, 3.52; N, 3.50. Found: C, 45.05;H, 3.70; N, 3.36.

EXAMPLE 181

9-(4-bromo-2-thienyl)-2,3,5,6,7,9-hexahydrothieno[3,2-b]quinolin-8(4H)-one 1,1-dioxide From the chiral chromatography of the above example was obtained the title compound as the more polar enantiomer.
mp >250;
$^1$H NMR (DMSO-$d_6$) δ 1.81 (m, 1H), 1.94 (m, 1H), 2.55 (m, 2H), 2.84 (m, 1H), 3.05 (m, 1H), 3.42 (m, 2H), 5.12 (s, 1H), 6.80 (s, 1H), 7.40 (s, 1H), 9.95 (br s, 1H);
MS (ESI+) m/z 400 (M+H)+;
Anal. Calcd for $C_{15}H_{14}BrNO_3S_2$: C, 45.01;H, 3.52; N, 3.50. Found: C, 45.07;H, 3.38; N, 3.62.

EXAMPLE 182

9-(34-difluorophenyl)-7,7-dimethyl-2,3,5,6,7,9-hexahydrothieno[3,2-b]quinolin-8(4H)-one 1,1-dioxide 3,4-Difluorobenzaldehyde (0.2 mmol) was processed according to the method of Example 116 to provide the title compound.
$^1$H NMR (DMSO-$d_6$) δ 0.90 (s, 3H), 0.98 (s, 3H), 1.75 (m, 2H), 2.56 (m, 2H), 2.80 (m, 1H), 3.00 (m, 1H), 3.30 (m, 2H), 4.80 (s, 1H), 7.00 (m, 1H), 7.10 (m, 1H), 7.24 (m, 1H), 9.70 (br s, 1H);
MS (APCI+) m/z 380 (M+H)+.

EXAMPLE 183

9-(3-chloro-4-fluorophenyl)-7,7-dimethyl-2,3,5,6,7,9-hexahydrnthieno [32-b]quinolin-.8(4H)-one 1,1-dioxide 3-Chloro-4-fluorobenzaldehyde (0.2 mmol) was processed according to the method of Example 116 to provide the title compound.
$^1$H NMR (DMSO-$d_6$) δ 0.90 (s, 3H), 0.98 (s, 3H), 1.76 (m, 2H), 2.56 (m, 2H), 2.80 (m, 1H), 3.00 (m, IFH), 3.30 (m, 2H), 4.80 (s, 1H), 7.16 (m, 1H), 7.24 (m, 2H), 9.72 (br s, 1H);
MS (APCI+) m/z 396 (M+H)+.

EXAMPLE 184

9-[4-fluoro-3-(trifluoromethyl)phenyl]-7,7-dimethyl-2,3,5,6,7,9-hexahydrothieno[3,2-b]quinolin-8(4H)-one 1,1-dioxide 4-Fluoro-3-trifluoromethylbenzaldehyde (0.2 mmol) was processed according to the method of Example 116 to provide the title compound.
$^1$H NMR (DMSO-$d_6$) δ 0.90 (s, 3H), 0.98 (s, 3H), 1.75 (m, 2H), 2.56 (m, 2H), 2.80 (m, 1H), 3.00 (m, 1H), 3.30 (m, 2H), 4.90 (s, 1H), 7.35 (m, 1H), 7.45 (m, 1H), 7.52 (m, 1H), 9.78 (br s, 1H);
MS (APCI+) m/z 430 (M+H)+.

EXAMPLE 185

9-(4-chloro-3-fluorophenyl)-7,7-dimethyl-2,3,5,6,7,9-hexahydrothieno[3.2-b]quinolin-8(4H)-one 1,1-dioxide 4-Chloro-3-fluorobenzaldehyde (0.2 mmol) was processed according to the method of Example 116 to provide the title compound.
$^1$H NMR (DMSO-$d_6$) δ 0.90 (s, 3H), 0.98 (s, 3H), 1.75 (m, 2H), 2.56 (m, 2H), 2.80 (m, 1H), 3.00 (m, 1H), 3.30 (m, 2H), 4.81 (s, 1H), 7.02 (m, 1H), 7.10 (m, 1H), 7.42 (m, 1H), 9.78 (br s, 1H);
MS (APCI+) m/z 396 (M+H)+.

EXAMPLE 186

9-(4-chloro-3-nitrophenyl)-7,7-dimethyl-2,3,5,6,7,9-hexahydrothieno[3.2-b]quinolin-8(4H)-one 1,1-dioxide 4-Chloro-3-nitrobenzaldehyde (0.2 mmol) was processed according to the method of Example 116 to provide the title compound.
$^1$H NMR (DMSO-$d_6$) δ 0.90 (s, 3H), 0.98 (s, 3H), 1.77 (m, 2H), 2.58 (m, 2H), 2.82 (m, 1H), 3.00 (m, 1H), 3.30 (m, 2H), 4.92 (s, 1H), 7.52 (m, 1H), 7.63 (d, 1H), 7.78 (s, 1H), 9.80 (br s, 1H);
MS (APCI+) m/z 423 (M+H)+.

EXAMPLE 187

9-(3.4-dibromophenyl)-7,7-dimethyl-2,3,5,6,7,9-hexahydrothieno[3.2-b]quinolin-8(4H)-one, 1,1-dioxide 3,4-Dibromobenzaldehyde (0.2 mmol) was processed according to the method of Example 116 to provide the title compound.
$^1$H NMR (DMSO-$d_6$) δ 0.90 (s, 3H), 0.98 (s, 3H), 1.77 (m, 2H), 2.58 (m, 2H), 2.82 (m, 1H), 3.00 (m, 1H), 3.30 (m, 2H), 4.79 (s, 1H), 7.08 (m, 1H), 7.44 (s, 1H), 7.62 (d, 1H), 9.78 (br s, 1H);
MS (APCI+) m/z 500 (M+H)+.

EXAMPLE 188

9-[3-fluoro4-(trifluoromethyl)phenyl]-7.7-dimethyl-2,3,5,6,7,9-hexahydrothieno[3.2-b]quinolin-8(4H)-one 1,1-dioxide 3-Fluoro-4-trifluoromethylbenzaldehyde (0.2 mmol) was processed according to the method of Example 116 to provide the title compound.
$^1$H NMR (DMSO-$d_6$) δ 0.90 (s, 3H), 0.98 (s, 3H), 1.75 (m, 2H), 2.56 (m, 2H), 2.82 (m, 1H), 3.00 (m, 1H), 3.30 (m, 2H), 4.90 (s, 1H), 7.22 (m, 2H), 7.63 (m, 1H), 9.80 (br s, 1H);
MS (APCI+) m/z 430 (M+H)+.

EXAMPLE 189

7,7-dimethyl-9-(3-nitrophenyl)-2,3,5,6,7,9-hexahydrothieno[3.2-b]quinolin-8(4H)-one 1,1-dioxide 3-Nitrobenzaldehyde (0.2 mmol) was processed according to the method of Example 116 to provide the title compound.

¹H NMR (DMSO-d₆) δ 0.90 (s, 3H), 0.98 (s, 3H), 1.75 (m, 2H), 2.56 (m, 2H), 2.80 (m, 1H), 3.00 (m, 1H), 3.30 (m, 2H), 4.80 (s, 1H), 7.00 (m, 1H), 7.10 (m, 1H), 7.24 (m, 1H), 9.70 (br s, 1H);
MS (APCI+) m/z 380 (M+H)⁺.

EXAMPLE 190

9-(3-cyanophenyl)-7,7-dimethyl-2,3,5,6,7,9-hexahydrothieno[3.2-b]quinolin-8(4H)-one 1,1-dioxide 3-Cyanobenzaldehyde (0.2 mmol) was processed according to the method of Example 116 to provide the title compound.
¹H NMR (DMSO-d₆) δ 0.90 (s, 3H), 0.98 (s, 3H), 1.75 (m, 2H), 2.56 (m, 2H), 2.82 (m, 1H), 3.02 (m, 1H), 3.30 (m, 2H), 4.88 (s, 1H), 7.42–7.62 (m, 4H), 9.78 (br s, 1H);
MS (APCI+) m/z 369 (M+H)⁺.

EXAMPLE 191

9-(4-bromo-2-thienyl)-7,7-dimethyl-2,3,5,6,7,9-hexahydrothieno[3.2-b]quinolin-8(4H)-one 1,1-dioxide 4-Bromo-2-thiophenecarboxaldehyde (0.2 mmol) was processed according to the method of Example 116 to provide the title compound.
¹H NMR (DMSO-d₆) δ 0.97 (s, 3H), 0.99 (s, 3H), 1.77 (m, 2H), 2.56 (m, 2H), 2.82 (m, 1H), 3.02 (m, 1H), 3.30 (m, 2H), 5.10 (s, 1H), 6.80 (s, 1H), 7.40 (s, 1H), 9.78 (br s, 1H);
MS (APCI+) m/z 428 (M+H)⁺.

EXAMPLE 192

9-(5-chloro-2-thienyl)-7,7-dimethyl-2,3,5,6,7,9-hexahydrothieno[3.2-b]quinolin-8(4H)-one 1,1-dioxide 5-Chloro-2-thiophenecarboxaldehyde (0.2 mmol) was processed according to the method of Example 116 to provide the title compound.
¹H NMR (DMSO-d₆) δ 0.97 (s, 3H), 0.99 (s. 3H), 1.77 (m, 2H), 2.56 (m, 2H), 2.82 (m, 1H), 3.02 (m, 1H), 3.40 (m, 2H), 5.03 (s, 1H), 6.66 (s, 1H), 6.82 (s, 1H), 9.80 (br s, 1H);
MS (APCI+) m/z 384 (M+H)⁺.

EXAMPLE 193

9-(5-bromo-2-thienyl)-7,7-dimethyl-2,3,5,6,7,9-hexahydrothieno[3,2-b]quinolin-8(4H)-one 1,1-dioxide 5-Bromo-2-thiophenecarboxaldehyde (0.2 mmol) was processed according to the method of Example 116 to provide the title compound.
¹H NMR (DMSO-d₆) δ 0.97 (s, 3H), 0.99 (s, 3H), 1.77 (m, 2H), 2.56 (m, 2H), 2.82 (m, 1H), 3.02 (m, 1H), 3.40 (m, 2H), 5.04 (s, 1H), 6.65 (s, 1H), 6.96 (s, 1H), 9.82 (br s, 1H);
MS (APCI+) m/z 428 (M+H)⁺.

EXAMPLE 194

7.7-dimethyl-9-(5-nitro-3-thienyl)-2,3,5,6,7,9-hexahydrothieno[3,2-b]quinolin-8(4H)-one, 1,1-dioxide 5-Nitro-3-thiophenecarboxaldehyde (0.2 mmol) was processed according to the method of Example 116 to provide the title compound.
¹H NMR (DMSO-d₆) δ 0.97 (s, 3H), 1.02 (s, 3H), 1.78 (m, 2H), 2.58 (m, 2H), 2.82 (m, 1H), 3.02 (m, 1H), 3.40 (m, 2H), 4.94 (s, 1H), 7.62 (s, 1H), 7.82 (s, 1H), 9.80 (br s, 1H);
MS (APCI+) m/z 395 (M+H)⁺.

EXAMPLE 195

9-(5-chloro-2-hydroxyvhenyl)-7.7-dimethyl-2,3,5,6,7,9-hexahydrothieno[3.2-b]quinolin-8(4H)-one, 1,1-dioxide 5-Chlorosalicylaldehyde (0.2 mmol) was processed according to the method of Example 116 to provide the title compound.
¹H NMR (DMSO-d₆) δ 0.90 (s, 3H), 0.98 (s, 3H), 1.77 (m, 2H), 2.58 (m, 2H), 2.82 (m, 1H), 3.00 (m, 1H), 3.30 (m, 2H), 5.09 (s, 1H), 6.64 (d, 1H), 6.82 (s, 1H), 6.98 (m, 1H), 9.60 (br s, 1H), 9.62 (s, 1H);
MS (APCI+) m/z 394 (M+H)⁺.

EXAMPLE 196

9-(2-hydroxy-5-nitrophenyl)-7,7-dimethyl-2,3,5,6,7,9-hexahydrothieno[3.2-b]quinolin-8(4H)-one 1,1-dioxide 5-Nitrosalicylaldehyde (0.2 mmol) was processed according to the method of Example 116 to provide the title compound.
¹H NMR (DMSO-d₆) o 0.90 (s, 3H), 0.98 (s, 3H), 1.77 (m, 2H), 2.58 (m, 2H), 2.82 (m, 1H), 2.96 (m, 1H), 3.30 (m, 2H), 5.20 (s, 1H), 6.84 (d, 1H), 7.80 (s, 1H), 7.96 (m, 1H), 9.62 (br s, 1H), 11,12 (br s, 1H);
MS (APCI+) m/z 405 (M+H)⁺.

EXAMPLE 197

9-(2-hydroxy-3.5-dinitrophenyl)-7.7-dimethyl-2,3,5,6,7,9-hexahydrothieno[3.2-b]quinolin-8(4H)-one 1,1-dioxide 3,5-Dinitrosalicylaldehyde (0.2 mmol) was processed according to the method of Example 116 to provide the title compound.
¹H NMR (DMSO-d₆) o 0.90 (s, 3H), 0.98 (s, 3H), 1.77 (m, 2H), 2.58 (m, 2H), 2.76 (m, 1H), 2.86 (m, 1H), 3.30 (m, 2H), 5.16 (s, 1H), 7.52 (s, 1H), 8.42 (s, 1H), 9.42 (br s, 1H), 11,12 (br s, 1H);
MS (APCI+) m/z 450 (M+H)⁺.

EXAMPLE 198

9-(3.5-dibromo-2-hydroxyphenyl)-7,7-dimethyl-2,3,5,6,7,9-hexahydrothieno[3.2-b]quinolin-8(4H)-one 1,1-dioxide 3,5-Dibromosalicylaldehyde (0.2 mmol) was processed according to the method of Example 116 to provide the title compound.
¹H NMR (DMSO-d₆) δ 0.90 (s, 3H), 0.98 (s, 3H), 1.77 (m, 2H), 2.58 (m, 2H), 2.86 (m, 1H), 3.06 (m, 1H), 3.30 (m, 2H), 5.06 (s, 1H), 7.02 (s, 1H), 7.47 (s, 1H), 9.92 (br s, 2H);
MS (APCI+) m/z 518 (M+H)⁺.

EXAMPLE 199

9-(3-bromo-5-chloro-2-hydroxyphenyl)-7,7-dimethyl-2,3,5,6,7,9-hexahydrothieno[3.2-b]quinolin-8(4H)-one 1,1-dioxide 3-Bromo-5-chlorosalicylaldehyde (0.2 mmol) was processed according to the method of Example 116 to provide the title compound.

¹H NMR (DMSO-d₆) δ 0.96 (s, 3H), 1.02 (s, 3H), 1.77 (m, 2H), 2.58 (m, 2H), 2.82 (m, 1H), 3.06 (m, 1H), 3.30 (m, 2H), 5.04 (s, 1H), 6.92 (s, 1H), 7.40 (s, 1H), 9.98 (br s, 2H);
MS (APCI+) m/z 473 (M+H)⁺.

EXAMPLE 200

9-(3-bromo-2-hydroxy-5-nitrophenyl)-7,7-dimethyl-2,3,5,6,7,9-hexahydrothieno[3,2-b]quinolin-8(4H)-one 1,1-dioxide 3-Bromo-5-nitrosalicylaldehyde (0.2 mmol) was processed according to the method of Example 116 to provide the title compound.
¹H NMR (DMSO-d₆) δ 0.96 (s, 3H), 1.02 (s, 3H), 1.77 (m, 2H), 2.58 (m, 2H), 2.82 (m, 1H), 2.96 (m, 1H), 3.30 (m, 2H), 5.14 (s, 1H), 7.72 (s, 1H), 8.12 (s, 1H), 9.98 (br s, 2H);
MS (APCI+) m/z 484 (M+H)⁺.

EXAMPLE 201

9-(3,5-dichloro-2-hydroxyphenyl)-7,7-dimethyl-2,3,5,6,7,9-hexahydrothieno[3,2-b]quinolin-8(4H)-one 1,1-dioxide 3,5-Dichlorosalicylaldehyde (0.2.mmol) was processed according to the method of Example 116 to provide the title compound.
¹H NMR (DMSO-d₆) δ 0.96 (s, 3H), 1.02 (s, 3H), 1.77 (m, 2H), 2.58 (m, 2H), 2.82 (m, 1H), 3.04 (m, 1H), 3.30 (m, 2H), 5.06 (s, 1H), 6.86 (s, 1H), 7.22 (s, 1H), 9.82 (br s, 2H);
MS (APCI+) m/z 429 (M+H)⁺.

EXAMPLE 202

9-(2-hydroxy-3-nitrophenyl)-7,7-dimethyl-2,3,5,6,7,9-hexahydrothieno[3,2-b]quinolin-8(4H)-one 1,1-dioxide 3-Nitrosalicylaldehyde (0.2 mmol) was processed according to the method of Example 116 to provide the title compound.
¹H NMR (DMSO-d₆) 60.96 (s, 3H), 1.02 (s, 3H), 1.77 (m, 2H), 2.58 (m, 2H), 2.82 (m, 1H), 2.94 (m, 1H), 3.30 (m, 2H), 5.26 (s, 1H), 6.86 (m, 1H), 7.39 (m, 1H), 7.79 (m, 1H), 9.82 (br s, 2H);
MS (APCI+) mi/z 405 (M+H)⁺.

EXAMPLE 203

9-(5-bromo-2-hydroxy-3-nitrophenyl)-7,7-dimethyl-2,3,5,6,7,9-hexahydrothieno[3,2-b]quinolin-8(4H)-one 1,1-dioxide 5-Bromo-3-nitrosalicylaldehyde (0.2 mmol) was processed according to the method of Example 116 to provide the title compound.
¹H NMR (DMSO-d₆) δ 0.96 (s, 3H), 1.02 (s, 3H), 1.77 (m, 2H), 2.58 (m, 2H), 2.82 (m, 1H), 2.99 (m, 1H), 3.30 (m, 2H), 5.20 (s, 1H), 7.78 (s, 1H), 8.18 (s, 1H), 9.90 (br s, 2H);
MS (APCI+) m/z 484 (M+H)⁺.

EXAMPLE 204

7,7-dimethyl-9-(2,4,5-trifluorophenyl)-2,3,5,6,7,9-hexahydrothieno[3,2-b]quinolin-8(4H)-one 1,1-dioxide 2,4,5-Trifluorobenzaldehyde (0.2 mmol) was processed according to the method of Example 116 to provide the title compound.
¹H NMR (DMSO-d₆) δ 0.96 (s, 3H), 1.02 (s, 3H), 1.77 (m, 2H), 2.58 (m, 2H), 2.82 (m, 1H), 2.96 (m, 1H), 3.30 (m, 2H), 5.02 (s, 1H), 7.18 (m, 1H), 7.38 (m, 1H), 9.78 (br s, 1H);
MS (APCI+) m/z 398 (M+H)⁺.

EXAMPLE 205

7,7-dimethyl-9-(2,3,4-trifluorophenyl)-2,3,5,6,7,9-hexahydrothieno[3,2-b]quinolin-8(4H)-one 1,1-dioxide 2,3,4-Trifluorobenzaldehyde (0.2 mmol) was processed according to the method of Example 116 to provide the title compound.
¹H NMR (DMSO-d₆) δ 0.90 (s, 3H), 1.00 (s, 3H), 1.78 (m, 2H), 2.58 (m, 2H), 2.82–2.96 (m, 2H), 3.30 (m, 2H), 5.02 (s, 1H), 7.00 (m, 1H), 7.18 (m, 1H), 9.78 (br s, 1H);
MS (APCI+) m/z 398 (M+H)⁺.

EXAMPLE 206

7,7-dimethyl-9-(3,4,5-trifluorophenyl)-2,3,5,6,7,9-hexahydrothieno[3,2-b]quinolin-8(4H)-one 1,1-dioxide 3,4,5-Trifluorobenzaldehyde (0.2 mmol) was processed according to the method of Example 116 to provide the title compound.
¹H NMR (DMSO-d₆) δ 0.90 (s, 3H), 1.00 (s, 3H), 1.78 (m, 2H), 2.58 (m, 2H), 2.82 (m, 1H), 2.99 (m, 1H), 3.30 (m, 2H), 4.82 (s, 1H), 7.02 (m, 2H), 9.78 (br s, 1H);
MS (APCI+) m/z 398 (M+H)⁺.

EXAMPLE 207

9-(3,5-dibromo-4-hydroxyphenyl)-7,7-dimethyl-2.35.6.79-hexahydrothieno[3,2-b]quinolin-8(4H)-one, 1,1-dioxide 3,5-Dibromo-4-hydroxybenzaldehyde (0.2 mmol) was processed according to the method of Example 116 to provide the title compound.
¹H NMR (DMSO-d₆) δ 0.90 (s, 3H), 1.00 (s, 3H), 1.78 (m, 2H), 2.58 (m, 2H), 2.82 (m, 1H), 2.99 (m, 1H), 3.30 (m, 2H), 4.72 (s, 1H), 7.22 (s, 2H), 9.78 (br s, 2H);
MS (APCI+) m/z 518 (M+H)⁺.

EXAMPLE 208

9-(4-chlorophenyl)-7,7-dimethyl-2,3,5,6,7,9-hexahydrothieno[3,2-b]quinolin-8(4H)-one 1,1-dioxide 4-Chlorobenzaldehyde (0.2 mmol) was processed according to the method of Example 116 to provide the title compound.
¹H NMR (DMSO-d₆) δ 0.90 (s, 3H), 1.00 (s, 3H), 1.78 (m, 2H), 2.58 (m, 2H), 2.82 (m, 1H), 2.99 (m, 1H), 3.30 (m, 2H), 4.82 (s, 1H), 7.18 (d, 2H), 7.23 (d, 2H), 9.68 (br s, 1H);
MS (APCI+) m/z 378 (M+H)⁺.

EXAMPLE 209

9-(3-chloronhenyl)-7,7-dimethyl-2,3,5,6,7,9-hexahydrothieno[3,2-b]quinolin-8(4H)-one 1,1-dioxide 3-Chlorobenzaldehyde (0.2 mmol) was processed according to the method of Example 116 to provide the title compound.

¹H NMR (DMSO-d₆) δ0.90 (s, 3H), 1.00 (s, 3H), 1.78 (m, 2H), 2.58 (m, 2H), 2.82 (m, 1H), 2.99 (m, 1H), 3.30 (m, 2H), 4.80 (s, 1H), 7.16–7.26 (m, 4H), 9.67 (br s, 1H); MS (APCI+) m/z 378 (M+H)⁺.

EXAMPLE 210

9-(4-chloro-3-fluorophenyl)-2,3,5,6,7,9-hexahydrothieno[3,2-b]quinolin-8(4H)-one, 1,1-dioxide 4-Chloro-3-fluorobenzaldehyde (0.95 g, 6.0 mmol) was processed according to the method of Example 115C to provide the title compound.
mp >250;
¹H NMR (DMSO-d₆) δ 1.90 (m, 2H), 2.26 (m, 2H), 2.54 (m, 2H), 2.86 (m, 1H), 3.02 (m, 1H), 3.38 (m, 2H), 4.86 (s, 1H), 7.05 (dd, 1H, J=1.5,9.0Hz), 7.14 (dd, 1H, J=1.5;9.0Hz), 7.48 (t, 1H, J=9.0Hz), 9.85 (s, 1H);
MS (ESI+) m/z 368 (M+H)⁺;
Anal. Calcd for C₁₇H₁₅ClFNO₃S: C, 55.51;H, 4.11; N, 3.81. Found: C, 55.28;H, 4.13; N, 3.71.

EXAMPLE 211

9-[3-(trifluoromethoxy)phenyyl-2,3,5,6,7,9-hexahydrothieno[3,2-b]quinolin-8(4H)-one 1,1-dioxide 3-Trifluoromethoxybenzaldehyde (1.0 g, 4.7 mmol) was processed according to the method of Example 11 5C to provide 1.32 g of the title compound.
mp >250;
¹H NMR (DMSO-d₆) δ 1.60–1.97 (m, 2H), 2.17–2.32 (m, 2H), 2.45–2.56 (m, 2H), 2.77-3.06 (m, 2H), 3.26–3.43 (m, 2H), 4.89 (s, 1H), 7.08 (s, 1H), 7.10 (d, 1H, J=5.9Hz), 7.20 (d, 1H, J=7.72Hz), 7.36 (t, 1H, J=7.72Hz), 9.82 (S, 1H);
MS (ESI+) m/z 400 (M+H)⁺;
Anal. Calcd for C₁₈H₁₆F₃NO4S: C, 54.13;H, 4.04; N, 3.51. Found: C, 53.88;H, 4.01; N, 3.21.

EXAMPLE 212

9-(3-bromo-4-fluorophenyl)-5,5-dimethyl-2,3,5,6,7,9-hexahydrothieno[3,2-b-quinolin 8(4H)-one 1,1-dioxide

EXAMPLE 212A 3-methoxy-4,4-dimethyl-2-cyclohexen-1,1-one.

A stirred solution of 4,4-dimethyl-1,3-cyclohexanedione (3.04 g, 21.7 mmol) and p-toluenesulfonic acid monohydrate (413 mg, 2.17 mmol) in methanol (40 mL) was heated at reflux for 2 hours. The reaction mixture was cooled and concentrated to give an oily residue. The residue was purified by flash chromatography (elution with 3% methanol/ethyl acetate) to provide 805 mg of the title compound as a colorless liquid.
¹H NMR (DMSO-d₆) δ 1,12 (s, 6H), 1.83 (t, 3H, J=7.1Hz), 2.42 (t, 3H, J=7.1Hz), 3.68 (s, 3H), 5.26 (s, 1H);
MS (DCI'NH₃) 'n/z 155 (M+H)⁺.

EXAMPLE 212B 3-amino-4.4-dimethyl-2-cyclohexen-1-one

3-Methoxy-4,4-dimethyl-2-cyclohexen-1-one in condensed anhydrous ammonia (50 mL) was heated at 100 ° C. (850 psi) for 34 hours. Ammonia was removed by evaporation, the residue dissolved in ethyl acetate (5 mL) and filtered through Florisil to provide 1.14 g of the title compound as a pale tan oil.
¹H NMR (DMSO-d₆) δ 1,11 (s, 3H), 1,18 (s, 3H), 1.67 (t, 3H, J=7.1Hz), 2.15 (t, 3H, J=7.1Hz), 4.83 (s, 1H), 6.59 (br s, 2H);
MS (DCI/NH₃) m/Z 139 (M+H)⁺.

EXAMPLE 212C 9-(3-bromo-4-fluorophenyl)-5,5-dimethyl-2,3,5,6,7,9-hexahydrothieno[3 2-b]quinolin-8(4H)-one 1,1-dioxide A stirred solution of 3-bromo-4-fluorobenzaldehyde (725 mg, 3.57 mmol), 3-amino-4,4-dimethyl-2-cyclohexen-1-one (496 mg, 3.57 mmol), and tetrahydrothiophene-3-oxo-1,1-dioxide (473 mg, 3.57 mmol) in ethanol (30 mL) was heated at reflux for 96 hours. The reaction mixture was cooled and concentrated to give a yellow residue which redissolved in ethanol (30 mL) and treated with 2 M HCl in diethyl ether (2.0 mL). The solution was then heated at reflux for 9 hours, then cooled.ambient temperature and the white solid that precipitated was triturated with ethyl acetate. The solid was purified by flash chromatography (elution with 8% methanol/methylene chloride) to provide 267 mg of the title compound as an off-yellow solid.
mp >270 ° C.;
¹H NMR (DMSO-d₆) δ 1.30 (s, 3H), 1.34 (s, 3H), 1.83–1.92 (m, 2H), 2.14–2.21 (m, 1H), 2.36–2.45 (m 1H), 2.89–2.97 (m, 1H), 3.03–3.11 (m, 1H), 3.29–3.44 (m, 2H), 4.85 (s, 1H), 7.13–7.26 (m, 2H), 7.35–7.39 (m, 1H), 9.40 (br s, 1H);
MS (DCI/NH₃) m/z 457 (M+NH₄)⁺;
Anal. Calcd for C₁₉H₁₉BrFNO₃S: C, 51.83;H, 4.35; N, 3.18. Found: C, 51.68;H, 4.14; N, 3.34.

EXAMPLE 213

9-[4-(trifluoromethoxy)phenyyl-2,3,5,6,7,9-hexahydrothieno[3 2-b]quinolin-8(4H)-one 1,1-dioxide 4-Trifluoromethoxybenzaldehyde (1,14 g, 6.00 mmol) was processed according to the method of Example 115C to provide 2.0 g of the title compound.
mp >250;
¹H NMR (DMSO-d₆) δ 1.90 (m, 2H), 2.26 (m, 2H), 2.54 (m, 2H), 2.86 (m, 1H), 3.02 (m, 1H), 3.38 (m, 2H), 4.86 (s, 1H), 7.20 (m, 2H), 7.30 (m, 2H), 9.85 (s, 1H);
MS (ESI+) m/z 400 (M+H)⁺;
Anal. Calcd for C₁₈H₁₆F₃NO4S: C, 54.13;H, 4.04; N, 3.51. Found: C, 54.02;H, 4.05; N, 3.45.

EXAMPLE 214

9-(21,3-benzothiadiazol-5-yl)-2,3,5,6,7,9-hexahydrothieno[3,2-b]cuinolin-8(4H)-one 1,1-dioxide

EXAMPLE 214A 5-bromomethylbenzo-2.1.3-thiadiazole

5-Methylbenzo-2,1,3-thiadiazole (5.0 g, 33 mmol), N-bromosuccinimide (5.92g, 33.3 mmol) and catalytic 2,2'-azobisisobutyronitrile were heated at reflux for 16 hours in chloroform (75 mL). The reaction mixture was cooled and the resulting precipitate was filtered off and discarded. The filtrate was evaporated and recrystallized from ethanol to provide 4.8 g of the title compound.
¹H NMR (CDCl₃) 4.65 (s, 2H), 7.65 (dd, 1H), 8.01 (d, 2H).

EXAMPLE 214B 5-hydroxymethylbenzo-2,1,3-thiadiazole

5-Bromomethylbenzo-2,1,3-thiadiazole (4.8 g) and calcium carbonate (10 g) were heated at reflux in 1:1 dioxane/water (120 mL) for 3 hours. The solvents were evaporated and the residue was partitioned between 2N hydrochloric acid and methylene 6 3 chloride. The organic layers were dried (magnesium sulfate), evaporated and chromatographed on silica gel eluting with 1:1 ethyl acetate/hexane to provide 2.66 g of the title compound.
¹H NMR (CDCl₃) 1.92 (t, 1H), 4.9 (d, 1H), 7.6 (dd, 1H), 8.0 (m, 2H).

EXAMPLE 214C 2,1,3-benzothiadiazole-5-carboxaldehyde

5-Hydroxymethylbenzo-2, 1,3-thiadiazole (2.6 g, 16 mmol) and manganese dioxide (6.0 g, 64 mmol) in chloroform (150 mL) were stirred at room temperature overnight. The reaction mixture was filtered off and the filtrate was evaporated to provide 1.9 g of the title compound.
¹H NMR (CDCl₃) 8.12 (s, 2H), 8.51 (m, 1H), 10.21 (s, 1H).

EXAMPLE 214D 9-(2,1,3-benzothiadiazol-5-yl)-2,3,5,6,7,9-hexahydrothieno[3,2-b]quinolin-8(4H)-one 1,1-dioxide 2,1,3-Benzothiadiazole-5-carboxaldehyde (0.33g, 2 mmol), was processed according to the method of Example 115C to provide 0.35 g of the title compound.
¹H NMR (DMSO-d₆) δ 1.87 (m, 2H), 2.22 (m, 2H), 2.56 (m, 2H), 2.87 (m, 1H), 3.05 (m, 1H), 3.32 (m, 2H), 5.06 (s, 1H), 7.61 (dd, 1H), 7.75 (s, 1H), 7.98 (d, 1H), 9.89 (s, 1H);
MS (ES1-) m/z 372 (M-H)⁻;
Anal. Calcd for $C_{17}H_{15}N_3O_3S_2$: C, 54.68;H, 4.05; N, 11.25. Found: C, 54.43;H, 4.26; N, 11.08.

EXAMPLE 215

9-(4-bromo-3-nitrophenyl)-2,3,5,6,7,9-hexahydrothieno[3.2-b]quinolin-8(4H)-one 1,1-dioxide

EXAMPLE 215A

4-Bromo-3-nitrobenzaldehyde

4-Bromobenzaldehyde (5.0 g, 27 mmol) was slowly added to concentrated sulfuric acid (25 mL) at 0 IC followed by dropwise addition of fuiming nitric acid (1.7 mL, 40.5 mmol) in concentrated sulfuric acid (8 mL). The reaction mixture was stirred at room temperature overnight, then poured onto ice water to provide 5.7 g of the title compound.
¹H NMR (CDCl₃) 7.98 (m,2H), 8.33 (s,lH), 10.04 (s,lH).

EXAMPLE 215B 9-(4-bromo-3-nitrophenyl)-2,3,5,6,7,9-hexahydrothieno[3.2-b]quinolin-8(4H)-one 1,1-dioxide 4-Bromo-3-nitrobenzaldehyde (5.7 g, 24.6 mmol), was processed according to the method of Example 115C to provide 8.4 g of the title compound.
¹H NMR (DMSO-d₆) δ 1.87 (m, 2H), 2.21 (m, 2H), 2.53 (m, 2H), 2.85 (m, 1H), 3.02 (m, 1H), 3.35 (m, 2H), 4.92 (s, 1H), 7.42 (dd, 1H), 7.73 (dd, 1H), 7.76 (d, 1H), 9.89 (s, 1H);
MS (ES1-) m/z 439 (M-H)⁻;
Anal. Calcd for $C_{17}H_{15}N_2BrO_5S$: C, 46.48;H, 3.44; N, 6.38. Found: C, 46.50;H, 3.43; N, 6.19.

EXAMPLE 216

9-(4-ethyl-3-nitrophenyl)-2,3,5,6,7,9-hexahydrothieno[3,2-b]quinolin-8(4H)-one 1,1-dioxide 4-Ethyl-3-nitrobenzaldehyde (0.165 g, 1 mmol) (Rinkes, Recl. Trav. Chim. Pays-Bas 1945, 64, 205) was processed according to the method of Example 115C to provide 0.145 g of the title compound.
¹H NMR (DMSO-d₆) δ 1,18 (t,3H),1.88 (m, 2H), 2.25 (m, 2H), 2.53 (m, 2H),2.75 (q, 2H),2.85 (m, 1H), 3.0 (m, 1H), 4.91 (s, 1H), 7.39 (d, 1H), 7.47 (dd, 1H), 7.62 (d, 1H), 9.84 (s, 1H);
MS (ES1-) m/z 387 (M-H)⁻;
Anal. Calcd for $C_{19}H_{20}N_2O_5S$: C, 58.75;H, 5.19; N, 7.21. Found: C, 58.59;H, 5.32; N, 7.10.

EXAMPLE 217

9-[3-nitro-4-(trifluoromethoxy)phenyl]-2,3,5,6,7,9-hexahydrothieno[3.2-b]quinolin-8(4H)-one 1,1-dioxide

EXAMPLE 217A 3-nitro-4-trifluoromethoxybenzaldehyde

4-Trifluoromethoxybenzaldehyde (1.9 g, 10 mmol) was dissolved in concentrated sulfuric acid (8 mL) at 0 ° C. followed by dropwise addition of 70 % nitric acid (1,1 mL). The reaction mixture was stirred at 0 ° C. for 2 hours, then poured onto ice water and extracted with ethyl acetate. The organic layer was washed with water, aqueous sodium bicarbonate solution , dried (sodium sulfate), filtered and evaporated. The residue was chromatographed on silica gel, eluting with 20 % ethyl acetate/hexane to provide 1.55.g of the title compound.
¹H NMR (CDCl₃) 7.68 (d, 1H), 8.2 (d, 1H), 8.49 (s, 1H),10.07 (s, 1H).

EXAMPLE 217B

9-[3-nitro-4-(trifluoromethoxy)phenyl]-2,3,5,6,7,9-hexahydrothieno[3.2-b]quinolin-8(4H)-one 1,1-dioxide 3-Nitro-4-trifluoromethoxybenzaldehyde (0.35 g, 1.5 mmol), tetrahydrothiophene-3-oxo-1,1-dioxide (0.2 g, 1.5 mmol) and 3-amino-2-cyclohexene-1-one(0.17 g, 1.5 mmol) in ethanol (2 mL) were heated at reflux for 48 hours with triethylamine (0.1 mL). The reaction mixture was evaporated in vacuo and the residue was chromatographed on silica gel, eluting with 10% ethanol/methylene chloride to afford 0.4 g of the intermediate hemiaminal that was suspended in ethanol (10 mL) and heated at reflux for 2 hours with 2 mL of 1 M HCl/ether. The reaction mixture was cooled and the precipitate collected to provide 0.31 g of the title compound.
¹H NMR (DMSO-d₆) δ 1.88 (m, 2H), 2.25 (m, 2H), 2.53 (m, 2H), 2.87 (m, 1H), 3.0 (m, 1H), 3.38 (m, 2H), 4.99 (s, 1H), 7.62 (dd, 1H), 7.68 (dd, 1H), 7.89 (d, 1H), 9.91 (s, 1H);

MS (ES1-) m/z 443 (M-H)⁻;
Anal. Calcd for $C_{18}H_{15}N_2F_3O_6S$: C, 48.65;H, 3.40; N, 6.30. Found: C, 48.45;H, 3.49; N, 6.54.

EXAMPLE 218

9-[4-(difluoromethoxy)phenyyl-2,3,5,6,7,9-hexahydrothieno[3,2-b]quinolin-8(4H)-one, 1,1-dioxide 4-Difluoromethoxybenzaldehyde (0.50 g, 2.9 mmol) was processed according to the method of Example 115C to provide 0.82 g of the title compound.
mp >250;
$^1$H NMR (DMSO-d$_6$) δ 1.81–1.93 (M, 2H), 2.16–2.46 (M, 2H), 2.50–2.53 (M, 2H), 2.76-3.02 (M, 2H), 3.24–3.46 (M, 2H), 4.85 (S, 1H), 7.01 (d, 1H, J=8.45Hz), 7.17 (t, 1H, J=73.17Hz), 7.19 (m, 2H), 9.76 (s, 1H);
MS (ESI+) m/z 382 (M+H)⁺;
Anal. Calcd for $C_{18}H_{17}F_2NO_4S$: C, 56.69;H, 4.49; N, 3.67. Found: C, 56.67;H, 4.5; N, 3.59.

EXAMPLE 219

9-(3-methyl-4-nitrophenyl)-2,3,5,6,7,9-hexahydrothieno[3,2-b]quinolin-8(4H)-one 1,1-dioxide

EXAMPLE 219A 3-methyl-4-nitrobenzaldehyde

To a solution of 3-methyl-4-nitrobenzyl alcohol (3.0 g, 18 mmol), N-methylmorpholine-N-oxide (3.2 g, 27 mmol), and powdered 4A molecular sieves (8.98 g) in methylene chloride (40 mL) was added in one portion tetrapropylammonium perruthenate (0.315 g, 0.898 mmol), and the reaction stirred at room temperature. The reaction was filtered through silica gel, eluting with methylene chloride, solvent evaporated and the residue purified by flash chromatography to provide 2.2 g of the title compound.

EXAMPLE 219B 9-(3-methyl-4-nitrophenyl)-2,3,5,6,7,9-hexahydrothieno[3.2-b]quinolin-8(4H)-one 1,1-dioxide 3-Methyl-4-nitrobenzaldehyde (0.99 g, 6.0 mmol) was processed according to the method of Example 115C to provide the title compound.
mp>250;
$^1$H NMR (DMSO-d$_6$) δ 1.90 (m, 2H), 2.26 (m, 2H), 2.54 (m, 2H), 2.86 (m, 1H), 3.02 (m, 1H), 3.38 (m, 2H), 4.98 (s, 1H), 7.30 (m, 2H), 7.92 (d, 1H, J=6.0Hz)), 9.85 (s, 1H);
MS (ESI+) m/z 375 (M+H)⁺;
Anal. Calcd for $C_{18}H_{18}N_2O_5S.0.2H_2O$: C, 57.74;H, 4.85; N, 7.48. Found: C, 56.91;H, 5.07; N, 7.07.

EXAMPLE 220

9-[3-nitro-4-(trifluoromethyl)phenyl]-2,3,5,6,7,9-hexahydrothieno[3,2-b]quinolin-8(4H)-one 1,1-dioxide 20 3-Nitro-4-trifluoromethylbenzaldehyde (0.33 g, 1.5 mmol) (Clark, J. Fluorine Chem. 1990, 50, 411), tetrahydrothiophene-3-oxo-1,1-dioxide (0.2 g, 1.5 mmol) and 3-amino-2-cyclohexene-1-one(0. 17 g, 1.5 mmol) in ethanol (2 mL) were heated at reflux for 48 hours with triethylamine (0.1 mL). The reaction mixture was evaporated in vacuo and the residue was chromatographed on silica gel, eluting with 10% ethanol/methylene 25 chloride to afford 0.32 g of the intermediate hemiaminal that was suspended in ethanol (10 mL) and heated at reflux for 2 hours with 2 mL of 1M HCUether. The reaction mixture was cooled and the precipitate collected to provide 0.24 g of the title compound.
$^1$H NMR (DMSO-d$_6$) δ 1.88 (m, 2H), 2.24 (m, 2H), 2.55 (m, 2H), 2.87 (m, 1H), 3.02 (m, 1H), 3.4 (m, 2H), 5.03 (s, 1H), 7.73 (d, 1H), 7.88 (d, 1H), 7.91 (t, 1H), 9.95 (s, 1H);
MS (ES1-) m/z 427 (M-H)⁻;
Anal. Calcd for $C_{18}H_{15}N_2F_3O_5S$: C, 50.47;H, 3.53; N, 6.54. Found: C, 50.49;H, 3.51; N, 6.25.

EXAMPLE 221

9-r4-(difluoromethoxy)-3-nitrophenyl]-2,3,5,6,7,9-hexahydrothieno[3,2-b]quinolin-8(4H)-one 1,1-dioxide

EXAMPLE 221 A 4-difluoromethoxy-3-nitrobenzaldehyde 10 4-Difluoromethoxybenzaldehyde (1.7 g, 10 mmol) was dissolved in concentrated sulfuric acid (8 mL) at 0 ° C. followed by dropwise addition of 70 % nitric acid (1,1 mL).
The reaction mixture was stirred at 0 ° C. for 2 hours, then poured onto ice water and extracted with ethyl acetate.. The organic layer was washed with water, aqueous sodium bicarbonate solution , dried (sodium sulfate), filtered and evaporated. The residue was 1 5 chromatographed on silica gel, eluting with 25 % ethyl acetate/hexane to provide 1,1 g of the title compound.
$^1$H NMR (CDCl$_3$) δ 6.71 (t, 1H), 7.59 (d, 1H), 8.15 (dd, 1H), 8.41 (s, 1H), 10.04 (s, 1H).

EXAMPLE 221 B

9-[4-(difluoromethoxy)-3-nitrophenyl]-2,3,5,6,7,9-hexahydrothieno[3,2-b]quinolin-8(4H)-one 1,1-dioxide 4-Difluoromethoxy-3-nitrobenzaldehyde (0.32 g, 1.5 mmol), tetrahydrothiophene-3-oxo-1,1-dioxide (0.2 g, 1.5 mmol) and 3-amino-2-cyclohexene-1-one(0.17 g, 1.5 mmol) in ethanol (2 mL) were heated at reflux for 48 hrs with triethylamine (0.1 mL). The 25 reaction mixture was evaporated in vacuo and the residue was chromatographed on silica gel, eluting with 10% ethanol/methylene chloride to afford 0.4 g of the intermediate hemiaminal that was suspended in ethanol (10 mL) and heated at reflux for 2 hours with 2 mL of 1M HCl ether. The reaction mixture was cooled and the precipite collected to provide 0.19 g of the title compound.
$^1$H NMR (DMSO-d$_6$) δ 1.89 (m, 2H), 2.23 (m, 2H), 2.53 (m, 2H), 2.85 (m, 1H), 3.02 (m, 1H), 3.37 (m, 2H), 4.96 (s, 1H), 7.32 (t, 1H), 7.39 (d, 1H), 7.59 (dd, 1H), 7.78 (d, 1H), 9.9 (s, 1H);
MS (ES1-) m/z 425 (M-H)⁻;
Anal. Calcd for $C_{,,}H_{16}N_2F_2O_6S$: C, 50.70;H, 3.75; N, 6.57. Found: C, 50.54;H, 3.74; N, 6.48.

EXAMPLE 222

9-(4-chloro-3-methylphenyl)-2,3,5,6,7,9-hexahydrothieno[3,2-b]quinolin-8(4H)-one 1,1-dioxide 4-Chloro-3-methylbenzaldehyde (0.93 g, 6.0 mmol) (Khanna J. Med. Chem. 1997, 40, 1634) was processed according to the method of Example 115C to provide the title compound.
mp >250;
$^1$H NMR (DMSO-$d_6$) δ 1.90 (m, 2H), 2.26 (m, 2H), 2.29 (s, 3H), 2.51 (m, 2H), 2.86 (m, 1H), 3.02 (m, 1H), 3.38 (m, 2H), 4.80 (s, 1H), 7.00 (dd, 1H, J=3; 7.5Hz), 7.12 (d, 1H, J=3.0Hz), 7.26 (d, 1H, J=9Hz), 9.75 (s, 1H);
MS (ESI+) m/z 364 (M+H)$^+$;
Anal. Calcd for $C_{18}H_{18}ClNO_3S$: C, 59.42;H, 4.99; N, 3.85. Found: C, 59.04;H, 5.14; N, 3.71.

EXAMPLE 223

9-(3-bromo-4-methylphenyl)-2,3,5,6,7,9-hexahydrothieno[3.2-b]quinolin-8(4H)-one 1,1-dioxide 3-Bromo-4-methylbenzaldehyde (0.70 g, 3.5 mmol) (Pearson.; Org. Synth. Coll. Vol. V, 1973, 117), was processed according to the method of Example 115C to provide 0.87 g of the title compound.
$^1$H NMR (DMSO-$d_6$) δ 1.76–1.94 (m, 2H), 2.17–2.24 (m, 2H), 2.26 (s, 3H), 2.49–2.57 (m, 2H), 2.78–2.85 (m, 1H), 2.98–3.04 (m, 1H), 3.25–3.35 (m, 2H), 4.80 (s, 1H), 7.07 (dd, 1H, J=8.0, 1.5Hz), 7.19 (d, 1H, J=8.0Hz), 7.30 (d, 1H, J=1.5Hz);
MS (ESI+) m/z 410, 408 (M+H)$^+$;
Anal. Calcd for $C_{18}H_{18}BrNO_3S0.25H_2O$: C, 52.37;H, 4.52; N, 3.39. Found: C, 52.29; H, 4.34; N, 3.03.

EXAMPLE 224

9-(3-bromo-4-methylphenyl)-2,3,5,6,7,9-hexahydrothieno[3.2-b]quinolin-8(4H)-one 1,1-dioxide The product from Example 223 (600 mg) was chromatographed on a 2×25 cm Regis Whelk-O1 column, eluting with hexane:methanol:methylene chloride (65:24:11) as the mobile phase at a flow rate of 10 mL/min to provide 250 mg of the less polar enantiomer as a white solid.
$^1$H NMR (DMSO-$d_6$) δ 1.76–1.94 (m, 2H), 2.17–2.24 (m, 2H), 2.26 (s, 3H), 2.49–2.57 (m, 2H), 2.78–2.85 (m, 1H), 2.98–3.04 (m, 1H), 3.25–3.35 (m, 2H), 4.80 (s, 1H), 7.07 (dd, 1H, J=8.0, 1.5Hz), 7.19 (d, 1H, J=8.0Hz), 7.30 (d, 1H, J=1.5Hz);
MS (ESI+) m/z 410, 408 (M+H)$^+$;
Anal. Calcd for $C_{18}H_{18}BrNO_3S0.75H_2O$: C, 51.25;H, 4.66; N, 3.32. Found: C, 51.22; H, 4.63; N, 3.29.

EXAMPLE 225

9-(3-bromo-4-methylphenyl)-2,3,5,6,7,9-hexahydrothieno[3,2-b]quinolin-8(4H)-one 1,1-dioxide The product from Example 223 (600 mg) was chromatographed on a 2×25 cm Regis Whelk-O1 column, eluting with hexane:methanol:methylene chloride (65:24:11) as the mobile phase at a flow rate of 10 mL/min to provide 230 mg of the more polar enantiomer as a white solid.
$^1$H NMR (DMSO-$d_6$) δ 1.76–1.94 (m, 2H), 2.17–2.24 (m, 2H), 2.26 (s, 3H), 2.49–2.57 (m, 2H), 2.78–2.85 (m, 1H), 2.98–3.04 (m, 1H), 3.25–3.35 (m, 2H), 4.80 (s, 1H), 7.07 (dd, 1H, J=8.0, 1.5Hz), 7.19 (d, 1H, J=8.0Hz), 7.30 (d, 1H, J=1.5Hz);
MS (ESI+) m/z 410,408 (M+H)$^+$;
Anal. Calcd for $C_{18}H_{18}BrNO_3S0.25H_2O$: C, 52.37;H, 4.52; N, 3.39. Found: C, 52.05; H, 4.43; N, 3.03.

EXAMPLE 226

9-[4-methyl-3-(methylsulfanyl)phenyl]-2,3,5,6,7,9-hexahydrothieno[3,2-b]quinolin-8(4H)-one 1l1-dioxide

EXAMPLE 226A

2-(3-bromo-4-methyl]phenyl)-1.3-dioxolane

To a solution of 3-bromo-4-methylbenzaldehyde (10.0 g, 50.5 mmol) in benzene (100 mL) was added ethylene glycol (10 mL) and p-toluenesulfonic acid (0.05 g). The reaction was heated at reflux for 4 hours and water was removed as an azeotrope with benzene using a Dean-Stark appartus. The reaction was cooled to room temperature, diluted with ethyl acetate (100 mL), and quenched with aqueous sodium bicarbonate. The organic layer was dried ($Na_2SO_4$), filtered and concentrated to provide 11.5 g of the title compound as an oil.
$^1$H NMR (DMSO-$d_6$) 8 2.35 (s, 3H), 3.91–4.07 (m, 4H), 5.71 (s, 1H), 7.32–7.39 (m, 2H), 7.60 (d, J=1.5Hz, 1H).

EXAMPLE 226B

2-[4-methyl-3-(methylsulfanyl)phenyl]-1.3-dioxolane

To a solution of the product from Example 226A (6.95 g, 28.7 mmol) in dry tetrahydrofuiran (100 mL) at -78 ° C. was added n-butyl]ithium (19.7 mL of 1.6 M, 31.5 mmol) and the reaction stirred for 30 minutes at -78 ° C. at which point a solution of dimethyldisulfide (4.05 g, 43.0 mmol) in tetrahydrofuran (10 mL) was added dropwise over 10 minutes. The reaction was allowed to stir at -78 ° C. for 30 minutes and then warmed to room temperature, quenched with saturated aqueous sodium bicarbonate, and extracted with ethyl acetate (2 x 50 mL). The organic layer was dried ($Na_2SO_4$), filitered and concentrated to provide 5.0 g of the title compound.
$^1$H NMR (DMSO-$d_6$) o 2.24 (s, 3H), 2.46 (s, 3H), 3.91–4.07 (m, 4H), 5.70 (s, 1H), 7.12 (dd, J=7.8, 1.5Hz, 1H), 7.20 (d, J=7.8Hz, 1H), 7.22 (d, J=1.5Hz, 1H).

EXAMPLE 226C

4-methyl-3-(methylsulfanyl)benzaldehyde

To a solution of the product from Example 226B (1.4 g, 6.7 mmol) in acetonitrile (50 mL) was added 2.OM HCI (50 mL) and the reaction mixture was allowed to stir for 2 hours at room temperature. The reaction mixture was poured onto a mixture of ice and saturated aqueous sodium bicarbonate, diluted with ethyl acetate, and the layers were separated. The organic layer was dried ($Na_2SO_4$), concentrated, and purified by flash chromatography (hexanes/ethyl acetate 5:1) to provide 1,1 g of the title compound.
$^1$H NMR (DMSO-$d_6$) δ 2.32 (s, 3H), 2.55 (s, 3H), 7.42 (d, J=7.8Hz, 1H), 7.60 (dd, J=7.8, 1.5Hz, 1H), 7.70 (d, J=1.5Hz, 1H), 9.98 (s, 1H).

EXAMPLE 226D

9-[4-methyl-3-(methylsulfanyl)phenyl]-2,3,5,6,7,9-hexahydrothieno[3,2-b]quinolin-8(4H)-one I1.-dioxide The product from Example 226C (0.77 g, 4.64 mmol) was processed according to the method of Example 115C to provide 0.725 g of the title compound.

¹H NMR (DMSO-d₆) δ 1.78–1.96 (m, 2H), 2.13 (s, 3H), 2.19–2.25 (m, 2H), 2.39 (s, 3H), 2.48–2.55 (m, 2H), 2.75–2.85 (m, 1H), 2.94–3.04 (m, 1H), 3.25–3.38 (m, 2H), 4.84 (s, 1H), 6.82 (dd, 1H, J=7.5,2.0Hz), 7.00 (d, 1H, J=2.0Hz), 7.01 (d, 1H, J=7.5Hz), 9.71 (s, 1H);
MS (ESI+) m/z 376 (M+H)⁺;
Anal. Calcd for $C_{19}H_{21}NO_3S_2 \cdot 0.2H_2O$: C, 60.20;H, 5.69; N, 3.69. Found: C, 59.87;H, 5.79; N, 3.59.

EXAMPLE 227

9-(4-chloro-3-fluorophenyl)-2,3,5,6,7,9-hexahydrothieno[3,2-b]quinolin-8(4H)-one 1,1-dioxide The product from Example 210 was chromatographed on a 2×25 cm Regis Whelk-O1 column, eluting with hexane:methanol:methylene chloride (60:27:13) as the mobile phase at a flow rate of 10 mL/min to provide the less polar enantiomer.
mp >250;
¹H NMR (DMSO-d₆) δ 1.90 (m, 2H), 2.26 (m, 2H), 2.54 (m, 2H), 2.86 (m, 1H), 3.02 (m, 1H), 3.38 (m, 2H), 4.86 (s, 1H), 7.05 (dd, 1H, J=1.5,9.0Hz), 7.14 (dd, 1H, J=1.5;9.0Hz), 7.48 (t, 1H, J=9.0Hz), 9.85 (s, 1H);
MS (ESI+) m/z 368 (M+H)⁺;
Anal. Calcd for $C_{17}H_{15}ClFNO_3S$: C, 55.51;H, 4.11; N, 3.81. Found: C, 55.28;H, 4.13; N, 3.71.

EXAMPLE 228

9-[4-methyl-3-(methylsulfonyl)phenyl]-2,3,5,6,7,9-hexahydrothieno[3,2-b]quinolin-8(4H)-one 1,1-dioxide

EXAMPLE 228A 4-methyl-3-(methylsulfonyl)benzaldehyde

To a solution of the product from Example 226B (3.6 g, 17.1 mmol) in methylene chloride (100 mL) at 0 °C. was added m-chlorobenzoic acid (11.81 g, 68.4 mmol) and the reaction stirred for 30 minutes at 0 °C. The reaction was quenched with saturated aqueous sodium bicarbonate, and the organic layer was dried (Na₂SO₄), filtered and concentrated to provide 3.8 g of the sulfone.

To a solution of the above sulfone (3.8 g, 15.7 mmol) in acetonitrile (50 mL) was added 2.0M HCl (50 mL) and the reaction mixture was allowed to stir for 2 hours at room temperature. The reaction mixture was poured onto a mixture of ice and saturated aqueous sodium bicarbonate, diluted with ethyl acetate, and the layers were separated. The organic layer was dried (Na₂SO₄), filtered, concentrated, and purified by flash chromatography (hexanes/ethyl acetate 2:1) to provide 2.2 g of the title compound.
¹H NMR (DMSO-d₆) δ 2.75 (s, 3H), 3.30 (s, 3H), 7.72 (d, J=7.8Hz, 1H), 8.13 (dd, J=7.8, 1.7Hz, 1H), 8.41 (d, J=1.7Hz, 1H), 10.07 (s, 1H).

EXAMPLE 228B

9-[4-methyl-3-(methylsulfonyl)phenyl]-2,3,5,6,7,9-hexahydrothieno[3.2-b]quinolin-8(4H)-one 1,1-dioxide A solution of the product from Example 228A (0.80 g, 4.04 mmol), was processed according to the method of Example 115C to provide 0.425 g of the title compound as a white solid.
¹H NMR (DMSO-d₆) δ 1.83–1.99 (m, 2H), 2.16–2.26 (m, 2H), 2.50–2.60 (m, 2H), 2.56 (s, 3H), 2.78–2.88 (m, 1H), 2.94–3.04 (m, 1H), 3.13 (s, 3H), 3.29–3.39 (m, 2H), 4.90 (s, 1H), 7.32 (d, 1H, J=7.8Hz), 7.39 (dd, 1H, J=7.8, 2.0Hz), 7.73 (d, 1H, J=2.0Hz), 9.81 (s, 1H);
MS (ESI+) m/z 408 (M+H)⁺;
Anal. Calcd for $C_{19}H_{21}NO_5S_2 \cdot H_2O$: C, 53.63;H, 5.45; N, 3.29. Found: C, 53.45;H, 5.21; N, 3.03.

EXAMPLE 229

(−)-9-(3-bromo-4-fluorophenyl)-5,5-dimethyl-2,3,5,6,7,9-hexahydrothieno[32-b]quinolin-8(4H)-one 1,1-dioxide The product from Example 212 was chromatographed on a (R₁R)-Whelk-O1 column (2.1 cm x 25 cm), gradient elution 3% MeOH-CH₂Cl₂ (2:1)/hexanes to 25% MeOH-CH₂Cl₂ (2:1)/hexanes, retention time 49 minuntes. [a]D23 −19.90 (c 0.6, DMSO);
mp >270 °C.;
¹H NMR (DMSO-d₆) δ 0.89 (s, 3H), 0.98 (s, 3H), 1.75 (t, 2H, J=6.1Hz), 2.50–2.64 (m, 2H), 2.68–3.07 (m, 3H), 3.29–3.41 (m, 1H), 4.80 (s, 1H), 7.13–7.32 (m, 2H), 7.38 (dd, 1H, J=6.7, 2.0Hz), 9.69 (br s, 1H);
MS (DCIINH₃) m/z 457 (M+NH₄)⁺;
Anal. Calcd for $C_9H_9BrFNO_3S$: C, 51.83;H, 4.35; N, 3.18. Found: C, 51.58;H, 4.09; N, 3.25.

EXAMPLE 230

(+)-9-(3-bromo-4-fluorolphenyl)-5.5-dimethyl-2,3,5,6,7,9-hexahydrothieno[3.2-b]quinolin-8(4H)-one 1,1-dioxide The product from Example 212 was chromatographed on a (R₁R)-Whelk-O1 column (2.1 cm x 25 cm), gradient elution 3% MeOH-CH₂Cl₂ (2:1)/hexanes to 25% MeOH-CH₂Cl₂ (2:1)/hexanes, retention time =53 minutes. [a]D23 +17.60 (c 0.4, DMSO);
mp >270 °C.;
¹H NMR (DMSO-d₆) δ 0.89 (s, 3H), 0.98 (s, 3H), 1.75 (t, 2H, J=6.1Hz), 2.50–2.64 (m, 2H), 2.68–3.07 (m, 3H), 3.29–3.41 (m, 1H), 4.80 (s, 1H), 7.13–7.32 (m, 2H), 7.38 (dd, 1H, J=6.7, 2.0Hz), 9.69 (br s, 1H);
MS (DCIINH₃) m/z 457 (M+NH₄)⁺;
Anal. Calcd for $C_{19}H_{19}BrFNO_3S$: C, 51.83;H, 4.35; N, 3.18. Found: C, 51.68;H, 4.14; N, 3.34.

EXAMPLE 231

(−)-9-(3-bromo-4-fluoroiphenyl)-7,7-dimethyl-2,3,5,6,7,9-hexahydrothieno[3.2-b]quinolin-8(4H)-one, 1,1-dioxide The product from Example 116 was chromatographed on a (R₁R)-Whelk-O 1 column (2.1 cm x 25 cm), gradient elution 3% MeOH-CH₂Cl₂ (2:1)/hexanes to 25% MeOH-CH₂Cl₂ (2:1)/hexanes, retention time =41 minutes. [a]D23 −21.60 (c 0.5, DMSO);
mp >270 °C.;
¹H NMR (DMSO-d₆) δ 1.30 (s, 3H), 1.34 (s, 3H), 1.83–1.92 (m, 2H), 2.14–2.21 (m, 1H), 2.36–2.45 (m 1H), 2.89–2.97 (m, 1H), 3.03–3.11 (m, 1H), 3.29–3.44 (m, 2H), 4.85 (s, 1H), 7.13–7.26 (m, 2H), 7.35–7.39 (m, 1H), 9.40 (br s, 1H); ¹³C NMR (DMSO-d₆) δ 199.2,157.9,155.5, 151.4, 144.4,143.3, 142.2,132.6,128.7, 116.2, 113.0, 107.1, 48.8, 33.9, 33,4, 24.7, 24.1, 23.4, 22.8;
MS (DCIINH₃) m/z 457 (M+NH₄)⁺;

Anal. Calcd for $C_{19}H_{19}BrFNO_3S$: C, 51.83;H, 4.35; N, 3.18. Found: C, 51.71;H, 4.20; N, 3.22.

EXAMPLE 232

(+)-9-(3-bromo-4-fluorophenyl)-7,7-dimethyl-2,3,5,6,7,9-hexahydrothieno[32-b]quinolin-8(4H)-one, 1,1-dioxide The product from Example 116 was chromatographed on a ($R_1R$)-Whelk-O1 column (2.1 cm x 25 cm), gradient elution 3% MeOH-$CH_2Cl_2$ (2:1 )/hexanes to 25% MeOH-$CH_2Cl_2$ (2: 1)/hexanes, retention time 47 minutes. D23 +30.50 (c 0.6, DMSO)
mp >270 C;
$^1$H NMR (DMSO-$d_6$) δ 1.30 (s, 3H), 1.34 (s, 3H), 1.83–1.92 (m, 2H), 2.14–2.21 (m, 1H), 2.36–2.45 (m 1H), 2.89–2.97 (m, 1H), 3.03–3.11 (m, 1H), 3.29–3.44 (m, 2H), 4.85 (s, 1H), 7.13–7.26 (m, 2H), 7.35–7.39 (m, 1H), 9.40 (br s, 1H);
MS (DCI/$NH_3$) m/z 457 $(M+NH_4)^+$;
Anal. Calcd for $C_{19}H_{19}BrFNO_3S$: C, 51.83;H, 4.35; N, 3.18. Found: C, 51.92;H, 4.26; N, 3.30.

EXAMPLE 233

9-(4-bromo-3-nitrophenyl)-2,3,5,6,7,9-hexahydrothienof3,2-b]quinolin-8(4H)-one 1,1-dioxide The product from Example 215 (1.48 g) was chromatographed on a Regis Whelk-O1 chiral column eluting with hexane:methanol:methylene chloride (20:54:27) to provide 0.64 g of the title compound as the more polar enantiomer.
$^1$H NMR (DMSO-$d_6$) δ 1.89 (m, 2H), 2.22 (m, 2H), 2.53 (m, 2H), 2.85 (m, 1H), 3.0 (m, 1H), 3.35 (m, 2H), 4.92 (s, 1H), 7.42 (dd, 1H), 7.75 (m, 2H), 9.89 (s, 1H);
MS (ESI) m/z 437 $(M-H)^-$;
Anal. Calcd for $C_{17}H_{15}N_2BrO_5S$: C, 46.48;H, 3.44; N, 6.38. Found: C, 46.09;H, 3.61; N, 6.18.

EXAMPLE 234

9-(4-bromo-3-nitrophenyl)-2,3,5,6,7,9-hexahydrothieno[3,2-b]quinolin-8(4H)-one 1,1-dioxide The product from Example 215 (1.48 g) was chromatographed on a Regis Whelk-O1 chiral column eluting with hexane:methanol:methylene chloride (20:54:27) to provide 0.64 g of the title compound as the less polar enantiomer.
$^1$H NMR (DMSO-$d_6$) 8 1.89 (m, 2H), 2.22 (m, 2H), 2.53 (m, 2H), 2.85 (m, 1H), 3.0 (m, 1H), 3.35 (m, 2H), 4.92 (s, 1H), 7.42 (dd, 1H), 7.75 (m, 2H), 9.89 (s, 1H);
MS (ESI) m/z 437 $(M-H)^-$;
Anal. Calcd for $C_{17}H_{15}N_2BrO_5S$: C, 46.48;H, 3.44; N, 6.38. Found: C, 46.09;H, 3.61; N, 6.18.

EXAMPLE 235

9-(3-iodo-4-methylphenyl)-2,3,5,6,7,9-hexahydrothieno[3.2-b]quinolin-8(4H)-one 1,1-dioxide

EXAMPLE 235 A 3-iodo-4-methylbenzaldehyde

To a slurry of 3-iodo-4-methylbenzoic acid (1.0 g,3.96 mmol) in 200ml of dry $CH_2Cl_2$-THF (1:1) was added oxalyl chloride (1 ml, 11.9 mmol) and several drops of DMF. This mixture was heated at 65° C. for 30 min, cooled to room temperature, and concentrated to form light yellow solids. The solids were dissolved in 200ml of THF and cooled to -78° C. A solution of lithium tri-tert-butoxyaluminohydride (4.1 ml, 4.1 mmol) was syringed into the reaction mixture. After 30 minutes at -78 ° C., a solution of saturated Rochelle's salt was added to quench the reaction at -78 ° C. The mixture was allowed to warm to ambient temperature and the layers separated. The organic layer was washed with IN HCl, sat $NaHCO_3$ and brine, dried ($Na_2SO_4$), concentrated and the resulting residue was purified by flash chromatography using hexane/EtOAc (4:1) as eluent to yield the title compound as a white solid (300 mg, 18%).

EXAMPLE 235 B 9-(3-iodo-4-methylphenyl)-2,3,5,6,7,9-hexahydrothieno [3,2-b]quinolin-8(4H)-one 1,1-dioxide To a slurry of the product from Example 235 A (300 mg, 1.63 mmol) in 8ml of ethanol was added 3-amino-2-cyclohexen-1-one (199 mg, 1.79 mmol), dihydro-3(2H)-thiophenone 1,1-dioxide (240mg, 1.79 mmol) and a drop of triethylamine. This mixture was heated in an oil bath at 110 IC in a sealed high pressure tube over night, cooled to ambient temperature, and concentrated. A solution of ethanol (5 mL) and 1M HCIVEt$_2$O (1 mL) was added and the resulting mixture was heated at 110 OC in a sealed pressure tube for 1 hour, cooled to room temperature, and filtered to provide the title compound as a white solid (314mg, 43%).
$^1$H NMR (DMSO-$d_6$) δ 1.75–1.94 (m, 4H), 2.20–2.24 (m, 2H), 2.28 (s, 3H), 2.83–2.86 (m, H), 2.96–3.06 (m, 1H), 3.2–3.5 (m, 2H), 4.76 (s, 1H), 7.08 (dd, 1H, J=7.67, 1.47Hz), 7.17 (d, 7.67H), 7.56 (d, 1.47H), 9.76 (s, 1H);
MS (ES1-) m/z 454 $(M-H)^-$;
Anal. Calcd for $C_{18}H_{18}1NO_3S$: C, 47.48;H, 3.98; N, 3.08. Found: C, 47.46;H, 3.90; N, 20 2.99.

EXAMPLE 236

9-[3-nitro-4-(trifluoromethyl)phenyyl-2,3,5,6,7,9-hexahydrothieno[3,2-b]quinolin-8(4H)-one 1,1-dioxide The product from Example 220 (0.16 g) was chromatographed on a Regis Whelk-O1 chiral column eluting with hexane:methanol:methylene chloride (40:40:20) to provide 0.05 g of the title compound as the less polar enantiomer.
$^1$H NMR (DMSO-$d_6$) δ 1.9 (m, 2H), 2.23 (m, 2H), 2.55 (m, 2H), 2.88 (m, 1H), 3.0 (m, 1H), 3.35 (m, 2H), 5.02 (s, 1H), 7.72 (d, 1H), 7.9 (m, 2H), 9.95 (S, 1H);
MS (ESI) m/z 427 $(M-H)^-$;
Anal. Calcd for $C_{18}H_{18}N_2F_3O_5S$: C, 50.47;H, 3.53; N, 6.54. Found: C, 50.81;H, 3.59; N, 6.25.

EXAMPLE 237

9-[3-nitro-4-(trifluoromethyl)phenyl]-2,3,5,6,7,9-hexahydrothieno[3,2-biquinolin-8(4H)-one 1,1-dioxide The product from Example 220 (0.16 g) was chromatographed on a Regis Whelk-O1 chiral column eluting with hexane:methanol:methylene chloride (40:40:20) to provide 0.06 g of the title compound as the more polar enantiomer. 10
$^1$H NMR (DMSO-$d_6$) δ 1.9 (m, 2H), 2.23 (m, 2H), 2.55 (m, 2H), 2.88 (m, 1H), 3.0 (m, 1H), 3.35 (m, 2H), 5.02 (s, 1H), 7.72 (d, 1H), 7.9 (m, 2H), 9.95 (S, lH);

MS (ESI) m/z 427 (M-H);
Anal. Calcd for $C_{18}H_{18}N_2F_3O_5S$: C, 50.47;H, 3.53; N, 6.54. Found: C, 50.65;H, 3.45; N, 6.22.

EXAMPLE 238

9-(2,13-benzothiadiazol-5-yl)-2,3,5,6,7,9-hexahydrothieno[3.2-b]quinolin-8(4H)-one, 1,1-dioxide The product from Example 214 (0.14 g) was chromatographed on a Regis Whelk-O1 chiral column eluting with hexane:methanol:methylene chloride (65:24:11) to provide 0.06 g of the title compound as the less polar enantiomer.
$^1$H NMR (DMSO-$d_6$) δ 1.9 (m, 2H), 2.22 (m, 2H), 2.48 (m, 2H), 2.88 (m, 1H), 3.04 (m, 1H), 5.05 (s, 1H), 7.61 (dd, 1H), 7.75 (s, 1H), 7.98 (d, 1H), 9.9 (s, 1H);
MS (ESI) m/z 372 (M-H)$^-$;
Anal. Calcd for $C_{17}H_{15}N_3O_3S_2$: C, 54.68;H, 4.05; N, 11.25. Found: C, 54.24;H. 3.89; N, 10.81.

EXAMPLE 239

9-(2 1,3-benzothiadiazol-5-yl)-2,3,5,6,7,9-hexahydrothieno[3,2-b]quinolin-8(4H)-one 1,1-dioxide The product from Example 214 (0.14 g) was chromatographed on a Regis Whelk-O1 chiral column eluting with hexane:methanol:methylene chloride (65:24:11) to provide 0.06 g of the title compound as the more polar enantiomer.
$^1$H NMR (DMSO-$d_6$) δ 1.9 (m, 2H), 2.22 (m, 2H), 2.48 (m, 2H), 2.88 (m, 1H), 3.04 (m, 1H), 5.05 (s, 1H), 7.61 (dd, 1H), 7.75 (s, 1H), 7.98 (d, 1H), 9.9 (s, 1H);
MS (ESI) m/z 372 (M-H)$^-$;
Anal. Calcd for $C_{18}H_{15}N_3O_3S_2$: C, 54.68;H, 4.05; N, 11.25. Found: C, 54.24;H, 3.89; N, 11.05.

EXAMPLE 240

9-(3-iodo-4-methylphenyl)-2,3,5,6,7,9-hexahydrothieno[3,2-b]quinolin-8(4H)-one 1,1-dioxide The product from Example 235 was chromatographed on a Regis Whelk-O1 chiral column eluting with hexane:methanol:methylene chloride (50:34:16) to provide the title compound as the less polar enantiomer.
$^1$H NMR (DMSO-$d_6$) δ 1.75–1.94 (m, 4H), 2.20–2.24 (m, 2H), 2.28 (s, 3H), 2.83–2.86 (m, 1H), 2.96–3.06 (m, 1H), 3.2–3.5 (m, 2H), 4.76 (s, 1H), 7.08 (dd, 1H, J=7.67, 1.47Hz), 7.17 (d, 7.67H), 7.56 (d, 1.47H), 9.76 (s, 1H);
MS (ES1-) n/z 454 (M-H)$^-$;
Anal. Calcd for $C_{18}H_{18}NO_3S$: C, 47.48;H, 3.98; N, 3.08. Found: C, 46.62;H, 4.09; N, 2.79.

EXAMPLE 241

9-(3-iodo-4-methylphenyl)-2,3,5,6,7,9-hexahydrothieno[3,2-b]quinolin-8(4H)-one 1,1-dioxide The product from Example 235 was chromatographed on a Regis Whelk-O1 chiral column eluting with hexane:methanol:methylene chloride (50:34:16) to provide the title compound as the more polar enantiomer.
$^1$H NMR (DMSO-$d_6$) 8 1.75–1.94 (m, 4H), 2.20–2.24 (m, 2H), 2.28 (s, 3H), 2.83–2.86 (m, 1H), 2.96–3.06 (m, 1H), 3.2–3.5 (m, 2H), 4.76 (s, 1H), 7.08 (dd, 1H, J=7.67, 1.47Hz), 7.17 (d, 7.67H), 7.56 (d, 1.47H), 9.76 (s, 1H);
MS (ES1-) m/z 454 (M-H);
Anal. Calcd for $C,H_{118}INO_3S$: C, 47.48;H, 3.98; N, 3.08. Found: C, 46.44;H, 4.14; N, .2.69.

Determination of Potassium Channel Opening Activity
Membrane Hyperpolarization Assays Compounds were evaluated for potassium channel opening activity using the rat thoracic aorta smooth muscle AI 0 cell line or primary cultured quinea-pig urinary bladder (GPB) cells.

The AI0 cell line was purchased from the American Type Culture Collection (Rockville, MD; Cat # 30–2002). Cells were grown in 96-well clear-bottomed black plates (Packard) in culture media (composition: Dulbecco's modified Eagle's medium supplemented with 20% Fetal Bovine Serum, 100 units/mL penicillin, 100 units/mL streptomycin and 0.25 mg/mL amphotericin B) at 37 ° C. with 5% C02 in a humidified chamber to form a confluent monolayer. 25 For the preparation of urinary bladder smooth muscle cells, urinary bladders were removed from male quinea-pigs (Hartley, Charles River, Wilmington, MA) weighing 300-400 g and placed in ice-cold $Ca^{2+}$-free Krebs solution (Composition, mM: KCl, 2.7; KH2PO4, 1.5; NaCl, 75; Na2HPO4, 9.6; Na2HPO4.7H2O, 8; MgSO4, 2; glucose, 5;HEPES, 10; pH 7.4). Cells were isolated by enzymatic dissociation as previously escribed with minor modifications (Klockner, U. and Isenberg, G., Pflugers Arch. 1985, 05, 329–339). The bladder was cut into small sections and incubated in 5 mL of the reb's solution containing I mg/mL collagenase (Sigma, St. Louis, MO) and 0.2 mg/mL ronase (Calbiochem, La Jolla, CA) with continuous stirring in a cell incubator for 30 minutes. The mixture was then centrifuged at 1300 x g for 5 minutes, and the pellet resuspended in Dulbecco's PBS (GIBCO, Gaithersburg, MD) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, TX). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% C02 until confluent. Cells were confirmed to be of smooth muscle type by cytoskeletal staining using a monoclonal mouse anti human-a-smooth muscle actin (Biomeda, Foster City, CA).

Functional activity at potassium channels was measured by evaluating changes in membrane potential using the bis-oxonol dye DiBAC(4)3 (Molecular Probes) in a 96-well cell-based kinetic assay system, Fluorescent Imaging Plate Reader (FLIPR) (K.S. Schroeder et al., J. Biomed. Screen., v. I pp. 75–81 (1996)). DiBAC(4)3 is an anionic potentiometric probe which partitions between cells and extracellular solution in a membrane potential-dependent manner. With increasing membrane potential (for example, K+depolarization), the probe further partitions into the cell; this is measured as an increase in fluorescence due to dye interaction with intracellular lipids and proteins.

Conyersely, decreasing membrane potential (hyperpolarization by potassium channel openers) evokes a decrease in fluorescence.

Confluent smooth muscle A10 or quinea-pig urinary bladder cells cultured in black clear-bottomed 96-well plates were rinsed twice with 200 mL assay buffer (composition, mM: HEPES, 20; NaCl, 120; KCl, 2; $CaC'_2$, 2; $MgCl_2$, 1;

glucose, 5; pH 7.4 at 25 ° C.) containing 5 lM DiBAC(4)$_3$ and incubated with 180 mL of the buffer in a cell incubator for 30 minutes at 37 OC to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 AM of the reference compound P1075 (assigned as 100%), a potent opener of smooth muscle KATP channels (Quast et al., Mol. Pharmacol., v. 43 pp. 474–481 (1993)).

Routinely, five concentrations of P1075 or test compounds (log or half-log dilutions) were evaluated and the maximal steady-state hyperpolarization values (expressed as % relative to P1075) plotted as a function of concentration. The EC$_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in A10 and Guinea-Pig Bladder (GPB) Cells

| Example # | MHP in A10 Cells | | MHP in GPB Cells | |
|---|---|---|---|---|
| | Maximal Response (% P1075) | EC50 ($\mu$M) | Maximal Response (% P1075) | EC50 ($\mu$M) |
| 1 | 93 | 2.1 | 80 | 1.4 |
| 2 | 73 | 0.70 | 77 | 2.1 |
| 3 | 90 | 1.6 | 110 | 1.3 |
| 4 | 110 | 0.50 | 120 | 0.38 |
| 5 | 78 | 5.5 | 41 | 18 |
| 6 | 48 | 12 | 31 | 17 |
| 7 | 94 | 4.8 | 100 | 2.8 |
| 8 | 66 | 7.5 | 100 | 2.5 |
| 9 | 39 | 16 | 67 | 7.2 |
| 10 | 61 | 4.5 | 100 | 15 |
| 11 | 42 | 11 | 29 | 20 |
| 12 | 34 | >10 | 16 | >10 |
| 13 | 110 | 2.0 | 100 | 1.6 |
| 14 | 83 | 5.2 | 100 | 1.8 |
| 15 | 74 | 5.7 | 95 | 2.0 |
| 16 | 83 | 6.3 | 47 | 3.5 |
| 17 | 79 | 4.2 | 73 | 5.1 |
| 18 | 64 | 7.6 | 66 | 1.4 |
| 19 | 100 | 0.39 | 120 | 0.43 |
| 20 | 52 | 10 | 76 | 3.0 |
| 21 | 33 | >10 | 15 | >10 |
| 22 | 15 | >10 | 71 | 3.6 |
| 23 | 49 | 3.6 | 91 | 3.0 |
| 24 | 76 | 3.9 | 100 | 1.4 |
| 25 | 90 | 1.8 | 110 | 0.84 |
| 26 | 42 | 4.4 | 93 | 3.2 |
| 27 | 40 | 3.7 | 75 | 3.0 |
| 28 | 42 | 3.6 | 78 | 2.9 |
| 29 | 110 | 0.24 | 120 | 0.46 |
| 30 | 91 | 3.8 | 97 | 2.3 |
| 31 | 100 | 0.27 | 100 | 0.16 |
| 32 | 100 | 0.64 | 110 | 0.44 |
| 33 | 100 | 3.0 | 100 | 2.0 |
| 34 | 97 | 0.28 | 110 | 0.53 |
| 35 | 93 | 2.4 | 91 | 1.1 |
| 36 | 96 | 1.7 | 110 | 0.48 |
| 37 | 100 | 0.15 | 110 | 0.20 |
| 38 | 100 | 0.51 | 140 | 0.44 |
| 39 | 120 | 0.35 | 120 | 0.17 |
| 40 | 120 | 0.23 | 130 | 0.15 |
| 41 | 120 | 1.0 | 120 | 0.62 |
| 42 | 57 | 3.7 | 69 | 3.9 |
| 43 | | | 111 | 0.049 |
| 44 | 100 | 0.28 | 120 | 0.15 |
| 45 | 77 | 3.8 | 92 | 2.4 |
| 48 | | | 100 | 0.13 |
| 49 | | | 92 | 0.56 |
| 50 | | | 87 | 1.4 |
| 51 | | | 102 | 0.93 |
| 52 | | | 79 | 4.3 |
| 53 | | | 103 | 0.40 |
| 54 | | | 107 | 3.2 |
| 55 | | | 103 | 2.6 |
| 54 | | | 133 | 0.11 |
| 57 | | | 104 | 0.12 |
| 58 | | | 124 | 0.37 |
| 59 | | | 27 | >10 |
| 60 | | | 117 | 0.076 |
| 61 | | | 101 | 0.059 |
| 62 | | | 12 | >10 |
| 63 | | | 50 | 3.2 |
| 64 | | | 88 | 0.39 |
| 65 | | | 96 | 0.24 |
| 66 | | | 90 | 0.21 |
| 67 | | | 84 | 0.74 |
| 68 | | | 99 | 1.9 |
| 69 | | | 99 | 0.24 |
| 70 | | | 93 | 0.15 |
| 71 | | | 57 | 5.4 |
| 72 | | | 97 | 0.042 |
| 73 | | | 102 | 2.7 |
| 74 | | | 90 | 0.52 |
| 75 | | | 79 | 1.7 |
| 76 | | | 67 | 1.8 |
| 77 | | | 109 | 0.22 |
| 78 | | | 111 | 2.7 |
| 79 | | | 116 | 0.73 |
| 80 | | | 108 | 0.52 |
| 81 | | | 110 | 0.078 |
| 82 | | | 63 | 6.5 |
| 83 | | | 91 | 0.063 |
| 84 | | | 95 | 0.11 |
| 85 | | | 79 | 0.83 |
| 86 | | | 85 | 1.1 |
| 87 | | | 93 | 0.044 |
| 88 | | | 90 | 0.38 |
| 89 | | | 79 | 0.060 |
| 90 | | | 83 | 0.028 |
| 91 | | | 44 | 15 |
| 92 | | | 93 | 0.052 |
| 93 | | | 114 | 1.21 |
| 94 | | | 86 | 0.058 |
| 95 | | | 96 | 0.11 |
| 96 | | | 81 | 0.27 |
| 97 | | | 86 | 0.216 |
| 98 | | | 96 | 0.215 |
| 99 | | | 92 | 0.26 |
| 100 | | | 91 | 0.41 |
| 101 | | | 72 | 3.3 |
| 102 | | | 84 | 2.3 |
| 103 | | | 84 | 3.6 |
| 104 | | | 102 | 0.084 |
| 105 | | | 69 | 4.9 |
| 106 | | | 87 | 1.8 |
| 107 | | | 91 | 1.1 |
| 108 | | | 71 | 0.58 |
| 109 | | | 97 | 0.081 |
| 110 | | | 88 | 0.14 |

TABLE 1-continued

Membrane Hyperpolarization (MHP) in A10 and Guinea-Pig Bladder (GPB) Cells

| Example # | MHP in A10 Cells Maximal Response (% P1075) | MHP in A10 Cells EC50 (μM) | MHP in GPB Cells Maximal Response (% P1075) | MHP in GPB Cells EC50 (μM) |
|---|---|---|---|---|
| 111 | | | 88 | 2.9 |
| 112 | | | 79 | 0.44 |
| 113 | | | 52 | 10 |
| 114 | | | 73 | 5.9 |
| 115 | | | | >10 |
| 116 | | | 92 | 0.24 |
| 117 | | | | >10 |
| 118 | | | | >10 |
| 119 | | | | >10 |
| 120 | | | 66 | 6.3 |
| 121 | | | 98 | 0.21 |
| 122 | | | 117 | 0.28 |
| 123 | | | 96 | 3.6 |
| 124 | | | 94 | 0.24 |
| 125 | | | 85 | 0.82 |
| 126 | | | 86 | 0.28 |
| 127 | | | 100 | 0.038 |
| 128 | | | 95 | 0.22 |
| 129 | | | 91 | 0.21 |
| 130 | | | 99 | 0.72 |
| 131 | | | 100 | 1.0 |
| 132 | | | 96 | 0.27 |
| 133 | | | 45 | 12 |
| 134 | | | | >10 |
| 135 | | | | >10 |
| 136 | | | 81 | 0.12 |
| 137 | | | 101 | 0.044 |
| 138 | | | 98 | 0.24 |
| 139 | | | 96 | 0.15 |
| 140 | | | | >10 |
| 141 | | | 61 | 6.6 |
| 142 | | | 92 | 0.17 |
| 143 | | | 80 | 0.47 |
| 144 | | | 72 | 0.58 |
| 145 | | | 80 | 1.7 |
| 146 | | | 97 | 0.038 |
| 147 | | | 93 | 0.055 |
| 148 | | | 85 | 0.047 |
| 149 | | | 97 | 0.028 |
| 150 | | | 96 | 0.033 |
| 151 | | | 74 | 0.42 |
| 152 | | | 93 | 0.35 |
| 153 | | | 94 | 0.70 |
| 154 | | | 82 | 2.2 |
| 155 | | | 86 | 0.20 |
| 156 | | | 77 | 3.9 |
| 158 | | | 100 | 0.028 |
| 159 | | | 100 | 0.32 |
| 160 | | | 109 | 1.8 |
| 161 | | | 91 | 0.099 |
| 162 | | | 25 | 21 |
| 163 | | | 106 | 0.68 |
| 164 | | | 83 | 2.8 |
| 165 | | | 92 | 0.21 |
| 166 | | | 86 | 0.69 |
| 167 | | | 90 | 0.60 |
| 168 | | | 91 | 0.66 |
| 169 | | | 74 | 4.2 |
| 170 | | | 84 | 0.29 |
| 171 | | | 103 | 0.031 |
| 172 | | | 93 | 0.75 |
| 173 | | | 72 | 0.42 |
| 174 | | | 98 | 2.7 |
| 175 | | | 91 | 0.42 |
| 176 | | | 95 | 3.2 |
| 177 | | | 95 | 1.4 |
| 178 | | | | >10 |
| 179 | | | 89 | 2.1 |
| 180 | | | 94 | 1.4 |
| 181 | | | 97 | 0.33 |
| 182 | | | 28 | >10 |
| 183 | | | 109 | 0.23 |
| 184 | | | 115 | 0.45 |
| 185 | | | 87 | 1.6 |
| 186 | | | 109 | 0.27 |
| 187 | | | 101 | 0.018 |
| 188 | | | 27 | >10 |
| 189 | | | 51 | 10 |
| 190 | | | 34 | >10 |
| 191 | | | 105 | 1.5 |
| 192 | | | 52 | 10 |
| 193 | | | 57 | 10 |
| 194 | | | 94 | 1.2 |
| 195 | | | 66 | 10 |
| 196 | | | 32 | >10 |
| 197 | | | 13 | >10 |
| 198 | | | 20 | >10 |
| 199 | | | 12 | >10 |
| 200 | | | 19 | >10 |
| 201 | | | 32 | >10 |
| 202 | | | 31 | >10 |
| 203 | | | 36 | >10 |
| 204 | | | 20 | >10 |
| 205 | | | 8 | >10 |
| 206 | | | 65 | 5.8 |
| 207 | | | 92 | 1.2 |
| 208 | | | 26 | >10 |
| 209 | | | 94 | 1.9 |
| 210 | | | 95 | 0.70 |
| 211 | | | 92 | 2.5 |
| 212 | | | 91 | 1.4 |
| 213 | | | 102 | 2.4 |
| 214 | | | 92 | 0.96 |
| 215 | | | 107 | 0.18 |
| 216 | | | 84 | 2.3 |
| 217 | | | 88 | 2.9 |
| 218 | | | 36 | >10 |
| 219 | | | 97 | 0.71 |
| 220 | | | 99 | 0.71 |
| 221 | | | 63 | 7.5 |
| 222 | | | 99 | 1.0 |
| 223 | | | 101 | 0.061 |

In vitro Functional models s were evaluated for functional potassium channel opening activity obtained from Landrace pig bladders and human bladders. pig bladders were obtained from female Landrace pigs of 9–30 kg. re euthanized with an intraperitoneal injection of pentobarbital solution, Webster Inc., Sterling MA. The entire bladder was removed and ed into Krebs Ringer bicarbonate solution (composition, mM: NaCl, ; dextrose, 1; KCl, 4.7; $CaC'_2$, 2.5; $MgSO_4$, 1.5; $KH_2PO_4$, 1.2; quilibrated with 5% $CO_2$/95% $O_2$ pH 7.4 at 37 ° C.). Propranolol (0.004 ed in all of the assays to block P-adrenoceptors. The trigonal and dome scarded. Strips 3–5 mm wide and 20 mm long were prepared from the cut in a circular fashion. The mucosal layer was removed. One end ationary glass rod and the other to a Grass FT03 transducer at a basal am. Two parallel platinum electrodes were included in the stationary ide field stimulation of 0.05Hz, 0.5 milli-seconds at 20 volts. This low ation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of 10–9 to 10-'M using 1/2 log increments. After a 60 minute rinsing period, a concentration response curve (cumulative) was generated for the test agonist in the same fashion as that used for the control agonist P1075. The maximal efficacy of each compound (expressed as % relative to P1075) is reported. The amount of agent necessary to cause 50% of the agents's maximal response ($ED_{50}$) was calculated using "ALLFIT" (DeLean et al., Am. J. Physiol. 235, E97 (1980)), and agonist potencies were expressed as pD2 (the negative logarithm). Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

Human bladders were obtained from women greater than 45 years old. The human tissue was obtained from the Anatomic Gift Foundation, Phoenix AZ. Human tissue was received via overnight delivery on wet ice placed into Krebs Ringer bicarbonate solution (composition, mM: NaCl, 120; $NaHCO_3$, 20; dextrose, 11; KCl, 4.7; 20 $CaC'_2$, 2.5; $MgSO_4$, 1.5; $KH_2PO_4$, 1.2; $K_2EDTA$, 0.01, equilibrated with 5% $CO_2$/95% 02 pH 7.4 at 37 ° C.). Propranolol (0.004 mM) was included in all of the assays to block P-adrenoceptors. The trigonal and dome portions were discarded. Strips 3–5 mm wide and 20 mm long were prepared from the remaining tissue cut in a circular fashion. The mucosal layer was removed. For the human detrusor strips the tissues were contracted 25 with 25 mM KCl which produced a steady state tension of approximately 400 centigrams. A control concentration response curve (cumulative) was generated for each tissue using the potassium channel opener P1075 as the control agonist. P1075 produced complete relaxation with concentrations from 10'9 to 1IO M using 1/2 log increments.

After a 60 minute rinsing period, a concentration response curve (cumulative) was 30 generated for the test agonist in the same fashion as that used for the control agonist P1075. The maxximal efficacies of the compounds (expressed as % relative to P1075) are reported. The amount of agent necessary to cause 50% of the agents's maximal response ($ED_{50}$) was calculated using "ALLFIT" (DeLean et al., Am. J. Physiol.. 235, E97 (1980)), and agonist potencies were expressed as pD2 (the negative logarithm). Agonist potencies were also expressed as an index relative to PI1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

| Example Number | Landrace Pig Bladder | | | Human Bladder | | |
|---|---|---|---|---|---|---|
| | Efficacy (% P1075) | pD2 | Index | Efficacy (% P1075) | pD2 | Index |
| 19 | 94 | 6.0 | 0.13 | 100 | 5.8 | 0.15 |
| 2 | 96 | 6.2 | 0.15 | | | |
| 1 | 100 | 5.5 | 0.022 | | | |
| 16 | 100 | 5.0 | 0.011 | | | |
| 11 | 100 | 4.1 | 0.0021 | | | |
| 5 | 96 | 4.8 | 0.0076 | | | |
| 3 | 85 | 6.0 | 0.11 | | | |
| 8 | 95 | 5.0 | 0.025 | | | |
| 4 | 93 | 6.2 | 0.18 | | | |
| 36 | 97 | 5.5 | 0.040 | | | |
| 26 | 78 | 4.5 | 0.0099 | | | |
| 25 | 88 | 5.4 | 0.038 | | | |
| 23 | 81 | 4.4 | 0.0053 | | | |
| 22 | 77 | 4.5 | 0.0069 | | | |
| 34 | 100 | 6.8 | 0.32 | | | |
| 38 | 98 | 6.2 | 0.14 | | | |
| 40 | 98 | 6.9 | 0.46 | | | |
| 30 | 99 | 5.5 | 0.018 | | | |
| 44 | 99 | 6.2 | 0.15 | | | |
| 43 | 98 | 6.6 | 0.41 | | | |
| 51 | 99 | 5.4 | 0.021 | | | |
| 52 | 100 | 5.6 | 0.018 | | | |
| 53 | 100 | 6.6 | 0.17 | | | |
| 54 | 89 | 4.9 | 0.015 | | | |
| 56 | 97 | 7.1 | 0.88 | | | |
| 57 | 100 | 6.8 | 0.42 | | | |
| 58 | 94 | 5.3 | 0.026 | | | |
| 60 | 100 | 6.9 | 0.60 | | | |
| 61 | 100 | 7.1 | 0.71 | | | |
| 65 | 100 | 6.0 | 0.048 | | | |
| 66 | 94 | 6.3 | 0.12 | | | |
| 69 | 98 | 6.2 | 0.15 | | | |
| 70 | 100 | 6.3 | 0.15 | | | |
| 72 | 97 | 6.6 | 0.53 | | | |
| 73 | 98 | 4.4 | 0.0022 | | | |
| 74 | 100 | 6.1 | 0.081 | | | |
| 77 | 93 | 5.5 | 0.046 | | | |
| 81 | 91 | 6.4 | 0.39 | | | |
| 83 | 100 | 7.0 | 0.57 | | | |
| 84 | 100 | 6.8 | 0.69 | | | |
| 86 | 100 | 6.5 | 0.069 | | | |
| 87 | 100 | 7.5 | 0.90 | | | |
| 91 | 95 | 4.6 | 0.0034 | | | |
| 92 | 100 | 6.5 | 0.44 | | | |
| 93 | 100 | 5.2 | 0.02 | | | |
| 94 | 94 | 6.4 | 0.31 | | | |
| 95 | 84 | 5.6 | 0.12 | | | |
| 96 | 97 | 6.5 | 0.37 | | | |
| 97 | 100 | 5.7 | 0.059 | | | |
| 98 | 100 | 5.6 | 0.057 | | | |
| 99 | 100 | 6.2 | 0.18 | | | |
| 100 | 100 | 6.4 | 0.17 | | | |
| 106 | 98 | 5.1 | 0.014 | | | |
| 107 | 100 | 5.2 | 0.015 | | | |
| 108 | 98 | 4.7 | 0.075 | | | |
| 109 | 100 | 6.6 | 0.36 | | | |
| 110 | 100 | 6.7 | 0.17 | | | |
| 112 | 99 | 5.7 | 0.032 | | | |
| 114 | 97 | 4.9 | 0.014 | | | |
| 116 | 100 | 6.3 | 0.16 | | | |
| 121 | 100 | 6.2 | 0.078 | | | |
| 122 | 94 | 4.8 | 0.012 | | | |
| 123 | 98 | 4.5 | 0.0047 | | | |
| 124 | 99 | 5.3 | 0.025 | | | |
| 126 | 99 | 6.3 | 0.20 | | | |
| 136 | 92 | 5.9 | 0.073 | | | |
| 139 | 100 | 6.0 | 0.13 | | | |
| 146 | 100 | 6.7 | 0.40 | | | |
| 147 | 99 | 6.2 | 0.24 | | | |
| 149 | 80 | 6.6 | 1.2 | | | |
| 155 | 98 | 5.4 | 0.026 | | | |
| 161 | 96 | 6.3 | 0.23 | | | |
| 164 | 94 | 5.0 | 0.0071 | | | |
| 165 | 94 | 5.8 | 0.035 | | | |
| 167 | 100 | 5.9 | 0.062 | | | |

TABLE 2-continued

Functional Potassium Channel Opening Activity in
Isolated Bladder Strips

| Example Number | Landrace Pig Bladder | | | Human Bladder | | |
|---|---|---|---|---|---|---|
| | Efficacy (% P1075) | pD2 | Index | Efficacy (% P1075) | pD2 | Index |
| 172 | 100 | 6.2 | 0.12 | | | |
| 180 | 71 | 5.5 | 0.036 | | | |

As shown by the data in Tables I and 2, the compounds of this invention reduce stimulated contractions of the bladder by opening potassium channels and therefore have utility in the treatment of diseases prevented by or ameliorated with potassium channel openers.

The utility of compounds of the invention for the treatment of urinary incontinence, bladder overactivity and bladder instability is illustrated by the ability of compounds of the invention to affect bladder contractions in-vivo. The following method is illustrative of the in-vivo bladder efficacy of compounds of the invention. In-vivo bladder efficacy protocol (isovolumetric contractions model) Male CD rats (400–450 g) were anesthetized with urethane (0.6 gikg ip +0.6 g/kg sc). The left femoral vein was cannulated with polyethylene (PE-50) tubing for test compound administration. A second polyethylene catheter (PE-60) was inserted 3–4 mm into the apex of the bladder dome and secured using a 5–0 silk purse string suture. The bladder was emptied via this catheter and additionally by applying slight manual pressure on the lower abdomen. The urinary catheter was connected using a Y-tube connector to both a pressure transducer and a syringe pump. The urethra was then ligated using 4–0 silk suture and the bladder was slowly filled using a constant infusion of room temperature saline at the rate of 0.1 ml/min until spontaneous rhythmic contractions were evident (1.0 –1.3 ml). After the contractions stabilized to a consistent pattern, bladder pressure was monitored for 20 minutes before and after a dose of the vehicle (equal parts of 0-cyclodextrin stock solution (lOg P-cyclodextrin dissolved in 200ml) and sterile water) alone. Then three doses of a test compound were administered cumulatively iv at 20 minute intervals. Each dosing solution (1 ml/kg) was warmed to body temperature before dosing and was infused over 3 minutes to minimize dosing rtifacts on the bladder pressure trace. Data were averaged over the last 10 minutes of ach period and presented as percent change from control. Area under the curve (AUC) of the bladder contractions was determined from the respective waveforms using a Modular Instruments, Inc. computerized data acquisition system and averaged over the last ten minutes of each twenty minute period. The dose required to reduce the area under the curve of the bladder contractions by 30% (AUC ED30%) relative to control was estimated using a customized Excel spreadsheet. Example 87 showed a dose dependent reduction in bladder AUC over the dose range of 0.01, 0.1 and I lmol/kg. The AUC $ED_{30}$ for Example 87 was determined to be 0.06 pmol/kg.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. Further included within the scope of the present invention arepharmaceutical compositions comprising one or more of the compounds of formula I prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally , intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be 'sterilized, for example, by filtration through a bacteria-retaining filter or by incorporation of sterilizing agents in the form of sterile solid compositions, which may be dissolved in sterile water or some other sterile injectable medium immediately before use. The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conyentionally employed as a solvent or suspending medium. For this purpose any bland fixed oil can be employed including synthetic mono-or diglycerides. In addition, fatty acids such as oleic acid are used in the preparation of injectables.

Solid dosage forms for oral administration include capsules, tablets, pills, ; powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydroftufuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfunning agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono-or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology. Volume XIV, Academic Press, New York, N. Y., (1976), p 33 et seq.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, anmuonium, alkylammonium, dialkylammonium, trialkylammonium, tetraalkylammonium, diethanolammmonium, and choline. Cations may be interchanged by methods known in the art, such as ion exchange. Where compounds of the present invention are prepared in the carboxylic acid form, addition of a base (such as a hydroxide or a free amine) will yield the appropriate cationic form.

The term "pharmaceutically acceptable salt, ester, amide, and prodrug," as used herein, refers to carboxylate salts, amino acid addition salts, zwitterions, esters, amides, and prodrugs of compounds of formula I which are within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I may be prepared according to conventional methods.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5-or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I may be prepared according to conyentional methods. It is intended that amides of the present invention include amino acid and peptide derivatives of the compounds of formula I, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The term "prodrug ester group," as used herein refers, to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book "Pro-drugs as Novel Delivery Systems," by Higuchi and Stella, cited above.

The compounds of the invention, including but not limited to those specified in the examples, reduce stimulated contractions of the bladder by opening potassium channels and therefore may have utility in the treatment of diseases prevented by or ameliorated with potassium channel openers. As potassium channel openers, the compounds of the present invention are useful for the treatment and prevention of diseases such as asthma, epilepsy, hypertension, Raynaud's syndrome, migraine, pain, male sexual dysfunction, female sexual dysfunction, eating disorders, urinary incontinence, functional bowel disorders, neurodegeneration and stroke.

The ability of the compounds of the invention to treat asthma, epilepsy, hypertension, Raynaud's syndrome, male sexual dysfunction, female sexual dysfunction, migraine, pain, eating disorders, urinary incontinence, functional bowel disorders, neurodegeneration and stroke can be demonstrated according to the methods described (D. E. Nurse et al., Br. J. Urol., v. 68 pp. 27–31 (1991); B. B. Howe et al., J. Pharmacol. Exi). Ther., v. 274 pp. 884–890 (1995); K. Lawson, Pharmacol. Ther., v. 70 pp. 39–63 (1996); D. R. Gehlert, et al., Neuro-Psychopharmacol & Biol. Psychiat., v. 18 pp. 1093–1102 (1994); M. Gopalakrishnan et al., Drug Development Research, v. 28 pp. 95–127 (1993); J.E. Freedman et al., The Neuroscientist, v. 2 pp. 145–152 (1996); D. Spanswick et al., Nature, v. 390 pp. 521–25 (December 4, 1997)).

Aqueous liquid compositions of the present invention are particularly useful for the treatment and prevention of asthma, epilepsy, hypertension, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

We claim:

1. A compound of formula I:

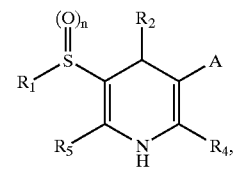

or a pharmacuetically acceptable salt, ester, amide, or prodrug thereof wherein, n is 1–2;

$R_2$ is selected from the group consisting of optionally substituted aryl and optionally substituted heteroaryl;

A is —$R_3$;

X is selected from the group consisting of C(O) and S(O)$_p$;

p is 1–2;

$R_3$ and $R_4$ together form a ring selected from the group consisting of a 5-, 6-, or 7-membered carbocyclic ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo, and a 5-, 6- or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo; and $R_1$ and $R_5$ together with the ring to which they are attached form a 5-, 6-or 7-membered sulfur-containing ring with 1–2 double bonds and 0–4 substituents selected from the group consisting of alkenyl, alkoxy, alkoxyalkoxy, alkoxyalkyl, alkyl, alkynyl, arylalkoxy, amino, aminoalkoxy, aminoalkyl, haloalkenyl, haloalkyl, halogen, hydroxy, hydroxyalkenyl, hydroxyalkyl, and oxo.

2. The compound according to claim 1 wherein A is —$XR_3$, X is C(O), and $R_3$ and $R_4$ together form a 6-membered carbocyclic ring with 1 double bond.

3. The compound according to claim 2 wherein $R_1$ and $R_5$ together with the ring to which they are attached form a 6-membered sulfur-containing ring with 1 double bond and n is 2.

4. The compound according to claim 3 wherein $R_2$ is an optionally substituted aryl.

5. The compound according to claim 4 selected from the group consisting of 3,4,6,7,8,10-hexahydro-10-(3-nitrophenyl)-2H-thiopyrano[3,2-b]quinolin-9(5H)-one, 1,1-dioxide, 10-(3,4-dichlorophenyl)-3,4,6,7,8, 10-hexahydro-2H-thiopyrano[3,2-b]quinolin-5 9(5H)-one, 1,1-dioxide, 10-(3-chloro-4-fluorophenyl)-3,4,6,7,8,10-hexahydro-2H-thiopyrano[3,2-b]quinolin-9(5H)-one, 1,1-dioxide, 10-(3-bromo-4-fluorophenyl)-3,4,6,7,8,10-hexahydro-2H-thiopyrano[3,2-b]quinolin-9(5H)-one, 1,1-dioxide, 10-(3-cyanophenyl)-3,4,6,7,8,10-hexahydro-2H-thiopyrano[3,2-b]quinolin-9(5H)-one, 1,1-dioxide, 3,4,6,7,8,10-hexahydro-10-[3-(trifluoromethyl)phenyl]-2H-thiopyrano[3,2-b]quinolin-9(5H)-one, 1,1-dioxide, 10-(3,4-difluorophenyl)-3,4,6,7,8,10-hexahydro-2H-thiopyrano[3,2-b]quinolin-9(5H)-one, 1,1-dioxide, 10-(3-bromophenyl)-3,4,6,7,8,10-hexahydro-2H-thiopyrano[3,2-b]quinolin-9(5H)-one, 1,1-dioxide, 3,4,6,7,8,10-hexahydro-10-(3,4,5-trifluorophenyl)-2H-thiopyrano[3,2-b]quinolin-9(5H)-one, 1,1-dioxide, 10-[3-fluoro-5-(trifluoromethyl)phenyl]-3,4,6,7,8,10-hexahydro-2H-thiopyrano[3,2-b]quinolin-9(5H)-one, 1,1-dioxide, 10-(3-fluorophenyl)-3,4,6,7,8,10-hexahydro-2H-thiopyrano[3,2-b]quinolin-9(5H)-one, 1,1-dioxide, 3,4,6,7,8,10-hexahydro-10-phenyl-2H-thiopyrano[3,2-b]quinolin-9(5H)-one, 1,1-dioxide, 10-[4-fluoro-3-(trifluoromethyl)phenyl]-3,4,6,7,8,10-hexahydro-2H-thiopyrano[3,2-b]quinolin-9(5H)-one, 1,1-dioxide, 3,4,6,7,8,10-hexahydro-10-(4-methyl-3-nitrophenyl)2H-thiopyrano [3,2-b]quinolin-9(5H)-one, 1,1-dioxide, 10-(4-chloro-3-fluorophenyl)-3,4,6,7,8, 10-hexahydro-2H-thiopyrano[3,2-b]quinolin-9(5H)-one, 1,1-dioxide, 10-(3-chlorophenyl)-3,4,6,7,8,10-hexahydro-2H-thiopyrano[3,2-b]quinolin-9(5H)-one, 1,1-dioxide, 3,4,6,7,8,10-hexahydro-10-[4-(trifluoromethyl)phenyl]-2H-thiopyrano[3,2-b]quinolin-9(5H)-one, 1,1-dioxide, 10-(4-bromophenyl)-3,4,6,7,8,10-hexahydro-2H-thiopyrano[3,2-bJquinolin-9(5H)-one, 1,1-dioxide, 10-(4-chloro-3-nitrophenyl)-3,4,6,7,8, 10-hexahydro-2H-thiopyrano[3,2-b]quinolin-9(5H)-one, 1,1-dioxide, and (+)- 10-(3-bromo-4-fluorophenyl)-3,4,6,7,8,10-hexahydro-2H-thiopyrano[3,2-b]quinolin-9(5H)-one, 1,1-dioxide, and (−)-10-(3-bromo-4-fluorophenyl)-3,4,6,7,8,10-hexahydro-2H-thiopyrano[3,2-b]quinolin-9(5H)-one, 1,1-dioxide.

6. The compound according to claim 3 wherein $R_2$ is an optionally substituted heteroaryl.

7. The compound according to claim 6 selected from the group consisting of 10-(3-pyridyl)-3,4,6,7,8,10-hexahydro-2H-thiopyrano[3,2-b]quinolin-9(5H)-one, 1,1-dioxide and 10-(4-pyridyl)-3,4,6,7,8, 10-hexahydro-2H-thiopyrano[3,2-b]quinolin-9(5H)-one, 1,1-dioxide.

8. The compound according to claim 2 wherein $R_1$ and $R_5$ together with the ring to which they are attached form a 5-membered sulfur-containing ring with 1 double bond and n is 2.

9. The compound according to claim 8 wherein $R_2$ is an optionally substituted aryl.

10. The compound according to claim 9 selected from the group consisting of 9-(3,4-dichlorophenyl)-2,3,5,6,7,9-hexahydrothieno[3,2-b]quinolin-8(4H)-one, 1,1-dioxide, 9-(3-cyanophenyl)-2,3,5,6,7,9-hexahydrothieno[3,2-b]quinolin-8(4H)-one, 1,1-dioxide, 9-[4-fluoro-3-(trifluoromethyl)phenyl]-2,3,5,6,7,9-hexahydrothieno[3,2-b]quinolin-8(4H)-one, 1,1-dioxide, 2,3,5,6,7,9-hexahydro-9-(4-methyl-3-nitrophenyl)thieno[3,2-b]quinolin-8(4H)-one, 1,1-dioxide, 9-(3,4-difluorophenyl)-2,3,5,6,7,9-hexahydrothieno[3,2-b]quinolin-8(4H)-one, 1,1-dioxide, 9-(4-chloro-3-nitrophenyl)-2,3,5,6,7,9-hexahydrothieno[3,2-b]quinolin-8(4H)-one, 1,1-dioxide, 9-(3-nitrophenyl)-2,3,5,6,7,9-hexahydrothieno[3,2-b]quinolin-8(4H)-one, 1,1-dioxide, 9-(3-bromo-4-fluorophenyl)-2,3,5,6,7,9-hexahydrothieno[3,2-b]quinolin-8(4H)-one, 1,1-dioxide, 9-(3-chloro-4-fluorophenyl)-2,3,5,6,7,9-hexahydrothieno[3,2-b]quinolin-8(4H)-one, 1,1-dioxide, (+)-9-(3-bromo-4-fluorophenyl)-2,3,5,6,7,9-hexahydrothieno[3,2-b]quinolin-8(4H)-one, 1,1-dioxide, (−)-9-(3-bromo-4-fluorophenyl)-2,3,5,6,7,9-hexahydrothieno[3,2-b]quinolin-8(4H)-one, 1,1-dioxide, 9-(4-fluoro-3-iodophenyl)-2,3,5,6,7,9-hexahydrothieno[3,2-b]quinolin-8(4H)-one, 1,1-dioxide, (+)-9-(3,4-dichlorophenyl)-2,3,5,6,7,9-hexahydrothieno[3,2-b]quinolin-8(4H)-one, 1,1-dioxide, (−)-9-(3,4-dichlorophenyl)-2,3,5,6,7,9-hexahydrothieno[3,2-b]quinolin-8(4H)-one, 1,1-dioxide, (+)-9-(4-chloro-3-nitrophenyl)-2,3,5,6,7,9-hexahydrothieno[3,2-b]quinolin-8(4H)-one, 1,1-dioxide, (−)-9-(4-chloro-3-nitrophenyl)-2,3,5,6,7,9-hexahydrothieno[3,2-b]quinolin-8(4H)-one, 1,1-dioxide, 9-(5-bromo-2-hydroxyphenyl)-2,3,5,6,7,9-hexahydrothieno[3,2-b]quinolin-8(4H)-one, 1,1-dioxide, (+)-9-(3-chloro-4-fluorophenyl)-2,3,5,6,7,9-hexahydrothieno[3,2-b]quinolin-8(4H)-one, 1,1-dioxide, (−)-9-(3-chloro-4-fluorophenyl)-2,3,5,6,7,9-hexahydrothieno[3,2-b]quinolin-8(4H)-one, 1,1-dioxide, 9-(4-fluoro-3-methylphenyl)-2,3,5,6,7,9-hexahydrothieno[3,2-b]quinolin-8(4H)-one, 1,1-dioxide, (+)-9-(3-cyanophenyl)-2,3,5,6,7,9-hexahydrothieno[3,2-b]quinolin-8(4H)-one, 1,1-dioxide, (−)-9-(3-cyanophenyl)-2,3,5,6,7,9-hexahydrothieno[3,2-b]quinolin-8(4H)-one, 1,1-dioxide, 9-(5-bromo-4-fluoro-2-iodophenyl)-2,3,5,6,7,9-hexahydrothieno[3,2-b]quinolin-8(4H)-one, 1,1-dioxide, 9-(4-fluoro-2-hydroxyphenyl)-2,3,5,6,7,9-hexahydrothieno[3,2-b]quinolin-8(4H)-one, 1,1-dioxide, 9-(5-chloro-2-hydroxyphenyl)-2,3,5,6,7,9-hexahydrothieno[3,2-b]quinolin-8(4H)-one, 1,1-dioxide, 9-(5-bromo-4-fluoro-2-hydroxyphenyl)-2,3,5,6,7,9-hexahydrothieno[3,2-b]quinolin-8(4H)-one, 1,1-dioxide, (+)-9-(4-methyl-3-nitrophenyl)-2,3,5,6,7,9-hexahydro[3, 2-b]quinolin-8(4H)-one, 1,1-dioxide, (−)-9-(4-methyl-3-nitrophenyl)-2,3,5,6,7,9-hexahydro[3, 2-b]quinolin-8(4H)-one, 1,1-dioxide, 9-(4-fluoro-3-vinylphenyl)-2,3,5,6,7,9-hexahydrothieno [3,2-b]quinolin-8(4H)-one, 1,1-dioxide, 9-(3-acetyl-4-fluorophenyl)-2,3,5,6,7,9-hexahydrothieno[3,2-b]quinolin-8(4H)-one, 1,1-dioxide, 9-[4-fluoro-3-(2-furyl)phenyl]-2,3,5,6,7,9-hexahydrothieno[3,2-b]quinolin-8(4H)-one, 1,1- dioxide, 9-[6-fluoro-(1, 1'-biphenyl)-3-yl]-2,3,5,6,7,9-hexahydrothieno[3,2-b]quinolin-8(4H)-one, 1,1-dioxide, 9-[4-fluoro-3-(phenylethynyl)phenyl]-2,3,5,6,7,9-hexahydrothieno[3,2-b]quinolin-8(4H)-one, 1,1-dioxide, 9-(3,4-dibromophenyl)-2,3,5,6,7,9-hexahydrothieno[3,2-b]quinolin-8(4H)-one, 1, 1-dioxide, (+)-9-[4-fluoro-3-(trifluoromethyl)phenyl]-2,3,5,6,7,9-hexahydrothieno[3,2-b]quinolin-8(4H)-one, 1,1-dioxide, (−)-9-[4-fluoro-3-(trifluoromethyl)phenyl]-2,3,5,6,7,9-hexahydrothieno[3,2-b]quinolin-8(4H)-one, 1,1-dioxide, 9-[4-fluoro-3-(2-thienyl)phenyl]-2,3,5,6,7,9-hexahydrothieno[3,2-b]quinolin-8(4H)-one, 1,1-dioxide, 9-[4-fluoro-3-(3-hydroxy-3-methyl-1-butynyl)phenyl]-2,3,5,6,7,9-hexahydrothieno[3,2-b]quinolin-8(4H)-one, 1,1-dioxide, (+)-9-(3-cyano-4-fluorophenyl)-2,3,5,6,7,9-hexahydrothieno[3,2-b]quinolin-8(4H)-one, 1,1-dioxide, (−)-9-(3-cyano-4-fluorophenyl)-2,3,5,6,7,9-hexahydrothieno[3,2-b]quinolin-8(4H)-one, 1,1-dioxide, (+)-9-(3,4-dibromophenyl)-2,3,5,6,7,9-hexahydrothieno[3,2-b]quinolin-8(4H)-one, 1,1-dioxide, (−)-9-(3,4-dibromophenyl)-2,3,5,6,7,9-hexahydrothieno[3,2-b]quinolin-8(4H)-one, 1,1-dioxide, (+)-9-(4-fluoro-3-iodophenyl)-2,3,5,6,7,9-hexahydrothieno[3,2-b]quinolin-8(4H)-one, 1,1-dioxide, (−)-9-(4-fluoro-3-iodophenyl)-2,3,5,6,7,9-hexahydrothieno[3,2-b]quinolin-8(4H)-one, 1,1-dioxide, 9-[4-chloro-3-(trifluoromethyl)phenyl]-2,3,5,6,7,9-hexahydrothieno[3,2-b]quinolin-8(4H)-one, 1,1-dioxide, (+)-9-(3-ethynyl-4-fluorophenyl)-2,3,5,6,7,9-hexahydrothieno[3,2-b]quinolin-8(4H)-one, 1,1-dioxide, (−)-9-(3-ethynyl-4-fluorophenyl)-2,3,5,6,7,9-hexahydrothieno[3,2-b]quinolin-8(4H)-one, 1,1-dioxide, (+)-9-(3-cyano-4-methylphenyl)-2,3,5,6,7,9-hexahydrothieno[3,2-b]quinolin-8(4H)-one, 1,1-dioxide, (+)-9-(3-cyano-4-methylphenyl)-2,3,5,6,7,9-hexahydrothieno[3,2-b]quinolin-8(4H)-one, 1,1-dioxide, (−)-9-(3-cyano-4-methylphenyl)-2,3,5,6,7,9-hexahydrothieno[3,2-b]quinolin-8(4H)-one, 1,1-dioxide, 9-[4-fluoro-3-(3-pyridinyl)phenyl]-2,3,5,6,7,9-hexahydrothieno[3,2-b]quinolin-8(4H)-one, 1,1-dioxide, (+)-9-[4-fluoro-3-(2-ftiryl)phenyl]-2,3,5,6,7,9-hexahydrothieno[3,2-b]quinolin-8(4H)-one, 1,1-dioxide, (−)-9-[4-fluoro-3-(2-ftiryl)phenyl]-2,3,5,6,7,9-hexahydrothieno[3,2-b]quinolin-8(4H)-one, 1,1-dioxide, 9-(3-allyl-4-fluorophenyl)-2,3,5,6,7,9-hexahydrothieno[3,2-b]quinolin-8(4H)-one, 1, 1-dioxide, 9-[3-(1-ethoxyvinyl)-4-fluorophenyl]-2,3,5,6,7,9-hexahydrothieno[3,2-b]quinolin-8(4H)-one, 1, 1-dioxide, (−)-9-[4-chloro-3-(trifluoromethyl)phenyl]-2,3,5,6,7,9-hexahydrothieno[3,2-b]quinolin-8(4H)-one, 1,1-dioxide, (+)-9-[4-chloro-3-(trifluoromethyl)phenyl]-2,3,5,6,7,9-hexahydrothieno[3,2-b]quinolin-8(4H)-one, 1,1-dioxide, (9S)-9-(3-ethyl-4-fluorophenyl)-2,3,5,6,7,9-hexahydrothieno[3,2-b]quinolin-8(4H)-one, 1,1-dioxide, (+)-9-(3,4-difluoro)-2,3,5,6,7,9-hexahydrothieno[3,2-b]quinolin-8(4H)-one, 1,1-dioxide, (9S)-9-(3-ethenyl-4-fluorophenyl)-2,3,5,6,7,9-hexahydrothieno[3,2-b]quinolin-8(4H)-one, 1,1-dioxide, (−)-9-(3,4-difluorophenyl)-2,3,5,6,7,9-hexahydrothieno[3,2-b]quinolin-8(4H)-one 1,1-dioxide, 9-(4-chloro-3-fluorophenyl)-2,3,5,6,7,9-hexahydrothieno[3,2-b]quinolin-8(4H)-one 1,1-dioxide, 9-[3-(trifluoromethoxy)phenyl]-2,3,5,6,7,9-hexahydrothieno[3,2-b]quinolin-8(4H)-one 1,1-dioxide, 9-[4-(trifluoromethoxy)phenyl]-2,3,5,6,7,9-hexahydrothieno[3,2-b]quinolin-8(4H)-one 1,1-dioxide, 9-(4-bromo-3-nitrophenyl)-2,3,5,6,7,9-hexahydrothieno[3,2-b]quinolin-8(4H)-one 1,1-dioxide, 9-(4-ethyl-3-nitrophenyl)-2,3,5,6,7,9-hexahydrothieno[3,2-b]quinolin-8(4H)-one 1, 1-dioxide, 9-[3-nitro-4-(trifluoromethoxy)phenyl]-2,3,5,6,7,9-hexahydrothieno[3,2-b]quinolin-8(4H)-one 1,1-dioxide, 9-[4-(difluoromethoxy)phenyl]-2,3,5,6,7,9-hexahydrothieno[3,2-b]quinolin-8(4H)-one 1,1-dioxide, 9-(3-methyl-4-nitrophenyl)-2,3,5,6,7,9-hexahydrothieno[3,2-b]quinolin-8(4H)-one 1,1-dioxide, 9-[3-nitro-4-(trifluoromethyl)phenyl]-2,3,5,6,7,9-hexahydrothieno[3,2-b]quinolin-8(4H)-one 1,1-dioxide, 9-[4-(difluoromethoxy)-3-nitrophenyl]-2,3,5,6,7,9-hexahydrothieno[3,2-b]quinolin-8(4H)-one 1,1-dioxide, 9-(4-chloro-3-methylphenyl)-2,3,5,6,7,9-hexahydrothieno[3,2-b]quinolin-8(4H)-one 1,1-dioxide, 9-(3-bromo-4-methylphenyl)-2,3,5,6,7,9-hexahydrothieno[3,2-b]quinolin-8(4H)-one 1,1-dioxide, (+)-9-(3-bromo-4-methylphenyl)-2,3,5,6,7,9-hexahydrothieno[3,2-b]quinolin-8(4H)-one 1,1-dioxide, (−)-9-(3-bromo-4-methylphenyl)-2,3,5,6,7,9-hexahydrothieno[3,2-b]quinolin-8(4H)-one 1,1-dioxide, 9-[4-methyl-3-(methylsulfanyl)phenyl]-2,3,5,6,7,9-hexahydrothieno[3,2-b]quinolin-8(4H)-one 1,1-dioxide, (−)-9-(4-chloro-3-fluorophenyl)-2,3,5,6,7,9-hexahydrothieno[3,2-b]quinolin-8(4H)-one 1,1-dioxide, (+)-9-(4-chloro-3-fluorophenyl)-2,3,5,6,7,9-hexahydrothieno[3,2-b]quinolin-8(4H)-one 1,1-dioxide, 9-[4-methyl-3-(methylsulfonyl)phenyl]-2,3,5,6,7,9-hexahydrothieno[3,2-b]quinolin-8(4H)-one 1,1-dioxide, (+)-9-(4-bromo-3-nitrophenyl)-2,3,5,6,7,9-hexahydrothieno[3,2-b]quinolin-8(4H)-one 1,1-dioxide, (−)-9-(4-bromo-3-nitrophenyl)-2,3,5,6,7,9-hexahydrothieno[3,2-b]quinolin-8(4H)-one 1,1-dioxide, 9-(3-iodo-4-methylphenyl)-2,3,5,6,7,9-hexahydrothieno[3,2-b]quinolin-8(4H)-one 1,1-dioxide, (+)-9-[3-nitro-4-(trifluoromethyl)phenyl]-2,3,5,6,7,9-hexahydrothieno[3,2-b]quinolin-8(4H)-one 1,1-dioxide, (−)-9-[3-nitro-4-(trifluoromethyl)phenyl]-2,3,5,6,7,9-hexahydrothieno[3,2-b]quinolin-8(4H)-one 1,1-dioxide, (+)-9-(3-iodo-4-methylphenyl)-2,3,5,6,7,9-hexahydrothieno[3,2-b]quinolin-8(4H)-one 1,1-dioxide, and (−)-9-(3-iodo-4-methylphenyl)-2,3,5,6,7,9-hexahydrothieno[3,2-b]quinolin-8(4H)-one 1,1-dioxide.

11. The compound according to claim 8 wherein $R_2$ is an optionally substituted heteroaryl.

12. The compound according to claim 1 selected from the group consisting of 9-(2,1,3-benzoxadiazol-5-yl)-2,3,5,6,7,9-hexahydrothieno[3,2-b]quinolin-8(4H)-one, 1,1-dioxide, (+)-9-(2, 1,3-benzoxadiazol-5-yl)-2,3,5,6,7,9-hexahydrothieno[3,2-b]quinolin-8(4H)-one, 1,1-dioxide, (−)-9-(2, 1,3-benzoxadiazol-5-yl)-2,3,5,6,7,9-hexahydrothieno[3,2-b]quinolin-8(4H)-one, 1,1-dioxide, 9-(3-pyridinyl)-2,3,5,6,7,9-hexahydrothieno[3,2-b]quinolin-8(4H)-one, 1,1-dioxide, 9-(4-pyridinyl)-2,3,5,6,7,9-hexahydrothieno[3,2-b]quinolin-8(4H)-one, 1,1,-dioxide, 9-(5-bromo-2-thienyl)-2,3,5,6,7,9-hexahydrothieno[3,2-b]quinolin-8(4H)-one, 1,1-dioxide, 9-(4-bromo-2-thienyl)-2,3,5,6,7,9-hexahydrothieno[3,2-b]quinolin-8(4H)-one, 1,1-dioxide, (+)-9-(5-bromo-2-thienyl)-2,3,5,6,7,9-hexahydrothieno[3,2-b]quinolin-8(4H)-one, 1,1-dioxide, (−)-9-(5-bromo-2-thienyl)-2,3,5,6,7,9-hexahydrothieno[3,2-b]quinolin-8(4H)-one, 1,1-dioxide, 9-(5-cyano-2-thienyl)-2,3,5,6,7,9-hexahydrothieno[3,2-b]quinolin-8(4H)-one, 1,1-dioxide, (+)-9-(4-bromo-2-thienyl)-2,3,5,6,7,9-hexahydrothieno[3,2-b]quinolin-8(4H)-one 1,1-dioxide, (−)-9-(4-bromo-2-thienyl)-2,3,5,6,7,9-hexahydrothieno[3,2-b]quinolin-8(4H)-one 1,1-dioxide, 9-(2,1,3-benzothiadiazol-5-yl)-2,3,5,6,7,9-hexahydrothieno[3,2-b]quinolin-8(4H)-one 1,1-dioxide. (+)-9-(2,1,3-benzothiadiazol-5-yl)-2,3,5,6,7,9-hexahydrothieno[3,2-b]quinolin-8(4H)-one 1,1-dioxide, and (−)-9-(2,1,3-benzothiadiazol-5-yl)-2,3,5,6,7,9-hexahydrothieno[3,2-b]quinolin-8(4H)-one 1,1-dioxide.

13. The compound according to claim 2 wherein $R_1$ and $R_5$ together with the ring to which they are attached form a 5-membered sulfur-containing ring with 1 double bond and n is 1.

14. The compound according to claim 13 wherein $R_2$ is an optionally substituted aryl.

15. The compound according to claim 14 which is 9-(3-bromo-4-fluorophenyl)-2,3,5,6,7,9-hexahydrothieno[3,2-b]quinolin-8(4H)-one, 1-oxide.

16. The compound according to claim 2 wherein $R_1$ and $R_5$ together with the ring to which they are attached form a 7-membered sulfur-containing ring with 1 double bond and n is 2.

17. The compound according to claim 16 wherein $R_2$ is an optionally substituted aryl.

18. The compound according to claim 17 which is 1,1-(3-bromo-4-fluorophenyl)-2,3,4,5,7,8,9,11-octahydrothiepino[3,2-b]quinolin-10(6H)-one, 1,1-dioxide.

19. The compound according to claim 1 wherein A is —$XR_3$, X is C(O), and $R_3$ and $R_4$ together form a 5-membered carbocyclic ring with 1 double bond.

20. A compound according to claim 19 wherein $R_1$ and $R_5$ together with the ring to which they are attached form a 6-membered sulfur-containing ring with 1 double bond and n is 2.

21. A compound according to claim 20 wherein $R_2$ is an optionally substituted aryl.

22. A compound according to claim 24 selected from the group consisting of 9-(3,4-dichlorophenyl)-3,4,5,6,7,9-hexahydrocyclopenta[b]thiopyrano[2,3-e]pyridin-8(2H)-one, 1,1-dioxide, 9-(4-chloro-3-nitrophenyl)-3,4,5,6,7,9-hexahydrocyclopenta[b]thiopyrano[2,3-e]pyridin-8(2H)-one, 1,1-dioxide, 9-(3-chloro-4-fluorophenyl)-3,4,5,6,7,9-hexahydrocyclopenta[b]thiopyrano[23-e]pyridin-8(2H)-one, 1,1-dioxide, 9-(3-bromo-4-fluorophenyl)-3,4,5,6,7,9-hexahydrocyclopenta[b]thiopyrano[2,3-e]pyridin-8(2H)-one, 1,1-dioxide, 9-(3-cyanophenyl)-3,4,5,6,7,9-hexahydrocyclopenta[b]thiopyrano[2,3-e]pyridin-8(2H)-one, 1,1-dioxide, 9-(4-fluoro-3-trifluoromethylphenyl)-3,4,5,6,7,9-hexahydrocyclopenta[b]thiopyrano[2,3-e]pyridin-8(2H)-one, 1,1-dioxide, 9-(4-methyl-3-nitrophenyl)-3,4,5,6,7,9-hexahydrocyclopentafb]thiopyrano[2,3-e]pyridin-8(2H)-one, 1,1-dioxide, 9-(3,4-difluorophenyl)-3,4,5,6,7,9-hexahydrocyclopenta[b]thiopyrano[2,3-e]pyridin-8(2H)-one, 1,1-dioxide, 3,4,5,6,7,9-hexahydro-9-(3-nitrophenyl)cyclopenta[b]thiopyrano[2,3-e]pyridin-8(2H)-one, 1,1,-dioxide, (+)-9-(3-bromo-4-fluorophenyl)-3,4,5,6,7,9-hexahydrocyclopenta[b]thiopyrano[2,3-e]pyridin-8(2H)-one, 1,1-dioxide, (−)-9-(3-bromo-4-fluorophenyl)-3,4,5,6,7,9-hexahydrocyclopenta[b]thiopyrano[2,3-e]pyridin-8(2H)-one, 1,1-dioxide, 9-[3-(trifluoromethoxy)phenyl]-3,4,5,6,7,9-hexahydrocyclopenta[b]thiopyrano[2,3-e]pyridin-8(2H)-one, 1,1-dioxide, 9-(5-bromo-2-hydroxyphenyl)-3,4,5,6,7,9-hexahydrocyclopenta[b]thiopyrano[2,3-e]pyridin-8(2H)-one, 1,1-dioxide, and 9-(5-bromo-4-fluoro-2-nitrophenyl)-3,4,5,6,7,9-hexahydrocyclopenta[b]thiopyrano[2,3-e]pyridin-8(2H)-one, 1,1-dioxide.

23. A compound according to claim 20 wherein $R_2$ is an optionally substituted heteroaryl.

24. A compound according to claim 23 which is 9-(5-cyano-6-methylthiopyrid-2-yl)-3,4,5,6,7,9-hexahydrocyclopenta[b]thiopyrano[2,3-e]pyridin-8(2H)-one, 1,1-dioxide.

25. The compound according to claim 19 wherein $R_1$ and $R_5$ together with the ring to which they are attached form a 5-membered sulfur-containing ring with 1 double bond and n is 2.

26. The compound according to claim 25 wherein $R_2$ is an optionally substituted aryl.

27. The compound according to claim 26 selected from the group consisting of 8-(4-chloro-3-nitrophenyl)-2,3,4,5,6,8-hexahydro-7H-cyclopenta[b]thieno[2,3-e]pyridin-7-one 1,1-dioxide, 8-(3-cyanophenyl)-2,3,4,5,6,8-hexahydro-7H-cyclopenta[b]thieno[2,3-e]pyridin-7-one, 1,1-dioxide, 8-(3-bromo-4-fluorophenyl)-2,3,4,5,6,8-hexahydro-7H-cyclopenta[b]thieno[2,3-e]pyridin-7-one, 1,1-dioxide, 8-(4-fluoro-3-trifluoromethylphenyl)-2,3,4,5,6,8-hexahydro-7H-cyclopenta[b]thieno[2,3-e]pyridin-7-one, 1,1-dioxide, 2,3,4,5,6,8-hexahydro-8-(3-nitrophenyl)-7H-cyclopenta[b]thieno[2,3-e]pyridin-7-one, 1,1-dioxide, 8-(3,4-dichlorophenyl)-2,3,4,5,6,8-hexahydro-7H-cyclopenta[b]thieno[2,3-e]pyridin-7-one, 1,1-dioxide, 8-(3-chloro-4-fluorophenyl)-2,3,4,5,6,8-hexahydro-7H-cyclopenta[b]thieno[2,3-e]pyridin-7-one, 1,1-dioxide, 8-(3-bromophenyl)-2,3,4,5,6,8-hexahydro-7H-cyclopenta[b]thieno[2,3-e]pyridin-7-one, 1,1-dioxide, 8-(3,4-dibromophenyl)-2,3,4,5,6,8-hexahydro-7H-cyclopenta[b]thieno[2,3-e]pyridin-7-one, 1,1-dioxide, 8-(4-bromophenyl)-2,3,4,5,6,8-hexahydro-7H-cyclopenta[b]thieno[2,3-e]pyridin-7-one, 1,1-dioxide, 8-(3,4-difluorophenyl)-2,3,4,5,6,8-hexahydro-7H-cyclopenta[b]thieno[2,3-e]pyridin-7-one, 1,1-dioxide, 8-(4-chloro-3-fluorophenyl)-2,3,4,5,6,8-hexahydro-7H-cyclopenta[b]thieno[2,3-e]pyridin-7-one, 1,1-dioxide, (−)-8-(3-bromo-4-fluorophenyl)-2,3,4,5,6,8-hexahydro-7H-cyclopenta[b]thieno[2,3-e]pyridin-7-one, 1,1-dioxide, (+)-8-(3-bromo-4-fluorophenyl)-2,3,4,5,6,8-hexahydro-7H-cyclopenta[b]thieno[2,3-e]pyridin-7-one, 1,1-dioxide, 8-(4-fluoro-3-iodophenyl)-2,3,4,5,6,8-hexahydro-7H-cyclopenta[2,3-e]pyridin-7-one, 1,1-dioxide, (+)-8-(3,4-dichlorophenyl)-2,3,4,5,6,8-hexahydrocyclopenta[b]thieno[2,3-e]pyridin-7-one, 1,1-dioxide, (−)-8-(3,4-dichlorophenyl)-2,3,4,5,6,8-hexahydrocyclopenta[b]thieno[2,3-e]pyridin-7-one, 1,1-dioxide, (+)-8-(4-chloro-3-nitrophenyl)-2,3,4,5,6,8-hexahydrocyclopenta[b]thieno[2,3-e]pyridin-7-one, 1,1-dioxide, (−)-8-(4-chloro-3-nitrophenyl)-2,3,4,5,6,8-hexahydrocyclopenta[b]thieno[2,3-e]pyridin-7-one, 1,1-dioxide, (−)-8-(3-cyanophenyl)-2,3,4,5,6,8-hexahydrocyclopenta[b]thieno[2,3-e]pyridin-7-one, 1,1-dioxide, and (+)-8-(3-cyanophenyl)-2,3,4,5,6,8-hexahydrocyclopenta[b]thieno[2,3-e]pyridin-7-one, 1,1-dioxide.

28. The compound according to claim 25 wherein $R_2$ is an optionally substituted heteroaryl.

29. The compound according to claim 28 selected from the group consisting of 8-(2-cyano-4-pyridinyl)-2,3,4,5,6,8-hexahydro-7H-cyclopenta[b]thieno[2,3-e]pyridin-7-one, 1,1-dioxide, 8-(4-bromo-2-thienyl)-2,3,4,5,6,8-hexahydro-7H-cyclopenta[b]thieno[2,3-e]pyridin-7-one, 1,1-dioxide, 8-(5-bromo-2-thienyl)-2,3,4,5,6,8-hexahydro-7H-cyclopenta[b]thieno[2,3-e]pyridin-7-one, 1,1-dioxide, 2,3,4,5,6,8-hexahydro-8-(5-nitro-3-thienyl)-7H-cyclopenta[b]thieno[2,3-e]pyridin-7-one, 1,1-dioxide, 2,3,4,5,6,8-hexahydro-8-(5-nitro-2-thienyl)-7H-cyclopenta[b]thieno[2,3-e]pyridin-7-one, 1,1-dioxide, 2,3,4,5,6,8-hexahydro-8-(5-nitro-2-furyl)-7H-cyclopenta[b]thieno[2,3-e]pyridin-7-one, 1,1-dioxide, and 8-(2,1,3-benzoxadiazol-5-yl)-2,3,4,5,6,8-hexahydro-7H-cyclopenta[b]thieno[2,3-e]pyridin-7-one, 1,1-dioxide.

30. The compound according to claim 19 wherein $R_1$ and $R_5$ together with the ring to which they are attached form a 7-membered sulfur-containing ring with 1 double bond and n is 2.

31. The compound according to claim 30 wherein $R_2$ is an optionally substituted aryl.

32. The compound according to claim 31 which is 10-(3-bromo-4-fluorophenyl)-2,3,4,5,6,7,8,10-octahydro-9H-cyclopenta[b]thiepino[2,3-e]pyridin-9-one.

33. The compound according to claim 1 wherein $R_1$ and $R_5$ together with the ring to which they are attached form a 6-membered sulfur-containing ring with 1 double bond and n is 2.

34. The compound according to claim 1 wherein A is —$XR_3$, X is $S(O)_p$, $R_3$ and $R_4$ form a 6-membered sulfur-containing ring with 1 double bond.

35. The compound according to claim 34 wherein $R_1$ and $R_5$ together with the ring to which they are attached form a 6-membered sulfur-containing ring with 1 double bond and n is 2.

36. The compound according to claim 35 wherein $R_2$ is an optionally substituted aryl.

37. The compound according to claim 36 selected from the group consisting of 10-(4-chloro-3-nitrophenyl)-3,4,6,7,8,10-hexahydro-2H,5H-bisthiopyrano[3,2-b:2',3'-e]pyridine, 1,1,9,9-tetraoxide, 10-(3-bromo-4-fluorophenyl)-3,4,6,7,8,10-hexahydro-2H,5H-dithiopyrano[3,2-5 b:2',3'-e]pyridine, 1,1,9,9-tetraoxide, and 3,4,6,7,8,10-hexahydro-10-(3-nitrophenyl)-2H,5H-dithiopyrano[3,2-b:2',3'-e]pyridine, 1,1,9,9-tetraoxide.

38. The compound according to claim 1 wherein A is —$XR_3$, X is $S(O)_p$, $R_3$ and $R_4$ together form a 5-membered sulfur-containing ring with 1 double bond.

39. The compound according to claim 38 wherein $R_1$ and $R_5$ together with the ring to which they are attached form a 5-membered sulfur-containing ring with 1 double bond and n is 2.

40. The compound according to claim 39 wherein $R_2$ is an optionally substituted aryl.

41. The compound according to claim 40 selected from the group consisting of 8-(4-chloro-3-nitrophenyl)-2,3,4,5,6,8-hexahydrodithieno[3,2-b:2',3'-e]pyridine, 1,1,7,7-tetraoxide, 8-(3-bromo-4-fluorophenyl)-2,3,4,5,6,8-hexahydrodithieno[3,2-b:2',3'-e]pyridine, 1,1,7,7-tetraoxide, 8-(3-cyanophenyl)-2,3,4,5,6,8-hexahydrodithieno[3,2-b:2',3'-e]pyridine, 1,1,7,7-tetraoxide, 8-(4-fluoro-3-trifluoromethylphenyl)-2,3,4,5,6,8-hexahydrodithieno[3,2-b:2',3'-e]pyridine, 1,1,7,7-tetraoxide, 2,3,4,5,6,8-hexahydro-8-(3-nitrophenyl)dithieno[3,2-b:2',3'-e]pyridine, 1,1,7,7-tetraoxide, 8-(3-chloro-4-fluorophenyl)-2,3,4,5,6,8-hexahydrodithieno[3,2-b:2',3'-e]pyridine, 1, 1,7,7-tetraoxide, 8-(3,4-dichlorophenyl)-2,3,4,5,6,8-hexahydrodithieno[3,2-b:2',3'-e]pyridine, 1,1,7,7-tetraoxide, 8-(3-cyano-4-fluorophenyl)-2,3,4,5,6,8-hexahydrodithieno[3,2-b:2',3 '-e]pyridine, 1,1,7,7-tetraoxide, 8-[4-chloro-3-(trifluoromethyl)phenyl]-2,3,4,5,6,8-hexahydrodithieno[3,2-b:2',3'-e]pyridine-1,1,7,7-tetraoxide, 8-(3,4-dibromophenyl)-2,3,4,5,6,8-hexahydrodithieno[3,2-b:2',3'-e]pyridine-1,1,7,7-tetraoxide, and 8-(4-fluoro-3-iodophenyl)-2,3,4,5,6,8-hexahydrodithieno[3,2-b:2'3'-e]pyridine-1,1,7,7-tetraoxide.

42. The compound according to claim 39 wherein $R_2$ is an optionally substituted heteroaryl.

43. The compound according to claim 42 which is 8-(2,1,3-benzoxadiazol-5-yl)-2,3,4,5,6,8-hexahydrodithieno[3,2-b:2',3i-e]pyridine-1,1,7,7-tetraoxide.

44. The compound according to claim 1 wherein $R_1$ and $R_5$ together with the ring to which they are attached form a 5-membered sulfur-containing ring with 1 double bond and n is 2.

45. The compound according to claim 1 wherein A is —$XR_3$, X is C(O), $R_3$ and $R_4$ together form a 6-membered-carbocyclic ring with 1 double bond and 1–2 substituents independently selected from alkyl.

46. The compound according to claim 45 wherein $R_1$ and $R_5$ together with the ring to which they are attached form a 5-membered sulfur-containing ring with 1 double bond and n is 2.

47. The compound according to claim 46 wherein $R_2$ is an optionally substituted aryl.

48. The compound according to claim 47 selected from the group consisting of 9-(3-bromo-4-fluorophenyl)-7,7-dimethyl-2,3,5,6,7,9-hexahydrothieno[3,2-b]quinolin-8(4H)-one, 1,1-dioxide, 9-(3,4-dichlorophenyl)-7,7-dimethyl-2,3,5,6,7,9-hexahydrothieno[3,2-b]quinolin-8(4H)-one, 1,1-dioxide, 9-(3,4-difluorophenyl)-7,7-dimethyl-2,3,5,6,7,9-hexahydrothieno[3,2-b]quinolin-8(4H)-one 1,1-dioxide, 9-(3-chloro-4-fluorophenyl)-7,7-dimethyl-2,3,5,6,7,9-hexahydrothieno[3,2-b]quinolin-8(4H)-one 1,1-dioxide, 9-[$4$-fluoro-3-(trifluoromethyl)phenyl]-7,7-dimethyl-2,3,5,6,7,9-hexahydrothieno[3,2-b]quinolin-8(4H)-one 1,1-dioxide, 9-(4-chloro-3-fluorophenyl)-7,7-dimethyl-2,3,5,6,7,9-hexahydrothieno[3,2-b]quinolin-8(4H)-one 1,1-dioxide, 9-(4-chloro-3-nitrophenyl)-7,7-dimethyl-2,3,5,6,7,9-hexahydrothieno[3,2-b]quinolin-8(4H)-one 1,1-dioxide, 9-(3,4-dibromophenyl)-7,7-dimethyl-2,3,5,6,7,9-hexahydrothieno[3,2-b]quinolin-8(4H)-one 1,1-dioxide, 9-[3-fluoro-4-(trifluoromethyl)phenyl]-7,7-dimethyl-2,3,5,6,7,9-hexahydrothieno[3,2-b]quinolin-8(4H)-one 1,1-dioxide, 7,7-dimethyl-9-(3-nitrophenyl)-2,3,5,6,7,9-hexahydrothieno[3,2-b]quinolin-8(4H)-one 1,1-dioxide, 9-(3-cyanophenyl)-7,7-dimethyl-2,3,5,6,7,9-hexahydrothieno[3,2-b]quinolin-8(4H)-one 1,1-dioxide, 9-(5-chloro-2-hydroxyphenyl)-7,7-dimethyl-2,3,5,6,7,9-hexahydrothieno[3,2-b]quinolin-8(4H)-one 1,1-dioxide, 9-(2-hydroxy-5-nitrophenyl)-7,7-dimethyl-2,3,5,6,7,9-hexahydrothieno[3,2-b]quinolin-8(4H)-one 1,1-dioxide, 9-(2-hydroxy-3,5-dinitrophenyl)-7,7-dimethyl-2,3,5,6,7,9-hexahydrothieno[3,2-b]quinolin-8(4H)-one 1,1-dioxide, 9-(3,5-dibromo-2-hydroxyphenyl)-7,7-dimethyl-2,3,5,6,7,9-hexahydrothieno[3,2-b]quinolin-8(4H)-one 1,1-dioxide, 9-(3-bromo-5-chloro-2-hydroxyphenyl)-7,7-dimethyl-2,3,5,6,7,9-hexahydrothieno[3,2-b]quinolin-8(4H)-one 1,1-dioxide, 9-(3-bromo-2-hydroxy-5-nitrophenyl)-7,7-dimethyl-2,3,5,6,7,9-hexahydrothieno[3,2-b]quinolin-8(4H)-one 1,1-dioxide, 9-(3,5-dichloro-2-hydroxyphenyl)-7,7-dimethyl-2,3,5,6,7,9-hexahydrothieno [3,2-b]quinolin-8(4H)-one 1,1-dioxide, 9-(2-hydroxy-3-nitrophenyl)-7,7-dimethyl-2,3,5,6,7,9-hexahydrothieno[3,2-b]quinolin-8(4H)-one 1,1-dioxide, 9-(5-bromo-2-hydroxy-3-nitrophenyl)-7,7-dimethyl-2,3,5,6,7,9-hexahydrothieno[3,2-b]quinolin-8(4H)-one 1,1-dioxide, 7,7-dimethyl-9-(2,4,5-trifluorophenyl)-2,3,5,6,7,9-hexahydrothieno[3,2-b]quinolin-8(4H)-one 1,1-dioxide, 7,7-dimethyl-9-(2,3,4-trifluorophenyl)-2,3,5,6,7,9-hexahydrothieno[3,2-b]quinolin-8(4H)-one 1,1-dioxide, 7,7-dimethyl-9-(3,4,5-trifluorophenyl)-2,3,5,6,7,9-hexahydrothieno[3,2-b]quinolin-8(4H)-one 1,1-dioxide, 9-(3,5-dibromo-4-hydroxyphenyl)-7,7-dimethyl-2,3,5,6,7,9-hexahydrothieno[3,2-b]quinolin-8(4H)-one 1,1-dioxide, 9-(4-chlorophenyl)-7,7-dimethyl-2,3,5,6,7,9-hexahydrothieno[3,2-b]quinolin-8(4H)-one 1,1-dioxide, 9-(3-chlorophenyl)-7,7-dimethyl-2,3,5,6,7,9-hexahydrothieno[3,2-b]quinolin-8(4H)-one 1,1-dioxide, 9-(3-bromo-4-fluorophenyl)-5,5-dimethyl-2,3,5,6,7,9-hexahydrothieno[3,2-b]quinolin-8(4H)-one 1,1-dioxide, (–)-9-(3-bromo-4-fluorophenyl)-5,5-dimethyl-2,3,5,6,7,9-hexahydrothieno[3,2-b]quinolin-8(4H)-one 1,1-dioxide, (+)-9-(3-bromo-4-fluorophenyl)-5,5-dimethyl-2,3,5,6,7,9-hexahydrothieno[3,2-b]quinolin-8(4H)-one 1,1-dioxide, (–)-9-(3-bromo-4-fluorophenyl)-7,7-dimethyl-2,3,5,6,7,9-hexahydrothieno[3,2-b]quinolin-8(4H)-one, 1,1-dioxide, and (+)-9-(3-bromo-4-fluorophenyl)-7,7-dimethyl-2,3,5,6,7,9-hexahydrothieno[3,2-b]quinolin-8(4H)-one, 1,1-dioxide.

49. The compound according to claim 46 wherein $R_2$ is an optionally substituted heteroaryl.

50. The compound according to claim 49 selected from the group consisting of 9-(4-bromo-2-thienyl)-7,7-dimethyl- 2,3,5,6,7,9-hexahydrothieno[3,2-b]quinolin-8(4H)-one 1,1-dioxide, 9-(5-chloro-2-thienyl)-7,7-dimethyl-2,3,5,6,7,9-hexahydrothieno[3,2-b]quinolin-5 8(4H)-one 1,1-dioxide, 9-(5-bromo-2-thienyl)-7,7-dimethyl-2,3,5,6,7,9-hexahydrothieno[3,2-b]quinolin-8(4H)-one 1,1-dioxide, and 7,7-dimethyl-9-(5-nitro-3-thienyl)-2,3,5,6,7,9-hexahydrothieno [3,2-b]quinolin-8(4H)-one 1,1-dioxide.

51. A compound selected from the group consisting of 3,4,6,7,8,10-hexahydro-10-(3-nitrophenyl)-2H-thiopyrano[3,2-b]quinolin-9(5H)-one, 1,1-dioxide, 10-(3,4-dichlorophenyl)-3,4,6,7,8,10-hexahydro-2H-thiopyrano[3,2-b]quinolin-5 9(5H)-one, 1,1-dioxide, 10-(3-chloro-4-fluorophenyl)-3,4,6,7,8,10-hexahydro-2H-thiopyrano[3,2-b]quinolin-9(5H)-one, 1,1-dioxide, 10-(3-bromo-4-fluorophenyl)-3,4,6,7,8,10-hexahydro-2H-thiopyrano[3,2-b]quinolin-9(5H)-one, 1,1-dioxide, 10-(3-cyanophenyl)-3,4,6,7,8,10-hexahydro-2H-thiopyrano[3,2-b]quinolin-9(5H)-one, 1,1-dioxide, 3,4,6,7,8,10-hexahydro-10-[3-(trifluoromethyl)phenyl]-2H-thiopyrano[3,2-b]quinolin-9(5H)-one, 1,1-dioxide, 10-(3,4-difluorophenyl)-3,4,6,7,8,10-hexahydro-2H-thiopyrano[3,2-b]quinolin-9(5H)-one, 1,1-dioxide, 10-(3-bromophenyl)-3,4,6,7,8,10-hexahydro-2H-thiopyrano[3,2-b]quinolin-9(5H)-one, 1,1-dioxide, 3,4,6,7,8,10-hexahydro-10-(3,4,5-trifluorophenyl)-2H-thiopyrano[3,2-b]quinolin-9(5H)-one, 1,1-dioxide, 10-[3-fluoro-5-(trifluoromethyl)phenyl]-3,4,6,7,8,10-hexahydro-2H-thiopyrano[3,2-b]quinolin-9(5H)-one, 1,1-dioxide, 10-(3-fluorophenyl)-3,4,6,7,8,10-hexahydro-2H-thiopyrano[3,2-b]quinolin-9(5H)-one, 1,1-dioxide, 3,4,6,7,8,10-hexahydro-10-phenyl-2H-thiopyrano[3,2-b]quinolin-9(5H)-one, 1,1-dioxide, 10-[4-fluoro-3-(trifluoromethyl)phenyl]-3,4,6,7,8, 10-hexahydro-2H-thiopyrano[3,2-b]quinolin-9(5H)-one, 1,1-dioxide, 3,4,6,7,8,10-hexahydro-10-(4-methyl-3-nitrophenyl)2H-thiopyrano[3,2-b]quinolin-9(5H)-one, 1,1-dioxide, 10-(4-chloro-3-fluorophenyl)-3,4,6,7,8,10-hexahydro-2H-thiopyrano[3,2-b]quinolin-9(5H)-one, 1,1-dioxide, 10-(3-chlorophenyl)-3,4,6,7,8,10-hexahydro-2H-thiopyrano[3,2-b]quinolin-9(5H)-one, 1,1-dioxide, 3,4,6,7,8,10-hexahydro-10-[4-(trifluoromethyl)phenyl]-2H-thiopyrano[3,2-b]quinolin-9(5H)-one, 1,1-dioxide, 10-(4-bromophenyl)-3,4,6,7,8, 10-hexahydro-2H-thiopyrano[3,2-b]quinolin-9(5H)-one, 1,1-dioxide, 10-(4-chloro-3-nitrophenyl)-3,4,6,7,8, 10-hexahydro-2H-thiopyrano[3,2-b]quinolin-9(5H)-one, 1,1-dioxide, 9-(3,4-dichlorophenyl)-2,3,5,6,7,9-hexahydrothieno[3,2-b]quinolin-8(4H)-one, 1,1-dioxide, 9-(3-cyanophenyl)-2,3,5,6,7,9-hexahydrothieno[3,2-b]quinolin-8(4H)-one, 1,1-dioxide, 9-[4-fluoro-3-(trifluoromethyl)phenyl]-2,3,5,6,7,9-hexahydrothieno[3,2-b]quinolin-8(4H)-one, 1,1-dioxide, 2,3,5,6,7,9-hexahydro-9-(4-methyl-3-nitrophenyl)thieno[3,2-b]quinolin-8(4H)-one, 1,1-dioxide, 9-(3,4-difluorophenyl)-2,3,5,6,7,9-hexahydrothieno[3,2-b]quinolin-8(4H)-one, 1,1-dioxide, 9-(4-chloro-3-nitrophenyl)-2,3,5,6,7,9-hexahydrothieno[3,2-b]quinolin-8(4H)-one, 1,1-dioxide, 9-(3,4-dichlorophenyl)-3,4,5,6,7,9-hexahydrocyclopenta[b]thiopyrano[2,3-e]pyridin-8(2H)-one, 1,1-dioxide, 9-(4-chloro-3-nitrophenyl)-3,4,5,6,7,9-hexahydrocyclopenta[b]thiopyrano[2,3-e]pyridin-8(2H)-one, 1,1-dioxide, 9-(3-chloro-4-fluorophenyl)-3,4,5,6,7,9-hexahydrocyclopenta[b]thiopyrano[2,3-e]pyridin-8(2H)-one, 1,1-dioxide, 9-(3-bromo-4-fluorophenyl)-3,4,5,6,7,9-hexahydrocyclopenta[b]thiopyrano[2,3-e]pyridin-8(2H)-one, 1,1-dioxide, 9-(3-nitrophenyl)-2,3,5,6,7,9-hexahydrothieno[3,2-b]quinolin-8(4H)-one, 1,1-dioxide, 9-(3-cyano)-3,4,5,6,7,9-hexahydrocyclopenta[b]thiopyrano[2,3-e]pyridin-8(2H)-one, 1,1-dioxide, 9-(3-bromo-4-fluorophenyl)-2,3,5,6,7,9-hexahydrothieno[3,2-b]quinolin-8(4H)-one, 1,1-dioxide, 8-(4-chloro-3-nitrophenyl)-2,3,4,5,6,8-hexahydro-7H-cyclopenta[b]thieno[2,3-e]pyridin-7-one 1,1-dioxide, 10-(4-chloro-3-nitrophenyl)-3,4,6,7,8,10-hexahydro-2H,5H-bisthiopyrano[3,2-b:2',3'-e]pyridine, 1,1,9,9-tetraoxide, 10-(3-pyridyl)-3,4,6,7,8,10-hexahydro-2H-thiopyrano[3,2-b]quinolin-9(5H)-one, 1,1-dioxide, 10-(4-pyridyl)-3,4,6,7,8,10-hexahydro-2H-thiopyrano[3,2-b]quinolin-9(5H)-one, 1,1-dioxide, 9-(4-fluoro-3-trifluoromethyl)-3,4,5,6,7,9-hexahydrocyclopenta[b]thiopyrano[2,3-e]pyridin-8(2H)-one, 1,1-dioxide, 9-(4-methyl-3-nitro)-3,4,5,6,7,9-hexahydrocyclopenta[b]thiopyrano[2,3-e]pyridin-8(2H)-one, 1,1-dioxide, 9-(3,4-difluorophenyl)-3,4,5,6,7,9-hexahydrocyclopenta[b]thiopyrano[2,3-e]pyridin-8(2H)-one, 1,1,7,7-tetraoxide, 8-(4-chloro-3-nitrophenyl)-2,3,4,5,6,8-hexahydrodithieno[3,2-b:2',3 '-e]pyridine, 1, 1,7,7-tetraoxide, 8-(3-cyanophenyl)-2,3,4,5,6,8-hexahydro-7H-cyclopenta[b]thieno[2,3-e]pyridin-7-one, 1,1-dioxide, 8-(3-bromo-4-fluorophenyl)-2,3,4,5,6,8-hexahydrodithieno[3,2-b:2',3'-e]pyridine, 1,1,7,7-tetraoxide, 10-(3-bromo-4-fluorophenyl)-3,4,6,7,8,10-hexahydro-2H,5H-dithiopyrano[3,2-b:2',3'-e]pyridine, 1,1,9,9-tetraoxide, 3,4,5,6,7,9-hexahydro-9-(3-nitrophenyl)cyclopenta[b]thiopyrano[2,3-e]pyridin-8(2H)-one, 1,1-dioxide, 8-(3-bromo-4-fluorophenyl)-2,3,4,5,6,8-hexahydro-7H-cyclopenta[b]thieno[2,3-e]pyridin-7-one, 1,1-dioxide, 8-(4-fluoro-3-trifluoromethylphenyl)-2,3,4,5,6,8-hexahydro-7H-cyclopenta[b]thieno[2,3-e]pyridin-7-one, 1,1-dioxide, 2,3,4,5,6,8-hexahydro-8-(3-nitrophenyl)-7H-cyclopenta[b]thieno[2,3-e]pyridin-7-one, 1,1-dioxide, 3,4,6,7,8,10-hexahydro-10-(3-nitrophenyl)-2H,5H-dithiopyrano[3,2-b:2',3'-e]pyridine, 1,1,9,9-tetraoxide, 8-(3,4-dichlorophenyl)-2,3,4,5,6,8-hexahydro-7H-cyclopenta[b]thieno[2,3-e]pyridin-7-one, 1,1-dioxide, 8-(3-chloro-4-fluorophenyl)-2,3,4,5,6,8-hexahydro-7H-cyclopenta[b]thieno[2,3-e]pyridin-7-one, 1,1-dioxide, 8-(3-cyanophenyl)-2,3,4,5,6,8-hexahydrodithieno[3,2-b:2',3'-e]pyridine, 1,1,7,7-tetraoxide, 8-(2-cyano-4-pyridinyl)-2,3,4,5,6,8-hexahydro-7H-cyclopenta[b]thieno[2,3-e]pyridin-7-one, 1,1-dioxide, 8-(3-bromophenyl)-2,3,4,5,6,8-hexahydro-7H-cyclopenta[b]thieno[2,3-e]pyridin-7-one, 1,1-dioxide, 8-(4-fluoro-3-trifluoromethylphenyl)-2,3,4,5,6,8-hexahydrodithieno[3,2-b:2',3'-e]pyridine, 1,1,7,7-tetraoxide, 8-(4-bromo-2-thienyl)-2,3,4,5,6,8-hexahydro-7H-cyclopenta[b]thieno[2,3-e]pyridin-7-one, 1,1-dioxide, 8-(5-bromo-2-thienyl)-2,3,4,5,6,8-hexahydro-7H-cyclopenta[b]thieno[2,3-e]pyridin-7-one, 1,1-dioxide, 2,3,4,5,6,8-hexahydro-8-(5-nitro-3-thienyl)-7H-cyclopenta[b]thieno[2,3-e]pyridin-7-one, 1,1-dioxide, 2,3,4,5,6,8-hexahydro-8-(5-nitro-2-thienyl)-7H-cyclopenta[b]thieno[2,3-e]pyridin-7-one, 1,1-dioxide, 2,3,4,5,6,8-hexahydro-8-(5-nitro-2-furyl)-7H-cyclopenta[b]thieno[2,3-e]pyridin-7-one, 1,1-dioxide, 8-(3,4-dibromophenyl)-2,3,4,5,6,8-hexahydro-7H-cyclopenta[b]thieno[2,3-e]pyridin-7-one, 1,1-dioxide, 2,3,4,5,6,8-hexahydro-8-(3-nitrophenyl)dithieno[3,2-b:2',3'-e]pyridine, 1,1,7,7-tetraoxide, 8-(3-chloro-4-fluorophenyl)-2,3,4,5,6,8-hexahydrodithieno[3,2-b:2',3'-e]pyridine, 1,1,7,7-tetraoxide, 8-(3,4-dichlorophenyl)-2,3,4,5,6,8-hexahydrodithieno[3,2-b:2',3'-e]pyridine, 1,1,7,7-tetraoxide, 8-(4-bromophenyl)-2,3,4,5,6,8-hexahydro-7H-cyclopenta[b]thieno[2,3-e]pyridin-7-one, 1,1-dioxide, 8-(3,4-difluorophenyl)-2,3,4,5,6,8-hexahydro-7H-cyclopenta[b]thieno[2,3-e]pyridin-7-one, 1,1-dioxide, 8-(4-chloro-3-fluorophenyl)-2,3,4,5,6,8-hexahydro-7H-cyclopenta[b]thieno[2,3-e]pyridin-7-one, 1,1-dioxide, 9-(3-chloro-4-fluorophenyl)-2,3,5,6,7,9-hexahydrothieno[3,2-b]quinolin-8(4H)-one, 1,1-dioxide, 8-(3-cyano-4-fluorophenyl)-2,3,4,5,6,8-hexahydrodithieno[3,2-b:2',3'-e]pyridine, 1, 1,7,7- tetraoxide, (+)-9-(3-bromo-4-fluorophenyl)-2,3,5,6,7,9-hexahydrothieno[3,2-b]quinolin-8(4H)-one, 1,1-dioxide, (−)-9-(3-bromo-4-fluorophenyl)-2,3,5,6,7,9-hexahydrothieno[3,2-b]quinolin-8(4H)-one, 1,1-dioxide, 8-(2,1,3-benzoxadiazol-5-yl)-2,3,4,5,6,8-hexahydro-7H-cyclopenta[b]thieno[2,3-e]pyridin-7-one, 1,1-dioxide, (−)-8-(3-bromo-4-fluorophenyl)-2,3,4,5,6,8-hexahydro-7H-cyclopenta[b]thieno[2,3-e]pyridin-7-one, 1,1-dioxide, (+)-8-(3-bromo-4-fluorophenyl)-2,3,4,5,6,8-hexahydro-7H-cyclopenta[b]thieno[2,3-e]pyridin-7-one, 1,1-dioxide, 9-(2,1,3-benzoxadiazol-5-yl)-2,3,5,6,7,9-hexahydrothieno[3,2-b]quinolin-8(4H)-one, 1,1-dioxide, 9-(4-fluoro-3-iodophenyl)-2,3,5,6,7,9-hexahydrothieno[3,2-b]quinolin-8(4H)-one, 1,1-dioxide, 8-(4-fluoro-3-iodophenyl)-2,3,4,5,6,8-hexahydro-7H-cyclopenta[b]thieno[2,3-e]pyridin-7-one, 1,1-dioxide, (+) 9-(3-bromo-4-fluorophenyl)-3,4,5,6,7,9-hexahydrocyclopenta[b]thiopyrano[2,3-e]pyridin-8(2H)-one, 1,1-dioxide, (−)-9-(3-bromo-4-fluorophenyl)-3,4,5,6,7,9-hexahydrocyclopenta[b]thiopyrano[2,3-e]pyridin-8(2H)-one, 1,1-dioxide, (+) 10-(3-bromo-4-fluorophenyl)-3,4,6,7,8,10-hexahydro-2H-thiopyrano[3,2-b]quinolin-9(5H)-one, 1,1-dioxide, (−)-10-(3-bromo-4-fluorophenyl)-3,4,6,7,8,10-hexahydro-2H-thiopyrano[3,2-b]quinolin-9(5H)-one, 1,1-dioxide, (+)-9-(3,4-dichlorophenyl)-2,3,5,6,7,9-hexahydrothieno[3,2-b]quinolin-8(4H)-one, 1,1-dioxide, (−)-9-(3,4-dichlorophenyl)-2,3,5,6,7,9-hexahydrothieno[3,2-b]quinolin-8(4H)-one, 1,1-dioxide, (+)-9-(2,1,3-benzoxadiazol-5-yl)-2,3,5,6,7,9-hexahydrothieno[3,2-b]quinolin-8(4H)-one, 1,1-dioxide, (−)-9-(2,1,3-benzoxadiazol-5-yl)-2,3,5,6,7,9-hexahydrothieno[3,2-b]quinolin-8(4H)-one, 1,1-dioxide, (+)-9-(4-chloro-3-nitrophenyl)-2,3,5,6,7,9-hexahydrothieno[3,2-b]quinolin-8(4H)-one, 1,1-dioxide, (−)-9-(4-chloro-3-nitrophenyl)-2,3,5,6,7,9-hexahydrothieno[3,2-b]quinolin-8(4H)-one, 1,1-dioxide, 10-(3-bromo-4-fluorophenyl)-2,3,4,5,7,8,9,11-octahydrothiepino[3,2-b]quinolin-10(6H)-one, 1,1-dioxide, 10-(3-bromo-4-fluorophenyl)-2,3,4,5,6,7,8,10-octahydro-9H-cyclopenta[b]thiepino[2,3-e]pyridin-9-one, 9-[3-(trifluoromethoxy)phenyl]-3,4,5,6,7,9-hexahydrocyclopenta[b]thiopyrano[2,3-e]pyridin-8(2H)-one, 1,1-dioxide, 9-(5-bromo-2-hydroxyphenyl)-3,4,5,6,7,9-hexahydrocyclopenta[b]thiopyrano[2,3-e]pyridin-8(2H)-one, 1,1-dioxide, 9-(5-cyano-6-methylthiopyrid-2-yl)-3,4,5,6,7,9-hexahydrocyclopenta[b]thiopyrano[2,3-e]pyridin-8(2H)-one, 1,1-dioxide, 9-(5-bromo-2-hydroxyphenyl)-2,3,5,6,7,9-hexahydrothieno[3,2-b]quinolin-8(4H)-one, 1,1-dioxide, (+)-9-(3-chloro-4-fluorophenyl)-2,3,5,6,7,9-hexahydrothieno[3,2-b]quinolin-8(4H)-one, 1,1-dioxide, (−)-9-(3-chloro-4-fluorophenyl)-2,3,5,6,7,9-hexahydrothieno[3,2-b]quinolin-8(4H)-one, 1,1-dioxide, 9-(4-fluoro-3-methylphenyl)-2,3,5,6,7,9-hexahydrothieno[3,2-b]quinolin-8(4H)-one, 1,1-dioxide, 7-(3-bromo-4-fluorophenyl)-5-(trifluoromethyl)-2,3,4,7-tetrahydrothieno[3,2-b]pyridine, 1,1-dioxide, (+)-9-(3-cyanophenyl)-2,3,5,6,7,9-hexahydrothieno[3,2-b]quinolin-8(4H)-one, 1,1-dioxide, (−)-9-(3-cyanophenyl)-2,3,5,6,7,9-hexahydrothieno[3,2-b]quinolin-8(4H)-one, 1,1-dioxide, 9-(5-bromo-4-fluoro-2-iodophenyl)-2,3,5,6,7,9-hexahydrothieno[3,2-b]quinolin-8(4H)-one, 1,1-dioxide, 9-(3-bromo-4-fluorophenyl)-7,7-dimethyl-2,3,5,6,7,9-hexahydrothieno[3,2-b]quinolin-8(4H)-one, 1,1-dioxide, 9-(3-pyridinyl)-2,3,5,6,7,9-hexahydrothieno[3,2-b]quinolin-8(4H)-one, 1,1-.dioxide, 9-(4-pyridinyl)-2,3,5,6,7,9-hexahydrothieno[3,2-b]quinolin-8(4H)-one, 1,1, dioxide, 9-(4-fluoro-2-hydroxyphenyl)-2,3,5,6,7,9-hexahydrothieno[3,2-b]quinolin-8(4H)-one, 1,1-dioxide, 9-(5-chloro-2-hydroxyphenyl)-2,3,5,6,7,9-hexahydrothieno[3,2-b]quinolin-8(4H)-one, 1,1-dioxide, 9-(5-bromo-4-fluoro-2-hydroxyphenyl)-2,3,5,6,7,9-hexahydrothieno[3,2-b]quinolin-8(4H)-one,1,1-dioxide, 8-(2,1,3-benzoxadiazol-5-yl)-2,3,4,5,6,8-hexahydrodithieno[3,2-b:2',3'-e]pyridine-1,1,7,7-tetraoxide, 8-(3,4-dibromophenyl)-2,3,4,5,6,8-hexahydrodithieno[3,2-b:2',3'-e]pyridine-1,1,7,7-tetraoxide, 9-(3-bromo-4-fluorophenyl)-2,3,5,6,7,9-hexahydrothieno[3,2-b]quinolin-8(4H)-one, 1-oxide, (+)-9-(4-methyl-3-nitrophenyl)-2,3,5,6,7,9-hexahydro[3,2-b]quinolin-8(4H)-one, 1,1-dioxide, (−)-9-(4-methyl-3-nitrophenyl)-2,3,5,6,7,9-hexahydro[3,2-b]quinolin-8(4H)-one, 1,1-dioxide, 9-(3,4-dichlorophenyl)-7,7-dimethyl-2,3,5,6,7,9-hexahydrothieno[3,2-b]quinolin-8(4H)-one, 1,1-dioxide, 9-(5-bromo-2-thienyl)-2,3,5,6,7,9-hexahydrothieno[3,2-b]quinolin-8(4H)-one, 1,1-dioxide, 9-(4-bromo-2-thienyl)-2,3,5,6,7,9-hexahydrothieno[3,2-b]quinolin-8(4H)-one, 1,1-dioxide, 9-(4-fluoro-3-vinylphenyl)-2,3,5,6,7,9-hexahydrothieno[3,2-b]quinolin-8(4H)-one, 1,1-dioxide, 9-(3-acetyl-4-fluorophenyl)-2,3,5,6,7,9-hexahydrothieno[3,2-b]quinolin-8(4H)-one, 1,1-dioxide, 9-[4-fluoro-3-(2-furyl)phenyl]-2,3,5,6,7,9-hexahydrothieno[3,2-b]quinolin-8(4H)-one, 1,1-dioxide, 9-[6-fluoro-(1,1-biphenyl)-3-yl]-2,3,5,6,7,9-hexahydrothieno[3,2-b]quinolin-8(4H)-one, 1,1-dioxide, 9-[4-fluoro-3-(phenylethynyl)phenyl]-2,3,5,6,7,9-hexahydrothieno[3,2-b]quinolin-8(4H)-one, 1,1-dioxide, 9-(3,4-dibromophenyl)-2,3,5,6,7,9-hexahydrothieno[3,2-b]quinolin-8(4H)-one, 1,1-dioxide, (+)-9-[4-fluoro-3-(trifluoromethyl)phenyl]-2,3,5,6,7,9-hexahydrothieno[3,2-b]quinolin-8(4H)-one, 1,1-dioxide, (−)-9-[4-fluoro-3-(trifluoromethyl)phenyl]-2,3,5,6,7,9-hexahydrothieno[3,2-b]quinolin-8(4H)-one, 1,1-dioxide, 9-[4-fluoro-3-(2-thienyl)phenyl]-2,3,5,6,7,9-hexahydrothieno[3,2-b]quinolin-8(4H)-one, 1,1-dioxide, 9-[4-fluoro-3-(3-hydroxy-3-methyl-1-butynyl)phenyl]-2,3,5,6,7,9-hexahydrothieno[3,2-b]quinolin-8(4H)-one, 1,1-dioxide, 8-(4-fluoro-3-iodophenyl)-2,3,4,5,6,8-hexahydrodithieno[3,2-b:2'3'-e]pyridine-1,1,7,7-tetraoxide, (+)-9-(3-cyano-4-fluorophenyl)-2,3,5,6,7,9-hexahydrothieno[3,2-b]quinolin-8(4H)-one, 1,1-dioxide, (−)-9-(3-cyano-4-fluorophenyl)-2,3,5,6,7,9-hexahydrothieno[3,2-b]quinolin-8(4H)-one, 1,1-dioxide, (+)-8-(3,4-dichlorophenyl)-2,3,4,5,6,8-hexahydrocyclopenta[b]thieno[2,3-e]pyridin-7-one, 1,1-dioxide, (−)-8-(3,4-dichlorophenyl)-2,3,4,5,6,8-hexahydrocyclopenta[b]thieno[2,3-e]pyridin-7-one, 1,1-dioxide, (+)-9-(3,4-dibromophenyl)-2,3,5,6,7,9-hexahydrothieno[3,2-b]quinolin-8(4H)-one, 1,1-dioxide, (−)-9-(3,4-dibromophenyl)-2,3,5,6,7,9-hexahydrothieno[3,2-b]quinolin-8(4H)-one, 1,1-dioxide, (+)-9-(4-fluoro-3-iodophenyl)-2,3,5,6,7,9-hexahydrothieno[3,2-b]quinolin-8(4H)-one, 1,1-dioxide, (−)-9-(4-fluoro-3-iodophenyl)-2,3,5,6,7,9-hexahydrothieno[3,2-b]quinolin-8(4H)-one, 1,1-dioxide, 9-[4-chloro-3-(trifluoromethyl)phenyl]-2,3,5,6,7,9-hexahydrothieno[3,2-b]quinolin-8(4H)-one, 1,1-dioxide, (+)-9-(3-ethynyl-4-fluorophenyl)-2,3,5,6,7,9-hexahydrothieno[3,2-b]quinolin-8(4H)-one, 1,1-dioxide, (−)-9-(3-ethynyl-4-fluorophenyl)-2,3,5,6,7,9-hexahydrothieno[3,2-b]quinolin-8(4H)-one, 1,1-dioxide, 9-(3-cyano-4-methylphenyl)-2,3,5,6,7,9-hexahydrothieno[3,2-b]quinolin-8(4H)-one, 1,1-dioxide, (+)-9-(3-cyano-4-methylphenyl)-2,3,5,6,7,9-hexahydrothieno[3,2-b]quinolin-8(4H)-one, 1,1-dioxide, (−)-9-(3-cyano-4-methylphenyl)-2,3,5,6,7,9-hexahydrothieno[3,2-b]quinolin-8(4H)-one, 1,1-dioxide, 9-[4-fluoro-3-(3-pyridinyl)phenyl]-2,3,5,6,7,9-hexahydrothieno[3,2-b]quinolin-8(4H)-one, 1,1-dioxide, (+)-8-(4-chloro-3-nitrophenyl)-2,3,4,5,6,8-hexahydrocyclopenta[b]thieno[2,3-e]pyridin-7-one, 1,1-dioxide, (−)-8-(4-chloro-3-nitrophenyl)-2,3,4,5,6,8- hexahydrocyclopenta[b]thieno[2,3-e]pyridin-7-one, 1,1-dioxide, (−)-8-(3-cyanophenyl)-2,3,4,5,6,8-hexahydrocyclopenta[b]thieno[2,3-e]pyridin-7-one, 1,1-dioxide, (+)-8-(3-cyanophenyl)-2,3,4,5,6,8-hexahydrocyclopenta[b]thieno[2,3-e]pyridin-7-one, 1,1-dioxide, (+)-9-[4-fluoro-3-(2-hryl)phenyl]-2,3,5,6,7,9-hexahydrothieno[3,2-b]quinolin-8(4H)-one, 1,1-dioxide, (−)-9-[4-fluoro-3-(2-furyl)phenyl]-2,3,5,6,7,9-hexahydrothieno[3,2-b]quinolin-8(4H)-one, 1,1-dioxide, (+)-9-(5-bromo-2-thienyl)-2,3,5,6,7,9-hexahydrothieno[3,2-b]quinolin-8(4H)-one, 1,1-dioxide, (−)-9-(5-bromo-2-thienyl)-2,3,5,6,7,9-hexahydrothieno[3,2-b]quinolin-8(4H)-one, 1,1-dioxide, 9-(3-allyl-4-fluorophenyl)-2,3,5,6,7,9-hexahydrothieno[3,2-b]quinolin-8(4H)-one, 1, 1-dioxide, 9-[3-(1-ethoxyvinyl)-4-fluorophenyl]-2,3,5,6,7,9-hexahydrothieno [3,2-b]quinolin-8(4H)-one, 1, 1-dioxide, (−)-9-[4-chloro-3-(trifluoromethyl)phenyl]-2,3,5,6,7,9-hexahydrothieno[3,2-b]quinolin-8(4H)-one, 1,1-dioxide, (+)-9-[4-chloro-3-(trifluoromethyl)phenyl]-2,3,5,6,7,9-hexahydrothieno[3,2-b]quinolin-8(4H)-one, 1,1-dioxide, (9S)-9-(3-ethyl-4-fluorophenyl)-2,3,5,6,7,9-hexahydrothieno[3,2-b]quinolin-8(4H)-one, 1,1-dioxide, 9-(5-cyano-2-thienyl)-2,3,5,6,7,9-hexahydrothieno[3,2-b]quinolin-8(4H)-one, 1,1-dioxide, (+)-9-(3,4-difluoro)-2,3,5,6,7,9-hexahydrothieno[3,2-b]quinolin-8(4H)-one, 1,1-dioxide, (9S)-9-(3-ethenyl-4-fluorophenyl)-2,3,5,6,7,9-hexahydrothieno[3,2-b]quinolin-8(4H)-one, 1,1-dioxide, 9-(5-bromo-4-fluoro-2-nitrophenyl)-3,4,5,6,7,9-hexahydrocyclopenta[b]thiopyrano[2,3-e]pyridin-8(2H)-one, 1,1-dioxide, (−)-9-(3,4-difluorophenyl)-2,3,5,6,7,9-hexahydrothieno[3,2-b]quinolin-8(4H)-one, 1,1-dioxide, (+)-9-(4-bromo-2-thienyl)-2,3,5,6,7,9-hexahydrothieno[3,2-b]quinolin-8(4H)-one 1,1-dioxide, (−)-9-(4-bromo-2-thienyl)-2,3,5,6,7,9-hexahydrothieno [3,2-b]quinolin-8(4H)-one 1,1-dioxide, 9-(3,4-difluorophenyl)-7,7-dimethyl-2,3,5,6,7,9-hexahydrothieno[3,2-b]quinolin-8(4H)-one 1,1-dioxide, 9-(3-chloro-4-fluorophenyl)-7,7-dimethyl-2,3,5,6,7,9-hexahydrothieno[3,2-b]quinolin-8(4H)-one 1,1-dioxide, 9-[4-fluoro-3-(trifluoromethyl)phenyl]-7,7-dimethyl-2,3,5,6,7,9-hexahydrothieno[3,2-b]quinolin-8(4H)-one 1,1-dioxide, 9-(4-chloro-3-fluorophenyl)-7,7-dimethyl-2,3,5,6,7,9-hexahydrothieno[3,2-b]quinolin-8(4H)-one 1,1-dioxide, 9-(4-chloro-3-nitrophenyl)-7,7-dimethyl-2,3,5,6,7,9-hexahydrothieno[3,2-b]quinolin-8(4H)-one 1,1-dioxide, 9-(3,4-dibromophenyl)-7,7-.dimethyl-2,3,5,6,7,9-hexahydrothieno[3,2-b]quinolin-8(4H)-one 1,1-dioxide, 9-[3-fluoro-4-(trifluoromethyl)phenyl]-7,7-dimethyl-2,3,5,6,7,9-hexahydrothieno[3,2-b]quinolin-8(4H)-one 1,1-dioxide, 7,7-dimethyl-9-(3-nitrophenyl)-2,3,5,6,7,9-hexahydrothieno[3,2-b]quinolin-8(4H)-one 1,1-dioxide, 9-(3-cyanophenyl)-7,7-dimethyl-2 , 3,5,6,7, 9-hexahydrothieno [3,2-b]quinolin-8(4H)-one 1,1-dioxide, 9-(4-bromo-2-thienyl)-7,7-dimethyl-2,3,5,6,7,9-hexahydrothieno[3,2-b]quinolin-8(4H)-one 1,1-dioxide, -9-(5-chloro-2-thienyl)-7,7-dimethyl-2,3,5,6,7,9-hexahydrothieno[3,2-b]quinolin-8(4H)-one 1,1-dioxide, 9-(5-bromo-2-thienyl)-7,7-dimethyl-2,3,5,6,7,9-hexahydrothieno[3,2-b]quinolin-8(4H)-one 1,1-dioxide, 7,7-dimethyl-9-(5-nitro-3-thienyl)-2,3,5,6,7,9-hexahydrothieno[3,2-b]quinolin-8(4H)-one 1,1-dioxide, 9-(5-chloro-2-hydroxyphenyl)-7,7-dimethyl-2,3,5,6,7,9-hexahydrothieno[3,2-b]quinolin-8(4H)-one 1,1-dioxide, 9-(2-hydroxy-5-nitrophenyl)-7,7-dimethyl-2,3,5,6,7,9-hexahydrothieno[3,2-b]quinolin-8(4H)-one 1,1-dioxide, 9-(2-hydroxy-3,5-dinitrophenyl)-7,7-dimethyl-2,3,5,6,7,9-hexahydrothieno[3,2-b]quinolin-8(4H)-one 1,1-dioxide, 9-(3,5-dibromo-2-hydroxyphenyl)-7,7-dimethyl-2,3,5,6,7, 9-hexahydrothieno[3,2-b]quinolin-8(4H)-one 1,1-dioxide, 9-(3-bromo-5-chloro-2-hydroxyphenyl)-7,7-dimethyl-2,3,5,6,7,9-hexahydrothieno[3,2-b]quinolin-8(4H)-one 1,1-dioxide, 9-(3-bromo-2-hydroxy-5-nitrophenyl)-7,7-dimethyl-2,3,5,6,7,9-hexahydrothieno[3,2-b]quinolin-8(4H)-one 1,1-dioxide, 9-(3,5-dichloro-2-hydroxyphenyl)-7,7-dimethyl-2,3,5,6,7,9-hexahydrothieno[3,2-b]quinolin-8(4H)-one 1,1-dioxide, 9-(2-hydroxy-3-nitrophenyl)-7,7-dimethyl-2,3,5,6,7,9-hexahydrothieno[3,2-b]quinolin-8(4H)-one 1,1-dioxide, 9-(5-bromo-2-hydroxy-3-nitrophenyl)-7,7-dimethyl-2,3,5,6,7,9-hexahydrothieno[3,2-b]quinolin-8(4H)-one 1,1-dioxide, 7,7-dimethyl-9-(2,4,5-trifluorophenyl)-2,3,5,6,7,9-hexahydrothieno[3,2-b]quinolin-8(4H)-one 1,1-dioxide, 7,7-dimethyl-9-(2,3,4-trifluorophenyl)-2,3,5,6,7,9-hexahydrothieno[3,2-b]quinolin-8(4H)-one 1,1-dioxide, 7,7-dimethyl-9-(3,4,5-trifluorophenyl)-2,3,5,6,7,9-hexahydrothieno[3,2-b]quinolin-8(4H)-one 1,1-dioxide, 9-(3,5-dibromo-4-hydroxyphenyl)-7,7-dimethyl-2,3,5,6,7,9-hexahydrothieno [3,2-b]quinolin-8(4H)-one 1,1-dioxide, 9-(4-chlorophenyl)-7,7-dimethyl-2,3,5,6,7,9-hexahydrothieno[3,2-b]quinolin-8(4H)-one 1,1-dioxide, 9-(3-chlorophenyl)-7,7-dimethyl-2,3,5,6,7,9-hexahydrothieno[3,2-b]quinolin-8(4H)-one 1,1-dioxide, 9-(4-chloro-3-fluorophenyl)-2,3,5,6,7,9-hexahydrothieno[3,2-b]quinolin-8(4H)-one 1,1-dioxide, 9-[3-(trifluoromethoxy)phenyl]-2,3,5,6,7,9-hexahydrothieno[3,2-b]quinolin-8(4H)-one 1,1-dioxide, 9-(3-bromo-4-fluorophenyl)-5,5-dimethyl-2,3,5,6,7,9-hexahydrothieno[3,2-b]quinolin-8(4H)-one 1,1-dioxide, 9-[4-(trifluoromethoxy)phenyl]-2,3,5,6,7,9-hexahydrothieno[3,2-b]quinolin-8(4H)-one 1,1-dioxide, 9-(2,1,3-benzothiadiazol-5-yl)-2,3,5,6,7,9-hexahydrothieno[3,2-b]quinolin-8(4H)-one 1,1-dioxide, 9-(4-bromo-3-nitrophenyl)-2,3,5,6,7,9-hexahydrothieno[3,2-b]quinolin-8(4H)-one 1,1-dioxide, 9-(4-ethyl-3-nitrophenyl)-2,3,5,6,7,9-hexahydrothieno[3,2-b]quinolin-8(4H)-one 1,1-dioxide, 9-[3-nitro-4-(trifluoromethoxy)phenyl]-2,3,5,6,7,9-hexahydrothieno[3,2-b]quinolin-8(4H)-one 1,1-dioxide, 9-[4-(difluoromethoxy)phenyl]-2,3,5,6,7,9-hexahydrothieno[3,2-b]quinolin-8(4H)-one 1,1-dioxide, 9-(3-methyl-4-nitrophenyl)-2,3,5,6,7,9-hexahydrothieno[3,2-b]quinolin-8(4H)-one 1,1-dioxide, 9-[3-nitro-4-(trifluoromethyl)phenyl]-2,3,5,6,7,9-hexahydrothieno[3,2-b]quinolin-8(4H)-one 1,1-dioxide, 9-[4-(difluoromethoxy)-3-nitrophenyl]-2,3,5,6,7,9-hexahydrothieno[3,2-445 b]quinolin-8(4H)-one 1,1-dioxide, 9-(4-chloro-3-methylphenyl)-2,3,5,6,7,9-hexahydrothieno[3,2-b]quinolin-8(4H)-one 1,1-dioxide, 9-(3-bromo-4-methylphenyl)-2,3,5,6,7,9-hexahydrothieno[3,2-b]quinolin-8(4H)-one 1,1-dioxide, (+)-9-(3-bromo-4-methylphenyl)-2,3,5,6,7,9-hexahydrothieno[3,2-b]quinolin-8(4H)-one 1,1-dioxide, (−)-9-(3-bromo-4-methylphenyl)-2,3,5,6,7,9-hexahydrothieno[3,2-b]quinolin-8(4H)-one 1,1-dioxide, 9-[4-methyl-3-(methylsulfanyl)phenyl]-2,3,5,6,7,9-hexahydrothieno[3,2-b]quinolin-8(4H)-one 1,1-dioxide, (−)-9-(4-chloro-3-fluorophenyl)-2,3,5,6,7,9-hexahydrothieno[3,2-b]quinolin-8(4H)-one 1,1-dioxide, (+)-9-(4-chloro-3-fluorophenyl)-2,3,5,6,7,9-hexahydrothieno[3,2-b]quinolin-8(4H)-one 1,1-dioxide, 9-[4-methyl-3-(methylsulfonyl)phenyl]-2,3,5,6,7,9-hexahydrothieno[3,2-b]quinolin-8(4H)-one 1,1-dioxide (−)-9-(3-bromo-4-fluorophenyl)-5,5-dimethyl-2,3,5,6,7,9-hexahydrothieno[3,2-b]quinolin-8(4H)-one 1,1-dioxide, (+)-9-(3-bromo-4-fluorophenyl)-5,5-dimethyl-2,3,5,6,7,9-hexahydrothieno[3,2-b]quinolin-8(4H)-one 1,1-dioxide, (−)-9-(3-bromo-4-fluorophenyl)-7,7-dimethyl-2,3,5,6,7,9-hexahydrothieno[3,2-b]quinolin-8(4H)-one, 1,1-dioxide, (+)-9-(3-bromo-4-fluorophenyl)-7,7-dimethyl-2,3,5,6,7,9-hexahydrothieno [3,2-b]quinolin-8(4H)-one, 1,1-dioxide, (+)-9-(4-bromo-3-nitrophenyl)-2,3,5,6,7,9-hexahydrothieno [3,2-b]quinolin-8(4H)-one 1,1-dioxide, (−)-9-(4-bromo-3-nitrophenyl)-2,3,5,6,7,9-hexahydrothieno[3,2-b]quinolin-8(4H)-one 1,1-dioxide, 9-(3-iodo-4-methylphenyl)-2,3,5,6,7,9-hexahydrothieno[3,2-b]quinolin-8(4H)-one 1,1-dioxide, (+)-9-[3-nitro-4-(trifluoromethyl)phenyl]-2,3,5,6,7,9 hexahydrothieno[3,2-b]quinolin-8(4H)-one 1,1-dioxide, (−)-9-[3-nitro-4-(trifluoromethyl)phenyl]-2,3,5,6,7,9-hexahydrothieno[3,2-b]quinolin-8(4H)-one 1,1-dioxide, (+)-9-(2,1,3-benzothiadiazol-5-yl)-2,3,5,6,7,9-hexahydrothieno[3,2-b]quinolin-8(4H)-one 1,1-dioxide, (−)-9-(2,1,3-benzothiadiazol-5-yl)-2,3,5,6,7,9-hexahydrothieno[3,2-b]quinolin-8(4H)-one 1,1-dioxide, (+)-9-(3-iodo-4-methylphenyl)-2,3,5,6,7,9-hexahydrothieno [3,2-b]quinolin-8(4H)-one 1,1-dioxide, and (−)-9-(3-iodo-4-methylphenyl)-2,3,5,6,7,9-hexahydrothieno[3,2-b]quinolin-8(4H)-one 1,1-dioxide, or a pharmaceutically acceptable salt, ester, amide or prodrug thereof.

52. A pharmaceutical composition comprising a therapeutically effective amount of a compound of claim 1 in combination with a pharmaceutically acceptable carrier.

53. A method of treating a disease than can be ameliorated with a potassium channel opener in a host mammal, comprising administering to the mammal in need thereof a therapeutically effective amount of the compound of claim 1; said disease is selected from a group consisting of epilepsy, Raynaud's syndrome, male erectile dysfunction, premature ejaculation, female anoryasmia, clitoral erectile insufficiency, vaginal engorgement, dyspareunia, vaginismus, migraine, pain, eating disorders, urinary incontinence, functional bowel disorders, neurodegeneration and stroke. pyridin-8(2H)-one, 1,1-dioxide, 54. A method of claim 53 wherein said administration of administering a therapeutically effective amount of the compound of claim 1 is for treating urinary incontinence.

* * * * *

UNITED STATES PATENT AND TRADEMARK OFFICE
CERTIFICATE OF CORRECTION

PATENT NO. : 6,593,335 B1
DATED : July 15, 2003
INVENTOR(S) : William A. Carroll et al.

It is certified that error appears in the above-identified patent and that said Letters Patent is hereby corrected as shown below:

Column 152,
Line 58, replace "A is - $R_3$;" with -- A is -$XR_3$; --.

Column 153,
Line 59, replace "[3,2-bJquinolin-" with -- [3,2-b]quinolin- --.
Line 61, replace "delete the number" with -- 40 --.

Column 155,
Line 1, replace "(1,I'-biphenyl)" with -- (1,1'biphenyl) --.
Lines 39 and 41, replace "(2-ftiryl)" with -- (2-furyl) --.

Column 156,
Line 37, replace "Claim 1" with -- Claim 11 --.

Column 157,
Line 12, replace "1,1(3-bromo-" with -- 11-(3-bromo- --.
Line 38, replace "hexahydrocyclopentafb]" with -- hexahydrocyclopenta[b] --.

Column 159,
Line 14, replace "[3,2-5 b:2'3'-e]" with -- [3,2-b:2'3'-e] --.

Column 160,
Line 10, replace "9-[$^4$-fluoro-3-" with -- 9-[4-fluoro-3- --.

Column 161,
Line 12, replace "quinolin-5 9(5H)-one" with -- quinolin-9(5H)-one --.

Column 163,
Line 35, replace "10-(3-bromo-" with -- 11-(3-bromo- --.

Column 164,
Line 3, insert after the word "-dioxide," with "8-[4-chloro-3(trifluoromethyl)phenyl] 2,3,4,5,6,8-hexahydrodithieno[3,2-b:2', 3'-e]pyridine-1,1,7,7,-tetraoxide,".

UNITED STATES PATENT AND TRADEMARK OFFICE
CERTIFICATE OF CORRECTION

PATENT NO.    : 6,593,335 B1
DATED         : July 15, 2003
INVENTOR(S)   : William A. Carroll et al.

It is certified that error appears in the above-identified patent and that said Letters Patent is hereby corrected as shown below:

Column 166,
Line 45, replace "[3,2-445b]" with -- [3,2,-b --.

Signed and Sealed this

Thirteenth Day of April, 2004

JON W. DUDAS
*Acting Director of the United States Patent and Trademark Office*